(12) United States Patent
Peterson et al.

(10) Patent No.: US 10,350,062 B2
(45) Date of Patent: Jul. 16, 2019

(54) REPLACEMENT HEART VALVE PROSTHESIS

(71) Applicant: Edwards Lifesciences Corporation, Irvine, CA (US)

(72) Inventors: Matthew A. Peterson, Costa Mesa, CA (US); Seung-Beom Yi, Mission Viejo, CA (US); Siddharth Vad, Irvine, CA (US); Travis Zenyo Oba, Yorba Linda, CA (US); Lauren R. Freschauf, Rancho Santa Margarita, CA (US); Amanda French, Newport Beach, CA (US); Yaron Keidar, Irvine, CA (US); Yuanlong Du, Fountain Valley, CA (US); Gregory Bak-Boychuk, San Clemente, CA (US); Kevin M. Golemo, Mission Viejo, CA (US); Alexander H. Cooper, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 43 days.

(21) Appl. No.: 15/653,390

(22) Filed: Jul. 18, 2017

(65) Prior Publication Data

US 2018/0021129 A1    Jan. 25, 2018

Related U.S. Application Data

(60) Provisional application No. 62/471,213, filed on Mar. 14, 2017, provisional application No. 62/365,070, filed on Jul. 21, 2016.

(51) Int. Cl.
*A61F 2/24* (2006.01)

(52) U.S. Cl.
CPC .......... *A61F 2/2412* (2013.01); *A61F 2/2409* (2013.01); *A61F 2/2418* (2013.01);
(Continued)

(58) Field of Classification Search
CPC ........ A61F 2/24; A61F 2/2412; A61F 2/2409; A61F 2/2436; A61F 2/2427
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |
| | (Continued) | |

FOREIGN PATENT DOCUMENTS

| | | |
|---|---|---|
| CA | 2304325 A1 | 10/2000 |
| CA | 2827556 A1 | 7/2012 |
| | (Continued) | |

OTHER PUBLICATIONS

Int'l. Search Report for PCT/US2017/043162, dated Dec. 6, 2017.
(Continued)

*Primary Examiner* — Alvin J Stewart
(74) *Attorney, Agent, or Firm* — Knobbe Martens Olson & Bear LLP

(57) ABSTRACT

A prosthesis can be configured to grasp intralumenal tissue when deployed within a body cavity and prevent axial flow of fluid around an exterior of the prosthesis. The prosthesis can include an expandable frame configured to radially expand and contract for deployment within the body cavity and a valve body. The expandable frame can include a frame body and a supplemental frame. The valve body can include a plurality of leaflets and one or more intermediate components. The one or more intermediate components can couple at least a portion of the leaflets to the expandable frame. The prosthesis can include an annular flap positioned around an exterior of the expandable frame.

25 Claims, 71 Drawing Sheets

(52) U.S. Cl.
CPC .......... *A61F 2/2436* (2013.01); *A61F 2/2427* (2013.01); *A61F 2210/0014* (2013.01); *A61F 2220/0008* (2013.01); *A61F 2230/0013* (2013.01); *A61F 2230/0054* (2013.01); *A61F 2250/0003* (2013.01); *A61F 2250/0014* (2013.01); *A61F 2250/0039* (2013.01); *A61F 2250/0069* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,197,978 A | 3/1993 | Hess |
| 5,326,371 A | 7/1994 | Love et al. |
| 5,332,402 A | 7/1994 | Teitelbaum |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,554,185 A | 9/1996 | Block et al. |
| 5,575,818 A | 11/1996 | Pinchuk |
| 5,607,444 A | 3/1997 | Lam |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,855,601 A | 1/1999 | Bessler et al. |
| 5,868,782 A | 2/1999 | Frantzen |
| 5,879,381 A | 3/1999 | Moriuchi et al. |
| 5,902,334 A | 5/1999 | Dwyer et al. |
| 5,935,108 A | 8/1999 | Katoh et al. |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,527,800 B1 | 3/2003 | McGuckin, Jr. et al. |
| 6,602,281 B1 | 8/2003 | Klein |
| 6,610,088 B1 | 8/2003 | Gabbay |
| 6,623,518 B2 | 9/2003 | Thompson et al. |
| 6,629,534 B1 | 10/2003 | St. Goar et al. |
| 6,641,606 B2 | 11/2003 | Ouriel et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | McGuckin, Jr. et al. |
| 6,712,836 B1 | 3/2004 | Berg et al. |
| 6,730,118 B2 | 5/2004 | Spenser et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 7,018,401 B1 | 3/2006 | Hyodoh et al. |
| 7,018,406 B2 | 3/2006 | Seguin et al. |
| 7,044,962 B2 | 5/2006 | Elliott |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| D553,747 S | 10/2007 | Fliedner |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,569,071 B2 | 8/2009 | Haverkost et al. |
| 7,585,321 B2 | 9/2009 | Cribier |
| 7,608,114 B2 | 10/2009 | Levine et al. |
| 7,615,072 B2 | 11/2009 | Rust et al. |
| 7,621,948 B2 | 11/2009 | Herrmann et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| D635,261 S | 3/2011 | Rossi |
| D635,262 S | 3/2011 | Rossi |
| 7,914,569 B2 | 3/2011 | Nguyen et al. |
| 7,981,151 B2 | 7/2011 | Rowe |
| 7,993,392 B2 | 8/2011 | Righini et al. |
| 8,016,877 B2 | 9/2011 | Seguin et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,109,996 B2 | 2/2012 | Stacchino et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,934 B2 * | 5/2012 | Styrc .......... A61F 2/2418 623/2.18 |

(56) References Cited

U.S. PATENT DOCUMENTS

| | | |
|---|---|---|
| 8,177,799 B2 | 5/2012 | Orban, III |
| 8,182,528 B2 | 5/2012 | Salahieh et al. |
| 8,182,530 B2 | 5/2012 | Huber |
| 8,197,528 B2 | 6/2012 | Colgan et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| D665,079 S | 8/2012 | Zago |
| D665,080 S | 8/2012 | Zago |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,052 B2 | 8/2012 | Salahieh et al. |
| 8,303,653 B2 | 11/2012 | Bonhoeffer et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,353,953 B2 | 1/2013 | Giannetti et al. |
| 8,361,137 B2 | 1/2013 | Perouse |
| 8,403,983 B2 * | 3/2013 | Quadri .................. A61F 2/2412 623/2.17 |
| 8,414,645 B2 | 4/2013 | Dwork et al. |
| 8,444,689 B2 | 5/2013 | Zhang |
| 8,449,599 B2 * | 5/2013 | Chau .................... A61F 2/2418 623/1.26 |
| 8,449,625 B2 | 5/2013 | Campbell et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,798 B2 * | 8/2013 | Rowe .................... A61F 2/2409 623/2.1 |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,579,963 B2 | 11/2013 | Tabor |
| 8,579,964 B2 | 11/2013 | Lane et al. |
| 8,584,849 B2 | 11/2013 | McCaffrey |
| 8,585,749 B2 | 11/2013 | Shelso |
| 8,617,236 B2 | 12/2013 | Paul et al. |
| 8,640,521 B2 | 2/2014 | Righini et al. |
| 8,652,145 B2 | 2/2014 | Maimon et al. |
| 8,652,201 B2 | 2/2014 | Oberti et al. |
| 8,672,992 B2 | 3/2014 | Off |
| 8,679,174 B2 | 3/2014 | Ottma et al. |
| 8,679,404 B2 | 3/2014 | Liburd et al. |
| 8,707,957 B2 | 4/2014 | Callister et al. |
| 8,721,707 B2 | 5/2014 | Boucher et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 * | 5/2014 | Montorfano .......... A61F 2/2409 623/2.18 |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,753,384 B2 | 6/2014 | Leanna |
| 8,764,818 B2 | 7/2014 | Gregg |
| 8,771,344 B2 | 7/2014 | Tran et al. |
| 8,778,020 B2 | 7/2014 | Gregg et al. |
| 8,784,478 B2 | 7/2014 | Tuval et al. |
| 8,784,481 B2 * | 7/2014 | Alkhatib ............... A61F 2/2418 623/2.18 |
| 8,790,387 B2 | 7/2014 | Nguyen et al. |
| 8,795,357 B2 | 8/2014 | Yohanan et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,852,267 B2 | 10/2014 | Cattaneo |
| 8,870,947 B2 | 10/2014 | Shaw |
| 8,870,948 B1 | 10/2014 | Erzberger et al. |
| 8,870,950 B2 | 10/2014 | Hacohen |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,961,583 B2 | 2/2015 | Hojeibane et al. |
| 8,961,593 B2 | 2/2015 | Bonhoeffer et al. |
| 8,974,524 B2 | 3/2015 | Yeung et al. |
| 8,986,375 B2 | 3/2015 | Garde et al. |
| 8,998,979 B2 | 4/2015 | Seguin et al. |
| 8,998,980 B2 | 4/2015 | Shipley et al. |
| 9,005,270 B2 | 4/2015 | Perkins et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,029,418 B2 | 5/2015 | Dove et al. |
| 9,034,032 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,751 B2 | 7/2015 | Naor |
| 9,173,737 B2 * | 11/2015 | Hill ....................... A61F 2/2418 |
| 9,186,249 B2 | 11/2015 | Rolando et al. |
| 2001/0007956 A1 | 7/2001 | Letac et al. |
| 2001/0047200 A1 | 11/2001 | White et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0111619 A1 | 8/2002 | Keast et al. |
| 2003/0105517 A1 | 6/2003 | White et al. |
| 2003/0120333 A1 | 6/2003 | Outlet et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0078074 A1 | 4/2004 | Anderson et al. |
| 2004/0117009 A1 | 6/2004 | Cali et al. |
| 2004/0133273 A1 | 7/2004 | Cox |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 * | 6/2005 | Salahieh ............... A61F 2/2418 623/2.11 |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 * | 7/2005 | Lane .................... A61F 2/2412 623/2.14 |
| 2005/0182486 A1 | 8/2005 | Gabbay |
| 2005/0216079 A1 | 9/2005 | MaCoviak |
| 2005/0234546 A1 | 10/2005 | Nugent et al. |
| 2006/0020247 A1 | 1/2006 | Kagan et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0116625 A1 | 6/2006 | Renati et al. |

(56) References Cited

U.S. PATENT DOCUMENTS

| | | |
|---|---|---|
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0219620 A1 | 9/2007 | Eells et al. |
| 2007/0250151 A1 | 10/2007 | Pereira |
| 2007/0255394 A1 | 11/2007 | Ryan |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071366 A1 | 3/2008 | Tuval et al. |
| 2008/0077236 A1 | 3/2008 | Letac et al. |
| 2008/0082164 A1 | 4/2008 | Friedman |
| 2008/0082165 A1 | 4/2008 | Wilson et al. |
| 2008/0097571 A1 | 4/2008 | Denison et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0062901 A1* | 3/2009 | McGuckin, Jr. ...... A61F 2/2418 623/1.15 |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0125096 A1 | 5/2009 | Chu et al. |
| 2009/0138079 A1 | 5/2009 | Tuval et al. |
| 2009/0149946 A1 | 6/2009 | Dixon |
| 2009/0171438 A1 | 7/2009 | Chuter et al. |
| 2009/0171456 A1 | 7/2009 | Kveen et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0287296 A1 | 11/2009 | Manasse |
| 2010/0114299 A1 | 5/2010 | Ben Muvhar et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1* | 12/2011 | Quadri ...... A61F 2/2415 623/2.2 |
| 2011/0319991 A1 | 12/2011 | Hariton et al. |
| 2012/0022639 A1* | 1/2012 | Hacohen ...... A61B 17/068 623/2.11 |
| 2012/0041550 A1 | 2/2012 | Salahieh et al. |
| 2012/0053685 A1* | 3/2012 | Cerf ...... A61F 2/2418 623/2.17 |
| 2012/0078353 A1* | 3/2012 | Quadri ...... A61F 2/2418 623/2.11 |
| 2012/0078360 A1* | 3/2012 | Rafiee ...... A61F 2/2418 623/2.37 |
| 2012/0101572 A1 | 4/2012 | Kovalsky et al. |
| 2012/0123529 A1 | 5/2012 | Levi et al. |
| 2012/0215303 A1* | 8/2012 | Quadri ...... A61F 2/2418 623/2.18 |
| 2012/0259405 A1 | 10/2012 | Weber et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0144375 A1 | 6/2013 | Giasolli et al. |
| 2013/0144378 A1* | 6/2013 | Quadri ...... A61F 2/2418 623/2.1 |
| 2013/0172983 A1 | 7/2013 | Clerc et al. |
| 2013/0211508 A1* | 8/2013 | Lane ...... A61F 2/2403 623/2.11 |
| 2013/0253635 A1 | 9/2013 | Straubinger et al. |
| 2013/0253642 A1 | 9/2013 | Brecker |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0005764 A1 | 1/2014 | Schroeder |
| 2014/0012368 A1* | 1/2014 | Sugimoto ...... A61L 31/022 623/2.11 |
| 2014/0018912 A1 | 1/2014 | Delaloye et al. |
| 2014/0025163 A1 | 1/2014 | Padala et al. |
| 2014/0046427 A1 | 2/2014 | Michalak |
| 2014/0052237 A1* | 2/2014 | Lane ...... A61F 2/2412 623/2.11 |
| 2014/0067054 A1 | 3/2014 | Chau et al. |
| 2014/0088685 A1 | 3/2014 | Yevzlin et al. |
| 2014/0100651 A1 | 4/2014 | Kheradvar et al. |
| 2014/0155990 A1 | 6/2014 | Nyuli et al. |
| 2014/0163668 A1 | 6/2014 | Rafiee |
| 2014/0172077 A1 | 6/2014 | Bruchman et al. |
| 2014/0194981 A1 | 7/2014 | Menk et al. |
| 2014/0207231 A1 | 7/2014 | Hacohen et al. |
| 2014/0215791 A1 | 8/2014 | Soundararajan et al. |
| 2014/0222136 A1* | 8/2014 | Geist ...... A61F 2/2466 623/2.11 |
| 2014/0222139 A1 | 8/2014 | Nguyen et al. |
| 2014/0222142 A1 | 8/2014 | Kovalsky et al. |
| 2014/0257467 A1 | 9/2014 | Lane et al. |
| 2014/0257475 A1 | 9/2014 | Gross et al. |
| 2014/0277390 A1 | 9/2014 | Ratz et al. |
| 2014/0277422 A1 | 9/2014 | Ratz et al. |
| 2014/0277427 A1* | 9/2014 | Ratz ...... A61F 2/2409 623/2.38 |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1* | 11/2014 | Gloss ...... A61F 2/2418 623/2.17 |
| 2014/0330372 A1 | 11/2014 | Weston et al. |
| 2014/0331475 A1 | 11/2014 | Duffy et al. |
| 2014/0336754 A1 | 11/2014 | Gurskis et al. |
| 2014/0343669 A1* | 11/2014 | Lane ...... A61F 2/2436 623/2.11 |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358221 A1 | 12/2014 | Ho et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379077 A1 | 12/2014 | Tuval et al. |
| 2015/0005863 A1 | 1/2015 | Para |

(56) References Cited

U.S. PATENT DOCUMENTS

| | | |
|---|---|---|
| 2015/0005873 A1 | 1/2015 | Chang et al. |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | McNamara et al. |
| 2015/0196390 A1* | 7/2015 | Ma .................. A61F 2/2418 623/2.17 |
| 2015/0209141 A1 | 7/2015 | Braido et al. |
| 2015/0265402 A1* | 9/2015 | Centola ............. A61F 2/2436 623/2.18 |
| 2015/0272737 A1* | 10/2015 | Dale .................. A61F 2/2442 623/2.37 |
| 2015/0328000 A1* | 11/2015 | Ratz .................. A61F 2/2418 623/2.37 |
| 2015/0328001 A1* | 11/2015 | McLean ............. A61F 2/2427 623/2.36 |
| 2015/0335429 A1 | 11/2015 | Morriss et al. |
| 2015/0351904 A1* | 12/2015 | Cooper .............. A61F 2/2418 623/2.1 |
| 2015/0359629 A1* | 12/2015 | Ganesan ............ A61F 2/2409 623/2.11 |
| 2015/0359631 A1* | 12/2015 | Sheahan ............ A61F 2/2418 623/2.19 |
| 2016/0000591 A1 | 1/2016 | Lei et al. |
| 2016/0030170 A1 | 2/2016 | Alkhatib et al. |
| 2016/0038281 A1* | 2/2016 | Delaloye ........... A61F 2/2409 623/2.18 |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0158007 A1* | 6/2016 | Centola ............. A61F 2/2439 623/1.26 |
| 2016/0213473 A1 | 7/2016 | Hacohen et al. |
| 2016/0235529 A1* | 8/2016 | Ma .................... A61F 2/2412 |
| 2017/0056166 A1* | 3/2017 | Ratz .................. A61F 2/2418 |
| 2017/0128199 A1* | 5/2017 | Gurovich ........... A61F 2/2418 |
| 2017/0333187 A1* | 11/2017 | Hariton ............. A61F 2/2418 |
| 2018/0071084 A1* | 3/2018 | Ma .................... A61F 2/2412 |
| 2018/0116790 A1* | 5/2018 | Ratz .................. A61F 2/243 |
| 2018/0153687 A1* | 6/2018 | Hariton ............. A61F 2/2412 |
| 2018/0221143 A1* | 8/2018 | Ratz .................. A61F 2/2409 |
| 2018/0250130 A1* | 9/2018 | Hariton ............. A61F 2/2418 |
| 2018/0303612 A1* | 10/2018 | Pasquino ........... A61F 2/2448 |

FOREIGN PATENT DOCUMENTS

| | | |
|---|---|---|
| DE | 102006052564 B3 | 12/2007 |
| EP | 1259194 B1 | 2/2005 |
| EP | 1255510 B1 | 4/2007 |
| EP | 1472996 B1 | 9/2009 |
| EP | 2308425 A1 | 4/2011 |
| EP | 1281375 B1 | 2/2012 |
| EP | 2496182 A1 | 9/2012 |
| EP | 2319458 B1 | 4/2013 |
| EP | 2124826 B1 | 7/2014 |
| EP | 1734903 B1 | 10/2015 |
| EP | 2815725 B1 | 4/2016 |
| EP | 2815723 B1 | 7/2016 |
| GB | 1264471 A | 2/1972 |
| GB | 1315844 A | 5/1973 |
| GB | 2245495 A | 1/1992 |
| GB | 2398245 A | 8/2004 |
| JP | 2002540889 A | 12/2002 |
| WO | 1997049355 A1 | 12/1997 |
| WO | 0053104 A1 | 9/2000 |
| WO | 0061034 A1 | 10/2000 |
| WO | 0135861 A1 | 5/2001 |
| WO | 0172239 A2 | 10/2001 |
| WO | 03092554 A1 | 11/2003 |
| WO | 2005011534 A1 | 2/2005 |
| WO | 2005041810 A2 | 5/2005 |
| WO | 2006085304 A2 | 8/2006 |
| WO | 2006089236 A1 | 8/2006 |
| WO | 2007025028 A1 | 3/2007 |
| WO | 2007034488 A2 | 3/2007 |
| WO | 2007058857 A2 | 5/2007 |
| WO | 2007123658 A1 | 11/2007 |
| WO | 2007134290 A2 | 11/2007 |
| WO | 2008005535 A2 | 1/2008 |
| WO | 2008013915 A2 | 1/2008 |
| WO | 2008070797 A2 | 6/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009094500 A1 | 7/2009 |
| WO | 2010004009 A2 | 1/2010 |
| WO | 2010008549 A1 | 1/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2012035279 A1 | 3/2012 |
| WO | 2012177942 A2 | 12/2012 |
| WO | 2013028387 A2 | 2/2013 |
| WO | 2013175468 A2 | 11/2013 |
| WO | 2014018432 A2 | 1/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

(56) References Cited

OTHER PUBLICATIONS

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.
Ratz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes this may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.
Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

(56) References Cited

OTHER PUBLICATIONS

The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Raiz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

Bavaria, Joseph E. M.D. et al.: "Transcatheter Mitral Valve Implantation: The Future Gold Standard for MR?," Applicant requests the Examiner to consider this reference to be prior art as of Dec. 2010.

\* cited by examiner

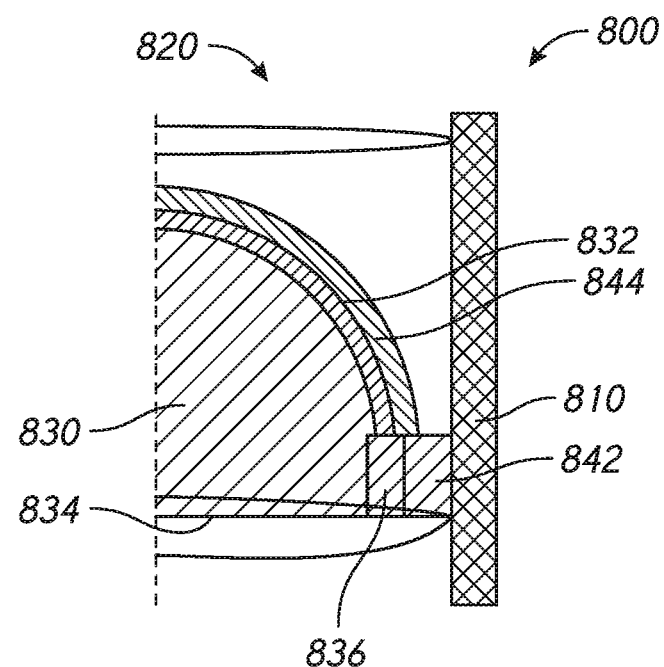
FIG. 15
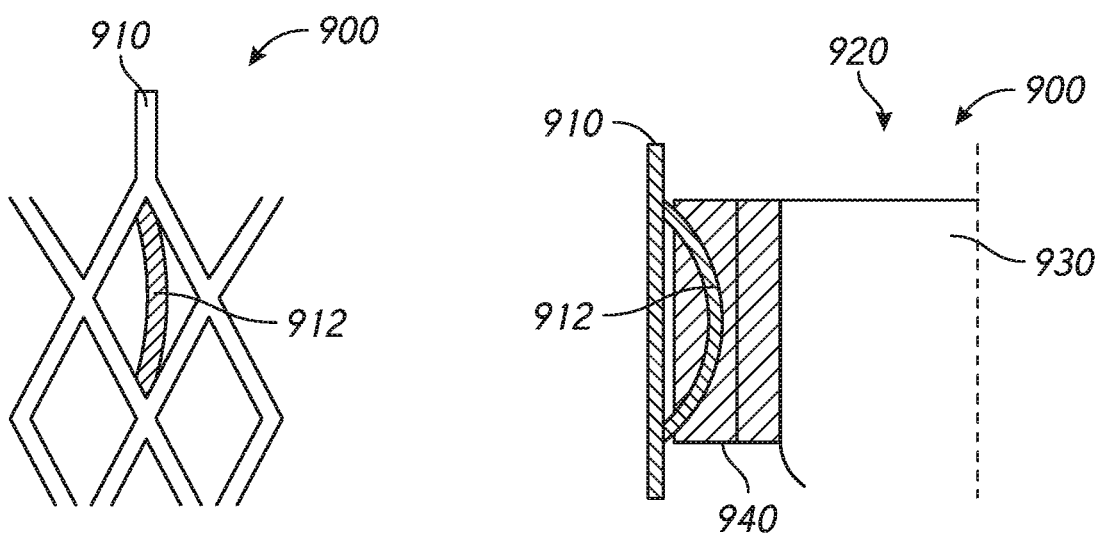
FIG. 16
FIG. 17

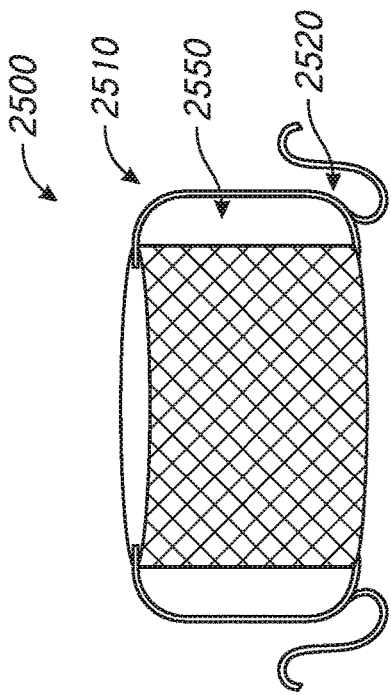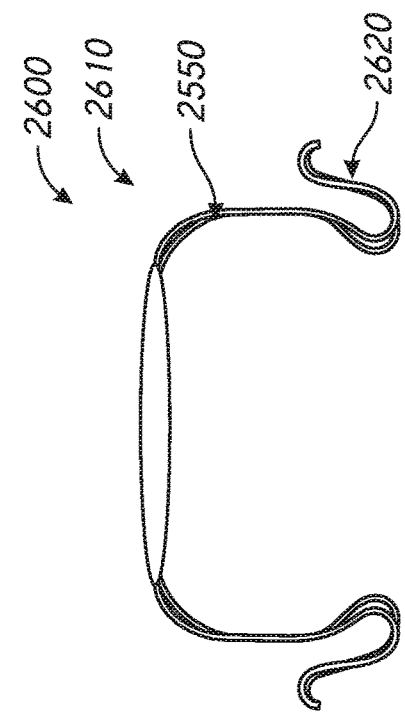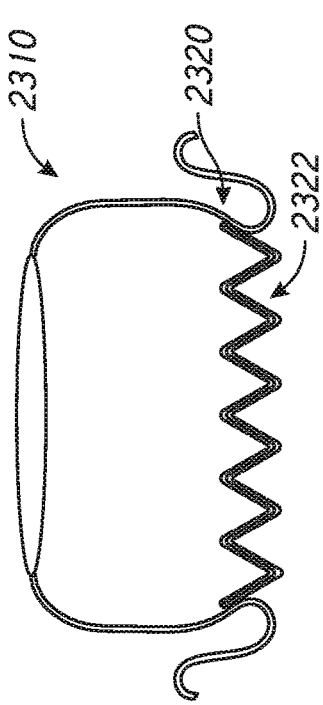

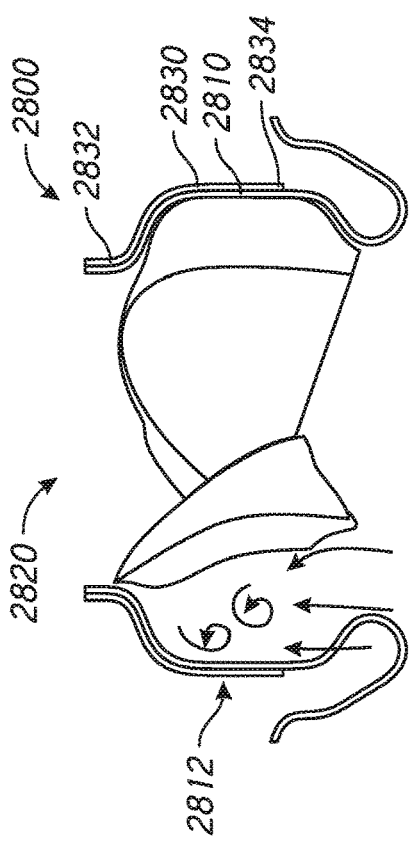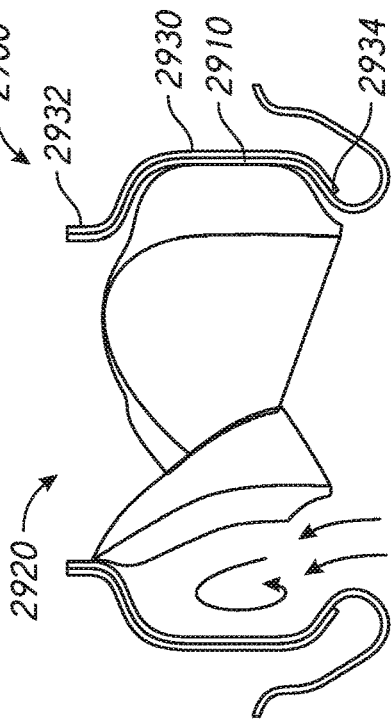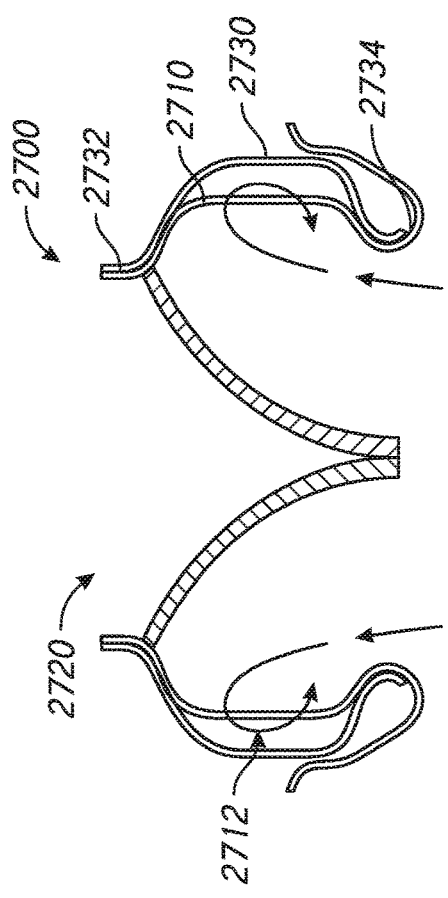
FIG. 39
FIG. 40
FIG. 38

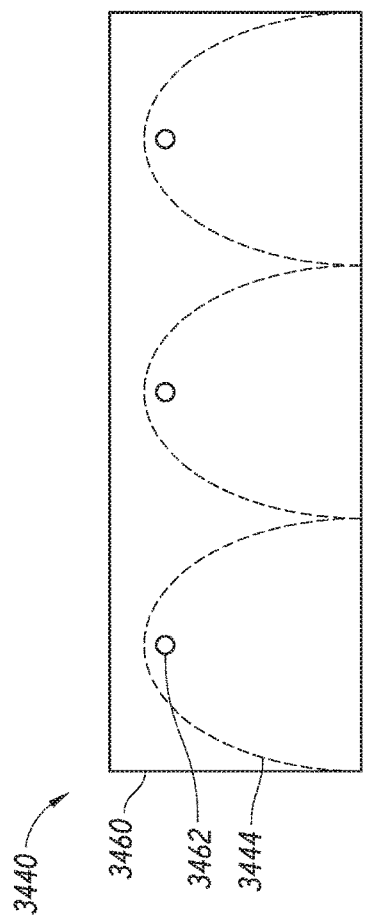
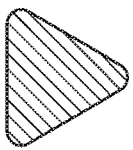
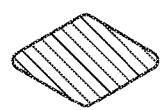
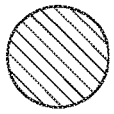
FIG. 50
FIG. 51
FIG. 52
FIG. 53

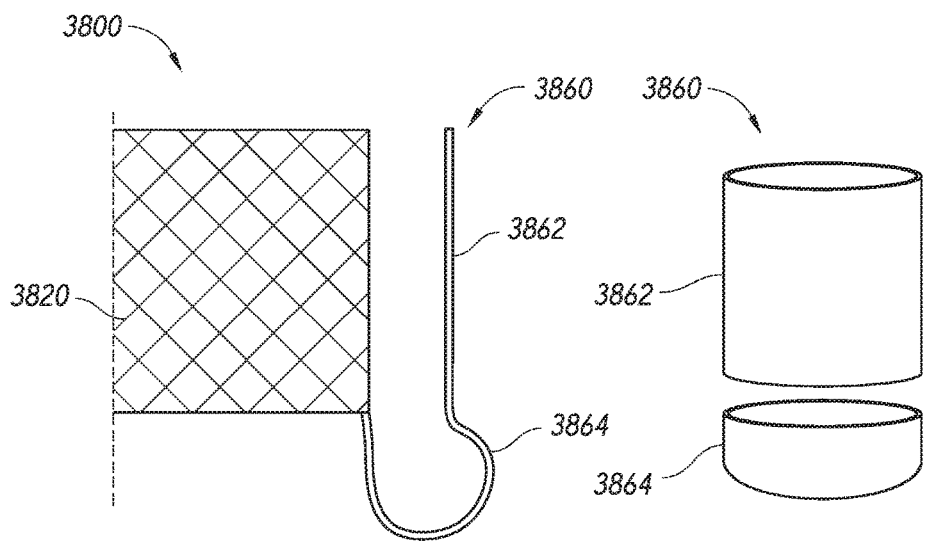
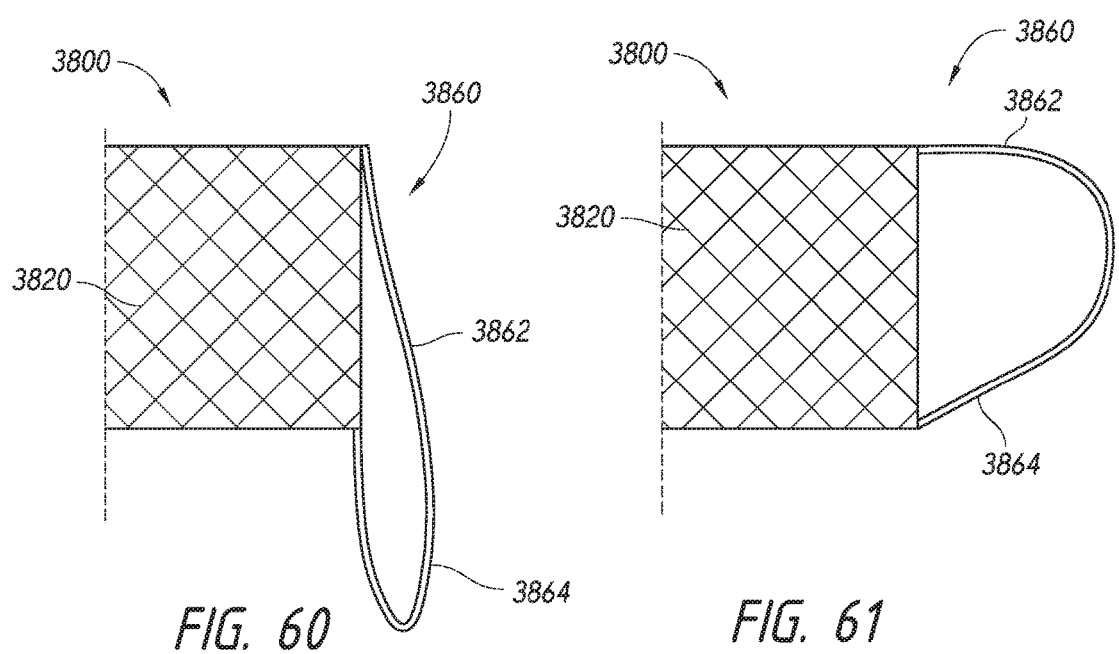

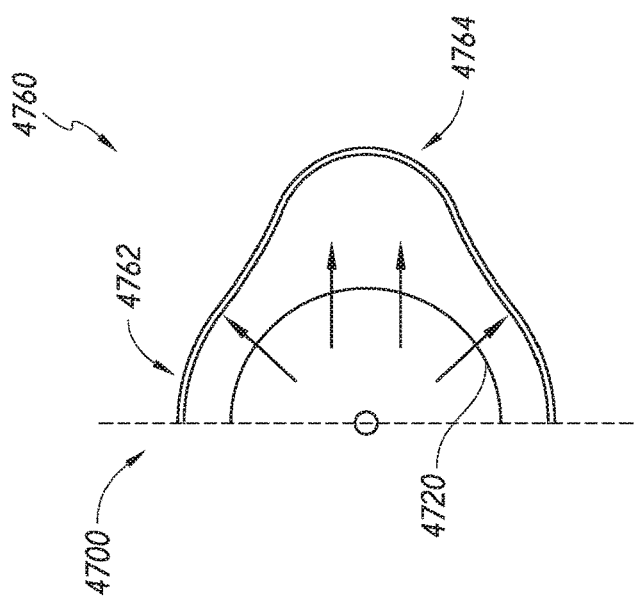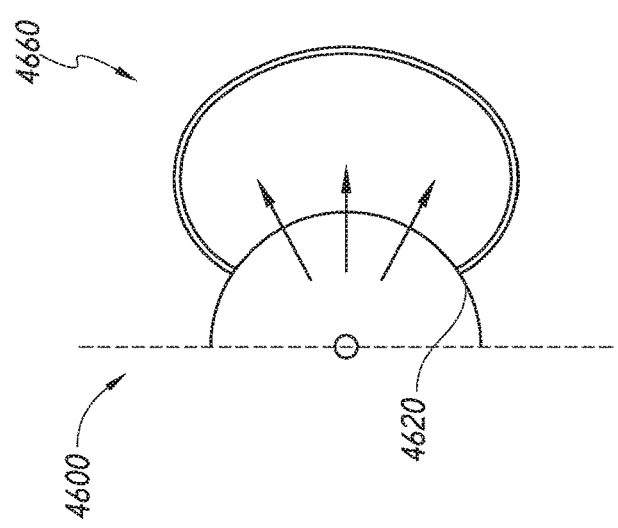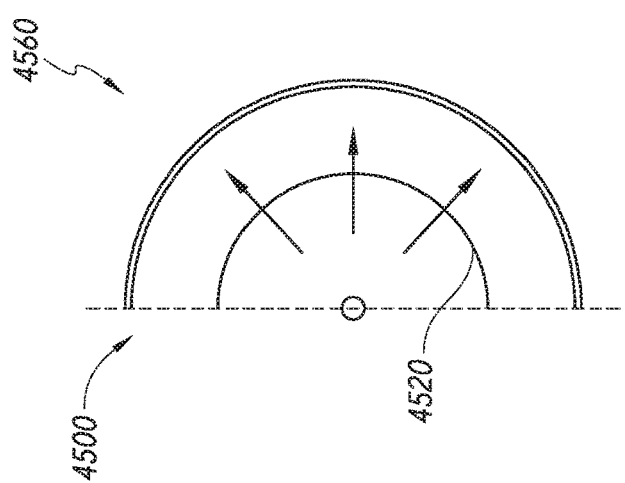

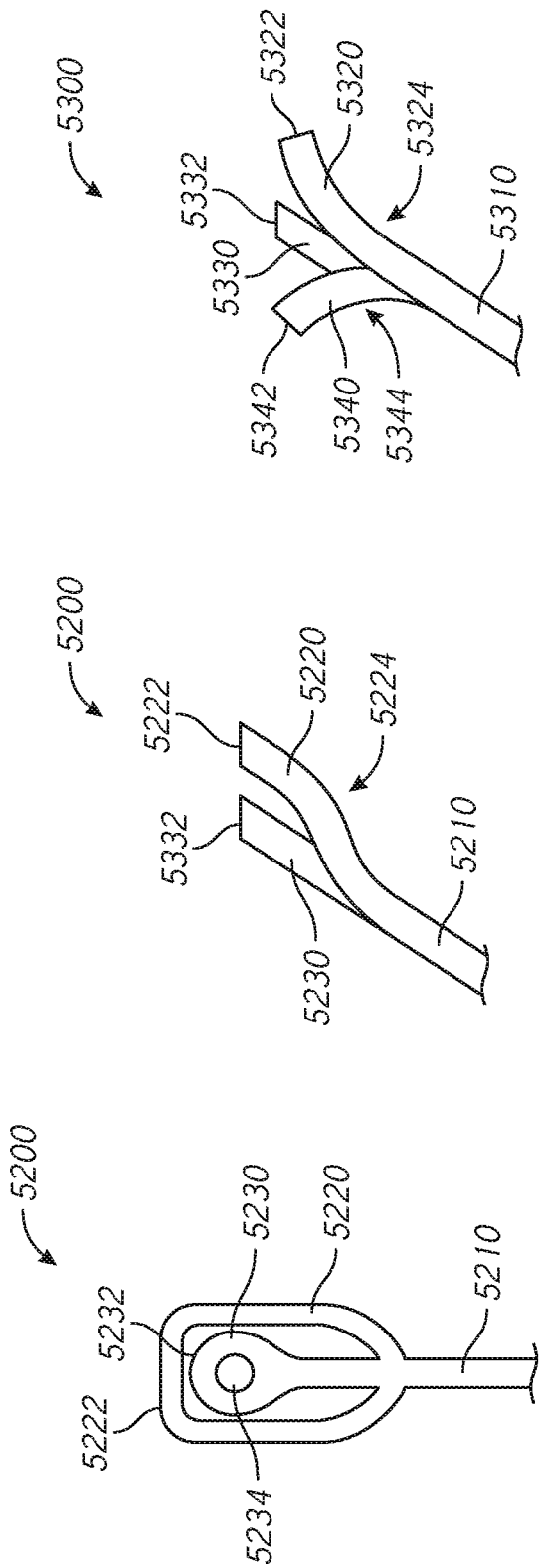

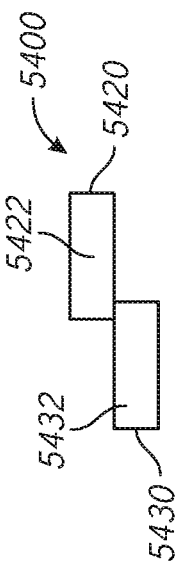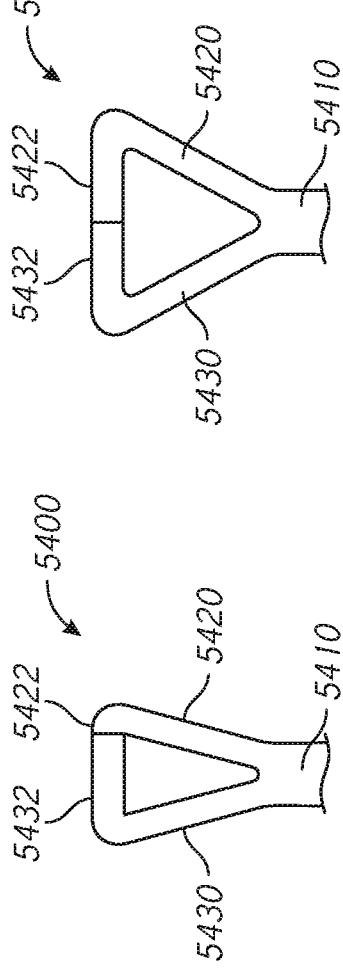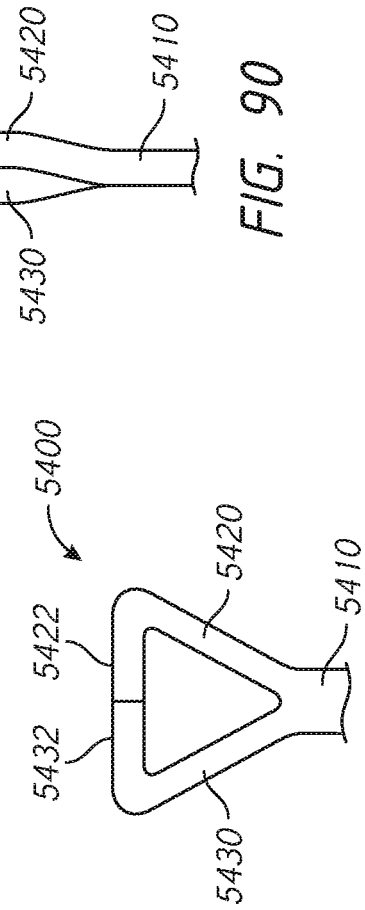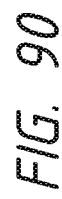

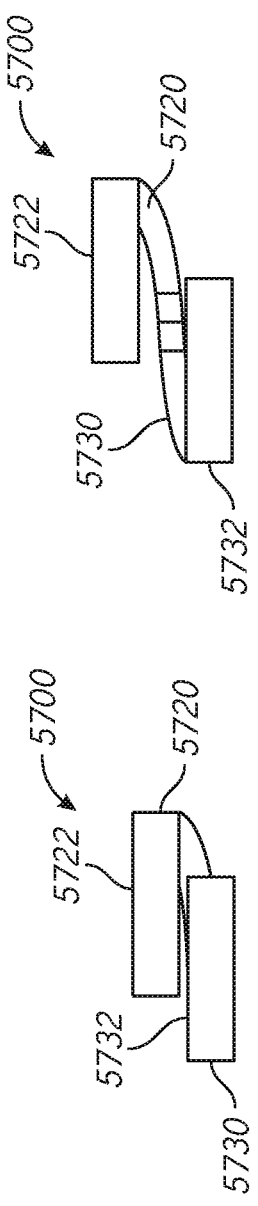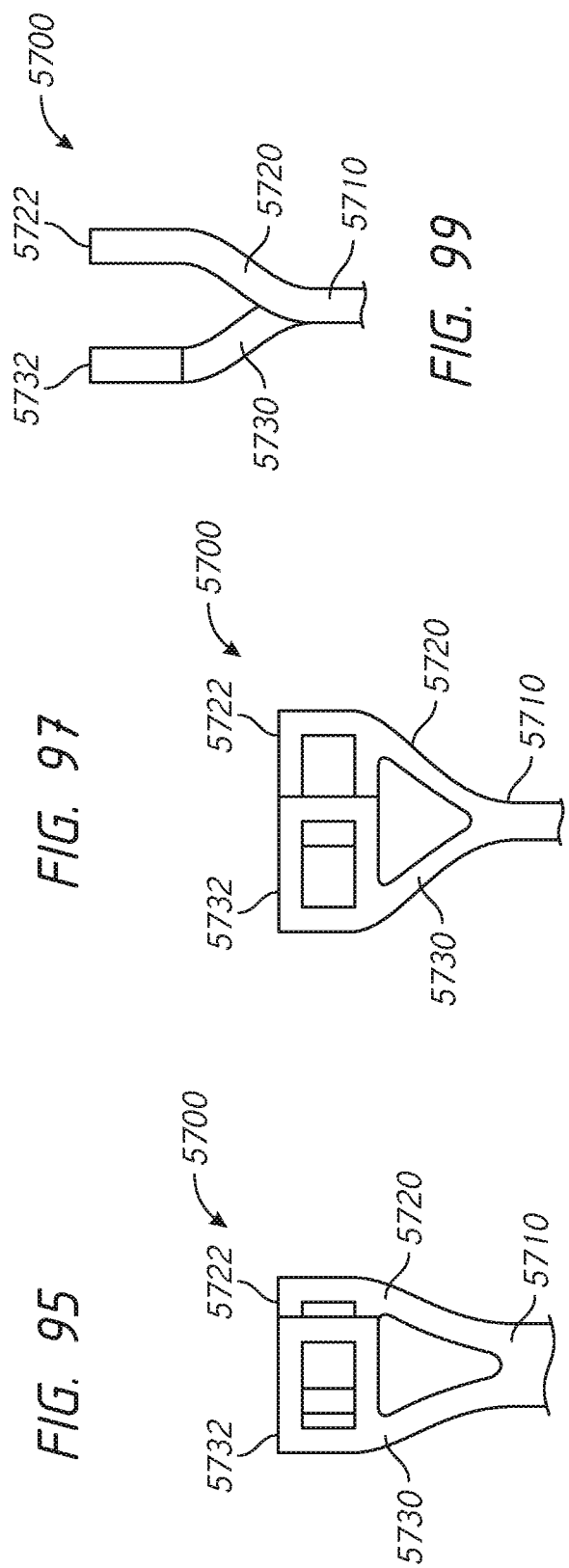

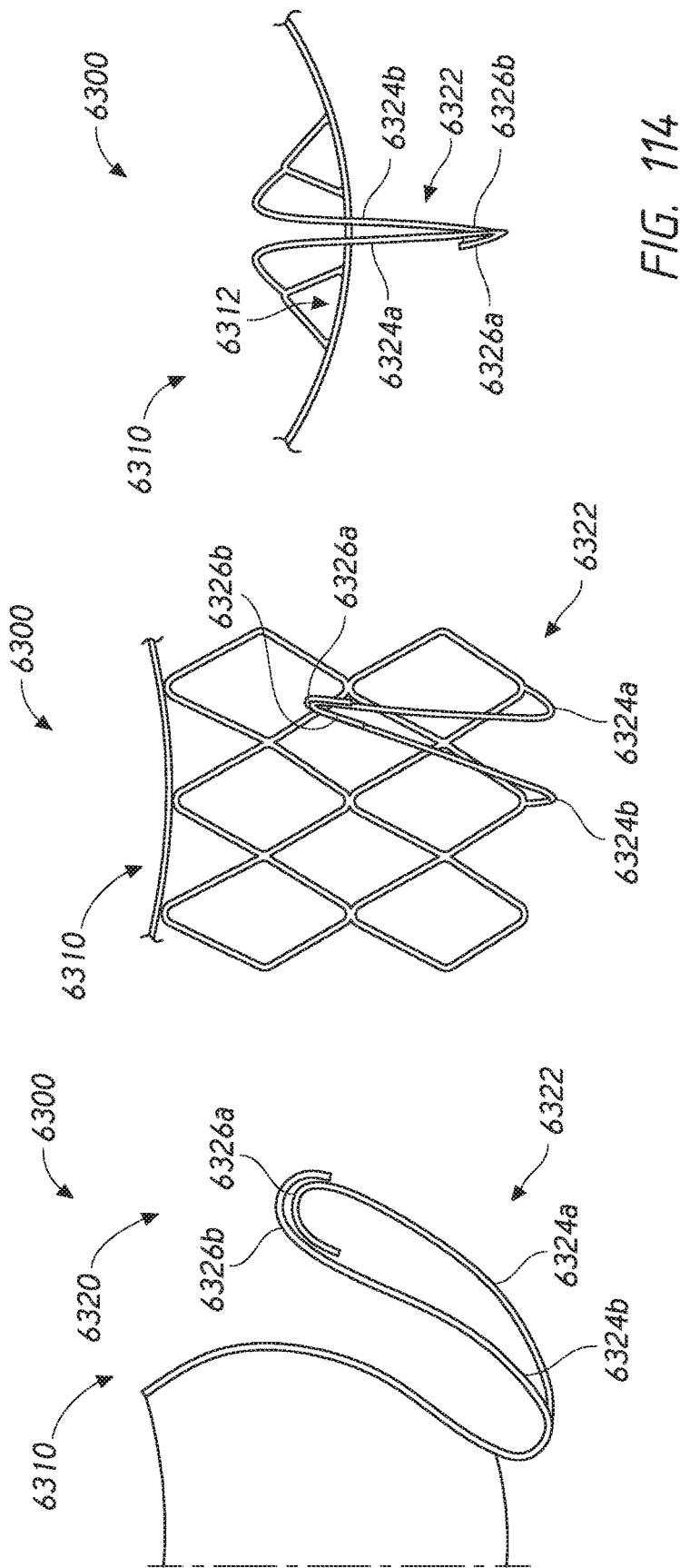

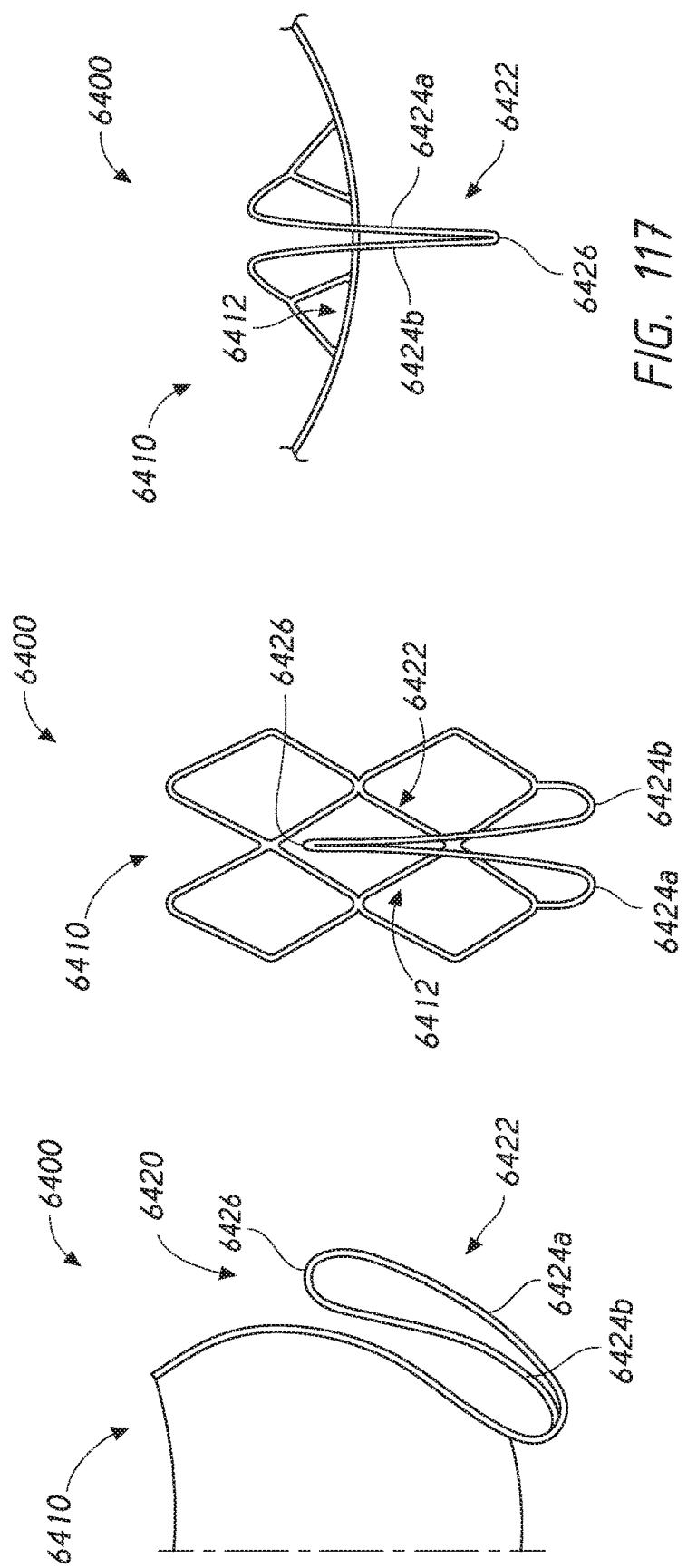

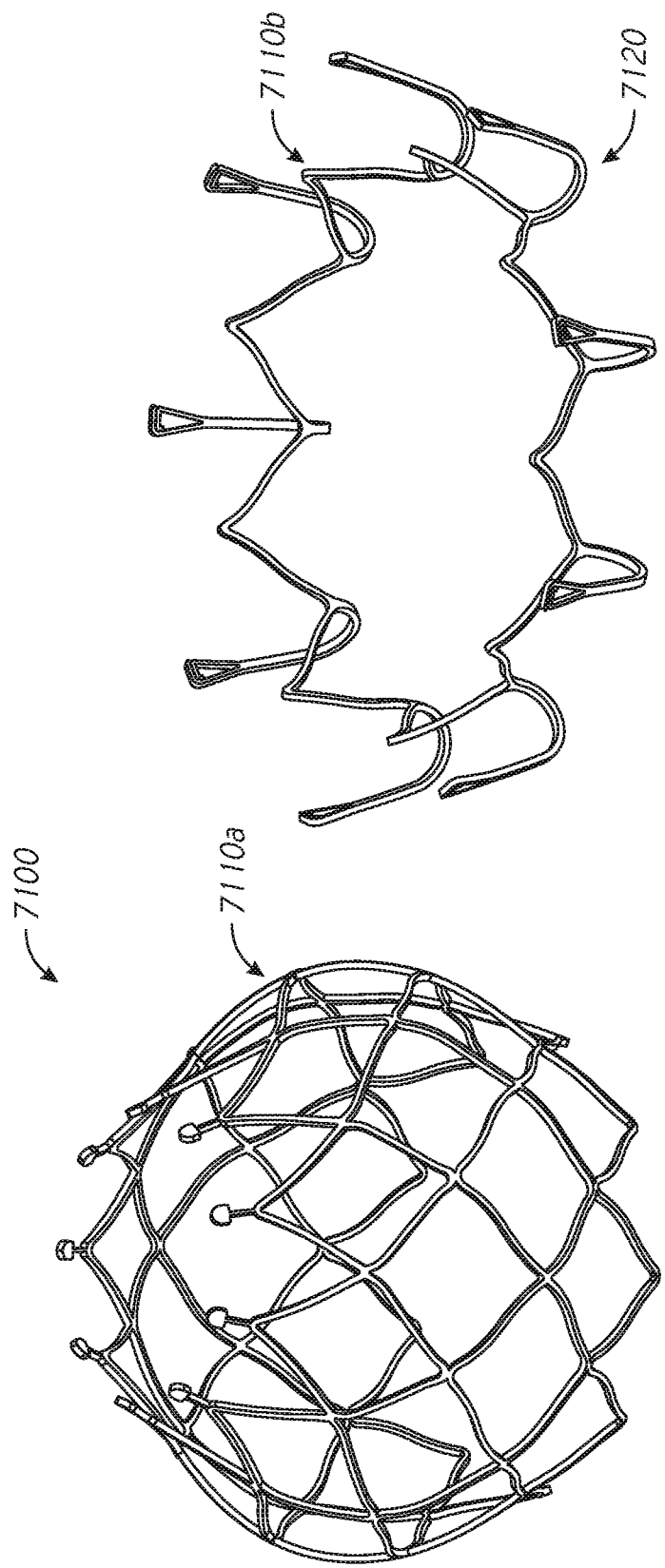

REPLACEMENT HEART VALVE PROSTHESIS

CROSS-REFERENCE TO RELATED APPLICATIONS

This application claims priority to U.S. Provisional App. No. 62/365,070 filed Jul. 21, 2016, titled REPLACEMENT HEART VALVE PROSTHESIS, and U.S. Provisional App. No. 62/471,213 filed Mar. 14, 2017, titled REPLACEMENT HEART VALVE PROSTHESIS, the entirety of each of which is hereby incorporated herein by reference in its entirety and is to be considered a part of this specification.

BACKGROUND

Field

Embodiments disclosed herein relate generally to prostheses for implantation within a lumen or body cavity. In particular, certain embodiments relate to expandable prostheses such as replacement heart valves, such as for the mitral valve, that are configured to be secured to intralumenal tissue and prevent paravalvular leakage.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage has proven particularly challenging. An additional challenge relates to the ability of such prostheses to be secured relative to intralumenal tissue, e.g., tissue within any body lumen or cavity, in an atraumatic manner. Yet another challenge arises when trying to reduce the likelihood of thrombosis within parts of the replacement valves and increasing the longevity of the replacement valve. Further challenges arise when trying to replace an already existing replacement valve with a new replacement valve.

SUMMARY

Embodiments of the present disclosure are directed to a prosthesis, such as but not limited to a replacement heart valve. According to some embodiments, a prosthesis can be configured to be deployed within a body cavity and prevent axial flow of fluid around an exterior of the prosthesis. The prosthesis can include an expandable frame configured to radially expand and contract for deployment within the body cavity, and an annular skirt positioned around an exterior of the expandable frame. The prosthesis can further include a valve body configured to provide one-way flow through the prosthesis. The prosthesis can further include a plurality of anchors for securing the prosthesis to intraluminal tissue such as the native valve anatomy. Further embodiments are directed to methods of delivering a prosthesis, e.g. a replacement heart valve, and methods of using a prosthesis to create a barrier to fluid flow exterior to the prosthesis (e.g., to prevent paravalvular leakage).

In some embodiments, a prosthesis can include an expandable frame having a proximal end and a distal end and a longitudinal axis extending therethrough. The expandable frame can be configured to radially expand and contract for deployment within a native heart valve. The prosthesis can include a valve body positioned within an interior of the expandable frame. The valve body can include a plurality of leaflets each having an arcuate proximal edge and a free distal edge, the plurality of leaflets being joined at commissures. The plurality of leaflets can be configured to allow flow in a proximal-to-distal direction and prevent flow in a distal-to-proximal direction. The valve body can include one or more intermediate components connecting the leaflets to the expandable frame, wherein at least a portion of the arcuate proximal edge of each leaflet and/or the commissures are indirectly coupled to the expandable frame via the one or more intermediate components such that when the frame is in an expanded configuration, the one or more intermediate components position at least a portion of the arcuate proximal edge of each leaflet and/or the commissures radially inward from an inner surface of the frame.

In some embodiments, at least a portion of the arcuate proximal edge of each leaflet can be directly coupled to the expandable frame. In some embodiments, the one or more intermediate components can be formed from a material having a stiffness greater than that of the plurality of leaflets and less than that of the expandable frame. In some embodiments, the one or more intermediate components can be formed from a sheet of material. In some embodiments, the one or more intermediate components can be formed from a sheet of at least one of fabric, polyurethane, and polyethylene terephthalate (PET).

In some embodiments, the one or more intermediate components can include a first intermediate component and a second intermediate component. The first intermediate component can be tensioned in a first direction and the second intermediate component can be tensioned in a second direction when the frame is in an expanded configuration. In some embodiments, the first direction can be oriented generally radially outwardly. In some embodiments, the second direction can be oriented generally axially. In some embodiments, the second direction can be oriented generally in a circumferential direction. In some embodiments, the one or more intermediate components can include a third intermediate component. The first intermediate component, the second intermediate component, and the third intermediate component can form a pocket at or proximate a commissure of the valve body.

In some embodiments, the one or more intermediate components can include a cylindrical conduit. In some embodiments, at least one of the one or more intermediate components can extend in a radial direction between the expandable frame and the plurality of leaflets. In some embodiments, at least one of the one or more intermediate components can extend tangentially to the plurality of leaflets. In some embodiments, at least one of the one or more intermediate components extends in a direction generally aligned with the longitudinal axis of the frame. In some embodiments, at least one of the one or more intermediate components extends in circumferential direction. In some embodiments, the prosthesis can include an annular skirt extending around the exterior of the expandable frame. In some embodiments, a proximal end of the annular skirt is attached to a proximal region of the expandable frame and a distal end of the annular skirt is attached to a distal region of the expandable frame. In some embodiments, an intermediate region of the frame can have a diameter greater than a diameter of the proximal region and/or a diameter of the distal region.

In some embodiments, a prosthesis can include an expandable frame configured to radially expand and contract for deployment within a native heart valve. The expandable frame can include a proximal end and a distal end and a longitudinal axis extending therethrough. The expandable frame can include a supplemental prosthesis retention structure. The prosthesis can include a valve body positioned within an interior of the expandable frame. The valve body can include a plurality of leaflets configured to allow flow in a first direction and prevent flow in a second opposite direction.

In some embodiments, the supplemental prosthesis retention structure can include an interfacing structure. The interfacing structure can include a plurality of V-shaped apices extending radially inward towards the longitudinal axis. The plurality of V-shaped apices can be configured to couple with a frame of a supplemental prosthesis. In some embodiments, the supplemental prosthesis retention structure can include an interfacing structure. The interfacing structure can include a plurality of protrusions extending radially inwardly from distal portions of cells of the expandable frame. In some embodiments, the supplemental prosthesis retention structure can include an internal expandable cage which can be configured to receive a supplemental prosthesis. In some embodiments, the internal expandable cage can include a plurality of circumferentially-expansible struts.

In some embodiments, a prosthesis can include an expandable frame which can be configured to radially expand and contract for deployment within a native heart valve. The expandable frame can include a frame body which can include a proximal region, a distal region, an intermediate region extending between the proximal and distal regions, and a longitudinal axis extending between proximal and distal ends of the frame body. The frame body can include a plurality of struts forming one or more rows of cells. The proximal region can include a first bend adjacent the intermediate region. A proximally extending portion of the first bend can be inclined or curved towards the longitudinal axis. The distal region can include a second bend adjacent the intermediate region. A distally extending portion of the second bend can be inclined or curved towards the longitudinal axis. The intermediate region can have a generally cylindrical shape. A diameter of the intermediate region can be greater than a diameter of the proximal region and a diameter of the distal region. A height of the intermediate region can be greater than a height of the proximal region and a height of the distal region.

The prosthesis can include a proximal anchoring feature attached to the frame body. The proximal anchoring feature can be sized to be positioned on a first side of an annulus of the native heart valve. The prosthesis can include a distal anchoring feature attached to the frame body. The distal anchoring feature can be sized to be positioned on a second side of an annulus of the native heart valve. The prosthesis can include a valve body positioned within an interior of the expandable frame, the valve body comprising a plurality of leaflets configured to allow flow in a first direction and prevent flow in a second opposite direction.

In some embodiments, when the expandable frame is in an expanded configuration, the height of the distal region can be greater than the height of the proximal region. In some embodiments, when the expandable frame is in an expanded configuration, a ratio of a largest diameter of the frame body to the height of the frame body can be between about 3:1 to about 1:1. In some embodiments, when the expandable frame is in an expanded configuration, a ratio of a largest diameter of the frame body to the height of the frame body can be between about 2:1 to about 3:2. In some embodiments, when the expandable frame is in an expanded configuration, a ratio of the height of the intermediate region to the combined heights of the proximal region and the distal region can be between about 2:1 to about 1:2. In some embodiments, when the expandable frame is in an expanded configuration, a ratio of the height of the intermediate region to the combined heights of the proximal region and the distal region can be between about 3:2 to about 1:1. In some embodiments, when the expandable frame is in an expanded configuration, a ratio of a largest diameter of the frame body to a smallest diameter of the frame body can be between about 2:1 to about 4:3.

In some embodiments, when the expandable frame is in an expanded configuration, the first bend can orient a portion of the proximal region, positioned proximally of the beginning of the first bend, such that the portion forms an angle of between about 30 degrees to about 60 degrees with a plane orthogonal to the longitudinal axis. In some embodiments, when the expandable frame is in an expanded configuration, the first bend can orient a portion of the proximal region, positioned proximally of the beginning of the first bend, such that the portion forms an angle of between about 40 degrees to about 50 degrees with a plane orthogonal to the longitudinal axis. In some embodiments, when the expandable frame is in an expanded configuration, the second bend can orient a portion of the distal region, positioned distally of the beginning of the second bend, such that the portion forms an angle of between about 30 degrees to about 60 degrees with a plane orthogonal to the longitudinal axis. In some embodiments, when the expandable frame is in an expanded configuration, the second bend can orient a portion of the distal region, positioned distally of the beginning of the second bend, such that the portion forms an angle of between about 40 degrees to about 50 degrees with a plane orthogonal to the longitudinal axis.

In some embodiments, the proximal anchoring feature can be attached to the proximal region of the frame body. In some embodiments, the proximal anchoring feature can include a plurality of anchors. In some embodiments, at least one of the anchors can include one or more eyelets. In some embodiments, at least one of the anchors can include two or more eyelets. In some embodiments, the distal anchoring feature can be attached to the distal region of the frame body. In some embodiments, the distal anchoring feature can include a plurality of distal anchors. In some embodiments, when the expandable frame is in an expanded configuration, at least one of the distal anchors can include ends extending radially outwardly away from the longitudinal axis. In some embodiments, when the expandable frame is in an expanded configuration, at least one of the distal anchors can include ends extending radially outwardly away from the longitudinal axis in a direction generally perpendicular to the longitudinal axis. In some embodiments, when the expandable frame is in an expanded configuration, all of the distal anchors can include ends extending radially outwardly away from the longitudinal axis. In some embodiments, when the expandable frame is in an expanded configuration, at least one of the distal anchors can include ends extending radially inwardly towards the longitudinal axis. In some embodiments, when the expandable frame is in an expanded configuration, at least one of the distal anchors can include ends extending radially inwardly towards the longitudinal axis in a direction generally perpendicular to the longitudinal axis. In some embodiments, when the expandable frame is in an expanded configuration, all of the distal anchors can include ends extending radially inwardly towards the longitudinal axis.

In some embodiments, the expandable frame further can include a plurality of locking tabs. In some embodiments, the locking tabs can include a bend in a direction opposite the first bend.

In some embodiments, the valve body further can include one or more intermediate components. At least a portion of each leaflet can be indirectly coupled to the expandable frame via the one or more intermediate components such that at least a portion of each leaflet is positioned radially inward from an inner surface of the frame body. In some embodiments, commissures of the valve body can be indirectly coupled to the expandable frame via the one or more intermediate components such that the commissures are positioned radially inward from the inner surface of the frame body. In some embodiments, at least a portion of an arcuate proximal edge of each leaflet can be indirectly coupled to the frame via the one or more intermediate components such that the arcuate proximal edge is positioned radially inward from the inner surface of the frame body. In some embodiments, at least a portion of an arcuate proximal edge of each leaflet can be directly coupled to the expandable frame.

In some embodiments, the one or more intermediate components can be formed from a material having a stiffness greater than that of the plurality of leaflets and less than that of the expandable frame. In some embodiments, the one or more intermediate components can include a first intermediate component and a second intermediate component. The first intermediate component can be tensioned in a first direction and the second intermediate component can be tensioned in a second direction when the frame is in an expanded configuration. In some embodiments, the first direction can be oriented generally radially outward. In some embodiments, the second direction can be oriented generally axially. In some embodiments, the second direction can be oriented generally in a circumferential direction.

In some embodiments, the one or more intermediate components can include a third intermediate component. The first intermediate component, the second intermediate component, and the third intermediate component can form a pocket at or proximate a commissure of the valve body. In some embodiments, the one or more intermediate components can include a cylindrical conduit. In some embodiments, at least one of the one or more intermediate components can extend in a radial direction between the expandable frame and the plurality of leaflets. In some embodiments, at least one of the one or more intermediate components can extend tangentially to the plurality of leaflets. In some embodiments, at least one of the one or more intermediate components can extend in a direction generally aligned with the longitudinal axis of the frame. In some embodiments, at least one of the one or more intermediate components can extend in circumferential direction.

In some embodiments, the prosthesis can include an annular skirt extending around the exterior of the expandable frame. In some embodiments, a proximal end of the annular skirt is attached to the proximal region of the frame body and a distal end of the annular skirt is attached to the distal region of the frame body.

In some embodiments, the prosthesis can include an expandable frame having a proximal end and a distal end and a longitudinal axis extending therethrough. The frame can be configured to radially expand and contract for deployment within a native heart valve. The prosthesis can include a valve body positioned within an interior of the expandable frame. The valve body can include a plurality of leaflets which can be configured to allow flow in a first direction and prevent flow in a second opposite direction. The prosthesis can include an annular skirt extending around the exterior of the expandable frame.

In some embodiments, the valve body can include one or more intermediate components. In some embodiments, at least one of the valve body and the annular skirt can include one or more openings which can be configured to allow at least one of: fluid ingress into a space between the valve leaflets and the annular skirt, and fluid egress out of the space between the valve leaflets and the annular skirt. In some embodiments, the one or more openings can be configured to allow fluid ingress into the space between the valve leaflets and the annular skirt when fluid flow is in the first direction. In some embodiments, the one or more openings can be configured to allow fluid egress out of the space between the valve leaflets and the annular skirt when fluid flow is in the second direction. In some embodiments, at least one of the one or more openings can be positioned within an area of the annular skirt between a first edge of a valve leaflet and the annular skirt.

In some embodiments, the prosthesis can include one or more conduits extending into the one or more openings. In some embodiments, the expandable frame can include an anchoring member sized and shaped to be positioned on an inflow side of a native valve annulus. In some embodiments, the one or more conduits can be configured to extend proximal of the anchoring member. In some embodiments, the anchoring member can be positioned along a proximal portion of the expandable frame.

In some embodiments, the inflow side of the native valve annulus is an atrial side of the native mitral valve annulus.

In some embodiments, when the annular skirt is in an expanded configuration, the annular skirt comprises a supplemental rib extending from a portion of the annular skirt. In some embodiments, when the annular skirt is in an expanded configuration, a proximal portion of the annular skirt bulges radially outward relative to the distal portion of the annular skirt. In some embodiments, when the annular skirt is in an expanded configuration, a distal portion of the annular skirt bulges radially outward relative to the proximal portion of the annular skirt. In some embodiments, when the annular skirt is in an expanded configuration, the annular skirt extends around the entire circumferential periphery of the frame to a generally equivalent radial dimension. In some embodiments, the annular skirt extends to different radial dimensions with a first peripheral region extending to a first radial dimension and a second peripheral region extending to a second radial dimension greater than the first radial dimension.

In some embodiments, the prosthesis can include one or more biasing members which can be configured to bias the skirt into an expanded configuration. In some embodiments, the one or more biasing members can include a radial spring. In some embodiments, the one or more biasing members can include a cantilever.

In some embodiments, the annular skirt can be configured to transition into an expanded configuration via blood flow into the annular skirt. In some embodiments, the prosthesis can include a one-way valve configured to allow blood flow into the annular skirt and inhibit blood flow out of the annular skirt. In some embodiments, the one-way valve can be positioned on a valve skirt, the valve skirt being positioned between the plurality of leaflets and the annular skirt. In some embodiments, the one-way valve can include a flap positioned on an exterior of the valve skirt. In some embodiments, the one-way valve can include a duckbill valve. In some embodiments, the one-way valve can be configured to allow blood flow into the annular skirt during systole and inhibit blood flow out of the annular skirt during diastole.

In some embodiments, the prosthesis can be a replacement mitral valve prosthesis, the expandable frame being configured for deployment within a native mitral valve.

In some embodiments, the prosthesis can include six distal anchors. In some embodiments, the prosthesis can include twelve distal anchors.

In some embodiments, the prosthesis can include an expandable frame which can be configured to radially expand and contract for deployment within a native heart valve. The expandable frame can include a frame body having a proximal region, a distal region, and an intermediate region extending between the proximal and distal regions. The frame body can include a first row of struts and a second row of struts. The expandable frame can include a supplemental frame having a first row of struts. The first row of struts can be configured to be generally aligned along the first row of struts of the frame body. The first row of struts of the supplemental frame can have a size and/or shape which generally matches the size and/or shape of the first row of struts of the frame body.

The expandable frame can include a distal anchoring feature. The distal anchoring feature can be sized to be positioned on a first side of an annulus of the native heart valve. For example, the distal anchoring feature can be positioned on a ventricular side of a native mitral valve annulus. The expandable frame can include a valve body positioned within an interior of the expandable frame. The valve body can include a plurality of leaflets which can be configured to allow flow in a first direction and prevent flow in a second opposite direction.

In some embodiments, the supplemental frame can be formed separately from the frame body. In some embodiments, the first row of struts of the supplemental frame can be configured to be attached to at least a portion of the first row of struts of the frame body. In some embodiments, the first row of struts of the supplemental frame can be attached to the first row of struts of the frame body via sutures. In some embodiments, the first row of struts of the supplemental frame and the first row of struts of the frame body can have an undulating shape.

In some embodiments, the first row of struts of the supplemental frame can be configured to be positioned radially inwardly of the first row of struts of the frame body. In some embodiments, the first row of struts of the supplemental frame can be configured to be positioned radially outwardly of the first row of struts of the frame body. In some embodiments, the distal anchoring feature can extend from the frame body. In some embodiments, the distal anchoring feature can extend distally from the frame body. In some embodiments, the distal anchoring feature can extend from the supplemental frame.

In some embodiments, the supplemental frame can include a second row of struts. The first and second rows of struts of the supplemental frame can form cells. In some embodiments, the second row of struts of the supplemental frame can have an undulating shape. In some embodiments, the second row of struts of the supplemental frame can be configured to extend distally of the frame body.

In some embodiments, the expandable frame can include a proximal anchoring feature. The proximal anchoring feature can be sized to be positioned on a second side of the annulus of the native heart valve. For example, the proximal anchoring feature can be positioned on an atrial side of a native mitral valve annulus. In some embodiments, the proximal anchoring feature can include a first row of struts. The first row of struts can be configured to be generally aligned along the second row of struts of the frame body. The first row of struts of the proximal anchoring feature can have a size and/or shape which generally matches the size and/or shape of the second row of struts of the frame body. In some embodiments, the proximal anchoring feature can be formed separately from the frame body. In some embodiments, the first row of struts of the proximal anchoring feature can be configured to be attached to at least a portion of the second row of struts of the frame body. In some embodiments, the first row of struts of the proximal anchoring feature can be attached to the second row of struts of the frame body via sutures. In some embodiments, the first row of struts of the proximal anchoring feature and the second row struts of cells of the frame body can have an undulating shape.

In some embodiments, the first row of struts of the proximal anchoring feature can be configured to be positioned radially outwardly of the second row of struts of the frame body. In some embodiments, the first row of struts of the proximal anchoring feature can be configured to be positioned radially inwardly of the second row of struts of the frame body. In some embodiments, the proximal anchoring feature can include a second row of struts. The first and second rows of struts of the proximal anchoring feature can form cells. In some embodiments, the second row of struts of the proximal anchoring feature can have an undulating shape. In some embodiments, the second row of struts of the proximal anchoring feature can be configured to be generally aligned along a third row of struts of the frame body. The second row of struts of the proximal anchoring feature can have a size and/or shape which generally matches the size and/or shape of the third row of struts of the frame body.

In some embodiments, the prosthesis can include a plurality of locking tabs. In some embodiments, at least some of the locking tabs can extend from the frame body. In some embodiments, at least some of the locking tabs can extend from the frame body. In some embodiments, at least some of the locking tabs can extend from the frame body and at least some of the locking tabs can extend from the proximal anchoring feature. The locking tabs of the proximal anchoring feature can be configured to be generally aligned along the locking tabs of the frame body. The locking tabs of the proximal anchoring feature can have a size and/or shape which generally matches the size and/or shape of the locking tabs of the frame body.

In some embodiments, the distal anchoring feature can include a plurality of distal anchors, at least one of the distal anchors can include two or more prongs. In some embodiments, the two or more prongs can be movable in a lateral direction relative to each other. In some embodiments, a lateral dimension of the distal anchor having two or more prongs can increase when the expandable frame transitions to an expanded configuration. In some embodiments, the two or more prongs can be movable in a radial direction relative to each other. In some embodiments, a radial offset of the two or more prongs can increase when the expandable frame transitions to an expanded configuration.

In some embodiments, the distal anchoring feature includes one or more anchors configured to be movable in an axial direction relative to the frame body. In some embodiments, the distal anchoring feature includes one or more anchors having an insert. In some embodiments, the insert can be configured to extend radially outwardly relative to the frame body when the expandable frame is in an expanded configuration. In some embodiments, the insert can include a platform. The platform can be configured to extend radially and/or laterally outwardly relative to the distal anchor when the expandable frame is in an expanded configuration.

In some embodiments, at least one of the distal anchors can include a strut which bifurcates into two or more struts proximate a base of the distal anchor.

In some embodiments, the plurality of leaflets can each have an arcuate proximal edge and a free distal edge. The plurality of leaflets can be joined at commissures. The plurality of leaflets can be configured to allow flow in a proximal-to-distal direction and prevent flow in a distal-to-proximal direction.

In some embodiments, the valve body can include one or more intermediate components connecting the leaflets to the expandable frame. The one or more intermediate components can connect the leaflets to the expandable frame. At least a portion of the arcuate proximal edge of each leaflet and/or the commissures can be indirectly coupled to the expandable frame via the one or more intermediate components such that when the frame is in an expanded configuration, the one or more intermediate components position at least a portion of the arcuate proximal edge of each leaflet and/or the commissures radially inward from an inner surface of the expandable frame In some embodiments, the one or more intermediate components can form a generally tangent surface with the expandable frame when the valve body is closed to prevent flow in the second direction. In some embodiments, the one or more intermediate components can form an angle between about 120° to about 195° with the expandable frame when the valve body is closed to prevent flow in the second direction. In some embodiments, the one or more intermediate components can form an angle between about 140° to about 190° with the expandable frame when the valve body is closed to prevent flow in the second direction. In some embodiments, the one or more intermediate components form an angle between about 160° to about 185° with the expandable frame when the valve body is closed to prevent flow in the second direction. In some embodiments, the one or more intermediate components can form an angle of about 180° with the expandable frame when the valve body is closed to prevent flow in the second direction.

In some embodiments, the prosthesis can include an annular skirt. The annular skirt can be at least partially formed from a material which can allow blood to flow therethrough. In some embodiments, the material can be a partially porous cloth. In some embodiments, the material can include one or more holes formed therethrough. In some embodiments, the material can be configured such that, after deployment at the native heart valve, a rate of blood flow through the material decreases. In some embodiments, the skirt can include a hydrogel which can reduce the rate of blood flow through the material.

BRIEF DESCRIPTION OF THE DRAWINGS

These and other features, aspects and advantages are described below with reference to the drawings, which are intended to illustrate embodiments of prostheses including embodiments of various components of these prostheses.

FIG. 15 is a cross-sectional schematic view of another embodiment of a floating valve.

FIG. 16 is a perspective schematic view of an embodiment of a portion of a frame.

FIG. 17 is a cross-sectional schematic view of the frame of FIG. 16 with a floating valve attached.

FIG. 34 is a side-oriented schematic view of another embodiment of a frame.

FIG. 35 is a side-oriented schematic view of another embodiment of a frame.

FIG. 36 is a side-oriented schematic view of another embodiment of a frame.

FIG. 37 is a side-oriented schematic view of another embodiment of a frame.

FIG. 38 is a cross-sectional schematic view of an embodiment of a frame, a plurality of anchors, an annular skirt, and a floating valve.

FIG. 39 is a cross-sectional schematic view of another embodiment of a frame, a plurality of anchors, an annular skirt, and a floating valve.

FIG. 40 is a cross-sectional schematic view of another embodiment of a frame, a plurality of anchors, an annular skirt, and a floating valve.

FIG. 50 illustrates a schematic representation of the valve body of the prosthesis of FIGS. 48 and 49.

FIGS. 51-53 illustrate schematics of embodiments of shapes of openings in skirts.

FIG. 58 illustrates a side-oriented cross-sectional schematic view of an embodiment of a frame and skirt.

FIG. 59 illustrates a perspective-oriented, exploded schematic of the annular skirt of FIG. 58.

FIG. 60 illustrates a side-oriented cross-sectional schematic view of the frame and skirt of FIG. 58 in a first configuration.

FIG. 61 illustrates a side-oriented cross-sectional schematic view of the frame and skirt of FIG. 58 in a second configuration.

FIG. 71 illustrates a top-oriented cross-sectional schematic view of another embodiment of a frame and skirt.

FIG. 72 illustrates a top-oriented cross-sectional schematic view of another embodiment of a frame and skirt.

FIG. 73 illustrates a top-oriented cross-sectional schematic view of another embodiment of a frame and skirt.

FIG. 83 illustrates a front view of an embodiment of an anchoring feature.

FIG. 84 illustrates a side view of the anchoring feature of FIG. 83.

FIG. 85 illustrates a side view of another embodiment of an anchoring feature.

FIG. 86 illustrates a top view of an embodiment of an anchoring feature, the anchoring feature being in a first configuration.

FIG. 87 illustrates a front view of the anchoring feature of FIG. 86, the anchoring feature being in a first configuration.

FIG. 88 illustrates a top view of the anchoring feature of FIG. 86, the anchoring feature being in a second configuration.

FIG. 89 illustrates a front view of the anchoring feature of FIG. 86, the anchoring feature being in a second configuration.

FIG. 90 illustrates a side view of the anchoring feature of FIG. 86, the anchoring feature being in a second configuration.

FIG. 95 illustrates a top view of another embodiment of an anchoring feature, the anchoring feature being in a first configuration.

FIG. 96 illustrates a front view of the anchoring feature of FIG. 95, the anchoring feature being in a first configuration.

FIG. 97 illustrates a top view of the anchoring feature of FIG. 95, the anchoring feature being in a second configuration.

FIG. 98 illustrates a front view of the anchoring feature of FIG. 95, the anchoring feature being in a second configuration.

FIG. 99 illustrates a side view of the anchoring feature of FIG. 95, the anchoring feature being in a second configuration.

FIG. 112 illustrates a side-oriented cross-sectional schematic view of an embodiment of a frame.

FIG. 113 illustrates a front-oriented schematic view of the frame of FIG. 112.

FIG. 114 illustrates a top-oriented schematic view of the frame of FIG. 112.

FIG. 115 illustrates a side-oriented cross-sectional schematic view of another embodiment of a frame.

FIG. 116 illustrates a front-oriented schematic view of the frame of FIG. 115.

FIG. 117 illustrates a top-oriented schematic view of the frame of FIG. 115.

FIG. 121 is a bottom-oriented perspective view of the components of FIG. 120.

FIG. 122 is a side view of a front-half of another embodiment of a frame and a plurality of anchors.

FIG. 123 is a close-up view of the components of FIG. 122.

FIG. 124 is a flat pattern of an embodiment of a frame having multiple frame components.

FIG. 125 is a flat, cutting pattern for the frame components of FIG. 124.

FIG. 126 is a flat pattern of another embodiment of a frame having multiple frame components.

FIG. 127 is a flat, cutting pattern for the frame components of FIG. 126.

FIG. 128 is a flat pattern of another embodiment of a frame having multiple frame components.

FIG. 129 is a flat, cutting pattern for the frame components of FIG. 128.

FIG. 130 is a side view of a front-half of another embodiment of a frame having multiple frame components.

FIG. 131 is a top-oriented perspective view of the frame components of FIG. 130.

DETAILED DESCRIPTION

Figure 1:
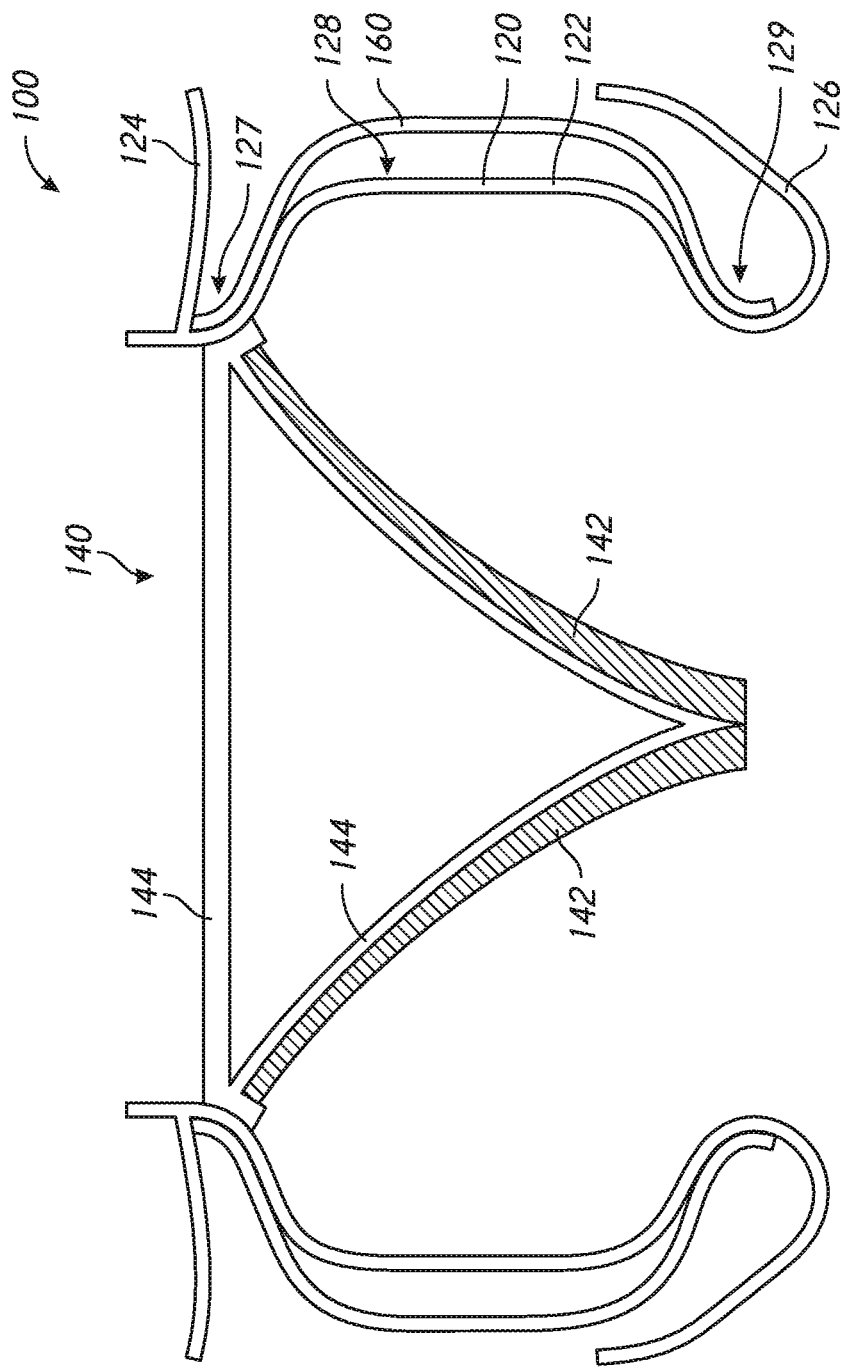
FIG. 1 is a side-oriented cross-sectional schematic view of an embodiment of a frame, a plurality of anchors, an annular skirt, and a floating valve.

The present specification and drawings provide aspects and features of the disclosure in the context of several embodiments of prostheses, replacement heart valves, and methods that are configured for use in the vasculature of a patient, such as for replacement of natural heart valves in a patient. These embodiments may be discussed in connection with replacing specific valves such as the patient's mitral valve. However, it is to be understood that the features and concepts discussed herein can be applied to replacing other types of valves including, but not limited to, the aortic valve, the pulmonary valve, and the tricuspid valve. Moreover, it is to be understood that the features and concepts discussed herein can be applied to products other than heart valve implants. For example, the controlled positioning, deployment, and/or securing features described herein can be applied to medical implants, for example other types of expandable prostheses, for use elsewhere in the body, such as within a vein, or the like. In addition, particular features of a prosthesis should not be taken as limiting, and features of any one embodiment discussed herein can be combined with features of other embodiments as desired and when appropriate.

Certain terminology may be used in the following description for the purpose of reference only, and thus are not intended to be limiting. For example, terms such as "upper", "lower", "upward", "downward", "above", "below", "top", "bottom" and similar terms refer to directions in the drawings to which reference is made. Terms such as "proximal", "distal", "radially outward", "radially inward," and "side" describe the orientation and/or location of portions of the components or elements within a consistent but arbitrary frame of reference which is made clear by reference to the text and the associated drawings describing the components or elements under discussion. Such terminology may include the words specifically mentioned above, derivatives thereof, and words of similar import. Similarly, the terms "first", "second", and other such numerical terms referring to structures neither imply a sequence or order unless clearly indicated by the context.

In some embodiments, the term "proximal" may refer to the parts of the prostheses, or components thereof, which are located closer to the operator of the device and system (e.g., the clinician implanting the prosthesis). The term "distal" may refer to the parts of the prostheses, or components thereof, which are located further from the operator of the device and system (e.g., the clinician implanting the prosthesis). However, it is to be understood that this terminology may be reversed depending on the delivery technique utilized (e.g., a transapical approach as compared to a transseptal approach).

Overview of Replacement Valves

With reference to FIGS. 1-4, embodiments of prostheses 100, 200 are illustrated. The illustrated prostheses 100, 200 may include components which are self-expanding or balloon expandable. The prostheses 100, 200, as well as other prostheses described herein, may be replacement valves that can be designed to replace a damaged or diseased native heart valve such as a mitral valve, as discussed above. It should be understood that the prostheses 100, 200, as well as other prostheses described herein, are not limited to being a replacement valve.

With reference first to the prosthesis 100 illustrated in FIG. 1, the prosthesis 100 includes a frame 120, a valve body 140, and a skirt 160. The frame 120 can be self-expanding or balloon expandable. The frame 120 provides a structure to which various components of the prosthesis 100 can be attached. As shown in the illustrated embodiment, the frame 120 includes a frame body 122, a first anchoring feature 124, and a second anchoring feature 126. As shown in the illustrated embodiment, the frame body 122 includes an upper region 127, an intermediate region 128, and a lower region 129. The intermediate region 128 can have a larger diameter than the upper region 127 and/or the lower region 129. In some embodiments, the frame 120 is oriented such that the upper region 127 is a proximal portion and the lower region 129 is a distal portion. The frame 120 can be formed from many different materials, including metals, such as Nitinol. The frame 120 is preferably formed from a plurality of struts forming open cells. As will be discussed in further detail below, components of the frame 120, such as the frame body 122, the first anchoring feature 124, and/or the second anchoring feature 126, can be used to attach or secure the prosthesis 100 to a native valve. For example, the frame body 122 and the second anchoring feature 126 can be used to attach or secure the prosthesis 100 to a native valve, such as a native mitral valve. In some embodiments, the frame 120 is sized to allow a supplemental prosthesis to be positioned within the frame 120. The frame 120 can include structural elements to secure the supplemental prosthesis to the frame 120. In some situations, this can allow for the use of a prosthesis designed for a different body cavity, such as a replacement aortic valve, to be positioned within the frame 120 when the frame 120 is positioned in another body cavity, such as a native mitral valve. However, it is to be understood that a prosthesis designed for the same body cavity can also be used. For example, in some situations, a supplemental prosthesis intended for the mitral valve can be used with the frame 120 when the frame 120 is positioned within the native mitral valve.

It is to be understood that the frame 120 can incorporate features and concepts which are the same as, or at least similar to, those of other frames described herein such as, but not limited to, frames 220, 300, 400, 500, 600, 700, 750, 810, 910, 1010, 1210, 1310, 1410, 1510, 1610, 1710, 1810, 1910, 2010, 2110, 2210, 2300, 2400, 2500, 2600, 2710, 2810, 2910, 3002, 3420, 3520, 3620, 3820, 3920, 4020, 4120, 4220, 4320, 4420, 4520, 4620, 4720, 4820, 4920, 5020, 5120, 5220, 6000, 6100, 6200, 6300, 6400, 6520, 6620, 6700, 6800, 6900, 7000, 7100 discussed below in connection with FIGS. 2-18, 20-43, 48-53, 58, 60-62, 64-80, 108-131. The frame 120, and any other frame described herein, may include features and concepts similar to those disclosed in U.S. Pat. Nos. 8,403,983, 8,414,644, and 8,652,203 and U.S. Publication Nos. 2010/0298931, 2011/0313515, 2014/0277390, 2014/0277427, 2014/0277422, and 2015/0328000, the entireties of each of which are hereby incorporated by reference and made a part of this specification. This is inclusive of the entire disclosure and is not in any way limited to the disclosure of the associated frames. Moreover, although the frame 120 has been described as including a frame body 122, a first anchoring feature 124, and a second anchoring feature 126, it is to be understood that the frame 120 need not include all components. For example, in some embodiments, the frame 120 can include the frame body 122 and the second anchoring feature 126 while omitting the first anchoring feature 124. Moreover, although the frame body 122, the first anchoring feature 124, and the second anchoring feature 126 have been illustrated as being unitarily or monolithically formed, it is to be understood that in some embodiments one or more of the frame body 122, the first anchoring feature 124, and the second anchoring feature 126 can be formed separately. In such embodiments, the separate components can be attached using any of the fasteners and techniques described herein, such as via sutures as shown, for example, in FIGS. 120-123. For example, the first anchoring feature 124 and/or the second anchoring feature 126 can be formed separately from the frame body 122. The first anchoring feature 124 and/or the second anchoring feature 126 can be attached to the frame body 122 via sutures.

With continued reference to the prosthesis 100 illustrated in FIG. 1, the valve body 140 is attached to the frame 120 within an interior of the frame 120. The valve body 140 functions as a one-way valve to allow blood flow in a first direction through the valve body 140 and inhibit blood flow in a second direction through the valve body 140. For example, in embodiments where the upper region 127 is a proximal portion and the lower region 129 is a distal portion, the valve body 140 can allow blood flow in a proximal-to-distal direction and inhibit blood flow in a distal-to-proximal direction. The valve body 140 preferably includes a plurality of valve leaflets 142, for example three leaflets 142, which are joined at commissures. As will be discussed in further detail below in connection with additional figures, the valve body 140 can include one or more intermediate components 144. The intermediate components 144 can be positioned between a portion of, or the entirety of, the leaflets 142 and the frame 120 such that at least a portion of the leaflets 142 are coupled to the frame 120 via the intermediate component 144. In this manner, a portion of, or the entirety of, the portion of the valve leaflets 142 at the commissures and/or an arcuate edge of the valve leaflets 142 are not directly coupled or attached to the frame 120 and are indirectly coupled or "float" within the frame 120. For example, a portion of, or the entirety of, the portion of the valve leaflets 142 proximate the commissures and/or the arcuate edge of the valve leaflets 142 can be spaced radially inward from an inner surface of the frame 120. This can beneficially allow valve leaflets 142 having various shapes and sizes to be incorporated into a frame 120 having a shape and size which does not correspond to the shape and size of the valve leaflets 142. For example, the valve leaflets 142 can be sized and shaped to form a generally cylindrical shape having a diameter. By using one or more intermediate components 144, the valve leaflets 142 can be attached to non-cylindrical frames 120 and/or frames 120 having a diameter larger than that of the diameter of the valve leaflets 142. Use of one or more intermediate components 144 can also beneficially reduce stress concentrations on valve leaflets 142. This can advantageously increase the effective lifespan of the valve leaflets 142. For example, the one or more intermediate components 144 can be formed from a material having a stiffness greater than that of the valve leaflet 142 yet less than that of the frame 120.

It is to be understood that the valve body 140 can incorporate features and concepts similar to, or the same as, those of other valve bodies described herein such as, but not limited to, valve bodies 240, 820, 920, 1020, 1110, 1220, 1320, 1420, 1520, 1620, 1720, 1820, 1920, 2020, 2120, 2220, 2720, 2820, 2920, 3440, 3540, 3640, 4830, 6540, 6640, discussed below in connection with FIGS. 2-4, 14-33, 38-40, 48-53, 57, 74, 118, 120, and 121. Moreover, although the valve body 140 has been described as including a plurality of leaflets 142 and one or more intermediate components 144, it is to be understood that the valve body 140 need not include all features. For example, the valve body 140 can include the plurality of valve leaflets 142 while omitting the intermediate components 144. In some embodiments, the valve leaflets 142 can be directly attached to the frame 120.

With continued reference the prosthesis 100 illustrated in FIG. 1, the skirt 160 can be attached to the frame 120. The skirt 160 can be positioned around and secured to an exterior of the frame 120. The skirt 160 can be annular and can extend entirely circumferentially around the frame 120. The skirt 160 can prevent or inhibit backflow of fluids, such as blood, around the prosthesis 100. For example, with the skirt 160 positioned annularly around an exterior of the frame 120, the skirt 160 can create an axial barrier to fluid flow exterior to the frame 120 when deployed within a body cavity such as a native valve annulus. The skirt 160 can encourage tissue in-growth between the skirt 160 and the natural tissue of the body cavity. This may further help to prevent leakage of blood flow around the prosthesis 100 and can provide further securement of the prosthesis 100 to the body cavity. In some embodiments, the skirt 160 can be loosely attached to the exterior of the frame 120. In some embodiments, the skirt 160 can be tautly secured around the frame 120.

It is to be understood that the skirt 160 can incorporate features and concepts similar to, or the same as, those of other skirts described herein such as, but not limited to, skirts 260, 2730, 2830, 2930, 3030, 3460, 3560, 3660, 3860, 3960, 4060, 4160, 4260, 4360, 4460, 4560, 4660, 4760, 4860, 4960, 5060, 5160, 6560, 6660 discussed below in connection with FIGS. 2-4, 38-43, 48-53, 58-79, 118, 120, and 121. Although the prosthesis 100 has been described as including a frame 120, a valve body 140, and a skirt 160, it is to be understood that the prosthesis 100 need not include all components. For example, in some embodiments, the prosthesis 100 can include only the frame 120 and the valve body 140 while omitting the skirt 160.

Figure 2:
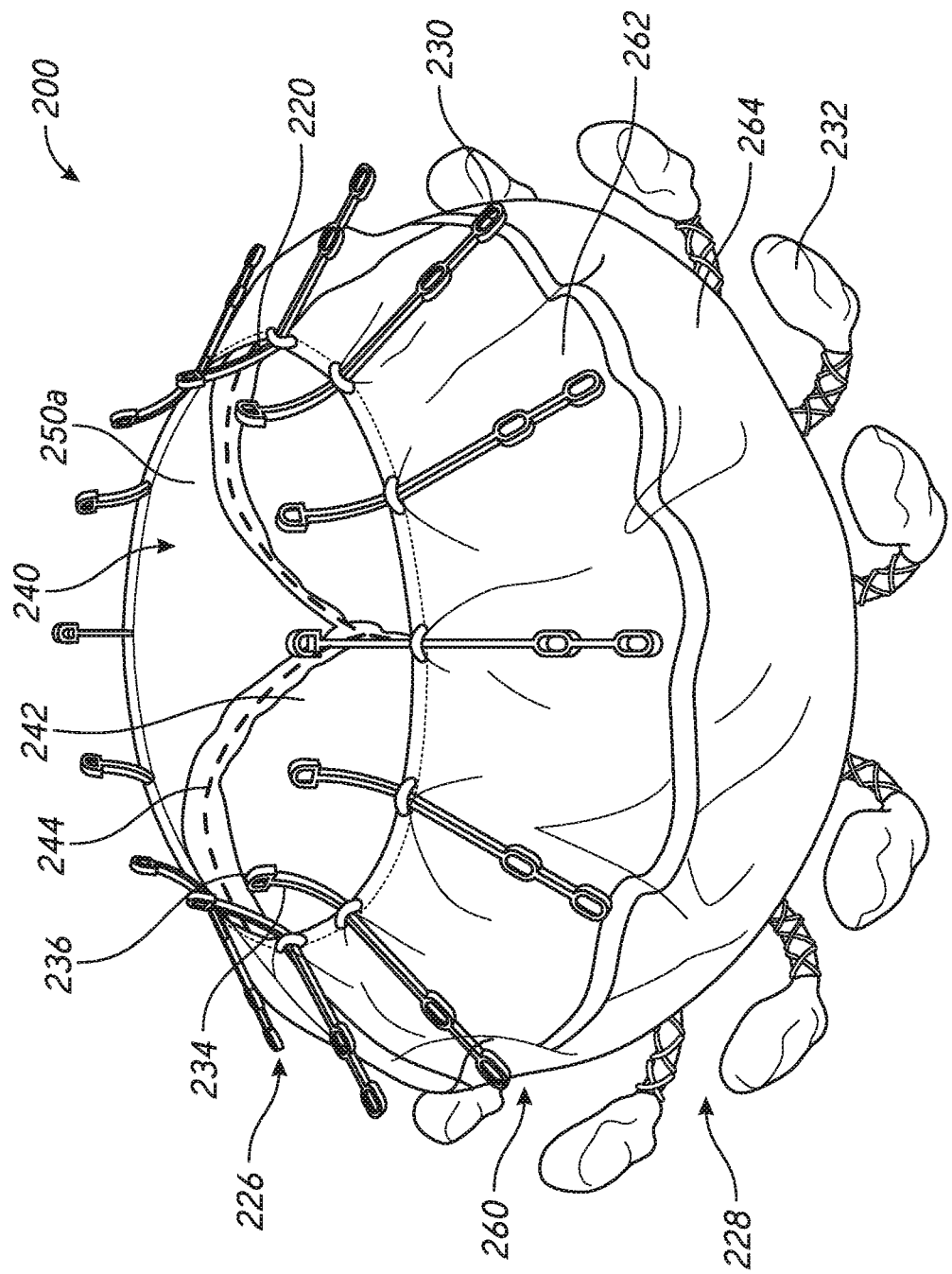
FIG. 2 is a top-oriented perspective view of another embodiment of a frame, a plurality of anchors, an annular skirt, and a valve body.
Figure 3:
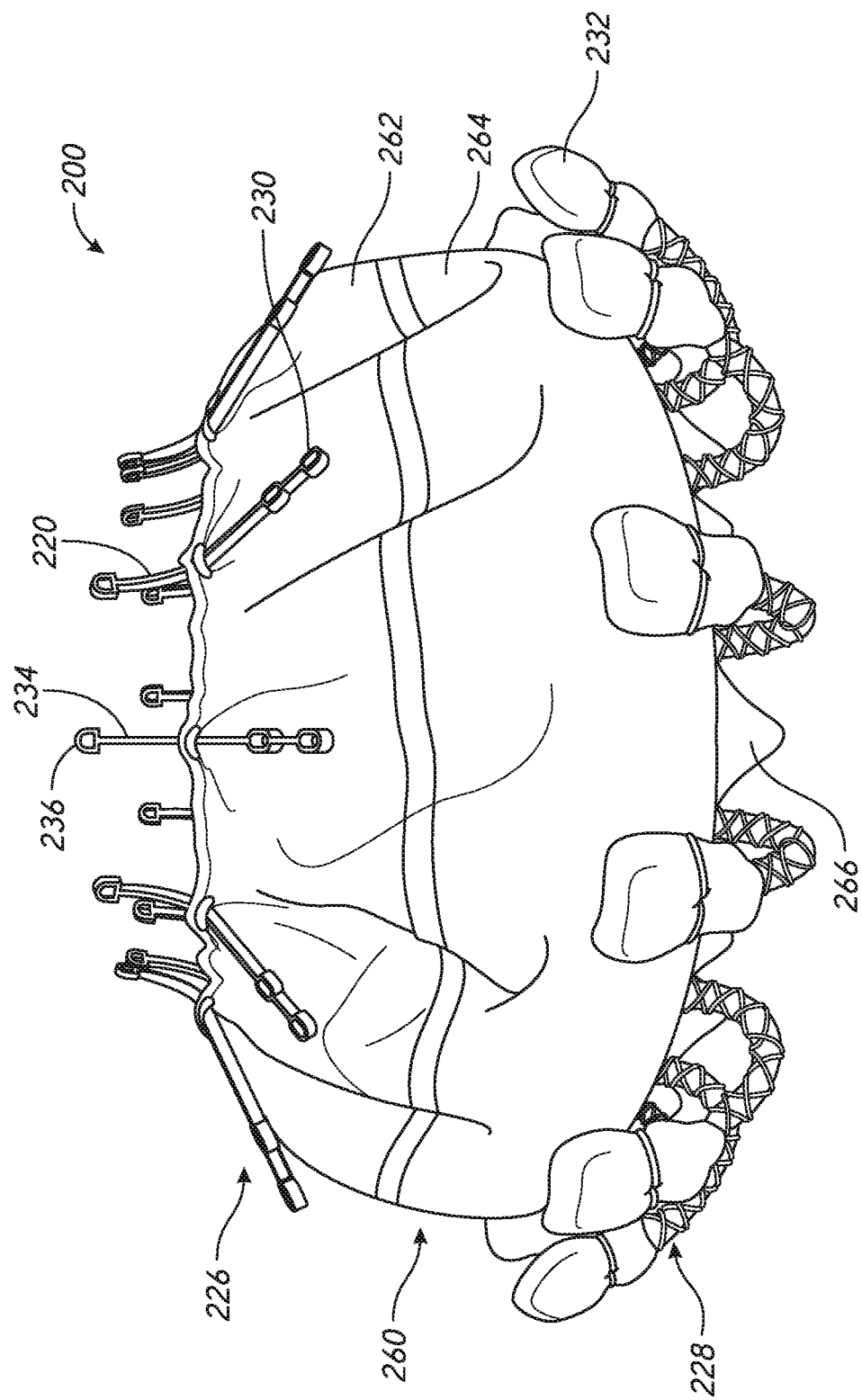
FIG. 3 is a side view of the prosthesis of FIG. 2.
Figure 4:
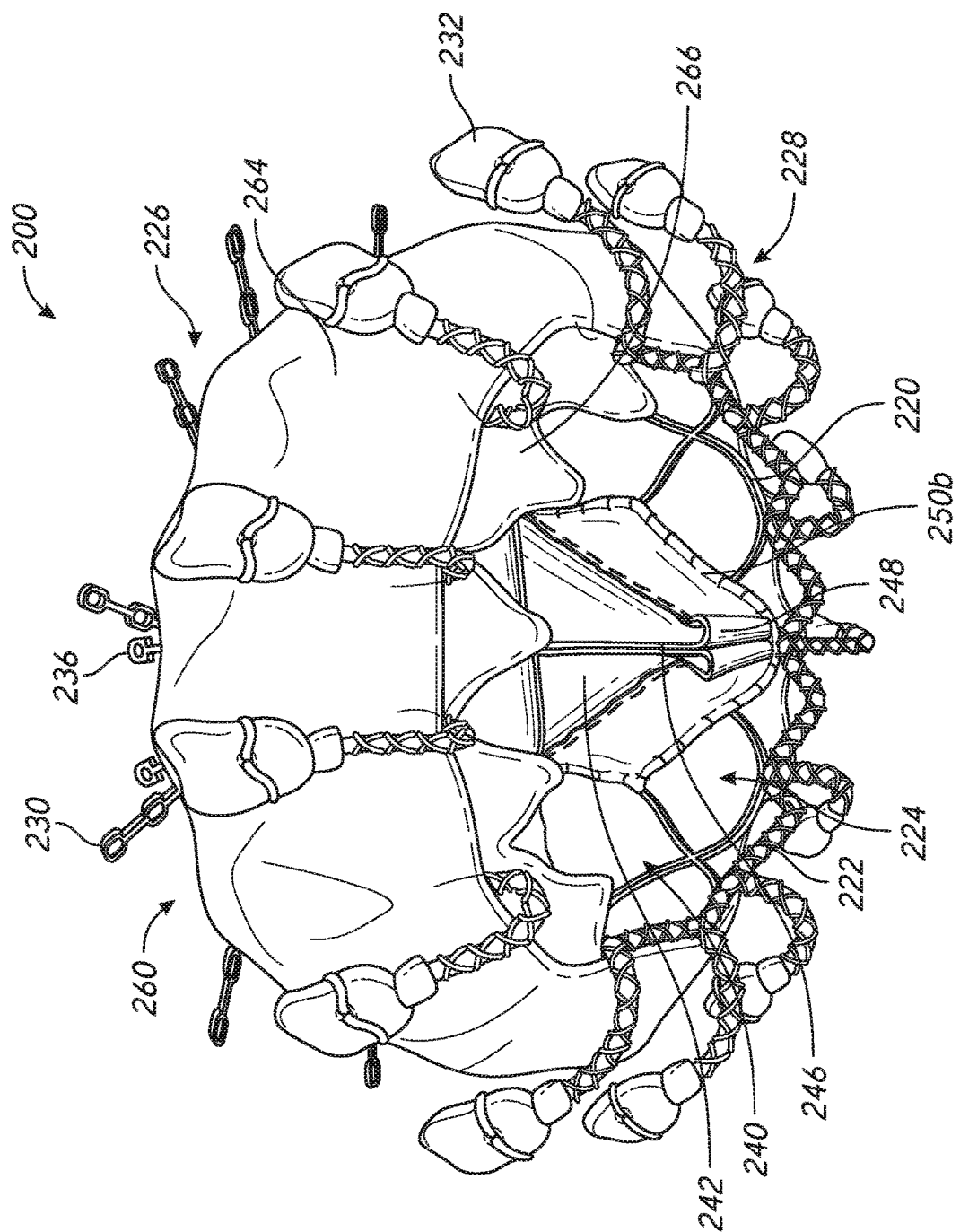
FIG. 4 is a bottom-oriented perspective view of the prosthesis of FIG. 2.

With reference next to the prosthesis 200 illustrated in FIGS. 2-4, the prosthesis 200 can include a frame 220, a valve body 240, and a skirt 260. The frame 220 can be self-expanding or balloon expandable. As shown in the illustrated embodiment, the frame 220 can include a frame body 222 formed from a plurality of struts defining a plurality of cells 224 (as shown in FIG. 4). One or more of the cells 224 can allow the frame 220 to longitudinally foreshorten when the frame 220 radially expands.

The frame 220 includes a first anchoring feature 226 and a second anchoring feature 228. As shown, the first anchoring feature 226 can be formed from a plurality of individual anchors extending from the frame body 222 in a direction radially outward from a longitudinal axis of the frame 220 and/or in a direction generally toward a lower end of the frame 220. The individual anchors of the first anchoring feature 226 can include tips or ends 230 having one or more eyelets. The eyelets can be used to facilitate attachment of a skirt, cover, and/or cushion to the first anchoring feature 226. As shown in the illustrated embodiment, the first anchoring feature 226 can include twelve individual anchors; however, it is to be understood that a greater number or lesser number of individual anchors can be used. For example, the number of individual anchors can be chosen as a multiple of the number of commissures for the valve body 240. As such, for a prosthesis 200 with a valve body 240 having three commissures, the first anchoring feature 226 can have three individual anchors, six individual anchors, nine individual anchors, twelve individual anchors, fifteen individual anchors, or any other multiple of three. It is to be understood that the number of individual anchors need not correspond to the number of commissures of the valve body 240.

As shown, the second anchoring feature 228 can be formed from a plurality of individual anchors extending from the frame body 222 in a direction radially toward the longitudinal axis of the frame 220 and bent to extend in a direction radially outward from the longitudinal axis of the frame 220. A portion of the individual anchors, such as tips or ends 230, can extend in a direction generally toward an upper end of the frame 220. The individual anchors of the second anchoring feature 228 can include tips or ends 230 having covers and/or cushions as shown. In some embodiments, the tips or ends 230 can be enlarged relative to the preceding portion of the second anchoring feature 228, such as a strut. The covers and/or cushions can reduce pressure applied to tissue of the body cavity, such as the native valve annulus, when the tips or ends 230 contact the native valve annulus. As shown in the illustrated embodiment, the second anchoring feature 228 can include twelve individual anchors; however, it is to be understood that a greater number or lesser number of individual anchors can be used. For example, the number of individual anchors can be chosen as a multiple of the number of commissures for the valve body 240. As such, for a prosthesis 200 with a valve body 240 having three commissures, the second anchoring feature 228 can have three individual anchors, six individual anchors, nine individual anchors, twelve individual anchors, fifteen individual anchors, or any other multiple of three. It is to be understood that the number of individual anchors need not correspond to the number of commissures of the valve body 240.

The frame 220 preferably includes a set of locking tabs 234 extending from the frame body 222 at its upper end. As shown, the frame 220 includes twelve locking tabs 234, however, it is to be understood that a greater number or lesser number of locking tabs can be used. The locking tabs 234 can extend generally upwardly from the frame body 222 in a direction generally aligned with the longitudinal axis of the frame 220. The locking tab 234 can include an enlarged head or end 236. As shown, the enlarged head or end 236 has a semi-circular or semi-elliptical shape forming a "mushroom" shape with the remaining portion of the locking tab 234. The locking tab 234 can include an eyelet which can be positioned through the enlarged head 236. It is to be understood that the locking tab 234 can include an eyelet at other locations, or can include more than a single eyelet. The locking tab 234 can be advantageously used with multiple types of delivery systems such as a "slot-based" delivery system and/or a "tether-based" delivery system.

With continued reference to the prosthesis 200 illustrated in FIGS. 2-4, the valve body 240 preferably includes a plurality of valve leaflets 242 each having a first edge 244, a second edge 246, and one or more tabs 248. The first edge 244, which may be considered a proximal edge, may be arcuate in shape. The tabs 248 can form part of the valve leaflets 242 positioned at the commissures of the valve body 240. The second edge 246 can be a freely moving edge which can allow the valve body 240 to open and close. The valve leaflet 242 can be similar to leaflet 1110 illustrated in FIG. 19A which includes a first edge 1112, a second edge 1114, and tabs 1116. The plurality of valve leaflets 242 can function in a manner similar to the native mitral valve, or to any other valves in the vascular system as desired.

As shown in the illustrated embodiment, the valve body 240 can include one or more first intermediate components 250a (as shown in FIG. 2) and one or more second intermediate component 250b (as shown in FIG. 4). The one or more first intermediate components 250a and the one or more second intermediate components 250b can be used to attach one or more of the valve leaflets 242, or a portion thereof, to the frame 220 such that the valve leaflet 242 is indirectly coupled to the frame 220 or "floats" within the frame 220. For example, as shown in the illustrated embodiment, at least a portion of the first edge 244 and the tabs 248 can be indirectly coupled to the frame 220 via the one or more intermediate components 250a, 250b with a portion of the first edge 244 directly coupled to the frame 220. The one or more first intermediate components 250a and/or one or more second intermediate components 250b can be formed from a combination of units, such as a combination of two, three, or more units. It is contemplated that the one or more intermediate components 250a, 250b can be formed from fewer units. As will be described in further detail, the intermediate components 250a, 250b can be attached to one or more third intermediate components to form a partially sealed or fully sealed pocket. The intermediate components 250 may be formed from a slightly porous material which allows fluid, such as blood, to enter into the pocket. In some instances, the blood can form a clot within the pocket.

With continued reference to the prosthesis 200 illustrated in FIGS. 2-4, the skirt 260 can be loosely attached to the exterior of the frame 220. The skirt 260 can be formed from multiple components such as an upper component 262, a middle component 264, and a lower component 266. The upper component 262 can be attached to an upper portion of the frame 220. As shown, the upper component 262 can be attached at or proximate the uppermost cusp or first edge 244 of the valve leaflet 242. The upper component 262 can extend downwardly and be attached to the middle component 264. The middle component 264 can extend downwardly towards a lower portion of the frame 220. As shown, the middle component 264 can be attached at or proximate the commissures of the valve body 240 and/or the base of the anchors of the second anchoring feature 228. The lower component 266 can be attached to the middle component 264 and can extend downwardly. As shown, the lower edge of the lower component 266 can follow the undulations of the struts of the frame 220. However, it is contemplated that the lower component 266 can have a lower edge with a different shape, such as a straight edge. Moreover, it is to be understood that the skirt 260 can be formed from a greater number or lesser number of components. For example, one or more of the upper component 262, the middle component 264, and/or the lower component 266 can be combined into a single component. The skirt 260 can be formed from a variety of materials, such as a knit polyester (e.g., polyethylene terephthalate (PET)) or any other biocompatible material.

As shown in the illustrated embodiment, the skirt 260 can be attached at or proximate the upper end of the frame 220 and at or proximate the lower end of the frame 220. The skirt 260 can be formed with sufficient material such that a portion of the skirt 260 positioned around a middle portion of the frame 220 is loose relative to an exterior of the frame 220.

Embodiments of Replacement Mitral Valve Frames and Anchoring Features

With reference to FIGS. 5A-13 and 83-117, embodiments of frames 300, 400, 500, 600, 700, and 750, 6000, 6100, 6200, 6300, 6400 and anchoring features 340, 350, 440, 450, 540, 550, 650, 710, 760, 5200, 5300, 5400, 5500, 5600, 5700, 5800, 5920, 5930, 6020, 6120, 6220, 6320, 6420 are illustrated. With reference first to the frame 300 illustrated in FIG. 5A, the frame 300 is shown in an expanded configuration. The frame 300 can include a frame body 302 having an upper region 310, an intermediate region 320, and a lower region 330. A longitudinal axis of the frame 300 may be defined as the central axis that extends through the center of the frame 300 between the upper and lower ends of the frame 300. In some embodiments, the frame 300 may be oriented such that the upper region 310 is a proximal portion and the lower region 330 is a distal portion. The frame 300 can include a first anchoring feature 340 and a second anchoring feature 350. In some embodiments, the frame 300 may be oriented such that the first anchoring feature 340 is a proximal anchoring feature and the second anchoring feature 350 is a distal anchoring feature.

One or both anchoring features 340, 350 can contact or engage a native valve annulus, such as the native mitral valve annulus, tissue beyond the native valve annulus, native leaflets, and/or other tissue at or around the implantation location during one or more phases of the cardiac cycle, such as systole and/or diastole. In some embodiments, one or both anchoring features 340, 350 do not contact or engage, or only partially contact or engage, a native valve annulus, such as the native mitral valve annulus, tissue beyond the native valve annulus, native leaflets, and/or other tissue at or around the implantation location during one or more phases of the cardiac cycle, such as systole and/or diastole. For example, when the frame 300 is used for a replacement mitral valve prosthesis, during at least systole, in some embodiments the second anchoring feature 350 is sized to contact or engage the native mitral valve annulus whereas the first anchoring feature 340 is sized to be spaced from the native mitral valve annulus. It is to be understood that in some embodiments, when the frame 300 is used for a replacement mitral valve prosthesis, during diastole and/or systole, in some embodiments both the first anchoring feature 340 and the second anchoring feature 350 are sized to contact or engage the native mitral valve annulus. In some instances, the first anchoring feature 340 may contact a portion of a skirt, such as skirts 160, 260, which can contact or engage the native mitral valve annulus. For example, the first anchoring feature 340 can be connected to a portion of a skirt. While the anchoring features 340, 350 have been illustrated as extending from the upper and lower regions 310, 330 of the frame 300 respectively, it is to be understood that the anchoring features 340, 350 can be positioned along any other portion of the frame 300 as desired. Moreover, while two anchoring features 340, 350 have been included in the illustrated embodiment, it is to be understood that a greater number or lesser number of sets of anchoring features can be utilized.

As shown, the frame body 302, when in an expanded configuration such as in a fully expanded configuration, has a bulbous or slightly bulbous shape, with an intermediate region 320 being larger than the upper region 310 and the lower region 330. The bulbous shape of the frame body 302 can advantageously allow the frame body 302 to engage a native valve annulus or other body cavity, while spacing the inlet and outlet from the heart or vessel wall. This can advantageously reduce undesired contact between the prosthesis and the heart or vessel, such as the atrial and ventricular walls of the heart.

As shown in the illustrated embodiment, the intermediate region 320 is preferably cylindrical or generally cylindrical in shape such that a diameter of an upper end of the intermediate region 320 and/or a diameter of a lower end of the intermediate region 320 is equal or generally equal to the diameter of a middle portion of the intermediate region 320. The general uniformity of the diameter of the intermediate region 320 from the upper end to the lower end, in conjunction with the axial dimension between the upper end and the lower end (i.e., the "height" of the intermediate region 320), provides for a significantly large circumferential area upon which a native valve annulus, or other body cavity, can be engaged. This can beneficially improve securement of the frame 300 to the native valve annulus or other body cavity. This can also improve sealing between the frame 300 and the native valve annulus, or other body cavity, thereby reducing paravalvular leakage. Although the frame body 302, such as the intermediate portion 302, has been described and illustrated as being cylindrical, it is to be understood that all or a portion of the frame body 302 can be have a non-circular cross-section such as, but not limited to, a D-shape, an oval or an otherwise ovoid cross-sectional shape.

In some embodiments, the diameter of the upper end of the intermediate region 320 and the lower end of the intermediate region 320 can be about the same. However, it is to be understood that the diameter of the upper end of the intermediate region 320 and the lower end of the intermediate region 320 can differ. In some embodiments, the frame body 302 in an expanded configuration can have a diameter at its widest portion of between about 30 mm to about 60 mm, between about 35 mm to about 55 mm, about 40 mm, any sub-range within these ranges, or any other diameter as desired. In some embodiments, the frame body 302 in an expanded configuration has a diameter at its narrowest portion between about 20 mm to about 40 mm, any sub-range within these ranges, or any other diameter as desired. In an expanded configuration, the ratio of the diameter of the frame body 302 at its widest portion to the diameter of the frame body 302 at its narrowest portion can be about 3:1, about 5:2, about 2:1, about 3:2, about 4:3, any ratio within these ratios, or any other ratio as desired. In the expanded configuration, the frame body 302 preferably has an axial dimension between the upper and lower ends of the frame body 302 (i.e., the "height" of the frame body 302) of between about 10 mm to about 40 mm, between about 18 mm to about 30 mm, about 20 mm, any sub-range within these ranges, or any other height as desired.

The frame body 302 can have an axially compact configuration relative to the radial dimension. For example, the ratio of the diameter of the largest portion of the frame body 302 to the height of the frame body 302 when the frame is in its expanded configuration can be about 3:1, about 5:2, about 2:1, about 3:2, about 4:3, about 13:10, about 5:4, or about 1:1. Thus, in some embodiments the width at the largest portion of the frame body 302 can be greater than the height of the frame body 302.

As shown in the illustrated embodiment, the height of the intermediate region 320 can be larger than the axial dimension between the upper and lower ends of the upper region 310 (i.e., the "height" of the upper region 310) and/or the axial dimension between the upper and lower ends of the lower region 330 (i.e., the "height" of the lower region 330). The height of the upper region 310 is preferably between about 3 mm to about 10 mm. In some embodiments, the height of the intermediate region 320 can be between about 6 mm to about 15 mm. In some embodiments, the height of the lower region 330 can be between about 3 mm to about 15 mm. The ratio of the height of the intermediate region 320 to the combined heights of the upper region 310 and lower region 330 can be about 1:2, about 2:3, about 3:5, about 1:1, about 5:3, about 3:2, about 2:1, any ratio within these ratios, or any other ratio as desired. The height of the intermediate region 320 can be greater than the height of the lower region 330 and the height of the lower region 330 can be greater than the height of the upper region 310.

Figure 5A:
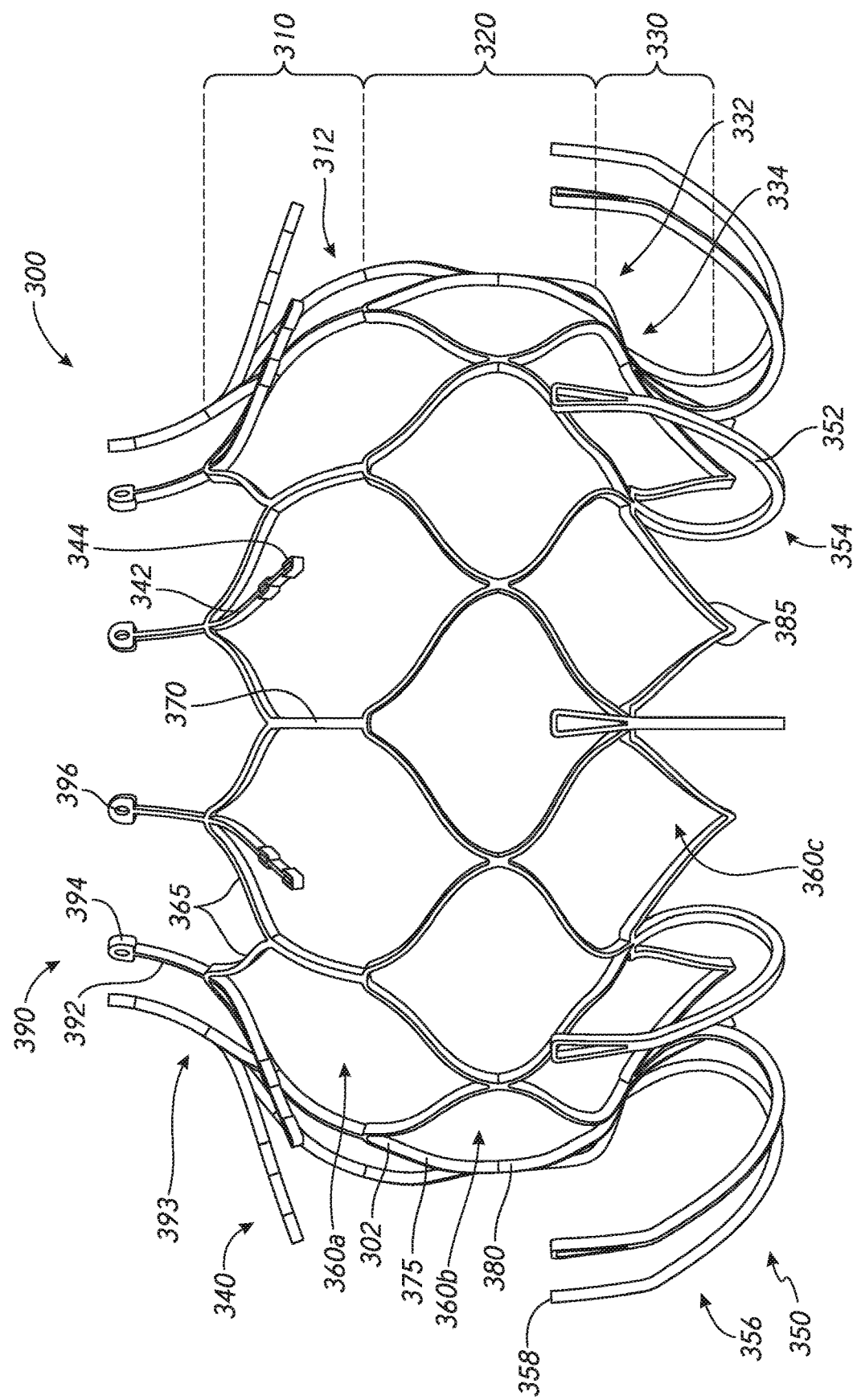
FIG. 5A is a side view of the front-half of an embodiment of a frame.

With continued reference to the frame 300 illustrated in FIG. 5A, at the juncture between the intermediate region 320 and the upper region 310, the frame body 302 can include a bend 312. The bend 312 can be a radially inward bend towards the longitudinal axis of the frame 300 such that a portion of the upper region 310, extending upwardly from the beginning of bend 312 adjacent the intermediate region 320, is inclined or curved towards the longitudinal axis of the frame 300. The radially inward inclination of the upper region 310 can allow for a substantial decrease in radial dimension over a relatively small axial dimension. The greater the degree of inclination, the greater the decrease in radial dimension per increase in axial dimension. This can beneficially provide a relatively compact or "squat" form factor for the frame body 302. Moreover, as will be discussed in further detail, the inclined or curved portion of the upper region 310 can facilitate the securement of a supplemental prosthesis within frame 300.

In some embodiments, the bend 312 can orient the portion of the upper region 310, positioned upward of the beginning of bend 312, such that it forms an angle of between about 20 degrees to about 70 degrees with a plane orthogonal to the longitudinal axis of the frame 300, an angle of between about 30 degrees to about 60 degrees with a plane orthogonal to the longitudinal axis of the frame 300, an angle of between about 40 degrees to about 50 degrees with a plane orthogonal to the longitudinal axis of the frame 300, an angle of about 45 degrees with a plane orthogonal to the longitudinal axis of the frame 300, any subrange within these ranges, or any other angle as desired. An angle of about 40 degrees to about 50 degrees can allow for a significant reduction in radial dimension per increase in axial dimension while still reducing strain when the frame 300 is in a crimped configuration. In some embodiments, the bend 312 can orient the portion of the upper region 310, positioned upward of the beginning of bend 312, such that it forms an angle of less than 70 degrees with a plane orthogonal to the longitudinal axis of the frame 300, an angle of less than 55 degrees with a plane orthogonal to the longitudinal axis of the frame 300, an angle of less than 40 degrees with a plane orthogonal to the longitudinal axis of the frame 300, an angle of less than 25 degrees with a plane orthogonal to the longitudinal axis of the frame 300, or less than any other angle as desired.

The bend 312 can generally form an arc with an angle between about 20 degrees to about 90 degrees. For example, as shown in the illustrated embodiment, the arc can have an angle of about 45 degrees. In other embodiments, the bend 312 can form an arc with an angle between about 30 degrees to about 60 degrees. The radius of curvature of the arc may be constant such that the bend 312 forms a circular arc or may differ along the length of the bend 312.

With continued reference to the frame 300 illustrated in FIG. 5A, at the juncture between the intermediate region 320 and the lower region 330, the frame body 302 can include a bend 332 toward the longitudinal axis of the frame 300. The bend 332 can be a radially inward bend towards the longitudinal axis of the frame 300 such that a portion of the lower region 330, extending downwardly from the beginning of bend 332 adjacent the intermediate region 320, is inclined or curved towards the longitudinal axis of the frame 300. The radially inward inclination of the lower region 330 can allow for a substantial decrease in radial dimension over a relatively small axial dimension. The greater the degree of inclination, the greater the decrease in radial dimension per increase in axial dimension. This can beneficially provide a relatively compact or "squat" form factor for the frame body 302. Moreover, when used at a native mitral valve, this can beneficially enhance the atraumatic nature of the device by allowing chordae tendineae to take a more natural trajectory, thereby relieving stress on the chordae and leaflets. Additionally, as will be discussed in further detail below, the inclined or curved portion of the lower region 330 can facilitate the securement of a supplemental prosthesis within frame 300.

The bend 332 can orient the portion of the lower region 330, positioned below of the beginning of bend 332, such that it forms an angle of between about 20 degrees to about 70 degrees with a plane orthogonal to the longitudinal axis, an angle of between about 30 degrees to about 60 degrees with a plane orthogonal to the longitudinal axis, an angle of between about 40 degrees to about 50 degrees with a plane orthogonal to the longitudinal axis, an angle of about 45 degrees with a plane orthogonal to the longitudinal axis, any subrange within these ranges, or any other angle as desired. An angle of about 40 degrees to about 50 degrees can allow for a significant reduction in radial dimension per increase in axial dimension while still reducing strain when the frame 300 is in a crimped configuration. In some embodiments, the bend 332 can orient the portion of the lower region 330, positioned below of the beginning of bend 332, such that it forms an angle of less than 70 degrees with a plane orthogonal to the longitudinal axis, an angle of less than 55 degrees with a plane orthogonal to the longitudinal axis, an angle of less than 40 degrees with a plane orthogonal to the longitudinal axis, an angle of less than 25 degrees with a plane orthogonal to the longitudinal axis, or less than any other angle as desired.

The bend 332 can generally form an arc with an angle between about 20 degrees to about 90 degrees. For example, as shown in the illustrated embodiment, the arc can have an angle of about 45 degrees. In some embodiments, the bend 332 can form an arc with an angle between about 30 degrees to about 60 degrees. The radius of curvature of the arc may be constant such that the bend 332 forms a circular arc or may differ along the length of the bend 332.

The lower region 330 can include a bend 334 below the bend 332. The bend 334 can be oriented opposite that of the bend 332 such that a portion of the lower region 330, extending downwardly from the beginning of the bend 334, is inclined or curved at less of an angle towards the longitudinal axis of the frame 300 than the portion above the beginning of bend 334, is generally parallel to the longitudinal axis, or is inclined or curved at an angle away from the longitudinal axis of the frame 300. This can beneficially reduce the rate of decrease in radial dimension over the remainder of the axial dimension of the lower region 330.

The bend 334 can orient the portion of the lower region 330, positioned below the beginning of bend 334, such that it forms an angle of between about 30 degrees to about 90 degrees with a plane orthogonal to the longitudinal axis, an angle of between about 45 degrees to about 85 degrees with a plane orthogonal to the longitudinal axis, an angle of between about 60 degrees to about 80 degrees with a plane orthogonal to the longitudinal axis, an angle of about 80 degrees with a plane orthogonal to the longitudinal axis, any subrange within these ranges, or any other angle as desired. In some embodiments, the bend 334 can orient the portion of the lower region 330, positioned below the beginning of bend 334, such that it forms an angle of greater than 25 degrees with a plane orthogonal to the longitudinal axis, an angle of greater than 40 degrees with a plane orthogonal to the longitudinal axis, an angle of greater than 55 degrees with a plane orthogonal to the longitudinal axis, an angle of greater than 70 degrees with a plane orthogonal to the longitudinal axis, or greater than any other angle as desired.

The diameter of the upper end of the upper region 310 and the lower end of the lower region 330 can be about the same. However, it should be understood that the diameter of the upper end of the upper region 310 and the lower end of the lower region 330 can differ. Moreover, in some embodiments, the frame body 302 may not have a bulbous portion, and can have substantially the same outer dimension along its entire length (e.g., cylindrical), or it may have one end larger than the other end. For example, the intermediate region 320 and the lower region 330 can have the same, or substantially the same, diameter.

With continued reference to the frame 300 illustrated in FIG. 5A, the frame body 302 can include a plurality of struts with at least some of the struts forming cells 360a, 360b, 360c. Any number of configurations of struts can be used, such as rings of undulating struts shown forming ellipses, ovals, rounded polygons, and teardrops, but also chevrons, diamonds, curves, and various other shapes. As shown in the illustrated embodiment, the frame body 302 can include three rows of cells 360a, 360b, 360c.

The upper row of cells 360a can have a hexagonal or generally hexagonal shape. The cell 360a can be formed via a combination of struts. As shown in the illustrated embodiment, the upper portion of cells 360a can be formed from a set of circumferentially-expansible struts 365 having a zig-zag or undulating shape forming a repeating "V" shape. The circumferentially-expansible struts 365 can be inclined or curved towards a longitudinal axis of the frame 300 such that an upper portion of the struts 365 are positioned closer to the longitudinal axis of the frame 300 than the lower portion of the struts 365.

The middle portion of cells 360a can be formed from a set of struts 370 extending downwardly from bottom ends of each of the "V" shapes. The struts 370 can extend generally longitudinally in a distal direction. As shown in the illustrated embodiment, the struts 370 can incorporate the bend 312 such that an upper portion of the struts 370 are inclined or curved towards the longitudinal axis of the frame 300 and the lower portion of the struts 370 extend in a direction generally parallel to the longitudinal axis of the frame 300.

The lower portion of cells 360a can be formed from a set of circumferentially-expansible struts 375 having a zig-zag or undulating shape forming a repeating "V" shape. As shown in the illustrated embodiment, circumferentially-expansible struts 375 can form a generally cylindrical portion of the frame 300 with the upper portion of the struts 375 having a radial dimension which is about the same as the radial dimension as the lower portion of the struts 375. The portion of the cells 360a extending upwardly from the bottom end of struts 370 may be considered to be a substantially non-foreshortening portion of the frame 300. As will be discussed in further detail below, foreshortening refers to the ability of the frame to longitudinally shorten as the frame radially expands.

As shown in the illustrated embodiment, the cells 360a can have an irregular hexagon shape. For example, hexagonal cells 360a can be symmetrical about a vertical axis extending from upper to lower ends of the cell 360a. In some embodiments, two of the sides of the hexagonal cells 360a can be one length, while the other four sides of the cells 360a can be a greater length. In some embodiments, the two sides with the same length can be generally parallel to one another.

As shown in the illustrated embodiment, the middle and/or lower rows of cells 360b, 360c can have a different shape from the cells 360a of the first row. The middle and lower row of cells 360b, 360c can have a diamond or generally diamond shape. The cells 360b, 360c may be considered to be a substantially foreshortening portion of the frame 300. The diamond or generally diamond shape can be formed via a combination of struts. The upper portion of cells 360b can be formed from the set of circumferentially-expansible struts 375 such that cells 360b share struts with cells 360a. The lower portion of cells 360b can be formed from a set of circumferentially-expansible struts 380. As shown in the illustrated embodiment, circumferentially-expansible struts 380 can extend generally in a downward direction. The circumferentially-expansible struts 380 can incorporate the bend 332 such that an upper portion of the struts 380 form a generally cylindrical portion of the frame 300 and the lower portion of the struts 380 can be inclined or curved towards the longitudinal axis of the frame 300.

The upper portion of cells 360c can be formed from the set of circumferentially-expansible struts 380 such that cells 360c share struts with cells 360b. The lower portion of cells 360c can be formed from a set of circumferentially-expansible struts 385. Circumferentially-expansible struts 385 can extend generally in a downward direction. The circumferentially-expansible struts 385 can be inclined or curved towards the longitudinal axis of the frame 300. As shown in the illustrated embodiment, the angle of inclination of the circumferentially-expansible struts 385 can be different from the angle of inclination of the lower portion of circumferentially-expansible struts 380. For example, the circumferentially-expansible struts 385 can be less inclined or curved towards the longitudinal axis of the frame 300 than the lower portion of circumferentially-expansible struts 380. As will be discussed in further detail, the angle of inclination of circumferentially-expansible struts 385 can be chosen based on the supplemental prosthesis the frame 300 is designed to receive.

While the cells 360a, 360b, 360c were described as generally hexagonal-shaped and generally diamond-shaped, it is to be understood that some or all of the struts 365, 370, 375, 380, 385 may not form entirely straight segments. As shown in the illustrated embodiments, the struts 365, 370, 375, 380, 385 can include some curvature such that the upper and/or lower apices are curved. For example, the struts 375, 380 forming apices of cells 360b can incorporate curvature such that the apices are generally "onion" shaped.

Figure 5B:
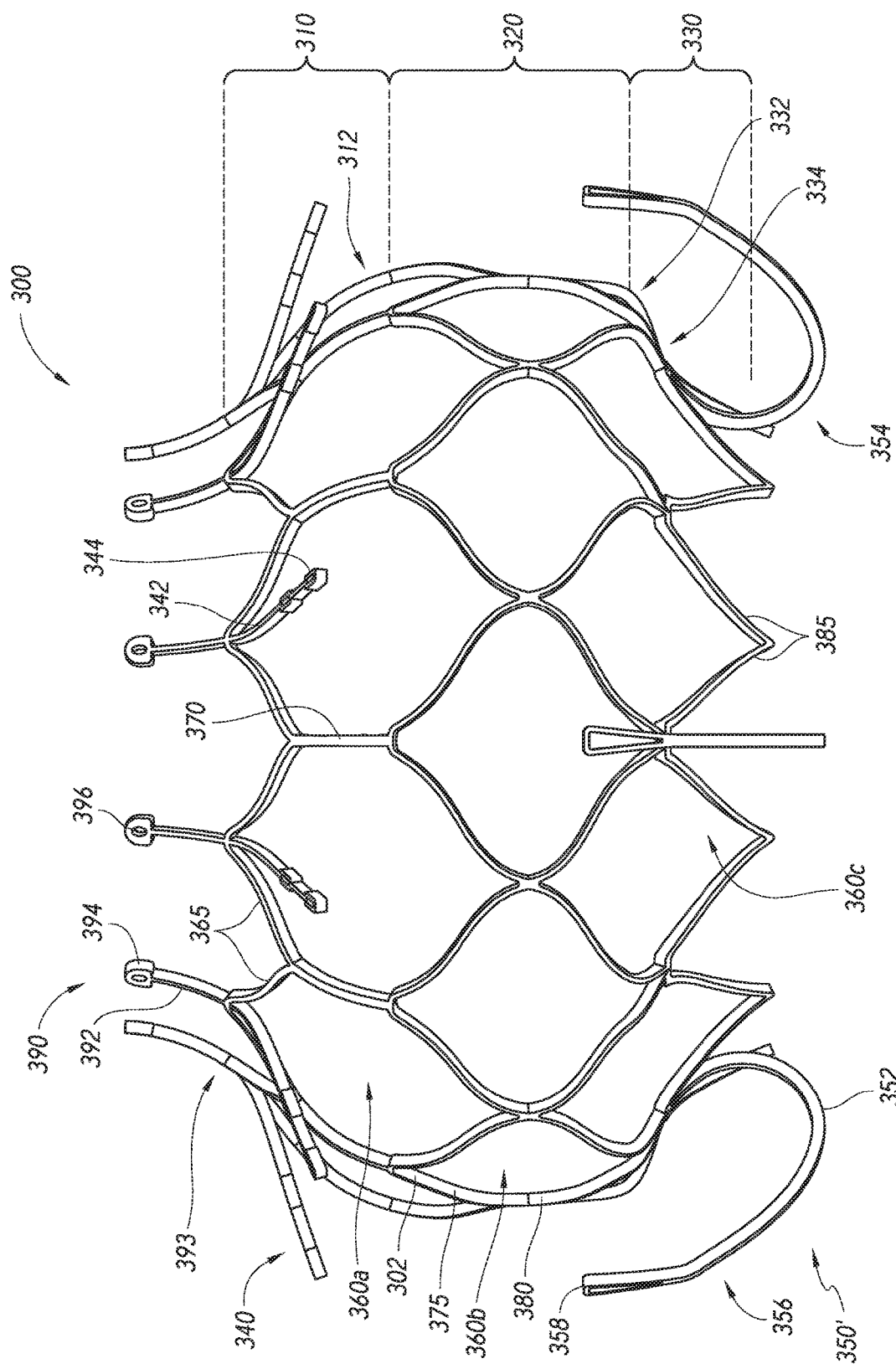
FIG. 5B is a side view of the front-half of another embodiment of a frame.

As shown in the illustrated embodiment, there can be a row of twelve cells 360a, a row of twelve cells 360b, and a row of twelve cells 360c. While each of the cells 360a, 360b, 360c are shown as having the same shape as other cells 360a, 360b, 360c of the same row, it is to be understood that the shapes of cells 360a, 360b, 360c within a row can differ. Moreover, it is to be understood that any number of rows of cells can be used and any number of cells may be contained in the rows. In some embodiments, the number of cells can correspond to the number of anchors or anchor tips forming the first anchoring feature and/or the number of anchors or anchor tips forming the second anchoring feature. As shown, the number of cells in each row of cells 360a, 360b, 360c have a 1:1 correspondence with the number of anchors in both the first anchoring feature 340 and the second anchoring feature 350 (i.e., twelve cells in each row of cells 360a, 360b, 360c and twelve anchors for the anchoring features 340, 350). It is to be understood that other ratios of numbers of cells per row to number of anchors per anchoring feature can be used such as, but not limited to, 2:1, 3:1, 4:1, 5:1, 6:1, and other ratios as desired. For example, as shown in the embodiment of frame 300 illustrated in FIG. 5B, the number of cells in some rows may be increased to a 2:1 ratio with anchors of one or both of the anchoring features, such as anchoring feature 350'. Although the anchors of anchoring feature 350' illustrated in FIG. 5B are equally spaced with two cells between each anchor, it is to be understood that the anchors can be unequally spaced. In some implementations, two anchors may be spaced apart by one cell whereas the remaining anchors are spaced apart by two or more cells. As another example, as shown in the embodiment of frame 600 illustrated in FIG. 9, the number of cells in some rows may be increased to a 2:1 ratio.

With continued reference to the frame 300 illustrated in FIG. 5A, the geometry of cells 360a, 360b, 360c can allow the cells 360a, 360b, 360c to foreshorten as the frame 300 is expanded. As such, one or more of cells 360a, 360b, 360c can allow the frame 300 to foreshorten as the frame 300 is expanded. Foreshortening of the frame 300 can be used to secure the prosthesis to intralumenal tissue in a body cavity, for example tissue at or adjacent a native valve, such as a native valve annulus and/or leaflets. The anchoring features 340, 350 and anchor tips 344, 358 are preferably located along the frame 300 with at least part of the foreshortening portion positioned between the anchoring features 340, 350 so that a portion of the anchoring features 340, 350 will move closer together with expansion of the frame 300.

As one example, this can allow the anchoring features 340, 350 to close in on opposite sides of the native mitral annulus to thereby secure the prosthesis at the mitral valve. In some embodiments, the anchoring features 340, 350 can be positioned such that the anchoring features 340, 350 do not contact opposing portions of the native mitral annulus at the same time. For example, in some situations, the anchoring feature 350 may contact the native mitral annulus while the anchoring feature 340 does not contact the native mitral annulus. This can be beneficial when anchoring feature 340 are used to provide stabilization and help align the prosthesis. In some embodiments, the anchoring features 340, 350 can be positioned such that the anchoring features 340, 350 grasp opposite side of the native mitral annulus.

With continued reference to the frame 300 illustrated in FIG. 5A, anchoring feature 340 can include one or more anchors. For example, as shown in the illustrated embodiment, the anchoring feature 340 can include twelve anchors. Each anchor can include one or more struts 342 extending from an upper region 310 of the frame body 302. As shown, struts 342 extend into the cells 360a. The struts 342 extend from an upper intersection of two segments of the cell 360a, for example, from the uppermost corner of the cells 360a between struts 365. However, it is to be understood that the struts 342 can extend from other portions of the frame body 302, such as other portions of the cell 360a. As shown, the struts 342 extend generally downwardly into the cells 360a while curving outwards away from the frame body 302. Thus, the anchoring feature 340 extends radially outwardly from the frame body 302 as it extends generally downwardly towards a tip 344. The tips 344 of the anchoring feature 340 can end after extending approximately between about one-third to about two-thirds of the height of hexagonal cells 360a when the frame 300 is expanded. Further, the tips 344 can extend farther outwards than the frame body 302.

As shown in the illustrated embodiment, the anchoring feature 340 can include one or more eyelets such as the two eyelets illustrated per strut 342. The one or more eyelets can form a portion of the tip 344 of the anchoring feature 340. The one or more eyelets can be used to attach other components of the prosthesis in which the frame 300 is used, such as a skirt. The shape of the one or more eyelets beneficially reduce the potential for trauma should the tips 344 contact tissue such as that of the native valve annulus or other body cavity.

Anchoring feature 350 can include one or more anchors. For example, as shown in the illustrated embodiment, the anchoring feature 350 can include twelve anchors. However, it is to be understood that the anchoring feature 350' can include a fewer or greater number of anchors. For example, as shown in FIG. 5B, the anchoring feature 350 can include six anchors. Each anchor can include one or more struts 352 extending from a lower region 330 of the frame 300. As shown, struts 352 extend from a lower intersection of two segments of the cell 360b, for example, from the lowermost corner of the cells 360b between struts 380. However, it is to be understood that the struts 352 can extend from other portions of the frame 300, such as other portions of the cell 360b and/or other portions of the cells 360c. For example, the struts 352 can extend from a lower intersection of two segments of the cell 360c, for example, from the lowermost corner of the cells 360c between struts 385.

As shown, the struts 352 extend generally downwardly while curving inwardly towards the longitudinal axis from the frame 300. Thus, the narrowest portion of the anchoring feature 340 can have a diameter which is about the same as, or less than, a diameter of the lower region 330 of the frame body 302. The struts 352 can incorporate a bend 354 to orient the strut 352 such that it extends radially outward away from the longitudinal axis of the frame 300. As shown in the illustrated embodiment, the bend can be generally semi-circular or semi-elliptical which can provide a space for the distal ends of the native valve leaflets to be stored. The anchors may then extend in a linear segment radially outwardly and upwardly. The struts 352 can include a second bend 356 along the linear segment. As shown in the illustrated embodiment, the bend 356 can orient the strut 352 such that it extends generally parallel to the longitudinal axis of the frame 300. For example, the tip 358 of anchoring feature 350 can extend generally parallel to the longitudinal axis of the frame 300. The tips 358 of the anchoring feature 350 can end after extending approximately above the base or connection point of the anchoring feature 350 to the frame body 302. In some embodiments, the tips 358 of the anchoring feature 350 can end after extending up to, or slightly past, the lower end of the intermediate region 320 of the frame body 302.

While the bend 356 orients the tip 358 such that it extends generally parallel to a longitudinal axis of the frame 300, it is to be understood that the bend 356 can orient the struts 352, such as the tips 358, in other directions. For example, the bend 356 can orient the struts 352, such as the tips 358, such that the they extend radially outward away from the longitudinal axis of the frame 300, such that struts 352 extends radially inward towards the longitudinal axis of the frame 300, or such that a portion of struts 352 extends radially outward away from the longitudinal axis of the frame 300 and another portion of struts 352. In some embodiments, the bend 356 can orient the struts 352, such as the tips 358, such that they extend generally perpendicular to a longitudinal axis of the frame 302 such as is shown with frame 400 illustrated in FIG. 6.

The tips or ends 344, 358 as described above can advantageously provide atraumatic surfaces that may be used to contact or engage intralumenal tissue without causing unnecessary or undesired trauma to tissue. For example, the tips or ends 344, 358 can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the frame 300 is deployed in-situ and the anchoring features 340, 350 expand away from the frame body 302, the movement of each loop from a delivered position to a deployed position avoids getting caught on the papillary muscles. As shown in the illustrated embodiment, the first anchoring feature 340 includes rounded eyelets at a tip or end 344 of the anchoring feature 340. The second anchoring feature 350 includes anchors tips or ends 358 having looped ends with a flattened or rounded top surface.

With continued reference to the frame 300 illustrated in FIG. 5A, the anchors of the first anchoring feature 340 can be circumferentially staggered with respect to the anchors of the second anchoring feature 350 meaning that the tips or ends 344 of the first anchoring feature 340 are not aligned, circumferentially, with the tips or ends 358 of the second anchoring feature 350. In other embodiments (not shown), the anchors of the first anchoring feature 340 and the anchors of the second anchoring feature 358 can be circumferentially aligned.

Preferably, each of the anchoring features 340, 350 are positioned or extend generally radially outwardly from the frame 300 so that the anchor tips 344, 358 are generally spaced away or radially outward from the rest of the frame body 302 and from where the base of the anchors connect to the frame body 302. For example, the anchor tips 344, 358 may be located radially outward from the intermediate region 320 of the frame body 302, with the tips 344, 358 being axially spaced from one another. In some embodiments, at least some of the anchoring features, such as anchoring features 340, 350, can extend to a radial distance from an exterior surface of the intermediate region 320 of the frame body 302 that is about 110% or more of the expanded diameter of the intermediate region 320 of the body 302 at the plane of tips 344, 358. In some embodiments, all of the anchors of the first anchoring feature 340 and/or all of the anchors of the second anchoring feature 350 extend at least to this radial distance. In other embodiments, fewer than all of the anchors of the first anchoring feature 340 and/or all of the anchors of the second anchoring feature 350 extend to this radial distance. The outermost diameter of the first anchoring feature 340 and/or the second anchoring feature 350 may be greater than the diameter of frame the body 302 as described above and may be in the range of about 35 mm to about 70 mm when expanded, in the range of about 35 mm to about 60 mm when expanded, in the range of about 40 mm to about 60 mm when expanded, in the range of about 45 mm to about 50 mm when expanded, any sub-range within these ranges when expanded, or any other diameter as desired.

The first anchoring feature 340 and the second anchoring feature 350 can extend radially outward from the longitudinal axis of the frame 300 to about the same radial dimension. However, it is to be understood that in other embodiments (not shown), the first anchoring feature 340 can be positioned to be not as far radially outward as the second anchoring feature 350 or the second anchoring feature 350 can be positioned to be not as far radially outward as the first anchoring feature 340. Such configurations may be advantageous in positioning and securing the prosthesis in a native valve annulus or other body location.

With continued reference to the frame 300 illustrated in FIG. 5A, it should be understood that the anchoring features 340, 350 can have various other configurations. For example, while the frame 300 includes anchoring features 340, 350 with twelve anchors each, it is to be understood that a greater number of anchors or a lesser number of anchors can be used. The number of anchors can correspond to the number of commissures of the internal valve used with the frame 300. For example, for a prosthesis with a valve having three commissures, the number of anchors can be chosen in multiples of three such as three anchors, six anchors, twelve anchors, fifteen anchors, and any other multiple of three. In some embodiments, instead of a 1:1 correspondence between the number of anchors in the first anchoring feature 340 and the second anchoring feature 350 (i.e., twelve anchors each), other ratios can be used. For example, a 1:2 or a 1:3 correspondence between the anchors, are possible such that the first anchoring feature 340 or the second anchoring feature 350 have fewer anchors than the other anchoring feature.

Individual anchors may extend radially outwardly from the frame at an anchor base and terminate at an anchor tip. The individual anchors can be connected to the frame at one of many different locations including apices, junctions, other parts of struts, etc. Moreover, the anchors forming the anchoring features 340, 350 can comprise first, second, third, or more spaced apart bending stages along the length of each anchor. Further details that may be incorporated and/or interchanged with the features described herein are disclosed in U.S. Publication Nos. 2014/0277422, 2014/0277427, 2014/0277390, and 2015/0328000, which have been incorporated by reference herein.

Covers and/or cushions (see, for example, covers and/or cushions 720, 770 illustrated in FIGS. 10-13) may be used to surround or partially surround at least a portion of the first anchoring feature 340 and/or the second anchoring feature 350, such as the tips or ends 344 of the first anchoring feature 340 and/or the tips or ends 358 of the second anchoring feature 350 and/or the struts to which the tips or ends 344, 458 are attached. The covers and/or cushions can be similar to those described in U.S. Publication No. 2015/0328000, which has been incorporated by reference in its entirety. For example, the covers and/or cushions can be formed from one or more pieces of material. In some embodiments, an inner portion can be positioned within a covering such that the covering forms a layer surrounding the inner portion. The inner portion can be formed of a foam material, such as a polymer foam, such that the inner portion is at least somewhat compliant. The covering can be formed of a biocompatible, fabric material such as a polymer woven or knitted cloth or sheet. In some embodiments, the cushions can be formed as a polymer molded insert. In some embodiments, the covers and/or cushions can be taut. In some embodiments, the covers and/or cushions can be loosely coupled to the anchoring feature. For example, a loosely coupled cover can be positioned along a side of a strut intended to be positioned against tissue.

In some embodiments, the covers and/or cushions can either fit snuggly around the tips 358 or can have extra padding so that the covers extend radially away from the frame 300. In some embodiments, all of the anchors of the second anchoring feature 350 can have the covers and/or cushions with some of the anchors having less cushioning than others. In some embodiments, all of the anchors of the second anchoring feature 350 can have the padded covers. In some embodiments, all of the anchors of the second anchoring feature 350 can have the snuggly fitting cushions. In some embodiments, not all of all of the anchors of the second anchoring feature 350 can have covers.

With continued reference to the frame 300 illustrated in FIG. 5A, the frame 300 can include a set of locking tabs 390 extending from the upper region 310 of the frame 300. As shown, the frame 300 includes twelve locking tabs 390, however, it is to be understood that a greater number or lesser number of locking tabs can be used. The locking tabs 390 can extend generally upwardly from the upper region 310 in a direction generally aligned with the longitudinal axis of the frame 300. As shown in the illustrated embodiment, the locking tabs 390 include a strut 392 which can include a bend 394 such that a portion of the strut 392, positioned upwards of the beginning of the bend 394, is inclined or curved at less of an angle towards the longitudinal axis of the frame 300 than the portion below the beginning of the bend 394, is generally parallel to the longitudinal axis, or is inclined or curved at an angle away from the longitudinal axis of the frame 300.

In some embodiments, the bend 394 can orient the portion of the strut 392, positioned upward of the beginning of bend 394, such that it forms an angle of between about 30 degrees to about 90 degrees with a plane orthogonal to the longitudinal axis, an angle of between about 45 degrees to about 85 degrees with a plane orthogonal to the longitudinal axis, an angle of between about 60 degrees to about 80 degrees with a plane orthogonal to the longitudinal axis, an angle of about 80 degrees with a plane orthogonal to the longitudinal axis, any subrange within these ranges, or any other angle as desired. In some embodiments, the bend 394 can orient the portion of the strut 392, positioned upward of the beginning of bend 394, such that it forms an angle of greater than 25 degrees with a plane orthogonal to the longitudinal axis, an angle of greater than 40 degrees with a plane orthogonal to the longitudinal axis, an angle of greater than 55 degrees with a plane orthogonal to the longitudinal axis, an angle of greater than 70 degrees with a plane orthogonal to the longitudinal axis, or greater than any other angle as desired.

At an upper end of the strut 392, the locking tab 390 can include an enlarged head 394. As shown, the enlarged head 394 has a semi-circular or semi-elliptical shape forming a "mushroom" shape with the strut 396. The locking tab 390 can include an eyelet 396 which can be positioned through the enlarged head 394. It is to be understood that the locking tab 234 can include an eyelet at other locations, or can include more than a single eyelet. The locking tab 390 can be advantageously used with multiple types of delivery systems. For example, the shape of the struts 392 and the enlarged head 394 can be used to secure the frame 300 to a "slot" based delivery system. The eyelets 396 can be used to secure the frame 300 to a "tether" based delivery system such as those which utilize sutures, wires, or fingers to control delivery of the frame 300. This can advantageously facilitate recapture and repositioning of the frame 300 in situ. In some embodiments, the frame 300 can be used with the delivery systems described in U.S. Pat. Nos. 8,414,644 and 8,652,203 and U.S. Publication Nos. 2015/0238315, the entireties of each of which are hereby incorporated by reference and made a part of this specification.

Figure 6:
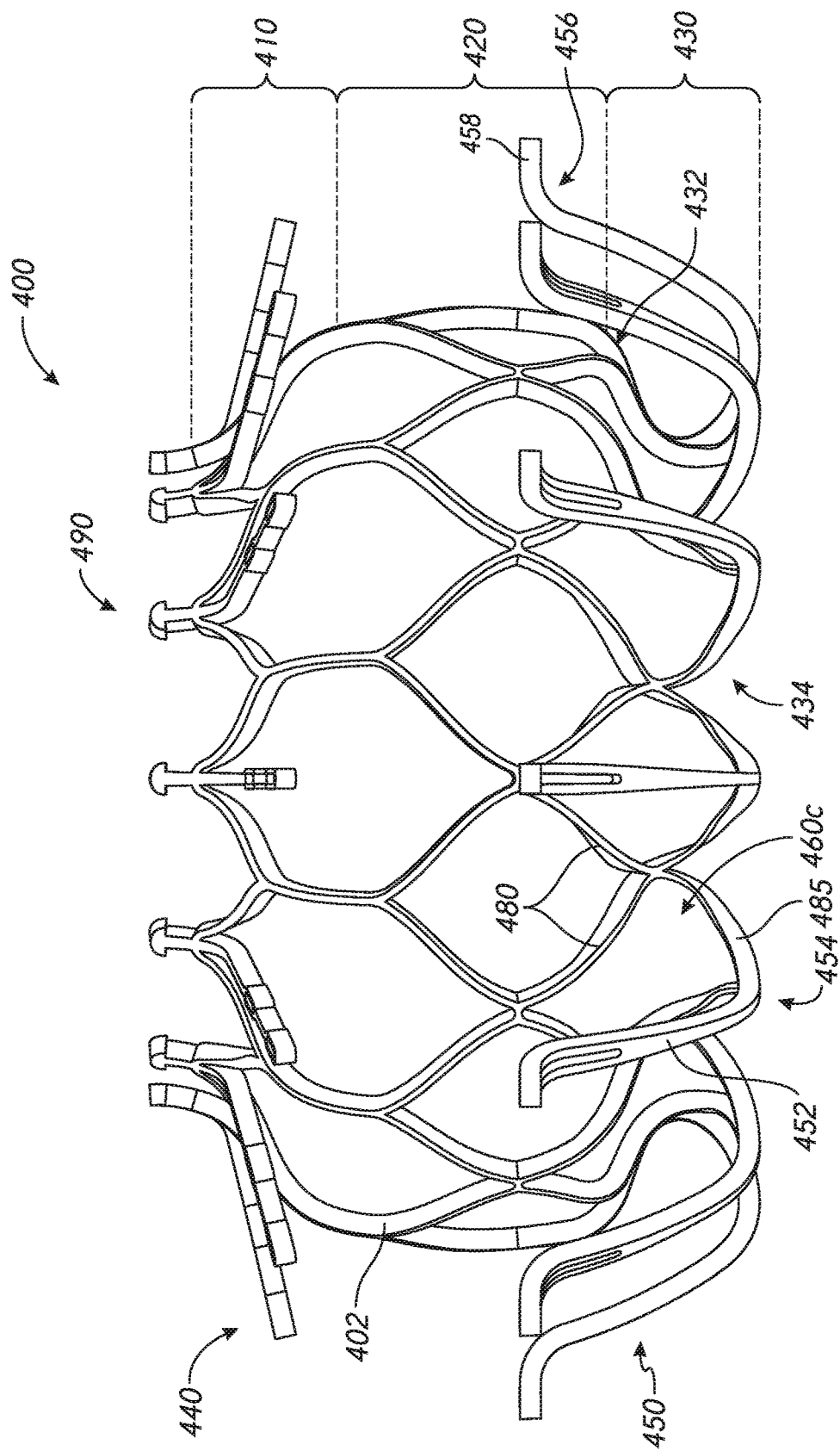
FIG. 6 is a side view of another embodiment of a frame.

With reference next to the frame 400 illustrated in FIG. 6, the frame 400 is shown in an expanded configuration. The frame 400 can include a frame body 402 having an upper region 410, an intermediate region 420, and a lower region 430. A longitudinal axis of the frame 400 may be defined as the central axis that extends through the center of the frame 400 between the upper and lower ends of the frame 400. In some embodiments, the frame 400 may be oriented such that the upper region 410 is a proximal portion and the lower region 430 is a distal portion. The frame 400 can include a first anchoring feature 440 and a second anchoring feature 450. In some embodiments, the frame 400 may be oriented such that the first anchoring feature 440 is a proximal anchoring feature and the second anchoring feature 450 is a distal anchoring feature.

As shown in the illustrated embodiment, the height of the intermediate region 420 can be larger relative to the heights of the upper region 410 and lower region 430 as compared to the height of the intermediate region 320 relative to the heights of the upper region 310 and lower region 330. This can advantageously provide a larger circumferential area upon which a native valve annulus can be engaged. This can also beneficially enhance securement of the frame 400 to the native valve annulus or other body cavity. Moreover, this can beneficially reduce the overall height of the frame 400.

At the juncture between the intermediate region 420 and the lower region 430, the frame 400 can include a bend 432 toward the longitudinal axis of the frame 400. The bend 432 can be a radially inward bend towards the longitudinal axis of the frame 400 such that a portion of the lower region 430, extending downwardly from the beginning of bend 432, is inclined or curved towards the longitudinal axis of the frame 400. The lower region 430 can include a second bend 434 below the bend 432. The bend 434 can be oriented opposite that of the bend 432 such that a portion of the lower region 430, extending downwardly from the beginning of the bend 434, is inclined or curved at an angle away from the longitudinal axis of the frame 400. This can beneficially allow at least a portion of the lower region 430 to form part of the second anchoring feature 450.

Figure 7:
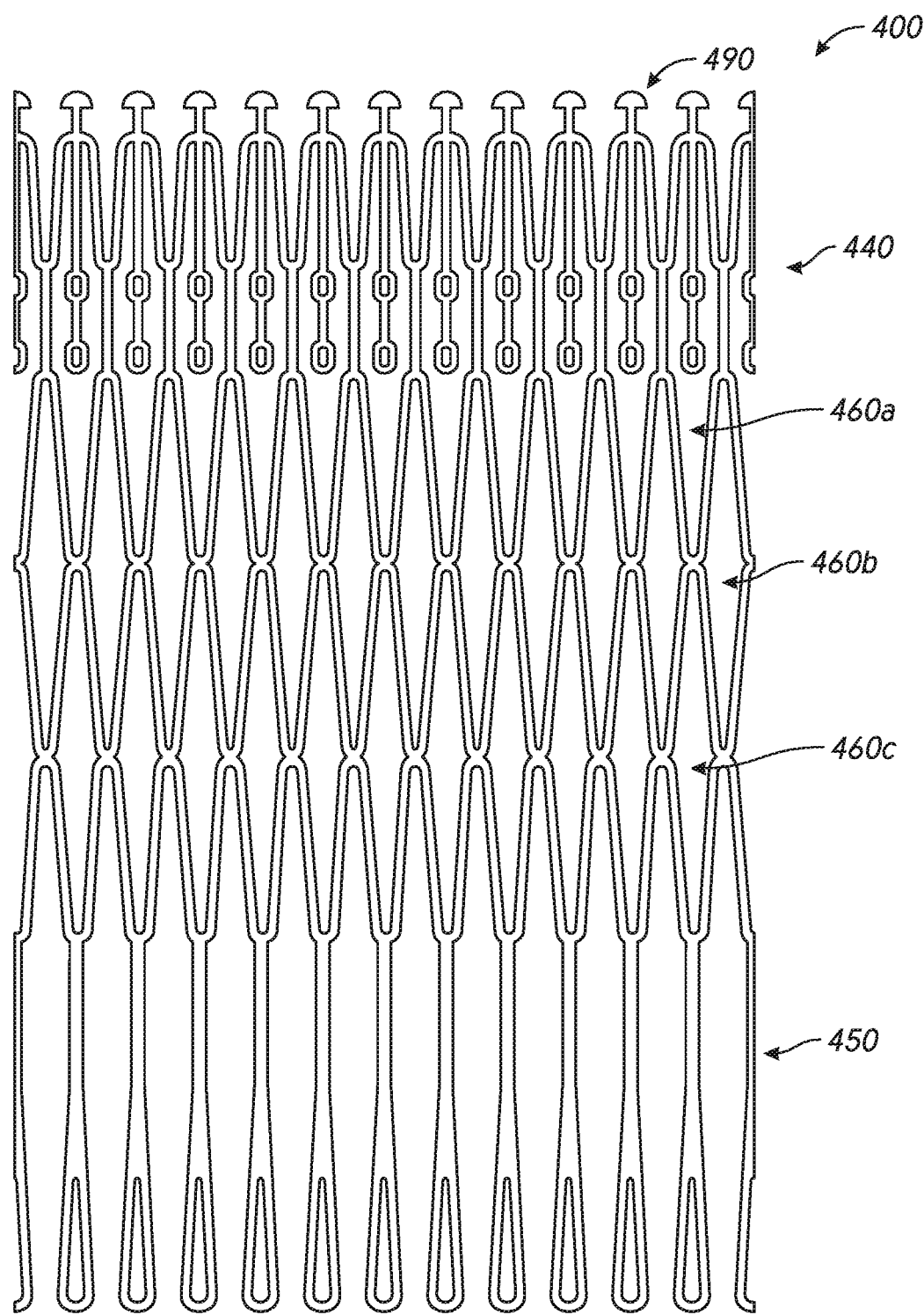
FIG. 7 is a flat, cutting pattern for the frame of FIG. 6.

The frame 400 can include a first row of cells 460a, a second row of cells 460b, and a third row of cells 460c (as shown in FIG. 7) which can share some similarities to cells 360a, 360b, 360c of frame 300. As shown in the illustrated embodiment, the upper portion of cells 460c can be formed from the set of circumferentially-expansible struts 480 such that cells 460c share struts with the cells of the row above. The lower portion of cells 460c can be formed from a set of circumferentially-expansible struts 485. Circumferentially-expansible struts 485 can extend generally in a downward direction. The circumferentially-expansible struts 485 can be inclined or curved away from the longitudinal axis of the frame 400 such that the upper portion of struts 485 are positioned closer to the longitudinal axis of the frame 400 than the lower portion of struts 485. As shown in the illustrated embodiment, the bend 434 can be formed by struts 485 and can be shaped similarly to the bend 354 discussed in connection with struts 352 of the second anchoring feature 350 of frame 300.

Anchoring feature 450 can include one or more anchors. For example, as shown in the illustrated embodiment, the anchoring feature 450 can include twelve anchors. Each anchor can include one or more struts 452 extending from a lower region 430 of the frame 400. As shown, struts 452 extend from a lower intersection of two segments of the cell 360c, for example, from the lowermost corner of the cells 460c between struts 485. However, it is to be understood that the struts 452 can extend from other portions of the frame 400, such as other portions of the cell 460b and/or other portions of the cells 460c. For example, the struts 452 can extend from a lower intersection of two segments of the cell 460b, for example, from the lowermost corner of the cells 460c between struts 480.

As shown, the struts 452 extend generally radially outward. The struts 452 can incorporate a bend 454 to orient the strut 452 such that it extends radially outward away from the longitudinal axis of the frame 400 and upwards. The anchors may then extend in a linear segment radially outwardly and upwardly. The struts 452 can include a second bend 456 along the linear segment. As shown in the illustrated embodiment, the bend 456 can orient the strut 452 such that it extends generally radially outward from the longitudinal axis of the frame 400 and generally perpendicular to the longitudinal axis of the frame 400. For example, the tip 458 of anchoring feature 450 can extend generally perpendicular to the longitudinal axis of the frame 400. This can beneficially increase the tissue contact area of the tip 458 of the anchor as compared to an anchor which does not incorporate such a bend. This increased tissue contact area can beneficially reduce the stress applied by the tip 458 to tissue thereby reducing the amount of pressure and potential for trauma to the tissue. In some embodiments, the uppermost portions of the anchoring feature 450 can extend up to, or slightly past, the lower end of the intermediate region 420 of the frame body 402.

With continued reference to the frame 400 illustrated in FIG. 6, the frame 400 can include locking tabs 490. These locking tabs 490 are similar to locking tabs 390 of frame 300; however, the locking tabs 490 have a lower axial dimension thereby providing for a more compact form factor. Although the locking tabs 490 do not include eyelets, it is to be understood that the locking tabs 490 can include eyelets.

With reference next to the frame 400 illustrated in FIG. 7, the frame 400 is shown as a flat pattern. Any of the frames described herein such as, but not limited to, frames 300, 400 can be made of many different materials, but is preferably made from metal. In some embodiments, the frames can be made from a shape memory material, such as nitinol. A wire frame or a metal tube can be used to make the frame. The wire frame of a metal tube can be cut or etched to remove all but the desired metal skeleton. In some embodiments a metal tube is laser cut in a repeating pattern to form the frame. The flat pattern can be cut from a metal tube and then the tube can be bent and expanded to the expanded configurations shown herein. The frames can further be expanded and/or compressed and/or otherwise worked to have the desired shape or shapes, such as for introduction and implantation.

Figure 8:
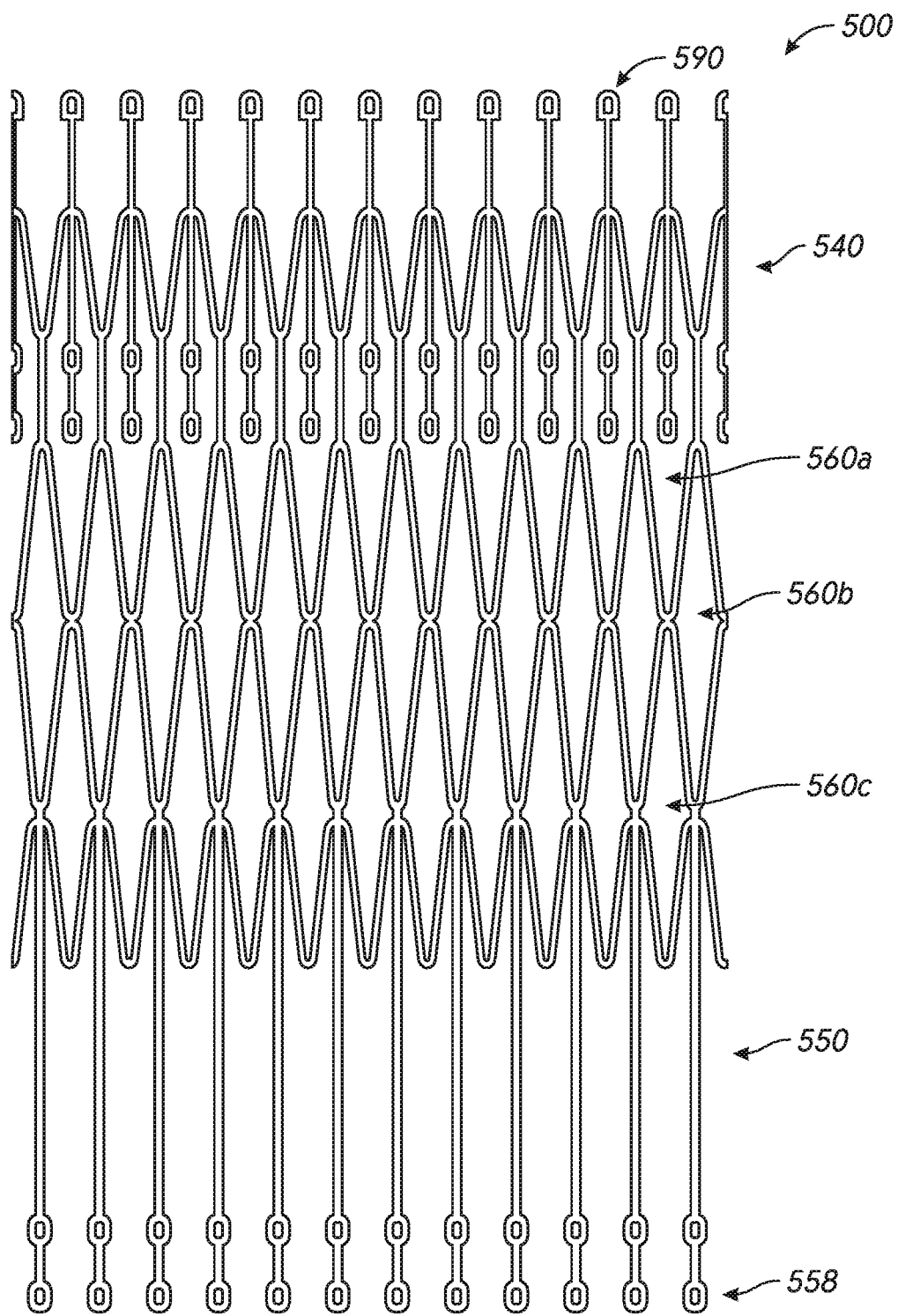
FIG. 8 is a flat, cutting pattern for another embodiment of a frame.

With reference next to the frame 500 illustrated in FIG. 8, the frame 500 is shown as a flat pattern. As shown in the illustrated embodiment, the frame 500 can include first anchoring feature 540, second anchoring feature 550, a first row of cells 560a, a second row of cells 560b, a third row of cells 560c, and a plurality of locking tabs 590. The second anchoring feature 550 can include anchors with tips 558 having one or more eyelets. As shown, each anchor can include two eyelets. The eyelets can beneficially facilitate attachment of other components, such as covers and/or cushions, to the tips 558.

Figure 9:
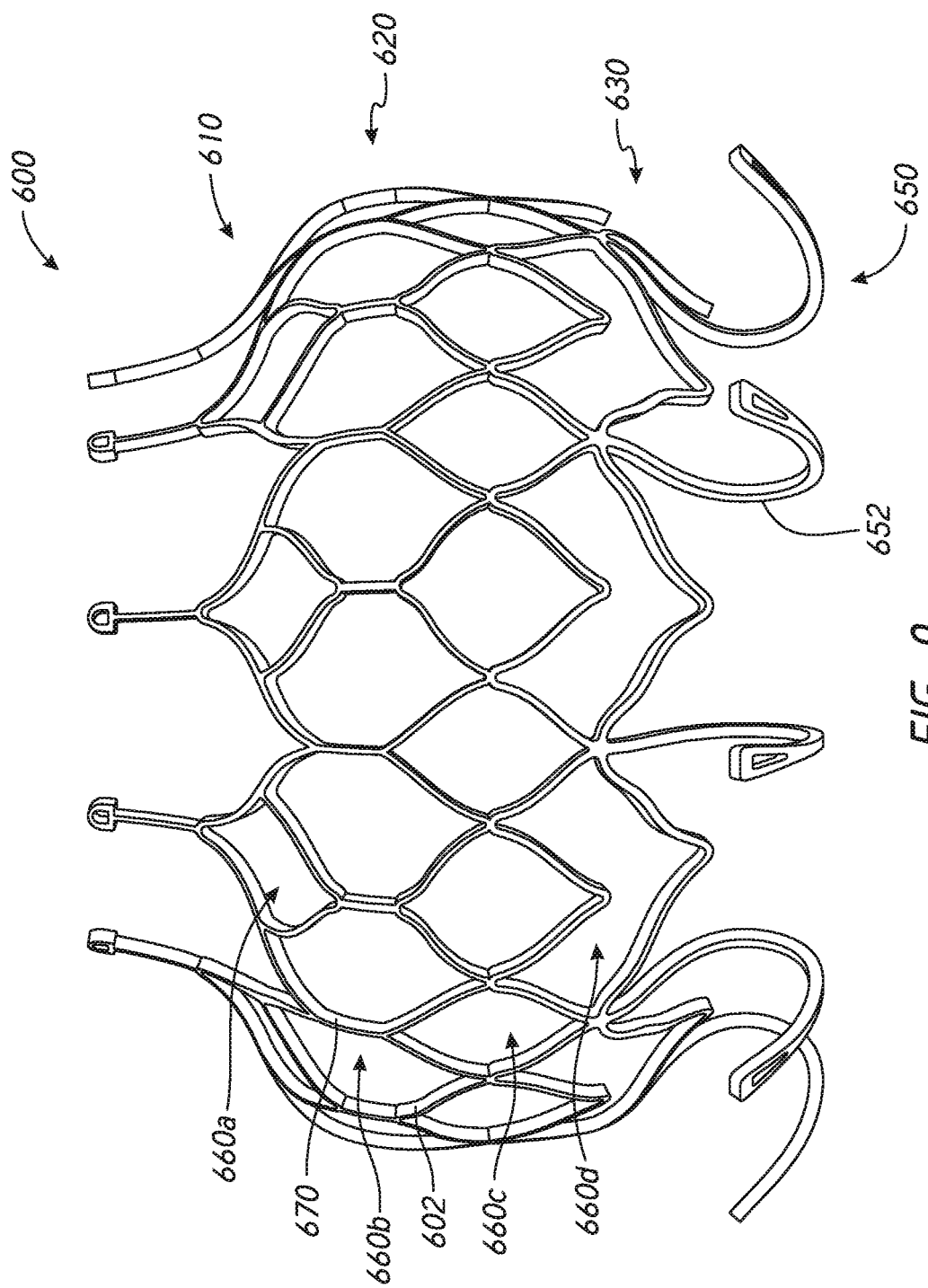
FIG. 9 is a side view of another embodiment of a frame.

With reference next to the frame 600 illustrated in FIG. 9, the frame 600 is shown in an expanded configuration. The frame 600 can include a frame portion 602 having an upper region 610, an intermediate region 620, and a lower region 630. A longitudinal axis of the frame 600 may be defined as the central axis that extends through the center of the frame 600 between the upper and lower ends of the frame 600. In some embodiments, the frame 600 may be oriented such that the upper region 610 is a proximal portion and the lower region 630 is a distal portion. The frame 600 can include an anchoring feature 650. In some embodiments, the frame 600 may be oriented such that the anchoring feature 650 is a distal anchoring feature.

As shown in the illustrated embodiment, anchoring feature 650 can include one or more anchors. For example, as shown in the illustrated embodiment, the anchoring feature 650 can include nine anchors each including a strut 652 extending from a lower region 630 of the frame body 602. The diameter of the frame body 602 at the widest portion is approximately the same as those of frames 300, 400, 500 are their widest portions. Moreover, when crimped into a collapsed configuration for delivery via a transcatheter delivery system, the overall length of the frame 600 can be similar to those of frames 300, 400, 500 when in a collapsed configuration for delivery. As shown in the illustrated embodiment, this can be achieved via strut and cell geometry.

As shown in the illustrated embodiment, there can be a first row of nine cells 660a, a second row of eighteen cells 660b, a third row of eighteen cells 660c, and a row of nine cells 660d. Cells 660b share similarities to cells 360a, 460a, 560a. For example, cells 660b can have a hexagonal or generally hexagonal shape. Cells 660 have generally longitudinally extending struts 670 which can extend generally parallel to the longitudinal axis of the frame 600. Cells 660a, 660c share similarities to cells 360b, 460b, 560b. For example, cells 660a, 660c can have a diamond or generally diamond shape. Cells 660d have an irregular polygonal shape. As shown, the number of cells in the first row of cells 660a and fourth row of cells 660d correspond to the number of anchors of the anchoring portion 650. The number of cells in the second row of cells 660b and the third row of cells 660c are twice that of the number of anchors. This can beneficially allow the frame to reach a desired width while maintaining a relatively axially compact profile when crimped into a collapsed configuration. Other ratios of the number of cells to the number of anchors can be chosen including 3:1, 4:1, 5:1, or any other ratio as desired.

Figure 10:
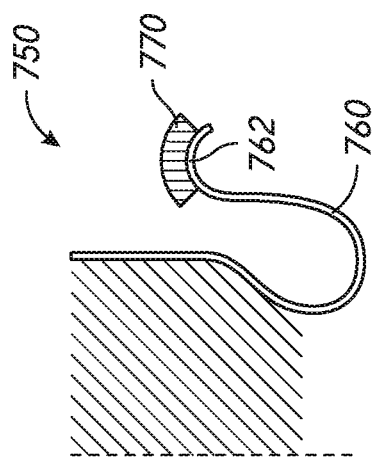
FIG. 10 is a side-oriented schematic view of an embodiment of a ventricular anchor.
Figure 11:
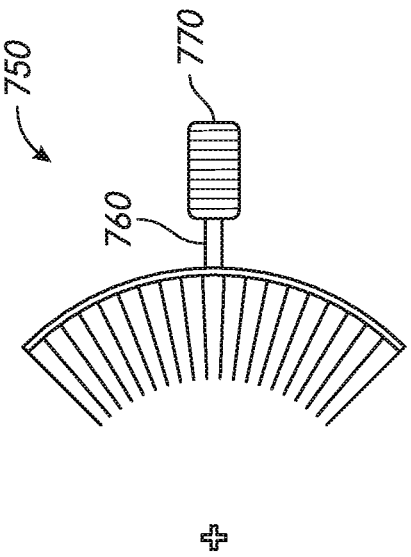
FIG. 11 is a top-oriented schematic view of the ventricular anchor of FIG. 10.

With reference next to the frame 700 illustrated in FIGS. 10 and 11, the frame 700 includes anchoring feature 710 having covers and/or cushions 720. As shown in the illustrated embodiment, the anchoring feature 710 can have a similar profile to those of anchoring feature 350. The anchoring feature 710 can include a cover and/or cushion 720 extending over a tip 712 of the anchors. In some embodiments, the cover and/or cushion 720 can be positioned such that it extends over the top of the tip 712. In some embodiments, the cover and/or cushion 720 can also be positioned such that it extends circumferentially around the tip 712. The cover and/or cushion 720 can be formed from a deformable material such as a foam. When the top portion of the cover and/or cushion 720 is subject to pressure due to a downwardly directed force, the cover and/or cushion 720 can compress and expand laterally outward. Such a force may be exerted upon the cover and/or cushion 720 when the cover and/or cushion 720, for example, when the cover and/or cushion 720 contacts a ventricular side of the mitral valve annulus during systole. The compression and lateral expansion of cover and/or cushion 720 can increase the surface area of the cover and/or cushion 720 in contact with the tissue, thereby exerting less pressure on the tissue and reducing the potential for trauma.

Figure 12:
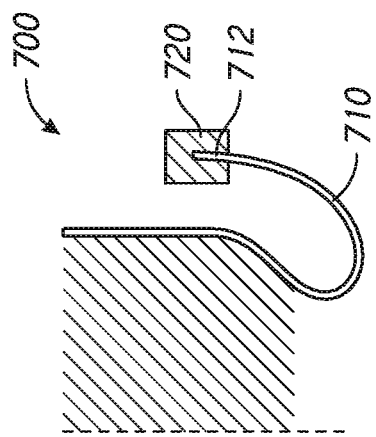
FIG. 12 is a side-oriented schematic view of another embodiment of a ventricular anchor.
Figure 13:
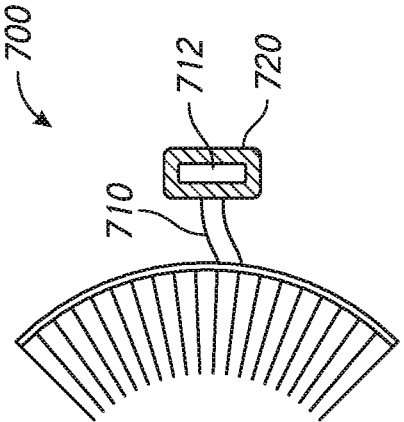
FIG. 13 is a top-oriented schematic view of the ventricular anchor of FIG. 12.
Figure 14:
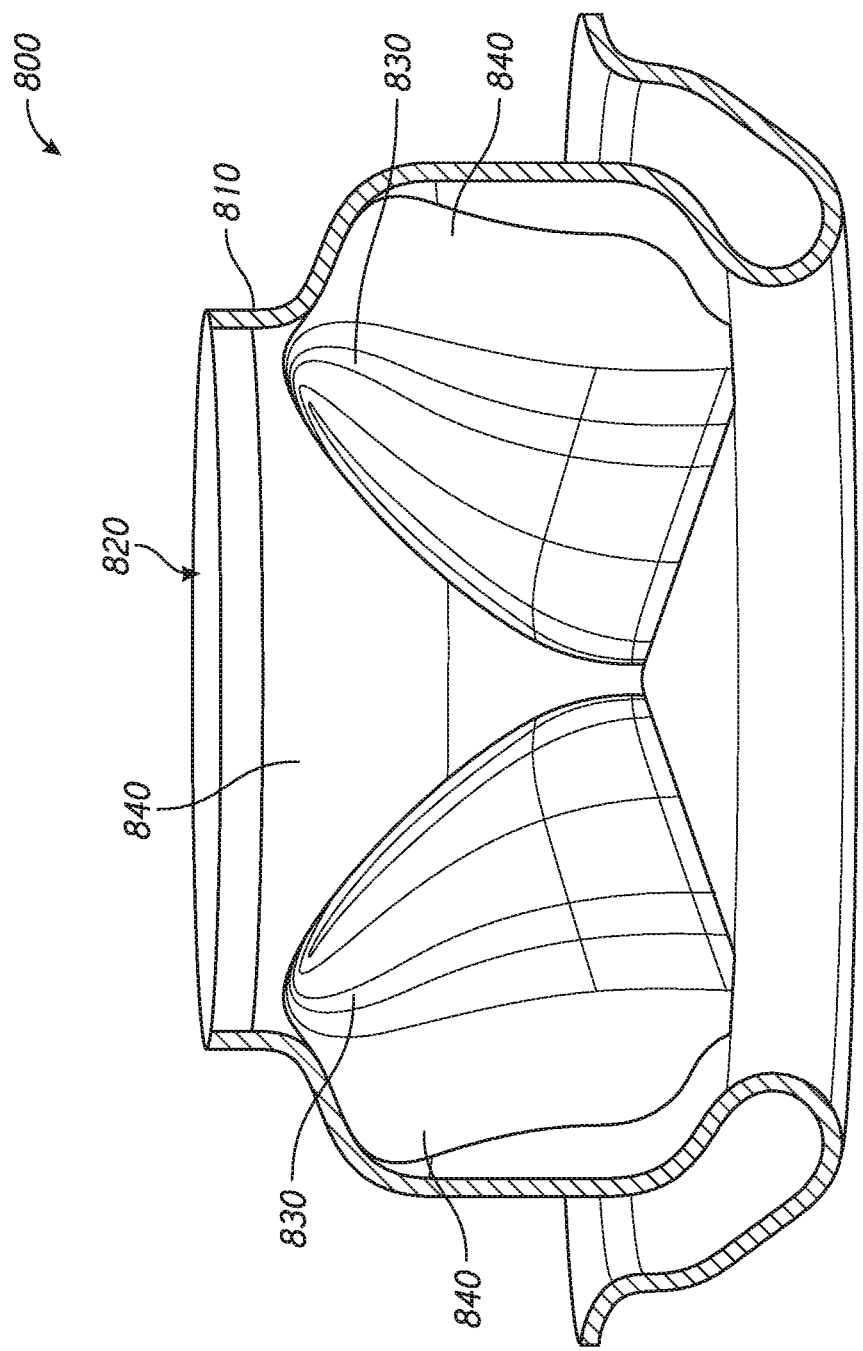
FIG. 14 is a side-oriented schematic view of an embodiment of a floating valve.

With reference next to the frame 750 illustrated in FIGS. 12 and 13, the frame 750 includes anchoring feature 760 having covers and/or cushions 770. As shown in the illustrated embodiment, the anchoring feature 760 can have a tip profile similar to that of anchoring feature 450. The anchoring feature 760 can include a cover and/or cushion 770 extending over a tip 762 of the anchors. In some embodiments, the cover and/or cushion 770 can be positioned such that it extends over the top of the tip 762. In some embodiments, the cover and/or cushion 770 can also be positioned such that it extends circumferentially around the tip 762. The cover and/or cushion 770 can be formed from a deformable material such as a foam. When the top portion of the cover and/or cushion 770 is subject to pressure due to a downwardly directed force, the cover and/or cushion 770 can compress and expand laterally outward. Such a force may be exerted upon the cover and/or cushion 770 when the cover and/or cushion 770, for example, when the cover and/or cushion 770 contacts a ventricular side of the mitral valve annulus during systole. The compression and lateral expansion of cover and/or cushion 770 can increase the surface area of the cover and/or cushion 770 in contact with the tissue, thereby exerting less pressure on the tissue and reducing the potential for trauma.

With reference next to FIGS. 83-85, embodiments of anchoring features 5200, 5300 are illustrated. In the expanded configuration, the anchoring features 5200, 5300 can include one or more prongs which are at least radially offset relative to each other. In this manner, tips of the one or more prongs can be at different radial positions relative to a longitudinal axis of a frame (not shown) to which the anchoring features 5200, 5300 are attached. This can beneficially increase the tissue contact area of the tips of the anchoring features 5200, 5300. This increased tissue contact area can beneficially reduce the stress applied by the anchoring features 5200, 5300 to tissue thereby reducing the amount of pressure and potential for trauma to the tissue. In some embodiments, the radial distance between the prongs of the anchoring features 5200, 5300 can be reduced or eliminated when in a collapsed configuration. This can beneficially reduce the crimp profile of the anchoring features 5200, 5300 such that a smaller delivery system can be utilized.

With reference first to FIGS. 83 and 84, anchoring feature 5200 is illustrated. The anchoring feature 5200 can be attached to a frame body (not shown) via one or more struts 5210. The anchoring feature 5200 can include one or more prongs 5220, 5230 having tips 5222, 5232. As shown in the illustrated embodiment, the first prong 5220 can form a loop similar to other anchoring features described herein. The second prong 5230 can be positioned within the first prong 5230. Positioning the second prong 5230 within the first prong 5220 can advantageously make use of an existing space within the first prong 5220.

The first prong 5220 and the second prong 5320 can be radially offset. As shown, the first prong 5220 can include a bend 5224 which directs the first prong 5220 radially outward relative to the second prong 5230 such that the tips 5222, 5232 are at different radial positions relative to each other. One or more coverings and/or cushions (not shown) can be attached to the anchoring feature 5200 which covers the tips 5222, 5232. The one or more coverings and/or cushions can span the gap between the tips 5222, 5232 to further increase the tissue contact area of the tips. The coverings and/or cushions can include the same or similar structure to those described herein. For example, the coverings and/or cushions can be formed from a foam material, woven or knitted cloth or sheet, and/or an insert. As shown in the illustrated embodiment, the tip 5222 of prong 5220 can be extend in a direction generally parallel to tip 5232 of prong 5230. While the tips 5222, 5232 are shown at or around the same axial position, it is to be understood that the tips 5222, 5232 can be axially offset. The prong 5230 can include an eyelet 5234.

With reference next to FIG. 85, anchoring feature 5300 is illustrated. The anchoring feature 5300 can be attached to a frame body (not shown) via one or more struts 5310. The anchoring feature 5300 can include one or more prongs 5320, 5330, 5340 having tips 5222, 5232, 5342.

The first prong 5320, the second prong 5320, and/or the third prong 5340 can be radially offset. As shown, the first prong 5320 can include a bend 5224 which directs the first prong 5320 radially outward relative to the second prong 5330 such that the tips 5322, 5332 are at different radial positions relative to each other. The third prong 5340 can include a bend 5344 which directs the third prong 5340 radially inward relative to the second prong 5330 such that the tips 5342, 5332 are at different radial positions relative to each other. One or more coverings and/or cushions (not shown) can be attached to the anchoring feature 5300 which covers the tips 5322, 5332, 5342. The one or more coverings and/or cushions can span the gap between the tips 5222, 5232, 5342 to further increase the tissue contact area of the tips. The coverings and/or cushions can include the same or similar structure to those described herein. For example, the coverings and/or cushions can be formed from a foam material, woven or knitted cloth or sheet, and/or an insert. While the tips 5322, 5332, 5342 are shown at or around the same axial position, it is to be understood that the tips 5322, 5332, 5342 can be axially offset.

With reference next to FIGS. 86-99, embodiments of anchoring features 5400, 5500, 5600, 5700 are illustrated. The anchoring features 5400, 5500, 5600, 5700 can transition between a crimped or collapsed configuration and an expanded configuration. In the collapsed configuration, the anchoring features 5400, 5500, 5600, 5700 can have a reduced crimp profile to facilitate delivery to a target location. In the expanded configuration, the anchoring features 5400, 5500, 5600, 5700 can increase in size which can advantageously increase the tissue contact area of the anchoring features 5400, 5500, 5600, 5700. This increased tissue contact area can beneficially reduce the stress applied by the anchoring features 5400, 5500, 5600, 5700 to tissue thereby reducing the amount of pressure and potential for trauma to the tissue.

With reference first to FIGS. 86-90, anchoring feature 5400 is illustrated. The anchoring feature 5400 can transition between a collapsed configuration (as shown in FIGS. 86 and 87) and an expanded configuration (as shown in FIGS. 88-90). In transitioning from the collapsed configuration to the expanded configuration, the lateral dimension (or width) of the anchoring feature 5400 can increase.

The anchoring feature 5400 can be attached to a frame body (not shown) via one or more struts 5410. The anchoring feature 5400 can include one or more prongs 5420, 5430 having tips 5422, 5432. As shown in the illustrated embodiment, the anchoring feature 5400 can have a looped profile similar to other anchoring features described herein. The first prong 5420 and the second prong 5430 can be radially offset such that the tip 5422 of first prong 5420 is radially outward relative to the tip 5432 of the second prong 5430. This can allow the tips 5422, 5432 to slide relative to each other when transitioning between the collapsed configuration and the expanded configuration. As shown, the tips 5422, 5432 can form a relatively flat surface of the anchoring feature 5400; however, it is to be understood that the tips 5422, 5432 can take on a more rounded shape similar to other anchoring features described herein. Moreover, while the tips 5422, 5432 are shown at or around the same axial position, it is to be understood that the tips 5422, 5432 can be axially offset. One or more cushions (not shown) can be attached to the anchoring feature 5400 which cover the tips 5422, 5432.

Figure 91:
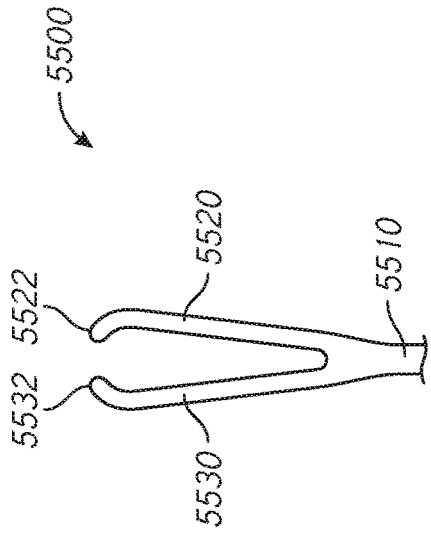
FIG. 91 illustrates a front view of another embodiment of an anchoring feature, the anchoring feature being in a first configuration.
Figure 92:
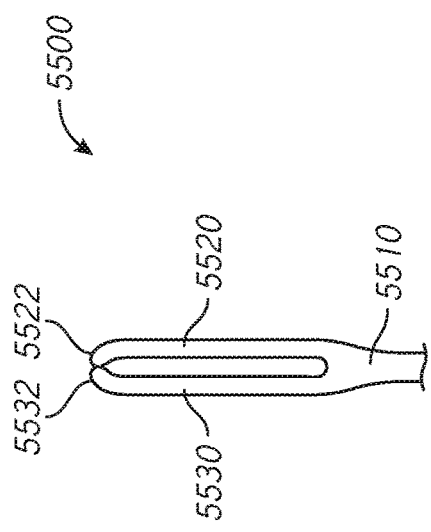
FIG. 92 illustrates a front view of the anchoring feature of FIG. 91, the anchoring feature being in a second configuration.

With reference next to FIGS. 91 and 92, anchoring feature 5500 is illustrated. The anchoring feature 5500 can transition between a collapsed configuration (as shown in FIG. 91) and an expanded configuration (as shown in FIG. 92). In transitioning from the collapsed configuration to the expanded configuration, the lateral dimension (or width) of the anchoring feature 5500 can increase.

The anchoring feature 5500 can be attached to a frame body (not shown) via one or more struts 5510. The anchoring feature 5500 can include one or more prongs 5520, 5530 having tips 5522, 5532. In the expanded configuration, the first prong 5520 and the second prong 5530 can be laterally offset such that a gap exists between tips 5522, 5532 of the prongs 5520, 5530. One or more coverings and/or cushions (not shown) can be attached to the anchoring feature 5500 which cover the tips 5522, 5532. The one or more coverings and/or cushions can span the gap between the tips 5522, 5532 to further increase the tissue contact area of the tips. The coverings and/or cushions can include the same or similar structure to those described herein. For example, the coverings and/or cushions can be formed from a foam material, woven or knitted cloth or sheet, and/or an insert. While the tips 5522, 5532 are shown at or around the same axial position, it is to be understood that the tips 5522, 5532 can be axially offset.

Figure 93:
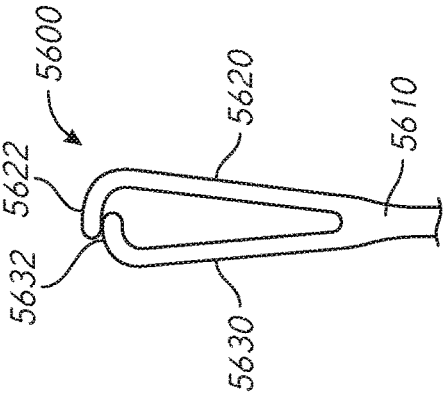
FIG. 93 illustrates a front view of another embodiment of an anchoring feature, the anchoring feature being in a first configuration.
Figure 94:
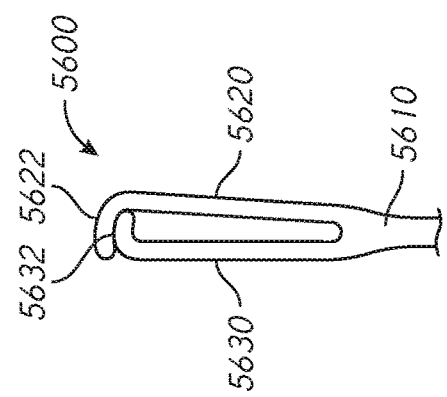
FIG. 94 illustrates a front view of the anchoring feature of FIG. 93, the anchoring feature being in a second configuration.
Figure 100:
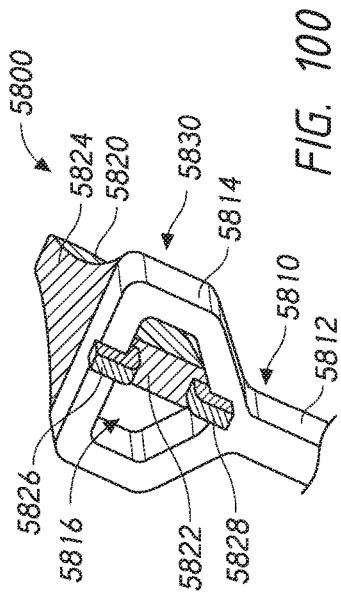
FIG. 100 illustrates a perspective view of an embodiment of a combined anchoring feature having a base anchor and an insert.
Figure 103:
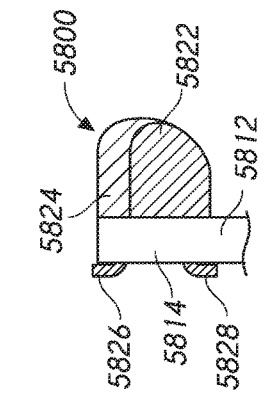
FIG. 103 illustrates a side view of the combined anchoring feature of FIG. 100.
Figure 102:
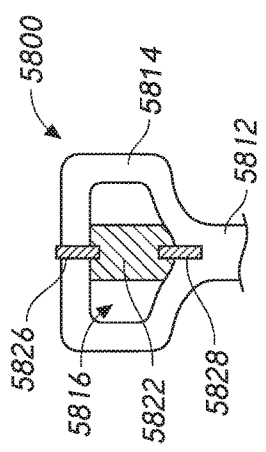
FIG. 102 illustrates a front view of the combined anchoring feature of FIG. 100.
Figure 101:
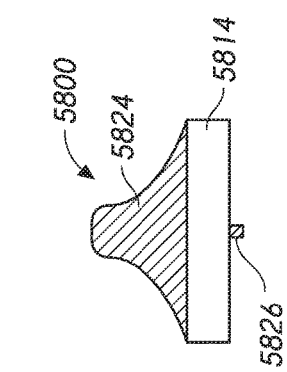
FIG. 101 illustrates a top view of the combined anchoring feature of FIG. 100.
Figure 106:
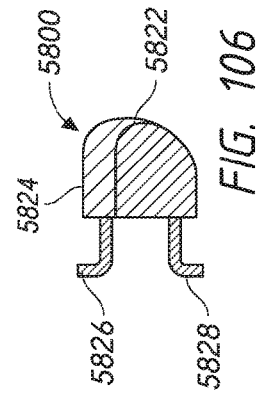
FIG. 106 illustrates a side view of the insert of the combined anchoring feature of FIG. 100.
Figure 105:
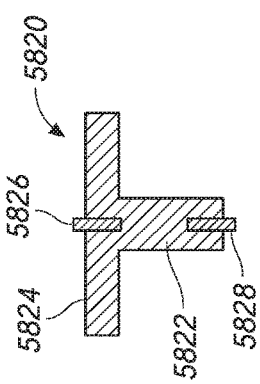
FIG. 105 illustrates a front view of the insert of the combined anchoring feature of FIG. 100.
Figure 104:
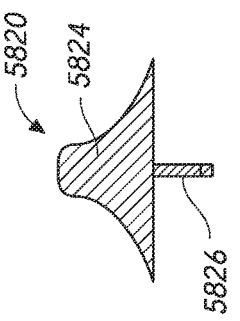
FIG. 104 illustrates a top view of the insert of the combined anchoring feature of FIG. 100.

With reference next to FIGS. 93 and 94, anchoring feature 5600 is illustrated. The anchoring feature 5600 can transition between a collapsed configuration (as shown in FIG. 93) and an expanded configuration (as shown in FIG. 94). In transitioning from the collapsed configuration to the expanded configuration, the lateral dimension (or width) of the anchoring feature 5600 can increase.

The anchoring feature 5600 can be attached to a frame body (not shown) via one or more struts 5610. The anchoring feature 5600 can include one or more prongs 5620, 5630 having tips 5622, 5632. As shown in the illustrated embodiment, the anchoring feature 5600 can have a generally looped profile similar to other anchoring features described herein. The first prong 5620 and the second prong 5630 can be axially offset such that the tip 5622 of first prong 5620 is positioned above tip 5632 of the second prong 5630. This can allow the tips 5622, 5632 to slide relative to each other when transitioning between the collapsed configuration and the expanded configuration. The tips 5622, 5432 can be at or around the same radial position. One or more coverings and/or cushions (not shown) can be attached to the anchoring feature 5600 which cover the tips 5622, 5632. The one or more coverings and/or cushions can span the axial offset between the tips 5622, 5632 to further increase the tissue contact area of the anchoring feature 5600. The coverings and/or cushions can include the same or similar structure to those described herein. For example, the coverings and/or cushions can be formed from a foam material, woven or knitted cloth or sheet, and/or an insert.

With reference next to FIGS. 95-99, anchoring feature 5700 is illustrated. The anchoring feature 5700 can transition between a collapsed configuration (as shown in FIGS. 95 and 96) and an expanded configuration (as shown in FIGS. 97-99). In transitioning from the collapsed configuration to the expanded configuration, the lateral dimension (or width) and/or a radial offset of the anchoring feature 5700 can increase.

The anchoring feature 5700 can be attached to a frame body (not shown) via one or more struts 5710. The anchoring feature 5700 can include one or more prongs 5720, 5730 having tips 5722, 5732. As shown in the illustrated embodiment, the tips 5722, 5732 can form an enlarged, looped shape. By increasing the area of contact between the tips 5722, 5732, the enlarged looped shape can reduce the likelihood that the tips 5722, 5732 are improperly aligned prior to crimping. For example, the enlarged loop shape can reduce the likelihood that the tips 5722, 5732 are in the same radial plane prior to crimping. It is to be understood that the tips 5722, 5732 can form other shapes such as those described in connection with other anchoring features described herein.

The first prong 5720 and the second prong 5730 can be radially offset such that the tip 5722 of first prong 5720 is radially outward relative to the tip 5732 of the second prong 5730. This can allow the tips 5722, 5732 to slide relative to each other when transitioning between the collapsed configuration and the expanded configuration. As shown, the tips 5722, 5732 can form a relatively flat surface of the anchoring feature 5700; however, it is to be understood that the tips 5722, 5732 can take on a more rounded shape similar to other anchoring features described herein. Moreover, while the tips 5722, 5732 are shown at or around the same axial position, it is to be understood that the tips 5722, 5732 can be axially offset. One or more coverings and/or cushions (not shown) can be attached to the anchoring feature 5700 which cover the tips 5722, 5732. The one or more coverings and/or cushions can span the radial offset and/or lateral offset between the tips 5722, 5732 to further increase the tissue contact area of the anchoring feature 5700. The coverings and/or cushions can include the same or similar structure to those described herein. For example, the coverings and/or cushions can be formed from a foam material, woven or knitted cloth or sheet, and/or an insert.

With reference next to FIGS. 100-106, anchoring feature 5800 is illustrated. The anchoring feature 5800 can include a base anchor 5810 to which one or more additional components, such as inserts 5820, can be attached. As shown in the illustrated embodiment, the insert 5820 can extend radially outward relative to the base anchor 5810 when the frame (not shown) is in an expanded configuration; however, it is to be understood that the insert 5820 can extend in other directions relative to the base anchor 5810. For example, the insert 5820 can extend in directions including, but not limited to, radially inward, laterally, and/or axially relative to the base anchor 5810.

In some embodiments, the base anchor 5810 can be attached to a frame body (not shown) of the replacement valve. For example, the base anchor 5810 can be unitarily formed with the frame body similar to other anchoring features described herein. In some instances, the base anchor 5810 can be unitarily formed with the frame body via laser-cutting a single tube. The insert 5820 can be formed separately from the base anchor 5810 and attached using any of the fasteners and techniques described herein, such as via sutures, welding, adhesives, and/or a snap-fit, such as via connectors 5826, 5828 described below. As will be described in further detail below, the insert 5820 can increase the tissue contact area of the anchoring feature 5800.

The anchoring feature 5800 can be attached to a frame body via one or more struts 5812 of the base anchor 5810. The base anchor 5810 can include a strut forming a portion of the tip 5830 of the anchoring feature 5800. As shown, the tip 5830 can have a looped shape which forms a hole or aperture 5816. In some implementations, the insert 5820 can be positioned at least partially within the hole or aperture 5816.

The insert 5820 can include a rib 5822 and a platform 5824. The insert 5820 may also include one or more connectors 5826, 5828. The rib 5822 can extend generally axially and radially when the insert 5820 is attached to the base anchor 5810. The rib 5822 can beneficially support other portions of the insert 5820 at least when the insert 5820 is subject to an axial load. As shown, the rib 5822 can have an arcuate shape when viewed from a side profile. The arcuate shape can reduce the likelihood of the rib 5822 catching onto to native anatomy, such as chordae tendineae when the anchoring feature 5800 is positioned at a target location.

The platform 5824 can form a contact surface for native anatomy, such as a ventricular side of the native mitral valve annulus. As shown, the platform 5824 can extend laterally outward relative to the base anchor 5810 and/or the rib 5822. The platform 5824 can form a generally planar surface. By increasing the lateral extent of the platform 5824, the tissue contact area of the anchoring feature 5800 can be significantly increased. This increased tissue contact area can beneficially reduce the stress applied by the anchoring feature 5800 to tissue thereby reducing the amount of pressure and potential for trauma to the tissue.

In some embodiments, the insert 5820 can include one or more connectors 5826, 5828. The connectors 5826, 5828 can be used to facilitate coupling of the insert 5820 to the base anchor 5810. In some embodiments, the one or more connectors 5826, 5828 can snap fit into openings of the base anchor 5810. For example, one or more complementary openings (not shown) can be formed along the strut within the hole or aperture 5816 of the base anchor 5810. In some embodiments, the one or more connectors 5826, 5828 can extend across the hole or aperture 5816 and clamp onto an opposite side of the base anchor 5810. However, it is to be understood that the one or more connectors 5826, 5828 can be omitted.

Use of separate components can beneficially allow for localized control over performance characteristics of the anchoring feature 5800. In some embodiments, the base anchor 5810 can be formed from a relatively rigid material and the insert 5820 can be formed from another material which may be more compliant than the material used for the base anchor 5810. This can increase the strength of the base anchor 5810 to allow the base anchor 5810 to resist loads imposed on the anchoring feature 5800 while in use. The compliancy of the insert 5820 can better conform to the native anatomy to enhance the tissue contact area and reduce the potential for trauma to tissue of the native anatomy. In some embodiments, the base anchor 5810 can be formed from a metal, such as nitinol, and the insert 5820 can be formed from a softer metal or plastic. The insert 5820 can have a cushion-like structure similar to other cushions described herein. For example, the insert 5820 can be formed at least partially from a foam material. This can beneficially enhance the compliancy of the insert 5820 and allow the insert 5820 to better conform to native anatomy. In some embodiments, at least the platform 5824 is formed from a foam material. As another example, at least the insert 5820 can be formed from a material that facilitates tissue ingrowth or formation. This can further enhance securement of the anchoring feature 5800 to tissue of the native anatomy.

It is to be understood that the base anchor 5810 and the insert 5820 can be formed from the same material. Use of separate components can facilitate manufacture of the anchoring feature 5800. As noted above, the base anchor 5810 can be unitarily formed with the frame body via laser-cutting a single tube. In such an embodiment, it may be difficult or impossible to form the geometry of the insert 5820. As such, the insert 5820 can be manufactured via an alternative manufacturing method.

Figure 107:
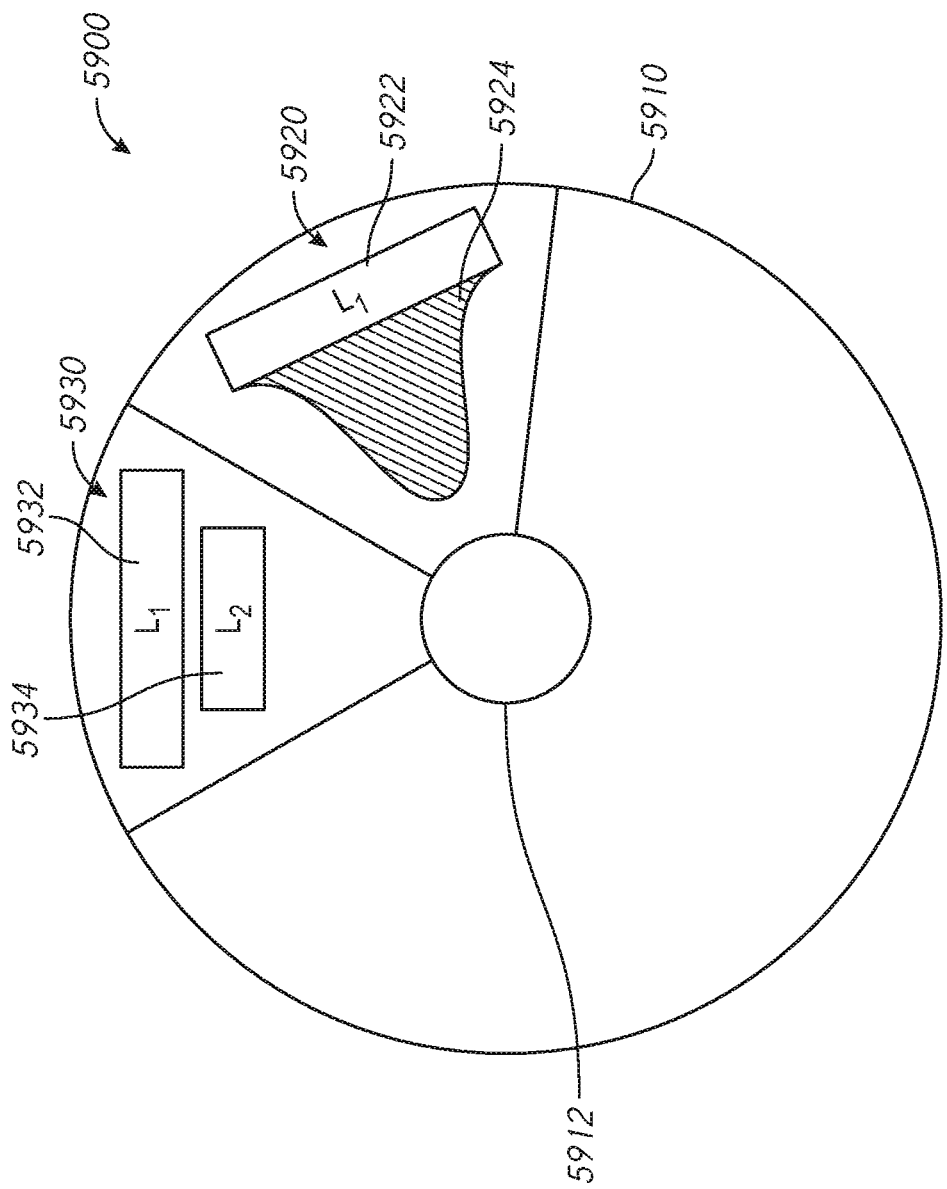
FIG. 107 illustrates a cross-sectional schematic of a delivery system having anchoring features positioned therein.

With reference next to FIG. 107, a cross-sectional schematic of an embodiment of a delivery system 5900 is illustrated. The delivery system 5900 can include an outer sheath 5910 and an inner sheath or rail 5912. Two anchoring features 5920, 5930 are illustrated within the outer sheath 5910 in a crimped or collapsed configuration. Although two anchoring features 5920, 5930 are shown, it is to be understood that a fewer or greater number of anchoring features can be used. Moreover, although two different anchoring features 5920, 5930 are illustrated, it is to be understood that the anchoring features can be the same.

Anchoring feature 5920 can share structures similar to anchoring feature 5800 described above. For example, the anchoring feature 5920 can include a base anchor 5922 and an insert 5924. In the illustrated embodiment, the insert 5924 of the anchoring feature 5920 extends radially inward relative to the base anchor 5922. This can more efficiently utilize the available space between the outer sheath 5910 and the inner sheath 5912. In some embodiments, when the replacement valve is released and transitioned into the expanded configuration, the anchoring feature 5920 can flip around in a manner similar to other anchoring features described herein. In so doing, the insert 5924 can be positioned radially outward relative to the base anchor 5920 similar to anchoring feature 5800.

Anchoring feature 5930 can share structures similar to anchoring features 5400, 5700 described above. For example, the anchoring feature 5930 can include a first prong 5932 and a second prong 5934 which are radially offset relative to each other. In the illustrated embodiment, the first prong 5932 of the anchoring feature 5930 is positioned radially outward of the second prong 5934 and is wider than the second prong 5934. This can more efficiently utilize the available space between the outer sheath 5910 and the inner sheath 5912.

Figure 108:
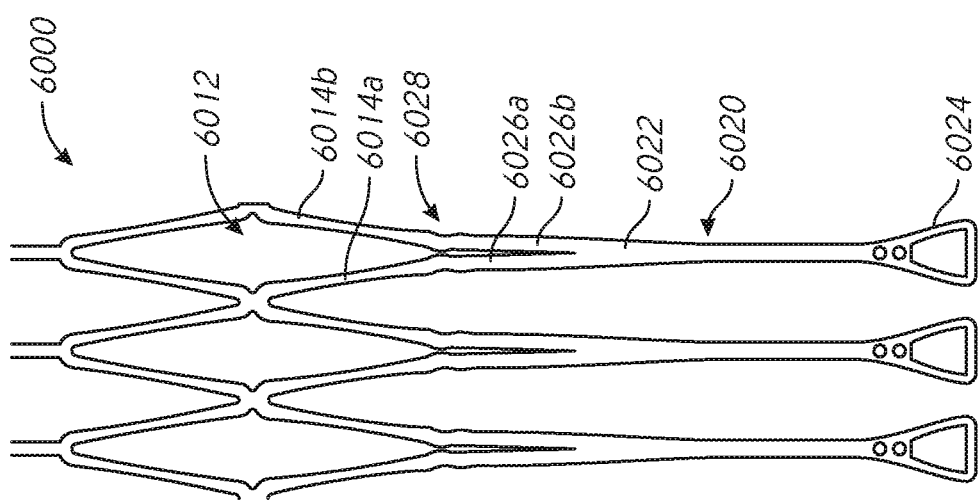
FIG. 108 illustrates a flat pattern of an embodiment of a frame.

With reference next to FIG. 108, a portion of an embodiment of a frame 6000 is illustrated. The frame 6000 can include a frame body 6010 having one or more struts forming cells 6012. The frame 6000 can include an anchoring feature 6020 having a strut 6022 and a tip 6024. As shown in the illustrated embodiment, the tip 6024 can form a looped shape; however, it is to be understood that the tip 6024 can incorporate any other tip configuration described herein. The strut 6022 can split into two or more struts 6026a, 6026b proximate a base or pivot location 6028 between the frame body 6010 and the anchoring feature 6020. As shown, the strut 6022 can bifurcate into two struts 6026a, 6026b which are each connected to struts 6014a, 6014b forming part of cells 6012. The struts 6014a, 6026a can be disconnected from struts 6014b, 6026b such that the struts 6014a, 6026a are movable relative to struts 6014b, 6026b.

This configuration can beneficially reduce strains imposed on the struts 6014a, 6014b, 6026a, 6026b when the frame 6000 is in a collapsed or crimped configuration and/or when the frame 6000 is subject to fatigue loading. The struts can effectively widen the outflow struts to allow for a greater distribution of strain during crimping and/or during fatigue loading since the struts are separated into two individual members. Moreover, as shown in the illustrated embodiment, the aspect ratio of the anchoring feature 6020 proximate the base or pivot location 6028 is larger than the aspect ratio of the anchoring feature 6020 further distal of the base or pivot location 6028. This can beneficially reduce resistance to side-loading and/or out-of-plane loading.

Moreover, in some implementations, localized stresses at the pivot location 6028 can be sufficient to effect at least a partial phase transformation of the material at the pivot location 6028. For example, in embodiments utilizing nitinol, localized stresses can be sufficient to cause at least partial "martensitic transformation" of nitinol at the pivot location 6028. This "martensitic transformation" can transform nitinol into the martensite phase from the austenite phase which has different material properties than the austentite phase. For example, nitinol in the austenite phase is less malleable and does not exhibit the same level of elastic deformation characteristics as nitinol in the martensite phase.

With respect to the geometry illustrated in FIG. 108, further crimping of the cells 6012 can cause the slot between struts 6026a, 6026b to increase in size. In implementations where the nitinol anchor flips from the collapsed configuration to the expanded configuration, this can be particularly advantageous. In such an implementation, when the nitinol anchor is released and allowed to expand while the cells 6012 remain in a compressed configuration, the nitinol anchor can flip to a lesser degree to facilitate positioning of the nitinol anchor between chordae tendineae and/or native leaflets. When such localized stresses at the pivot location 6028 are released, such as by allowing the cells 6012 to expand, material at the pivot location 6028 can revert back to the austenite phase.

Figure 109A:
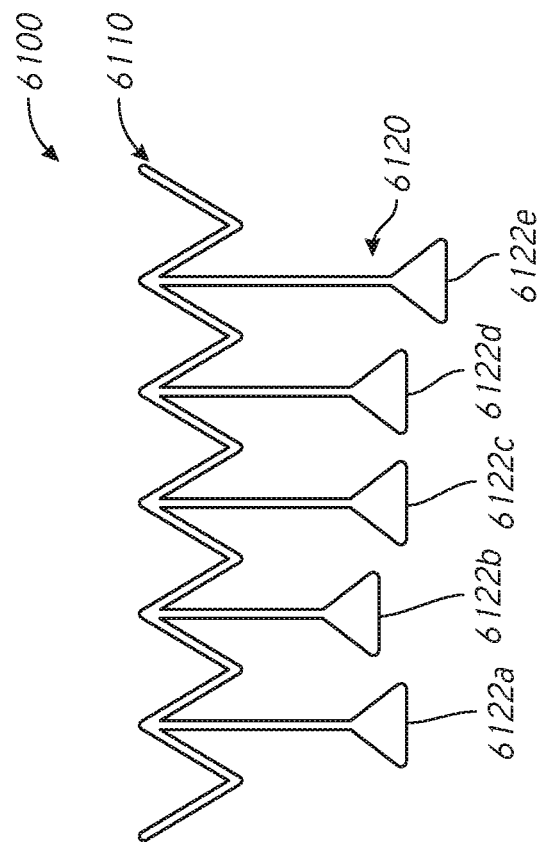
FIG. 109A illustrates a flat pattern of another embodiment of a frame.
Figure 109B:
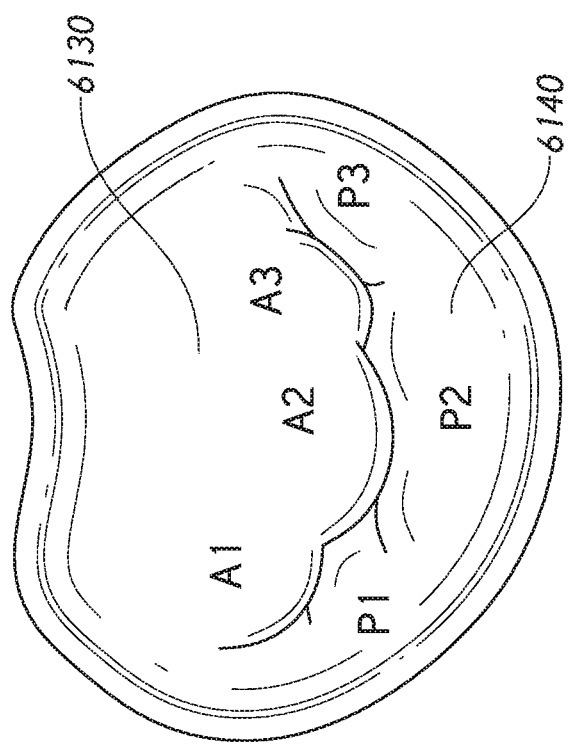
FIG. 109B illustrates a schematic of a native mitral valve.
Figure 111:
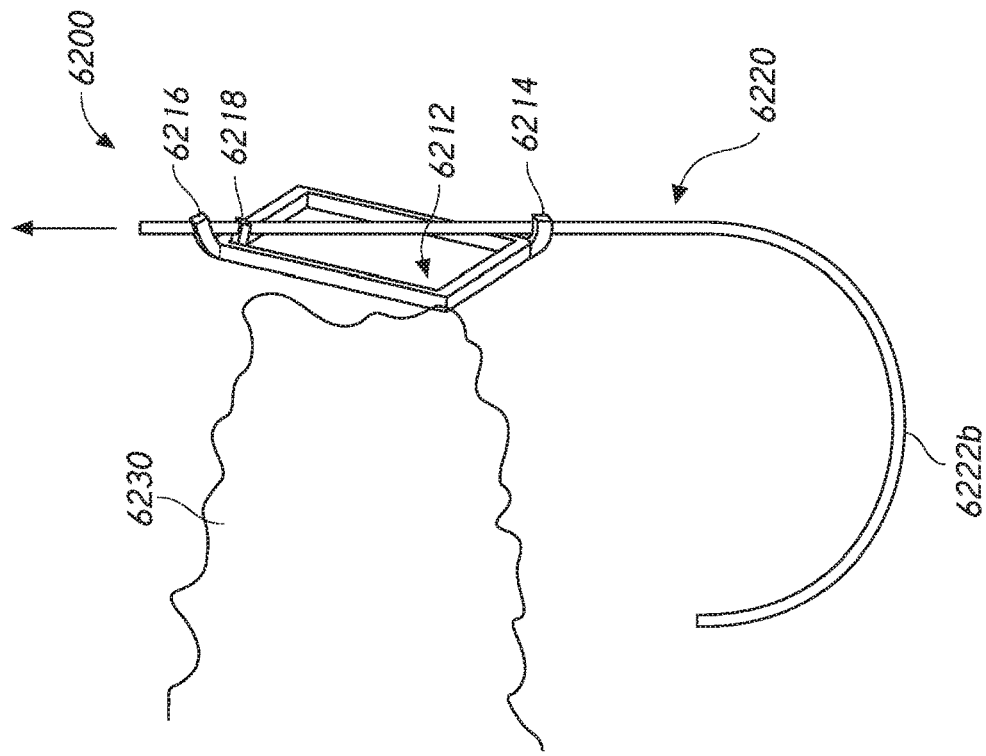
FIG. 111 illustrates a perspective view of a portion of the frame of FIG. 110.
Figure 110:
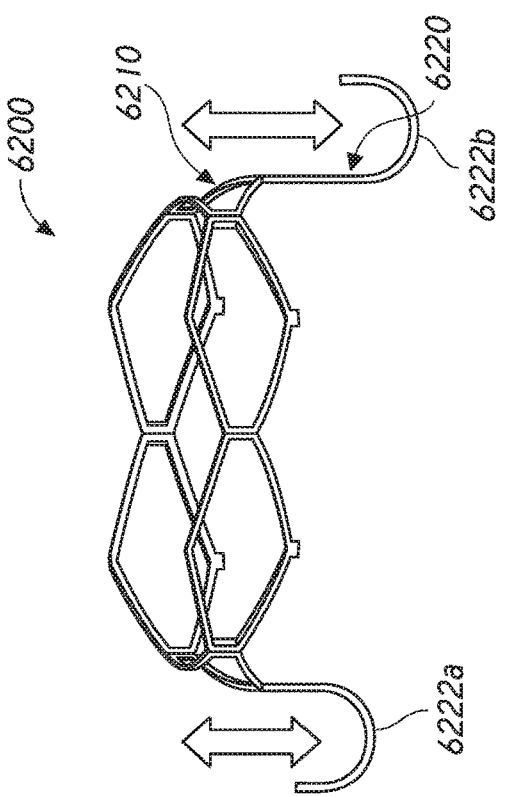
FIG. 110 illustrates a perspective view of an embodiment of a frame having an adjustable anchoring feature.

With reference next to FIGS. 109-111, portions of embodiments of frames 6100, 6200 are illustrated. The frames 6100, 6200 can include anchoring features 6120, 6220 with anchors having different lengths. This can allow the anchors to have different heights when the frames 6100, 6200 are in an expanded configuration. This can be particularly advantageous in situations where the native anatomy is non-planar. For example, the native mitral valve typically has a non-planar, saddle-shape. By better matching the length of the anchoring features 6120, 6220 with the shape of the native anatomy, the load distribution on frames 6100, 6200 as well as the native anatomy can be improved.

With reference first to FIG. 109A, frame 6100 is illustrated. The frame 6100 can include a frame body 6110 having one or more struts 6012 forming cells (not shown). The frame 6100 can include an anchoring feature 6120 in the form of multiple individual anchors 6122a-e. As shown in the illustrated embodiment, the individual anchors 6122a-e can have different lengths. The lengths can be chosen based on the contemplated position of the individual anchors 6122a-e on the native valve anatomy. For example, short anchors such as anchor 6122b can be positioned at an anterior or posterior location of the native mitral valve (e.g., the A2 and P2 lobes as shown in FIG. 109B) whereas longer anchors such as anchor 6122e can be positioned at or proximate commissures of the native mitral valve (e.g., the A1, A3, P1, or P3 lobes as shown in FIG. 109B).

Since certain regions of annular tissue may have greater stiffness than other regions of annular tissue, certain regions of annular tissue may be better suited for anchoring and load transfer. In some embodiments, the strength and/or compliancy of individual anchors 6122a-e can differ. For example, primary, load-bearing anchors can be stiffer than other anchors. These primary, load-bearing anchors can be designed to engage stiffer tissue at anterior or posterior locations of the native mitral valve. In some implementations, two primary anchors can be positioned behind the native anterior leaflet. Two or three primary anchors can be positioned behind the native posterior leaflet. This can beneficially enhance securement to the native annulus. For example, primary anchors can be positioned at the A1 and A3 lobes of the native anterior leaflet 6130 and/or the P1, P2, and P3 lobes of the native posterior leaflet 6140 (as shown in FIG. 109B). Moreover, this can beneficially increase the likelihood that at least one anchor extends behind the leaflets. Although four to five primary anchors have been described, it is to be understood that a fewer or greater number of primary anchors can be used. For example, in some embodiments, two to six primary anchors can be utilized.

Secondary anchors can be more compliant than other anchors. These secondary anchors can interact with more compliant tissue. In some implementations, these secondary anchors can be sized and shaped to isolate and/or immobilize the free edge of a native leaflet. This can beneficially reduce movement of the native leaflet during the cardiac cycle which can, in some instances, advantageously improve tissue ingrowth and/or reduction of paravalvular leakage. In some implementations, secondary anchors can be positioned at the A2 lobe of the native anterior leaflet 6130 and/or the commissures of the native mitral valve. The number of secondary anchors can be chosen to obtain a total number of desired anchors. For example, in embodiments having twelve anchors, the frame 6100 can have five primary anchors and seven secondary anchors. It is to be understood that a fewer or greater number of total anchors may be used as described above (e.g., nine total anchors).

With reference next to FIGS. 110 and 111, frame 6200 is illustrated. The frame 6200 can include a frame body 6210 having one or more struts forming cells 6212. The frame 6200 can include an anchoring feature 6220 having one or more anchors 6222a, 6222b. As shown in the illustrated embodiment, the individual anchors 6222a, 6222b can be adjustable to different heights. The heights can be changed based on the positioning of the individual anchors 6222a, 6222b relative to the native valve anatomy such as the native mitral valve annulus 6230. Individual placement of anchors can advantageously provide the user more controlled deployment of individual anchors. In some embodiments, a slight tug by the operator can be applied after each individual anchor is placed to verify that the anchor is well placed before moving onto the next anchor. In this manner, individual anchors can be more suitably positioned relative to the native valve anatomy. This can advantageously reduce the likelihood that the frame 6200 tilts or rocks during the various cardiac cycles of the patient's heart. Among other benefits, this can reduce the likelihood of paravalvular leakage which may be caused by tilting or rocking of the frame 6200.

With reference to FIG. 111, one or more of the anchors, such as anchor 6222b, can be attached to the frame body 6210 via one or more connector tabs 6214, 6216, 6218. The connector tabs 6214, 6216, 6218 can include apertures through which a strut 6224b of the anchor 6222b can be passed. As shown, a first connector tab 6214 can be positioned along a bottom region of a cell 6212. For example, the first connector tab 6214 can be positioned at or proximate a bottom apex of the cell 6212. A second connector tab 6216 can be positioned along a top region of a cell 6212. For example, the second connector tab 6216 can be positioned at or proximate a top apex of the cell 6212. A third connector tab 6218 can be positioned between the first and second connector tabs 6214, 6216.

In some embodiments, the connector tabs 6214, 6216, 6218 can be sized and shaped to retain the anchor 6222b in position. For example, as shown in the illustrated embodiment, the connector tabs 6216, 6218 can be biased in a direction which is non-perpendicular to a longitudinal axis of the frame body 6210. As such, the connector tabs 6216, 6218 can impose a frictional force on the strut 6224b which can resist translation of the strut 6224b relative to the connector tabs 6216, 6218. This frictional force is preferably sufficient to resist axially directed forces exerted on the anchor 6222b. In some embodiments, the connector tabs 6216, 6218 can allow the anchor 6222b to move axially in one direction (e.g., proximally) while inhibiting or preventing movement in the opposite direction (e.g., distally). For example, this can allow the operator to pull on the anchor 6222b in a proximal direction to shorten the anchor 6222b while inhibiting the anchor 6222b from moving distally and elongating during operation in the patient's heart. In some embodiments, the connector tabs 6216, 6218 can be pinched or squeezed towards each other to reduce this frictional force thereby facilitating adjustment of the length of the anchor 6222b.

While the frame 6200 includes connector tabs 6214, 6216, 6218, it is to be understood that other types of connection mechanisms can be used in conjunction with, or in lieu of, connector tabs 6214, 6216, 6218. For example, the frame 6200 can include a ratcheting mechanism which allows the length of the anchors to be reduced while inhibiting or preventing the length of the anchors to be increased. It is to be understood that the tips of the anchoring features 6220 can include any of the features and structures described herein with respect to other anchoring features.

With reference next to FIGS. 112-117, portions of embodiments of frames 6300, 6400 are illustrated. The frames 6300, 6400 can include anchoring features 6320, 6420 with anchors having struts attached to the frame 6300, 6400 at two or more locations. This can beneficially enhance the strength of the anchors of the anchoring features 6320, 6420.

With reference first to FIGS. 112-114, a portion of an embodiment of a frame 6300 is illustrated. The frame 6300 can include a frame body 6310 having one or more struts forming cells 6312. The frame 6300 can include an anchoring feature 6320 having one or more combined anchors 6322. As shown in the illustrated embodiment, the combined anchors 6322 can be formed from a first strut 6324a and a second strut 6324b which can extend from different portions of the frame body 6310. For example, the first strut 6324a and the second strut 6324b can extend from different cells of the frame body 6310. While the struts 6324a, 6324b are spaced apart about one cell length, it is to be understood that this distance can be increased or decreased.

In the expanded configuration, the tip 6326a of the first strut 6234a and the tip 6326b of the second strut 6324b can overlap. The overlap between the tips 6326a, 6326b can allow forces imposed on the tips 6326a, 6326b to be distributed between the two struts 6324a, 6324b. This can allow the struts 6324a, 6324b to be thinner which can facilitate delivery. For example, the use of thinner struts can facilitate crimping of the struts for positioning within a delivery system. As another example, the user of thinner struts can allow the struts to more easily pass between chordae tendineae when the frame 6300 is utilized in the native mitral valve and the anchoring feature 6320 is positioned within the left ventricle. As shown, the tips 6326a, 6326b overlap such that the tips are generally aligned along a plane passing through a longitudinal axis of the frame 6300. Moreover, the struts 6324a, 6324b can extend towards each other such that the lateral width of the combined anchor 6322 can be reduced. The reduced lateral width of the anchors can allow the combined anchor 6322 to more easily pass between chordae tendineae when the frame 6300 is utilized in the native mitral valve and the anchoring feature 6320 is positioned within the left ventricle.

In some embodiments, struts 6324a, 6324b can be positioned in a non-overlapping manner when the frame 6300 is in a collapsed or crimped configuration. As the frame 6300 transitions to the expanded configuration, the struts 6324a, 6324b can shift in position such that the struts overlap. This can beneficially allow the struts 6324a, 6324b to extend around chordae tendineae. It is to be understood that the struts 6324a, 6324b can be positioned in an overlapping manner when the frame 6300 is in a collapsed or crimped configuration.

With reference next to FIGS. 115-117, a portion of an embodiment of a frame 6400 is illustrated. The frame 6400 can include a frame body 6410 having one or more struts forming cells 6412. The frame 6400 can include an anchoring feature 6420 having one or more anchors 6422. As shown in the illustrated embodiment, the anchors 6422 can be formed from a first strut portion 6424a and a second strut portion 6424b which can extend from different portions of the frame body 6410. For example, the first strut portion 6424a and the second strut portion 6424b can extend from different cells of the frame body 6410. While the struts 6424a, 6424b are spaced apart about one cell length, it is to be understood that this distance can be increased or decreased.

Forces applied to the tip 6426 can be beneficially distributed between the two struts 6424a, 6424b. This can allow the struts 6424a, 6424b to be thinner which can facilitate delivery. For example, the use of thinner struts can facilitate crimping of the struts for positioning within a delivery system. The strut portions 6424a, 6424b can extend towards each other such that the lateral width of the anchor 6422 can be reduced. The reduced lateral width of the anchors can allow the anchor 6422 to more easily pass between chordae tendineae when the frame 6400 is utilized in the native mitral valve and the anchoring feature 6420 is positioned within the left ventricle.

Embodiments of Replacement Valves with Multi-Part Frames

With reference next to FIGS. 118-131, embodiments of prostheses 6500, 6600 and frames 6520, 6620, 6700, 6800, 6900, 7000, 7100 are illustrated. The illustrated prostheses 6500, 6600 and frames 6520, 6620, 6700, 6800, 6900, 7000, 7100 may include components which are self-expanding or balloon expandable. As will be discussed in further detail below, the illustrated prostheses 6500, 6600 and frames 6520, 6620, 6700, 6800, 6900, 7000, 7100 can include one or more components which are separately formed and subsequently attached. The components can be attached using any of the fasteners and techniques described herein, such as via sutures, welding, and/or adhesives. In some embodiments, the components can be attached in a similar manner to that described in U.S. Publication No. 2016/0310268, published Oct. 27, 2016, the entirety of which is incorporated herein by reference. The prostheses 6500, 6600 and frames 6520, 6620, 6700, 6800, 6900, 7000, 7100 as well as other prostheses described herein, may be replacement valves that can be designed to replace a damaged or diseased native heart valve such as a mitral valve, as discussed above. It should be understood that the prostheses 6500, 6600 and frames 6520, 6620, 6700, 6800, 6900, 7000, 7100 as well as other prostheses described herein, are not limited to being a replacement valve.

Figure 118:
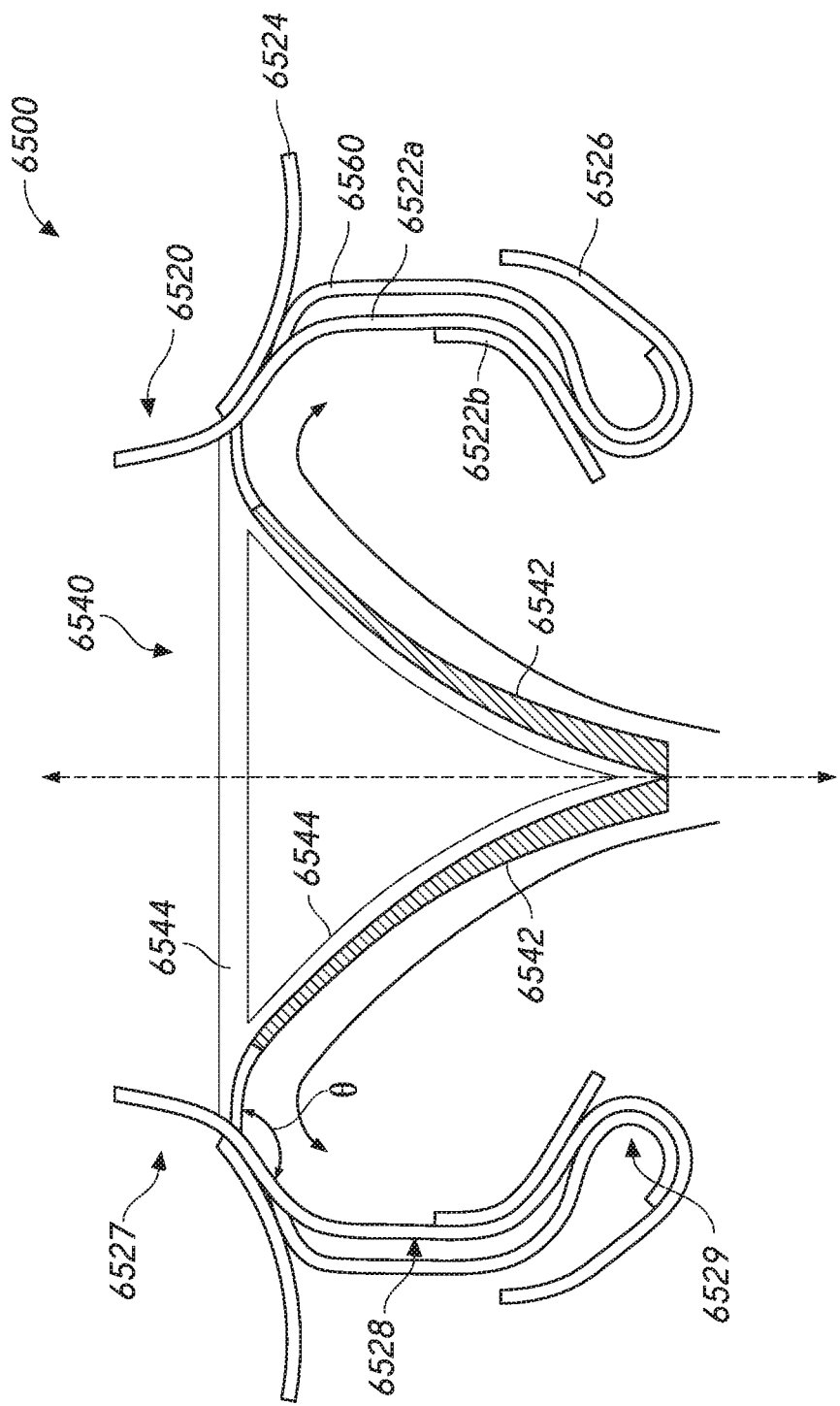
FIG. 118 is a side-oriented cross-sectional schematic view of an embodiment of a frame, a plurality of anchors, an annular skirt, and a floating valve, the components being a first configuration.
Figure 119:
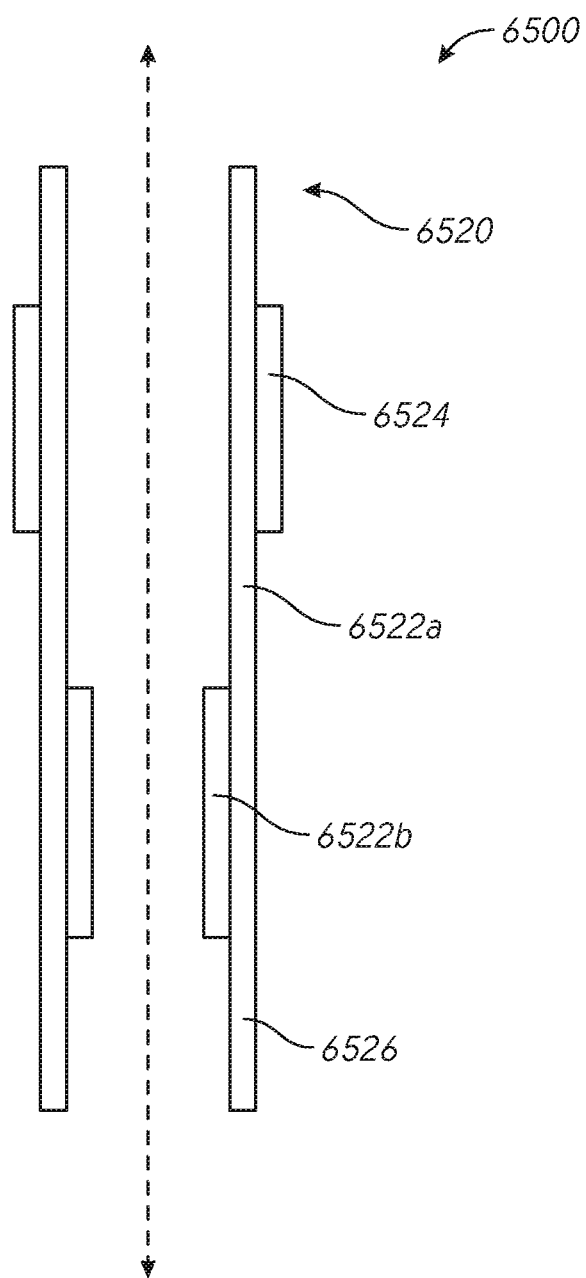
FIG. 119 is a side-oriented cross-sectional schematic view of the components of FIG. 118, the components being in a second configuration.

With reference first to FIGS. 118 and 119, the prosthesis 6500 can include a frame 6520, a valve body 6540, and a skirt 6560. The prosthesis 6500 can transition between an expanded configuration (shown in FIG. 118) and a collapsed or crimped configuration (shown in FIG. 119). The prosthesis 6500 can incorporate features and concepts which are the same as, or at least similar to, those of other frames described herein such as, but not limited to, prosthesis 100 described above in connection with FIG. 1. It is to be understood that structures, features, and/or functionality of the components described in connection with prosthesis 100 may be applicable to those described in connection with prosthesis 6500.

As shown in the illustrated embodiment, the frame 6520 can include a frame body 6522a, a first anchoring feature 6524, and a second anchoring feature 6526. As shown in the illustrated embodiment, the frame body 6522a includes an upper region 6527, an intermediate region 6528, and a lower region 6529. The intermediate region 6528 can have a larger diameter than the upper region 6527 and/or the lower region 6529. In some embodiments, the frame 6520 can be oriented such that the upper region 6527 is a proximal or inflow portion and the lower region 6529 is a distal or outflow portion. The frame 6520 can be formed from many different materials, including metals, such as Nitinol.

The frame 6520 is preferably formed from a plurality of struts forming open cells. As will be discussed in further detail below, components of the frame 6520, such as the frame body 6522a, the first anchoring feature 6524, and/or the second anchoring feature 6526, can be used to attach or secure the prosthesis 6500 to a native valve. For example, the frame body 6522a and the second anchoring feature 6526 can be used to attach or secure the prosthesis 6500 to a native valve, such as a native mitral valve. Although the frame 6520 has been described as including a frame body 6522a, a first anchoring feature 6524, and a second anchoring feature 6526, it is to be understood that the frame 6520 need not include all components. For example, in some embodiments, the frame 6520 can include the frame body 6522a and the second anchoring feature 6526 while omitting the first anchoring feature 6524.

With continued reference to FIGS. 118 and 119, one or more components of the frame 6520 can be formed separately from each other. This can beneficially allow the performance of the frame 6520 to be more precisely tuned for desired characteristics and uses. As shown in the illustrated embodiment, the frame body 6522a, the first anchoring feature 6524, and/or a supplemental frame 6522b can be formed separately from each other and subsequently attached. The frame body 6522a, the first anchoring feature 6524, and/or the supplemental frame 6522b can be attached using any of the fasteners and techniques described herein, such as via sutures, welding, and/or adhesives. In some embodiments, the frame body 6522a, the first anchoring feature 6524, and/or a supplemental frame 6522b can be delivered to the native valve separately from the frame 6520.

Use of separate components can beneficially allow for localized control over performance characteristics of the frame 6520. For example, the supplemental frame 6522b can locally reinforce a portion of the frame body 6522a by effectively increasing the wall thickness of the frame body 6522a. As shown, the supplemental frame 6522b can be positioned proximate a lower region 6529 of the frame 6520. In some implementations, such as those in which the replacement valve 6500 is used in a native mitral valve, the lower region 6529 of the frame 6520 can be subject to more stresses than the upper region 6527 of the frame 6520. By locally reinforcing portions of the frame body 6522a subject to greater stresses, the wall thickness in other portions of the frame 6520 which are subject to lower stresses can be remain thinner. This can allow other desirable characteristics, such as crimp diameter, to be generally maintained.

Moreover, as will be discussed in further detail below, use of separate components can allow different geometries to exist along different "layers" of the frame 6520. As shown in FIG. 119, the frame 6520 can have a multi-layer construction with supplemental frame 6522b forming an inner layer, frame body 6522a forming an intermediate layer, and/or first anchoring feature 6524 forming an outer layer. In this manner, supplemental frame 6522b, frame body 6522a, and/or first anchoring feature 6524 can be located in different circumferential planes. This can beneficially disassociate at least some impact of the various components on each other when the frame 6520 is in a crimped or collapsed configuration. This can advantageously reduce the crimp diameter of the frame 6520 since the components of frame 6520 crimp "in parallel" (i.e., along different planes) as compared to "in series" (i.e., within the same plane). Moreover, this can advantageously reduce the crimp length of the frame 6520 since the frame 6520 need not be designed to accommodate "in series" crimping of the anchoring features thereby allowing the frame 6520 to be made more compact.

As noted above, the frame components can be attached to each other using any of the fasteners and techniques described herein, such as via sutures, welding, and/or adhesives. In some implementations, the frame components can be attached in such a manner that some degree of movement may occur between the frame components. For example, in embodiments where the frame components are sutured together, the frame components may be capable of sliding relative to other frame components. This can beneficially reduce the effects each frame component has on each other during crimping. For example, this can allow the frame components to crimp together at the same or similar rate such that the frame components have about the same or similar strains.

With continued reference to the prosthesis 6500 illustrated in FIGS. 118 and 119, the valve body 6540 is attached to the frame 6520 within an interior of the frame 6520. The valve body 6540 functions as a one-way valve to allow blood flow in a first direction through the valve body 6540 and inhibit blood flow in a second direction through the valve body 6540. For example, in embodiments where the upper region 6527 is a proximal portion and the lower region 6529 is a distal portion, the valve body 6540 can allow blood flow in a proximal-to-distal direction and inhibit blood flow in a distal-to-proximal direction. The valve body 6540 preferably includes a plurality of valve leaflets 6542, for example three leaflets 6542, which are joined at commissures. As will be discussed in further detail below in connection with additional figures, the valve body 6540 can include one or more intermediate components 6544. The intermediate components 6544 can be positioned between a portion of, or the entirety of, the leaflets 6542 and the frame 6520 such that at least a portion of the leaflets 6542 are coupled to the frame 6520 via the intermediate component 6544. In this manner, a portion of, or the entirety of, the portion of the valve leaflets 6542 at the commissures and/or an arcuate edge of the valve leaflets 6542 are not directly coupled or attached to the frame 6520 and are indirectly coupled or "float" within the frame 6520.

Although the valve body 6540 has been described as including a plurality of leaflets 6542 and one or more intermediate components 6544, it is to be understood that the valve body 6540 need not include all features. For example, the valve body 6540 can include the plurality of valve leaflets 6542 while omitting the intermediate components 6544. In some embodiments, the valve leaflets 6542 can be directly attached to the frame 6520.

With continued reference the prosthesis 6500 illustrated in FIGS. 118 and 119, the skirt 6560 can be attached to the frame 6520. The skirt 6560 can be positioned around and secured to an exterior of the frame 6520. The skirt 6560 can be annular and can extend entirely circumferentially around the frame 6520. The skirt 6560 can prevent or inhibit backflow of fluids, such as blood, around the prosthesis 6500. For example, with the skirt 6560 positioned annularly around an exterior of the frame 6520, the skirt 6560 can create an axial barrier to fluid flow exterior to the frame 6520 when deployed within a body cavity such as a native valve annulus. The skirt 6560 can encourage tissue in-growth between the skirt 6560 and the natural tissue of the body cavity. This may further help to prevent leakage of blood flow around the prosthesis 6500 and can provide further securement of the prosthesis 6500 to the body cavity. In some embodiments, the skirt 6560 can be loosely attached to the exterior of the frame 6520. In some embodiments, the skirt 6560 can be tautly secured around the frame 6520. As shown in the illustrated embodiment, the skirt 6560 can extend along at least a portion of the second anchoring feature 6526. In some implementations, this can allow the skirt 6560 to form a flange along a lower region 6529 of the frame 6520 when the frame 6500 is in an expanded configuration. This can beneficially enhance sealing along the lower region 6529 of the frame 6520.

As shown, the shape of the frame 6520, in conjunction with the shape of the leaflets 6542 and intermediate components 6544, can beneficially enhance hemodynamic performance. For example, the shape of the frame 6520 with a larger intermediate region 6520 can allow for increased motion of the leaflets 6542 when transitioning between systole and diastole. This increased motion can help push or pull blood into and out of the region between the leaflets 6542 and the frame 6520 thereby increasing flow in the region. Moreover, the shape of the frame 6520, in conjunction with the shape of the leaflets 6542 and intermediate components 6544, can allow for significant washout on an underside of the valve body 6540. That is, the shape of the frame 6520, in conjunction with the shape of the leaflets 6542 and intermediate components 6544, can enhance the exchange of blood from a prior cardiac cycle—which may have stagnated and accumulated in crevices, pockets, and/or surfaces of the frame 6520, valve 6540, and/or skirt 6560—with fresh blood from a current cardiac cycle.

As shown, the connection between the frame 6520 and the intermediate component 6544 can be greater than 90°. Preferably, the connection between the frame 6520 and the intermediate component 6544 can be generally aligned when the leaflets 6542 such that the intermediate component 6544 forms a tangent surface with the frame 6520. That is, the connection between the frame 6520 and the intermediate component 6544 can be about 180° when the leaflets are in a closed position (e.g., during systole). In some implementations, the angle θ of the connection between the frame 6520 and the intermediate component 6544 can be between about 160° to about 185°, between about 140° to about 190°, between about 120° to about 195°, any sub-ranges within these ranges, or other angles as desired, when the leaflets 6542 are in a closed position. This tangent surface can enhance flow over the underside of the leaflets 6542 and/or intermediate components 6544 during systole. Moreover, the increased radius of curvature can reduce flow resistance and regions where flow could stagnate and initiate thrombus formation. In some embodiments, the radius of curvature can be about 15 mm, between about 12 mm to about 20 mm, between about 8 mm to about 25 mm, between about 5 mm to about 30 mm, any sub-ranges within these ranges, or other radii as desired, when the leaflets 6542 are in a closed position.

Although the prosthesis 6500 has been described as including a frame 6520, a valve body 6540, and a skirt 6560, it is to be understood that the prosthesis 6500 need not include all components. For example, in some embodiments, the prosthesis 6500 can include only the frame 6520 and the valve body 6540 while omitting the skirt 6560.

Figure 120:
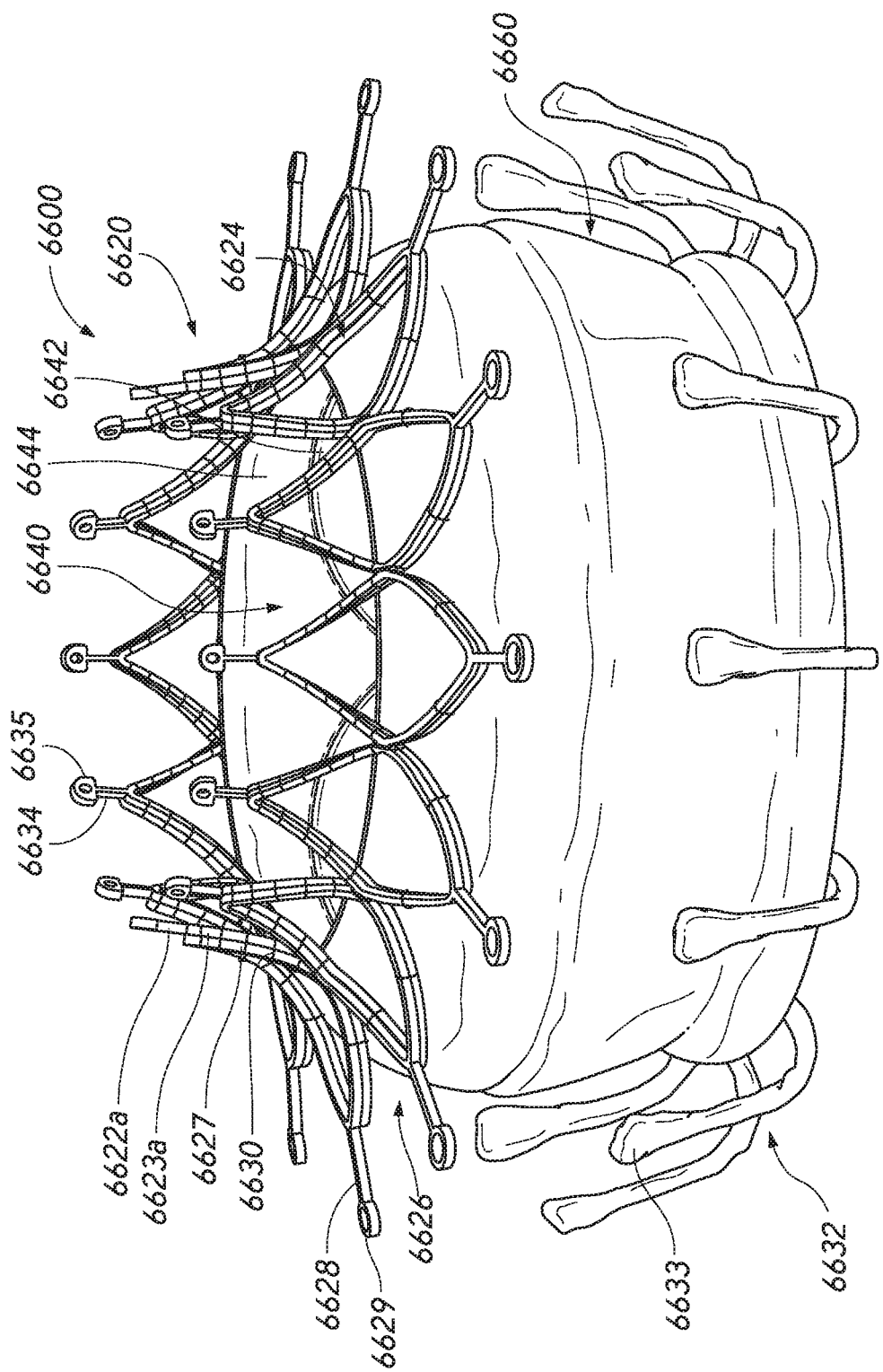
FIG. 120 is a top-oriented perspective view of another embodiment of a frame, a plurality of anchors, an annular skirt, and a valve body.
Figure 121:
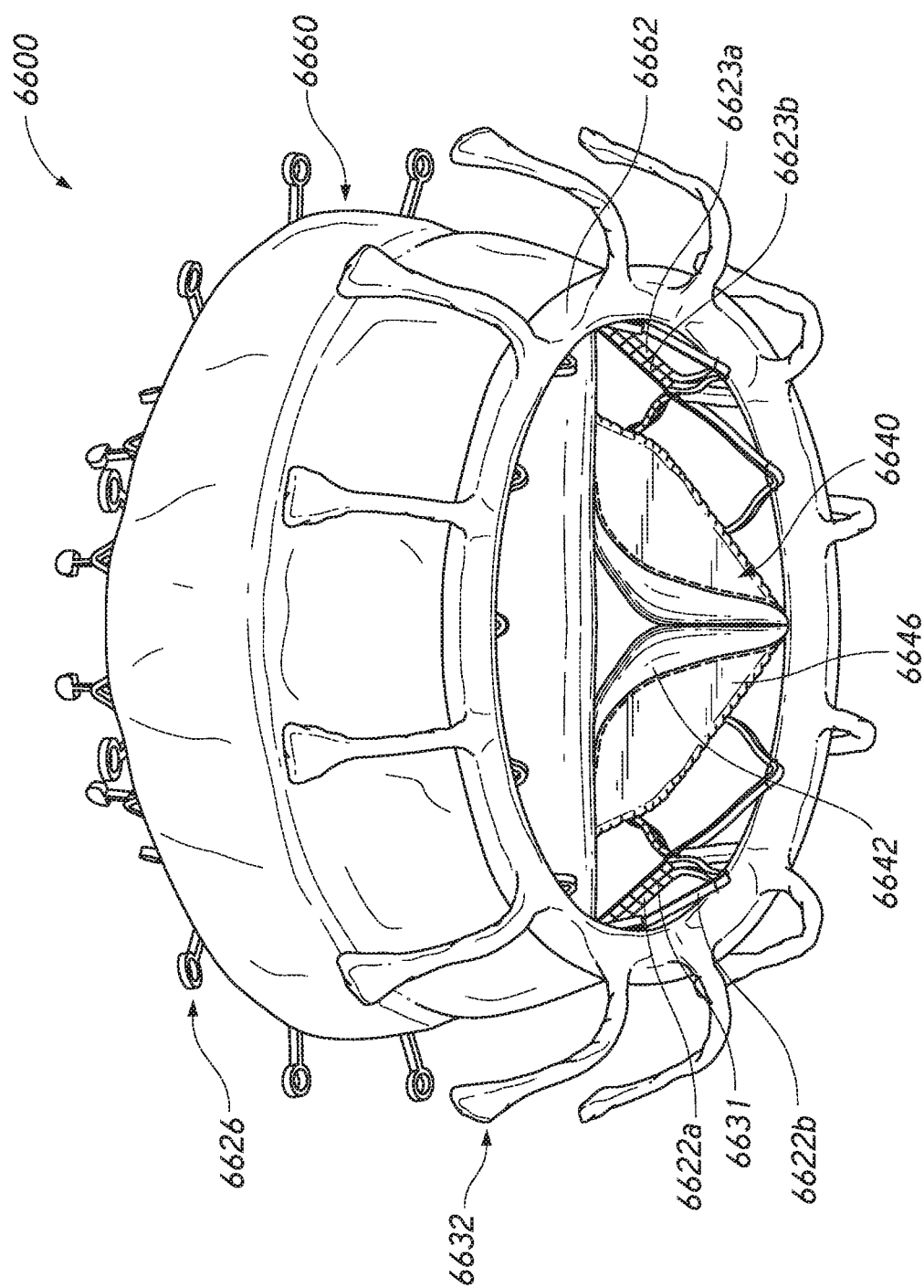

With reference next to the prosthesis 6600 illustrated in FIGS. 120 and 121, the prosthesis 6600 can include a frame 6620, a valve body 6640, and a skirt 6660. The frame 6620 can be self-expanding or balloon expandable. As shown in the illustrated embodiment, the frame 6620 can include a frame body 6622*a* formed from a plurality of struts defining a plurality of cells 6624. One or more of the cells 6624 can allow the frame 6620 to longitudinally foreshorten when the frame 6620 radially expands.

The frame 6620 can include a first anchoring feature 6626 and a second anchoring feature 6628. As shown, the first anchoring feature 6626 can be formed from a plurality of individual anchors extending from the frame body 6622*a* in a direction radially outward from a longitudinal axis of the frame 6620 and/or in a direction generally toward a lower end of the frame 6620. As shown in the illustrated embodiment, the first anchoring feature 6626 can include twelve individual anchors; however, it is to be understood that a greater number or lesser number of individual anchors can be used. For example, the number of individual anchors can be chosen as a multiple of the number of commissures for the valve body 6640. As such, for a prosthesis 6600 with a valve body 6640 having three commissures, the first anchoring feature 6626 can have three individual anchors, six individual anchors, nine individual anchors, twelve individual anchors, fifteen individual anchors, or any other multiple of three. It is to be understood that the number of individual anchors need not correspond to the number of commissures of the valve body 6640.

As shown in the illustrated embodiment, the first anchoring feature 6626 can be formed separately from the frame body 6622*a*. The first anchoring feature 6626 can include structures which generally match that of the frame body 6622*a*. For example, the first anchoring feature 6626 can include a plurality of struts 6627 forming cells which generally match the shape of the struts 6623*a* and/or cells of the frame body 6622*a*. This can allow at least some of the struts 6627 of the first anchoring feature 6626 to be aligned with struts 6623*a* of the frame body 6622*a*. This can beneficially facilitate attachment of the first anchoring feature 6626 to the frame body 6622*a*. The first anchoring feature 6626 can also include one or more struts 6628 which include tips 6629 in the form of eyelets. The one or more struts 6628 can extend radially outwardly and/or downwardly. As shown, sutures 6630 can wrap around struts 6627 of the first anchoring feature 6626 and struts 6623*a* of the frame body 6622*a* to couple the first anchoring feature 6626 and the frame body 6622*a* together; however, it is to be understood that other attachment mechanisms can be used such as those described herein including, but not limited to, welding and adhesives.

As shown, the second anchoring feature 6632 can be formed from a plurality of individual anchors extending from the frame body 6622*a* in a direction radially toward the longitudinal axis of the frame 6620 and bent to extend in a direction radially outward from the longitudinal axis of the frame 6620. A portion of the individual anchors, such as tips or ends 6633, can extend in a direction generally toward an upper end of the frame 6320. The individual anchors of the second anchoring feature 6632 can include tips or ends 6633 having covers and/or cushions as shown. In some embodiments, the tips or ends 6633 can be enlarged relative to the preceding portion of the second anchoring feature 6632, such as a strut. The covers and/or cushions can reduce pressure applied to tissue of the body cavity, such as the native valve annulus, when the tips or ends 6633 contact the native valve annulus. As shown in the illustrated embodiment, the second anchoring feature 6632 can include twelve individual anchors; however, it is to be understood that a greater number or lesser number of individual anchors can be used. For example, the number of individual anchors can be chosen as a multiple of the number of commissures for the valve body 6600. As such, for a prosthesis 6600 with a valve body 6640 having three commissures, the second anchoring feature 6632 can have three individual anchors, six individual anchors, nine individual anchors, twelve individual anchors, fifteen individual anchors, or any other multiple of three. It is to be understood that the number of individual anchors need not correspond to the number of commissures of the valve body 6640.

The frame 6620 preferably includes a set of locking tabs 6634 extending from the frame body 6622a at its upper end. As shown, the frame 6620 includes twelve locking tabs 6634, however, it is to be understood that a greater number or lesser number of locking tabs can be used. The locking tabs 6634 can extend generally upwardly from the frame body 6622a in a direction generally aligned with the longitudinal axis of the frame 6620. The locking tab 6634 can include an enlarged head or end 6635. As shown, the enlarged head or end 6636 has a semi-circular or semi-elliptical shape forming a "mushroom" shape with the remaining portion of the locking tab 6634. The locking tab 6634 can include an eyelet which can be positioned through the enlarged head 6635. It is to be understood that the locking tab 6635 can include an eyelet at other locations, or can include more than a single eyelet. The locking tab 6634 can be advantageously used with multiple types of delivery systems such as a "slot-based" delivery system and/or a "tether-based" delivery system.

As shown in FIG. 121, the frame 6620 can include a supplemental frame 6622b which can be used to reinforce portions of the frame body 6622a. The supplemental frame 6622b can be formed separately from the frame body 6622a. The supplemental frame 6622b can include structures which generally match that of the frame body 6622a. For example, the supplemental frame 6622b can include a plurality of struts 6623b forming cells which generally match the shape of the struts 6623a and/or cells of the frame body 6622a. This can allow at least some of the struts 6623b of the supplemental frame 6622b to be aligned with struts 6623a of the frame body 6622a. This can beneficially facilitate attachment of the supplemental frame 6622b to the frame body 6622a. As shown, the supplemental frame 6622b can extend along the entire circumferential periphery of the frame body 6622a (e.g., a loop); however, it is to be understood that the supplemental frame 6622b can extend along only a portion of the circumferential periphery of the frame body (e.g., an arc segment).

The supplemental frame 6622b can include struts which extend further below struts forming the frame body 6622a. This can beneficially increase the area to which the valve body 6640 can be attached to the frame 6620. For example, the valve body 6640 can be attached to portions of the supplemental frame 6622b extending below the frame body 6622a. In some implementations, the size of the supplemental frame 6622b can be chosen based on the type of valve body 6640 being used. For example, in some embodiments, the supplemental frame 6622b may not extend below the frame body 6622a. As shown, sutures 6631 can wrap around struts 6623b of the supplemental frame 6622b and struts 6623a of the frame body 6622a to couple the first supplemental frame 6622b and the frame body 6622a together; however, it is to be understood that other attachment mechanisms can be used such as those described herein including, but not limited to, welding and adhesives.

With continued reference to the prosthesis 6600 illustrated in FIGS. 120 and 121, the valve body 6640 preferably includes a plurality of valve leaflets 6642. The valve body 6640 can include one or more intermediate components such as first intermediate component 6644 and second intermediate component 6646. The valve leaflet 6642 can be similar to leaflet 1110 illustrated in FIG. 19A which includes a first edge 1112, a second edge 1114, and tabs 1116. The plurality of valve leaflets 6642 can function in a manner similar to the native mitral valve, or to any other valves in the vascular system as desired. As shown in the illustrated embodiment, a portion of the valve body is attached to the supplemental frame 6622b.

The skirt 6660 can be loosely attached to the exterior of the frame 6620. The skirt 6660 can be formed from one or more components. As shown, the skirt 6660 can extend from an upper region of the frame 6620 towards a lower region of the frame 6620. An upper portion of the skirt 6660 can extend between the frame body 6622a and the first anchoring feature 6626. The lower portion of the skirt 6660 can extend distally towards the second anchoring feature 6632. As shown, the lower portion of the skirt 6660 can extend around anchors of the second anchoring feature 6632 can form a flange 6662. This can beneficially enhance sealing along the lower region of the frame 6600. The skirt 260 can be formed from a variety of materials, such as a knit polyester (e.g., polyethylene terephthalate (PET)) or any other biocompatible material.

As shown in the illustrated embodiment, the skirt 6660 can be attached at or proximate the upper end of the frame 6620 and at or proximate the lower end of the frame 6620. The skirt 6660 can be formed with sufficient material such that a portion of the skirt 6660 positioned around a middle portion of the frame 6620 is loose relative to an exterior of the frame 6620.

Figure 122:
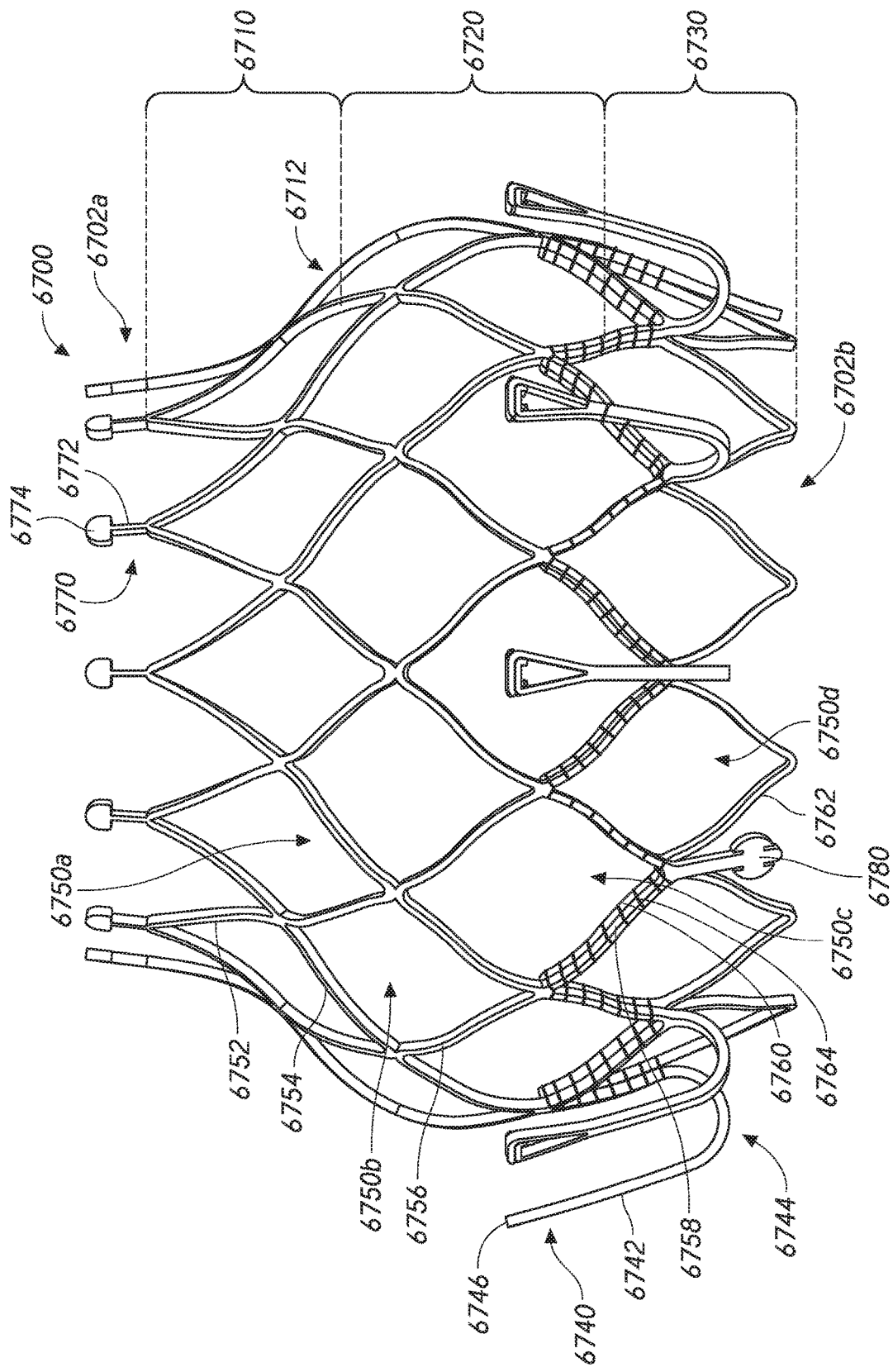
Figure 123:
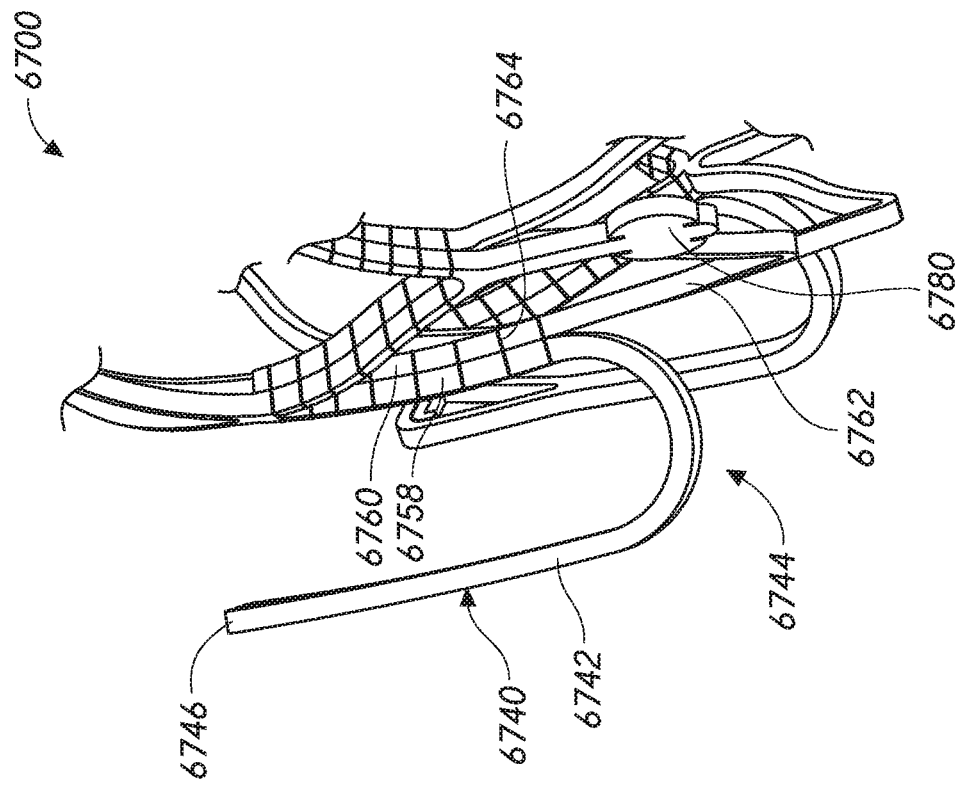

With reference next to the frame 6700 illustrated in FIGS. 122 and 123, the frame 6700 is shown in an expanded configuration. The frame 6700 can include a frame body 6702a and a supplemental frame 6702b. The frame 6700 can have an upper region 6710, an intermediate region 6720, and a lower region 6730. A longitudinal axis of the frame 6700 may be defined as the central axis that extends through the center of the frame 6700 between the upper and lower ends of the frame 6700. In some embodiments, the frame 6700 may be oriented such that the upper region 6710 is a proximal portion and the lower region 6730 is a distal portion. The frame 6700 can include an anchoring feature 6740 positioned at the intermediate region 6720 and/or lower region 6730. In some embodiments, the frame 6700 may be oriented such that the anchoring feature 6740 is a distal anchoring feature. It is to be understood that the frame 6700 can include other anchoring features. For example, the frame 6700 can include an anchoring feature positioned above the anchoring feature 6740 which can be a proximal anchoring feature.

Anchoring feature 6740 can contact or engage a native valve annulus, such as the native mitral valve annulus, tissue beyond the native valve annulus, native leaflets, and/or other tissue at or around the implantation location during one or more phases of the cardiac cycle, such as systole and/or diastole. For example, when the frame 6700 is used for a replacement mitral valve prosthesis, during at least systole, in some embodiments the anchoring feature 6740 is sized to contact or engage the native mitral valve annulus. While the anchoring feature 6740 has been illustrated as extending from between the intermediate and lower regions 6730 of the frame 6700, it is to be understood that the anchoring feature 6740 can be positioned along any other portion of the frame 6700 as desired.

As shown, the frame body 6702a and/or the supplemental frame 6702b, when in an expanded configuration such as in a fully expanded configuration, has a bulbous or slightly bulbous shape, with an intermediate region 6720 being larger than the upper region 6710 and the lower region 6730. The bulbous shape of the frame body 6702 can advantageously allow the frame body 6702 to engage a native valve annulus or other body cavity, while spacing the inlet and outlet from the heart or vessel wall. This can advantageously reduce undesired contact between the prosthesis and the heart or vessel, such as the atrial and ventricular walls of the heart.

As shown in the illustrated embodiment, the intermediate region 6720 is preferably cylindrical or generally cylindrical in shape such that a diameter of an upper end of the intermediate region 6720 and/or a diameter of a lower end of the intermediate region 6720 is equal or generally equal to the diameter of a middle portion of the intermediate region 320. The general uniformity of the diameter of the intermediate region 6720 from the upper end to the lower end, in conjunction with the axial dimension between the upper end and the lower end (i.e., the "height" of the intermediate region 6720), provides for a significantly large circumferential area upon which a native valve annulus, or other body cavity, can be engaged. Although the frame body 6702, such as the intermediate portion 6702, has been described and illustrated as being cylindrical, it is to be understood that all or a portion of the frame body 6702 can be have a non-circular cross-section such as, but not limited to, a D-shape, an oval or an otherwise ovoid cross-sectional shape.

In some embodiments, the diameter of the upper end of the intermediate region 6720 and the lower end of the intermediate region 6720 can be about the same. However, it is to be understood that the diameter of the upper end of the intermediate region 6720 and the lower end of the intermediate region 6720 can differ.

With continued reference to the frame 6700 illustrated in FIGS. 122 and 123, at the juncture between the intermediate region 6720 and the upper region 6710, the frame body 6702a can include a bend 6712. The bend 6712 can be a radially inward bend towards the longitudinal axis of the frame 6700 such that a portion of the upper region 6710, extending upwardly from the beginning of bend 6712 adjacent the intermediate region 6720, is inclined or curved towards the longitudinal axis of the frame 6700. The radially inward inclination of the upper region 6710 can allow for a substantial decrease in radial dimension over a relatively small axial dimension. The greater the degree of inclination, the greater the decrease in radial dimension per increase in axial dimension. This can beneficially provide a relatively compact form factor for the frame 6700.

As shown in the illustrated embodiment, the diameter of the upper end of the upper region 6710 can be less than the diameter of the lower end of the lower region 6730. However, it should be understood that the diameter of the upper end of the upper region 6710 can be the same as, or greater than, the diameter of the lower end of the lower region 6730. Moreover, in some embodiments, the frame 6700 may not have a bulbous portion, and can have substantially the same outer dimension along its entire length (e.g., cylindrical).

With continued reference to the frame 6700 illustrated in FIGS. 122 and 123, the frame body 6702a can include a plurality of struts with at least some of the struts forming cells 6750a, 6750b, 6750c. The supplemental frame 6702b can include a plurality of struts with at least some of the struts forming cells 6750d. Any number of configurations of struts can be used, such as rings of undulating struts shown forming ellipses, ovals, rounded polygons, and teardrops, but also chevrons, diamonds, curves, and various other shapes. As shown in the illustrated embodiment, the frame body 6702a and the supplemental frame 6702b such that the frame 6700 can include four rows of cells 6750a, 6750b, 6750c, 6750d. However, it is to be understood that the frame body 6702a and/or supplemental frame 6702b can include a fewer or greater number of rows of cells. Moreover, it is to be understood that the frame body 6702a and supplemental frame 6702b can be arranged with cells overlapping each other such that the frame 6700 has fewer rows of cells. For example, cells 6750c and cells 6750d can overlap such that the frame 6700 has three rows of cells.

The cell 6750a can be formed via a combination of struts. As shown in the illustrated embodiment, the upper portion of cells 6750a can be formed from a set of circumferentially-expansible struts 6752 having a zig-zag or undulating shape forming a repeating "V" shape. The circumferentially-expansible struts 6752 can be inclined or curved towards a longitudinal axis of the frame 6700 such that an upper portion of the struts 6752 are positioned closer to the longitudinal axis of the frame 6700 than the lower portion of the struts 6752.

The lower portion of cells 6750a can be formed from a set of circumferentially-expansible struts 6754 having a zig-zag or undulating shape forming a repeating "V" shape. As shown in the illustrated embodiment, the struts 6754 can incorporate the bend 6712 such that an upper portion of the struts 6754 are inclined or curved towards the longitudinal axis of the frame 6700 and the lower portion of the struts 6754 extend in a direction generally parallel to the longitudinal axis of the frame 6700.

The upper portion of cells 6750b can be formed from the set of circumferentially-expansible struts 6754 such that cells 6750b share struts with cells 6750a. The lower portion of cells 6750b can be formed from a set of circumferentially-expansible struts 6756. Circumferentially-expansible struts 6756 can extend generally in a downward direction. As shown in the illustrated embodiment, circumferentially-expansible struts 6756 can form a generally cylindrical portion of the frame 6700 with the upper portion of the struts 6756 having a radial dimension which is about the same as the radial dimension as the lower portion of the struts 6756.

The upper portion of cells 6750c can be formed from the set of circumferentially-expansible struts 6756 such that cells 6750c share struts with cells 6750b. The lower portion of cells 6750c can be formed from a set of circumferentially-expansible struts 6758 having a zig-zag or undulating shape forming a repeating "V" shape. Circumferentially-expansible struts 6758 can extend generally in a downward direction. As shown in the illustrated embodiment, circumferentially-expansible struts 6758 can be slightly inclined or curved towards the longitudinal axis of the frame 6700.

The upper portion of cells 6750d can be formed from the set of circumferentially-expansible struts 6760 having a zig-zag or undulating shape forming a repeating "V" shape. The lower portion of cells 6750d can be formed from a set of circumferentially-expansible struts 6762 having a zig-zag or undulating shape forming a repeating "V" shape. Circumferentially-expansible struts 6762 can extend generally in a downward direction. As shown in the illustrated embodiment, circumferentially-expansible struts 6762 can be slightly inclined or curved towards the longitudinal axis of the frame 6700.

As shown in the illustrated embodiment, struts 6752, 6754, 6756, 6758 can be monolithically or unitarily formed and define at least a portion of the frame body 6702a. Struts 6760, 6762 can be monolithically or unitarily formed and define at least a portion of the supplemental frame 6702b. The struts 6758 of the frame body 6702a and the struts 6760 of the supplemental frame 6702b can have the same general size and shape. Accordingly, when aligned together, the struts 6758, 6760 can form a "combined" strut with the combined wall thicknesses of the struts 6758, 6760. This can beneficially enhance the structural rigidity of the frame 6700 along the combined strut formed by struts 6758, 6760. The struts 6758, 6760 can be attached using sutures 6764 as shown; however, it is to be understood that the struts 6758, 6760 can be attached using any of the fasteners and techniques described herein, such as via welding and/or adhesives.

While the cells 6750a, 6750b, 6750c, 6750d are generally diamond-shaped, it is to be understood that some or all of the struts 6752, 6754, 6756, 6758, 6760, 6762 may not form entirely straight segments. The struts 6752, 6754, 6756, 6758, 6760, 6762 can include some curvature such that the upper and/or lower apices are curved. For example, one or more struts can incorporate curvature such that the apices are generally "onion" shaped.

As shown in the illustrated embodiment, there can be a row of twelve cells 6750a, a row of twelve cells 6750b, a row of twelve cells 6750c, and a row of twelve cells 6750d. While each of the cells 6750a, 6750b, 6750c, 6750d are shown as having the same shape as other cells 6750a, 6750b, 6750c, 6750d of the same row, it is to be understood that the shapes of cells 6750a, 6750b, 6750c, 6750d within a row can differ. Moreover, it is to be understood that any number of rows of cells can be used and any number of cells may be contained in the rows. In some embodiments, the number of cells can correspond to the number of anchors or anchor tips forming the first anchoring feature and/or the number of anchors or anchor tips forming the second anchoring feature. As shown, the number of cells in each row of cells 6750a, 6750b, 6750c, 6750d have a 4:3 correspondence with the number of anchors in the anchoring feature 6740 (i.e., twelve cells in each row of cells 6750a, 6750b, 6750c, 6750d and nine anchors for the anchoring feature 6740). It is to be understood that other ratios of numbers of cells per row to number of anchors per anchoring feature can be used such as, but not limited to, 1:1, 2:1, 3:1, 4:1, 5:1, 6:1, and other ratios as desired.

With continued reference to the frame 6700 illustrated in FIGS. 122 and 123, the geometry of cells 6750a, 6750b, 6750c, 6750d can allow the cells 6750a, 6750b, 6750c, 6750d to foreshorten as the frame 6700 is expanded. As such, one or more of cells 6750a, 6750b, 6750c, 6750d can allow the frame 6700 to foreshorten as the frame 6700 is expanded. Foreshortening of the frame 6700 can be used to secure the prosthesis to intralumenal tissue in a body cavity, for example tissue at or adjacent a native valve, such as a native valve annulus and/or leaflets.

Anchoring feature 6740 can include one or more anchors. For example, as shown in the illustrated embodiment, the anchoring feature 6740 can include nine anchors. In some implementations, the use of fewer anchors on anchoring feature 6740 can provide multiple advantages. Use of fewer anchors can enhance imaging of the frame 6700 during the delivery process which can beneficially facilitate implantation of the frame 6700. For example, this can reduce the amount of material, such as metal, and potential interference when used with echocardiography or other types of imaging techniques. Moreover, implantation can be facilitated since fewer anchors are to be positioned. In some implementations, the use of fewer anchors can reduce the amount of force applied on the delivery system. For example, in embodiments where the anchors expand radially outward when the frame 6700 transitions from a collapsed configuration to an expanded configuration, fewer anchors would impart a radially outward force on a component (e.g., a sheath) of the delivery system.

Each anchor can include one or more struts 6742 extending from an intermediate region 6720 and/or lower region 6730 of the frame 6700. As shown, struts 6752 extend from a lower intersection of two segments of the cell 6750c, for example, from the lowermost corner of the cells 6750c at the apex formed by struts 6758. However, it is to be understood that the struts 6752 can extend from other portions of the frame 6700, such as other portions of the cell 6750c and/or other portions of the cells 6750d. As shown in the illustrated embodiment, the anchoring feature 6740 can be monolithically or unitarily formed with the frame body 6702a. This can beneficially enhance structural stability of the anchoring feature 6740 as the anchoring feature 6740 is formed on a primary portion of the frame 6700.

As shown, the struts 6742 extend generally downwardly from the frame 6700. The struts 6742 can incorporate a bend 6744 to orient the strut 6742 such that it extends radially outward away from the longitudinal axis of the frame 300 and/or generally upwardly. As shown in the illustrated embodiment, the bend 6744 can be generally semi-circular or semi-elliptical which can provide a space for the distal ends of the native valve leaflets to be stored. The anchors may then extend in a linear segment radially outwardly and upwardly. As shown in the illustrated embodiment, the bend 6744 can orient the strut 6742 such that it extends generally parallel to the longitudinal axis of the frame 6700. For example, the tip 6746 of anchoring feature 6740 can extend generally parallel to the longitudinal axis of the frame 6700. The tips 6746 of the anchoring feature 6740 can end after extending approximately above the base or connection point of the anchoring feature 6740 to the frame body 6702a. In some embodiments, the tips 6746 of the anchoring feature 6740 can end after extending up to, or slightly past, the lower end of the intermediate region 6720 of the frame 6700. As shown in the illustrated embodiment, the tips 6746 can include multiple prongs which can be movable relative to each other. For example, the geometry of tips 6746 can be similar to that of anchoring feature 5600 discussed in connection with FIGS. 93 and 94.

While the bend 6744 orients the tip 6746 such that it extends generally parallel to a longitudinal axis of the frame 6700, it is to be understood that the bend 6744 can orient the struts 6742, such as the tips 6746, in other directions. For example, the bend 6746 can orient the struts 6742, such as the tips 6746, such that the they extend radially outward away from the longitudinal axis of the frame 6700, such that struts 6742 extends radially inward towards the longitudinal axis of the frame 6700, or such that a portion of struts 6742 extends radially outward away from the longitudinal axis of the frame 6700 and another portion of struts 6742. In some embodiments, the bend 6744 can orient the struts 6742, such as the tips 6746, such that they extend generally perpendicular to a longitudinal axis of the frame 6700 such as is shown with frame 400 illustrated in FIG. 6.

As shown in the illustrated embodiment, struts 6742 of the anchoring feature 6740 are positioned further radially outward from a longitudinal axis of the frame 6700 as compared to struts 6762 of the supplement frame 6702b. In other words, the struts 6742 and the struts 6762 are in different circumferential planes. When the frame 6700 transitions from the expanded configuration to a collapsed or crimped configuration for delivery, interference between the struts 6742 and the struts 6762 is reduced or eliminated. The removal or "un-nesting" of struts 6742 from the circumferential plane of struts 6762 effectively reduces the contribution to the circumference of material that does not circumferentially expand or crimp (e.g., the struts 6742). This can beneficially reduce stresses and strains imposed on the struts 6742, 6762 as compared to implementations in which the struts 6742, 6762 are within the same circumferential plane. In many instances, this can allow for the struts 6762 to compress further thereby allowing the frame 6700 to take on a smaller crimp profile when in the collapsed or crimped configuration.

Preferably, the anchoring feature 6740 is positioned or extend generally radially outwardly from the frame 300 so that the anchor tips 6746 are generally spaced away or radially outward from the rest of the frame body 6702*a* and from where the base of the anchors connect to the frame body 302. For example, the anchor tips 6746 may be located radially outward from the intermediate region 67720 of the frame 6700. Individual anchors may extend radially outwardly from the frame at an anchor base and terminate at an anchor tip. The individual anchors can be connected to the frame at one of many different locations including apices, junctions, other parts of struts, etc. Moreover, the anchors forming the anchoring feature 670 can comprise first, second, third, or more spaced apart bending stages along the length of each anchor. Further details that may be incorporated and/or interchanged with the features described herein are disclosed in U.S. Publication Nos. 2014/0277422, 2014/0277427, 2014/0277390, and 2015/0328000, which have been incorporated by reference herein.

Covers and/or cushions (see, for example, covers and/or cushions 720, 770 illustrated in FIGS. 10-13) may be used to surround or partially surround at least a portion of the anchoring feature 6740, such as the tips or ends 6746 and/or the struts to which the tips or ends 6746 are attached. The covers and/or cushions can be similar to those described in U.S. Publication No. 2015/032800, which has been incorporated by reference in its entirety. In some embodiments, the covers and/or cushions can either fit snuggly around the tips 6746 or can have extra padding so that the covers extend radially away from the frame 6700. In some embodiments, all of the anchors of the anchoring feature 6740 can have the covers and/or cushions with some of the anchors having less cushioning than others. In some embodiments, all of the anchors of the anchoring feature 6740 can have the padded covers. In some embodiments, all of the anchors of the anchoring feature 6740 can have the snuggly fitting cushions. In some embodiments, not all of all of the anchors of the second anchoring feature 6740 can have covers.

With continued reference to the frame 6700 illustrated in FIGS. 122 and 123, the frame 6700 can include a set of locking tabs 6770 extending from the upper region 6710 of the frame 6700. As shown, the frame 6700 includes twelve locking tabs 6770, however, it is to be understood that a greater number or lesser number of locking tabs can be used. The locking tabs 6770 can extend generally upwardly from the upper region 6710 in a direction generally aligned with the longitudinal axis of the frame 6700.

At an upper end of the strut 6772, the locking tab 6770 can include an enlarged head 6774. As shown, the enlarged head 6774 has a semi-circular or semi-elliptical shape forming a "mushroom" shape with the strut 6772. The locking tab 6770 can be advantageously used with multiple types of delivery systems. For example, the shape of the struts 6772 and the enlarged head 6774 can be used to secure the frame 6700 to a "slot" based delivery system. It is to be understood that the locking tab 6770 can include an eyelet at other locations, or can include more than a single eyelet. The eyelets can be used to secure the frame 6700 to a "tether" based delivery system such as those which utilize sutures, wires, or fingers to control delivery of the frame 6700. This can advantageously facilitate recapture and repositioning of the frame 6700 in situ. In some embodiments, the frame 6700 can be used with the delivery systems described in U.S. Pat. Nos. 8,414,644 and 8,652,203 and U.S. Publication Nos. 2015/0238315, the entireties of each of which are hereby incorporated by reference and made a part of this specification.

The frame 6700 can include one or more posts 6780. The posts 6780 can facilitate attachment of a valve body to the frame 6700. In some implementations, commissures of the valve body can be attached to the posts 6780. The commissures of the valve body can be attached to the posts 6780 via sutures and/or an intermediate component such as those described herein. For example, the commissures of the leaflets of the valve body can be indirectly coupled to the posts 6780 via an intermediate component which is sutured to and/or extends around the posts 6780.

As shown in the illustrated embodiment, the posts 6780 can extend distally from a lower portion of the frame body 6702*a*, such as the apices of cells 6750*c*. Extension of the posts 6780 from the frame body 6702*a* can reduce relative movement between the posts 6780 and the overall frame 6700. This can beneficially enhance the stability of a valve body positioned within the frame 6700. Moreover, distal extension of the posts 6780 can allow a longer valve body to be utilized within the frame 6700.

The number of posts 6780 can match the number of commissures of the valve body. For example, in implementations where a valve body having three leaflets is used, the frame 6700 can include three posts 6780 to which each commissure of the valve body can be attached. The posts 6780 can be generally equally spaced around the periphery of the frame 6700. Although the posts 6780 are positioned on the frame body 6702*a*, it is to be understood that the posts 6780 can extend from the supplemental frame 6702*b*. The posts 6780 can extend between the cells 6750*d* and/or can extend from a distal portion of cells 6750*d* (e.g., distal apices). In some embodiments, the posts 6780 can be positioned radially inwardly relative to the struts 6762 of the supplemental frame 6702*b*. For example, the posts 6780 can extend from an inner surface of the supplemental frame 6702*b*. In some embodiments, the posts 6780 can be positioned radially outwardly relative to the struts 6758 of the frame body 6702*a*. For example, the posts 6780 can extend from an outer surface of the frame body 6702*a*.

Figure 124:
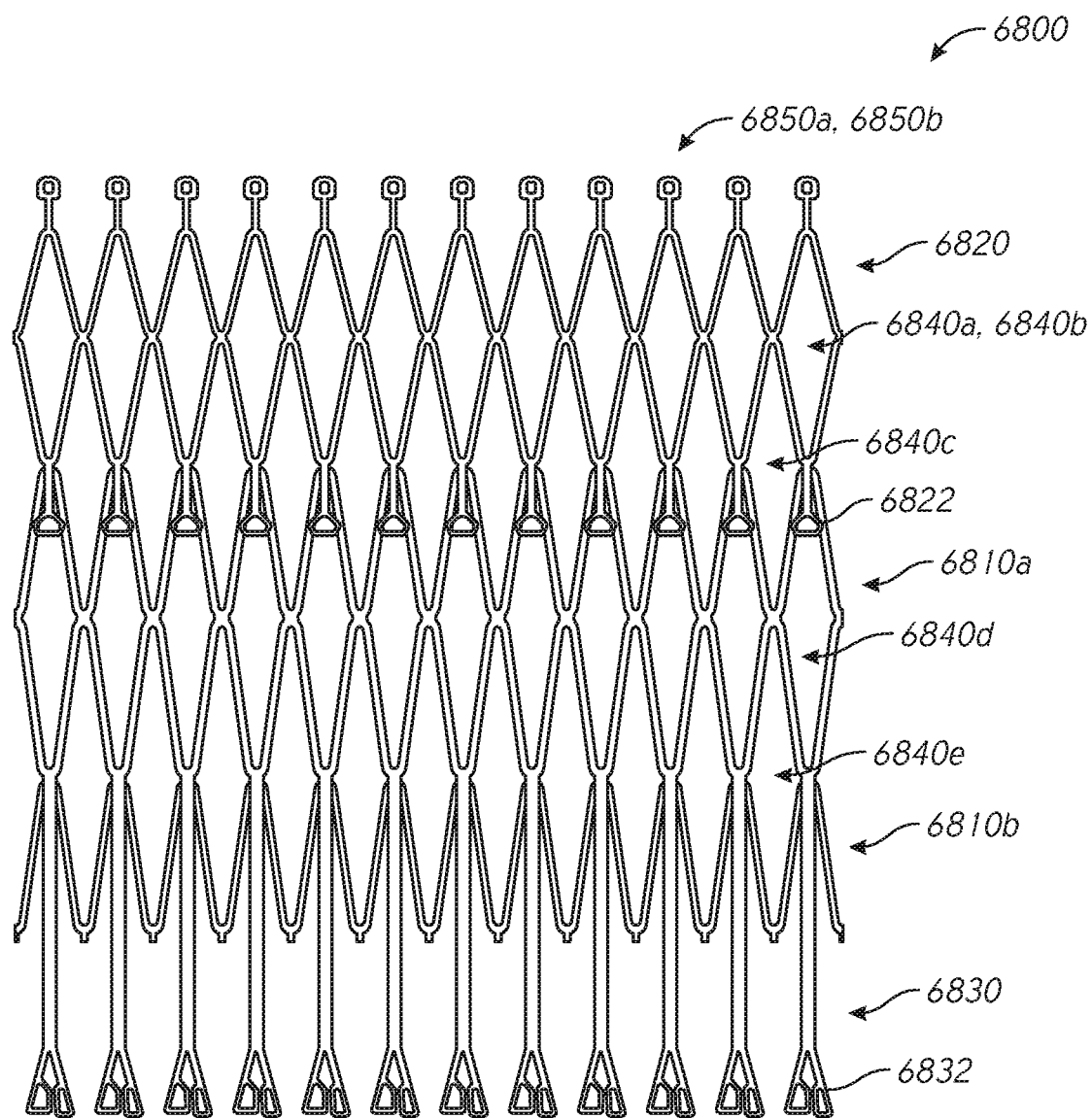
Figure 125:
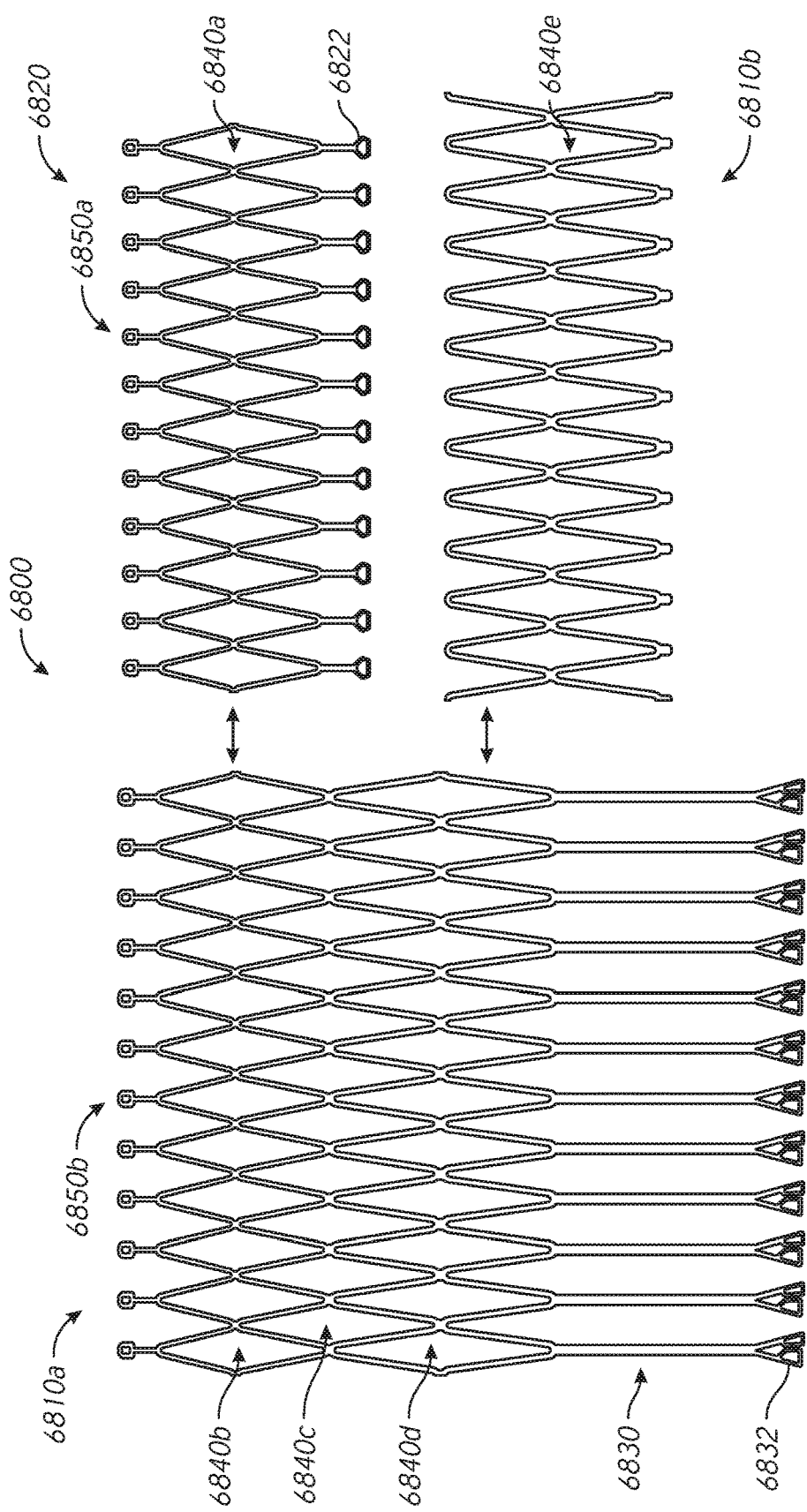

With reference next to the frame 6800 illustrated in FIGS. 124 and 125, the frame 6800 is shown as a flat pattern. The frame 6800 is shown in an assembled configuration in FIG. 124 and a disassembled configuration in FIG. 125. As shown in the illustrated embodiment, the frame 6800 can include a frame body 6810*a*, a supplemental frame 6810*b*, first anchoring feature 6820, and/or a second anchoring feature 6830. In the assembled configuration, the frame 6800 can include a first row of cells 6840*a*, 6840*b*, a second row of cells 6840*c*, a third row of cells 6840*d*, and/or a fourth row of cells 6840*e*. In some embodiments, in the assembled configuration, the frame 6800 can include a plurality of locking tabs 6850*a*, 6850*b*. The first anchoring feature 6820 can include anchors with tips 6822 having one or more eyelets. The second anchoring feature 6830 can include anchors with tips 6832. As shown in the illustrated embodiment, the tips 6832 can include multiple prongs which can be movable relative to each other. For example, the geometry of tips 6832 can be similar to that of anchoring feature 5700 discussed in connection with FIGS. 95-99 when shape-set.

One or more components of the frame 6800 can be formed separately from each other. As shown in the illustrated embodiment, the frame body 6810*a*, the supplemental frame 6810*b*, and/or the first anchoring feature 6820 can be formed separately from each other and subsequently attached. The first anchoring feature 6820 can be positioned in front of the frame body 6810*a*. The supplemental frame 6810*b* can be positioned behind the frame body 6810*a*. The frame body 6810*a*, the supplemental frame 6810*b*, and/or the first anchoring feature 6820 can be attached using any of the fasteners and techniques described herein, such as via sutures, welding, and/or adhesives.

With reference to FIG. 125, the frame body 6810*a* include one or more struts forming cells 6840*b*, 6840*c*, 6840*d* as shown in three separate rows. The one or more struts can be monolithically or unitarily formed to enhance the structural integrity of the frame body 6810*a*. The anchoring feature 6830 can be monolithically or unitarily formed with the frame body 6810*a*. The locking tabs 6850*b* can be monolithically or unitarily formed with the frame body 6810*a*.

The supplemental frame 6810*b* can include one or more struts forming cells 6840*e* as shown in a single row. The struts forming the lower portion of the lower row of cells 6840*d* and the struts forming the upper portion of the cells 6840*e* can have the same general size and shape. Accordingly, when aligned together, these struts can form a "combined" strut with the combined wall thicknesses of the struts. This can beneficially enhance the structural rigidity of the frame 6800 along the lower portion of the frame 6800. This can be advantageous since the second anchoring feature 6830, which can be subject to significant loading during operation, can be attached to at least a portion of this combined strut.

The first anchoring feature 6820 can include one or more struts forming cells 6840*a* as shown in a single row. The struts forming the upper portion of the upper row of cells 6840*b* and the struts forming the upper portion of the cells 6840*a* can have the same general size and shape. Accordingly, when aligned together, these struts can form a "combined" strut with the combined wall thicknesses of the struts. This can beneficially enhance the structural rigidity of the frame 6800 along the lower portion of the frame 6800. This can be advantageous since the tips 6822 of first anchoring feature 6820, which can be subject to loading during operation, can be attached to at least a portion of this combined strut.

The first anchoring feature 6820 can include a locking tab 6850*a*. The locking tabs 6850*a* of the frame body 6810*a* and the locking tabs 6850*b* of the first anchoring feature 6810*b* can have the same general size and shape. Accordingly, when aligned together, "combined" locking tabs 6850*a*, 6850*b* can have a larger wall thickness. This can beneficially enhance the structural rigidity of the locking tabs 6850*a*, 6850*b*. This can be advantageous since the tips 6850*a*, 6850*b* can be subject to loading during delivery.

While the cells 6840*a*, 6840*b*, 6840*c*, 6840*d*, 6840*e* are generally diamond-shaped, it is to be understood that some or all of the struts forming cells 6840*a*, 6840*b*, 6840*c*, 6840*d*, 6840*e* may not be entirely straight segments. The struts forming cells 6840*a*, 6840*b*, 6840*c*, 6840*d*, 6840*e* can include some curvature such that the upper and/or lower apices are curved. For example, one or more struts can incorporate curvature such that the apices are generally "onion" shaped.

As shown in the illustrated embodiment, each row of cells 6840*a*, 6840*b*, 6840*c*, 6840*d*, 6840*e* can include twelve cells. While each of the cells 6840*a*, 6840*b*, 6840*c*, 6840*d*, 6840*e* are shown as having the same shape as other cells 6840*a*, 6840*b*, 6840*c*, 6840*d*, 6840*e* of the same row, it is to be understood that the shapes of cells 6840*a*, 6840*b*, 6840*c*, 6840*d*, 6840*e* within a row can differ. Moreover, it is to be understood that any number of rows of cells can be used and any number of cells may be contained in the rows. For example, some rows of cells may have twelve cells whereas other rows of cells may have six cells.

Figure 126:
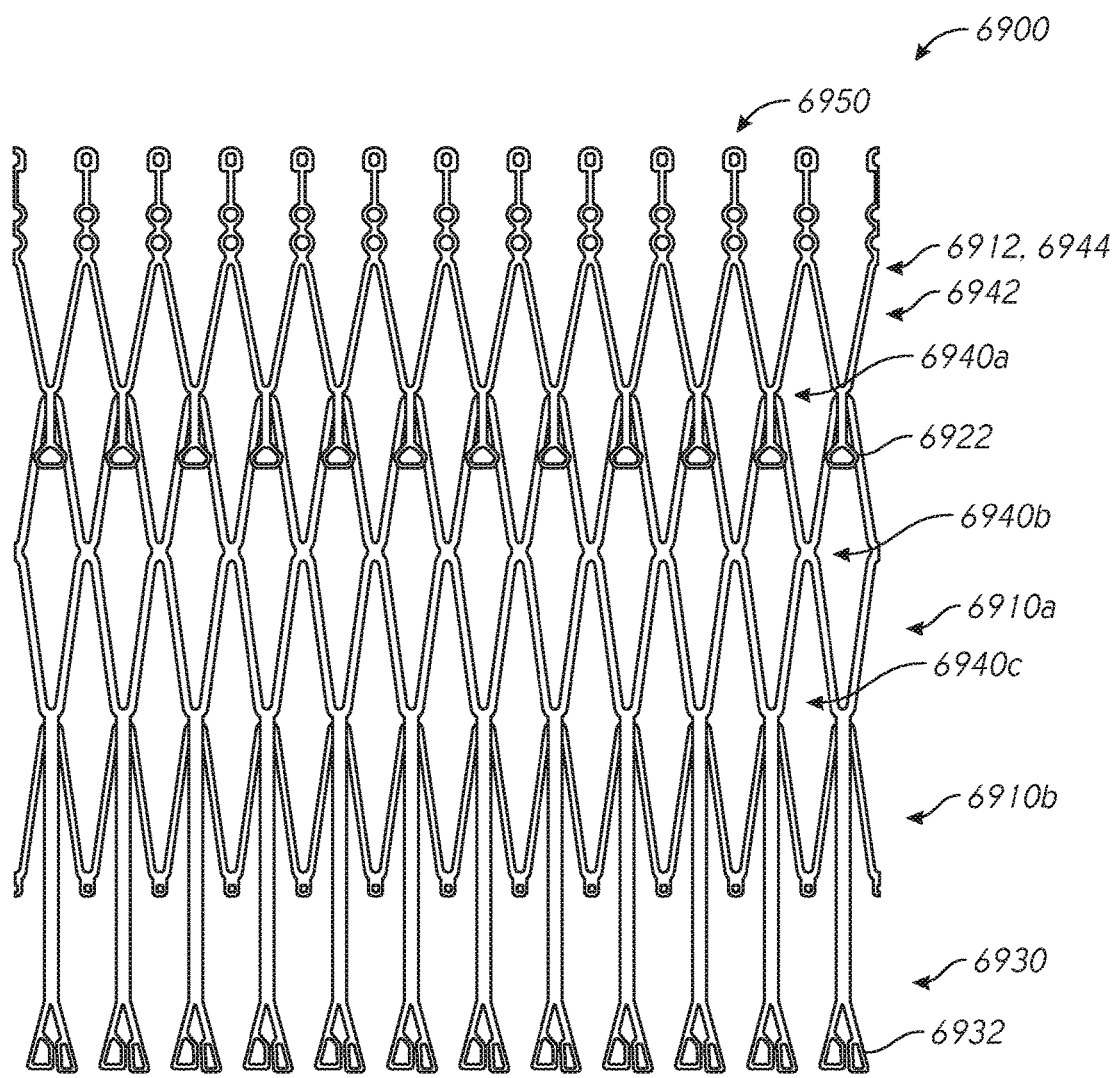
Figure 127:
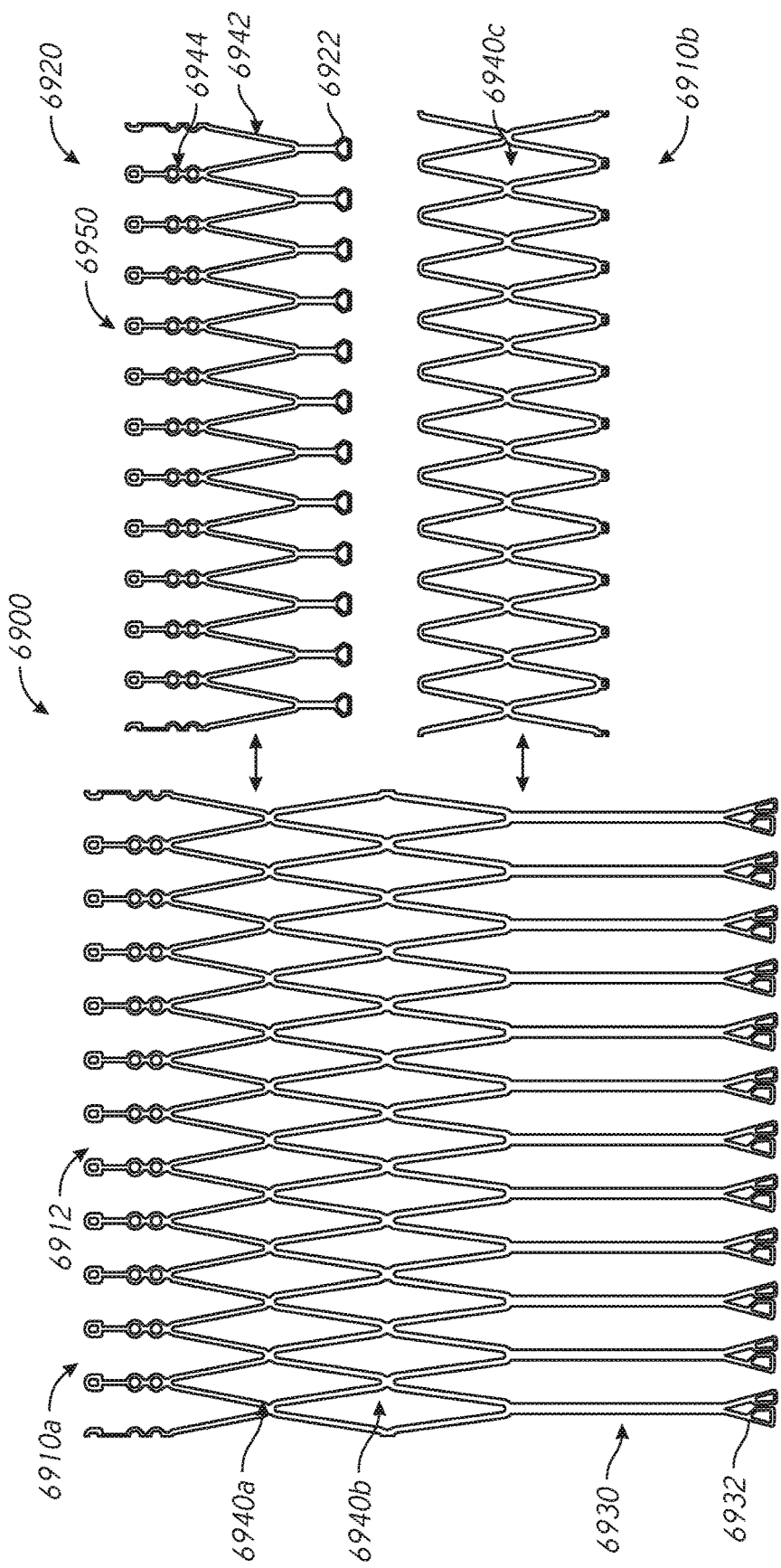

With reference next to the frame 6900 illustrated in FIGS. 126 and 127, the frame 6900 is shown as a flat pattern. The frame 6900 is shown in an assembled configuration in FIG. 126 and a disassembled configuration in FIG. 127. As shown in the illustrated embodiment, the frame 6900 can include a frame body 6910*a*, a supplemental frame 6910*b*, first anchoring feature 6920, and/or a second anchoring feature 6930. In the assembled configuration, the frame 6900 can include a first row of cells 6940*a*, a second row of cells 6940*b*, and/or a third row of cells 6940*c*. In some embodiments, in the assembled configuration, the frame 6900 can include a plurality of locking tabs 6950*a*, 6950*b*. The first anchoring feature 6920 can include anchors with tips 6922 having one or more eyelets. The second anchoring feature 6930 can include anchors with tips 6932.

As shown in the illustrated embodiment, the frame body 6910*a*, the supplemental frame 6910*b*, and/or the first anchoring feature 6920 can be formed separately from each other and subsequently attached. The first anchoring feature 6920 can be positioned in front of the frame body 6910*a*. The supplemental frame 6910*b* can be positioned behind the frame body 6910*a*. The frame body 6910*a*, the supplemental frame 6910*b*, and/or the first anchoring feature 6920 can be attached using any of the fasteners and techniques described herein, such as via sutures, welding, and/or adhesives.

With reference to FIG. 127, the frame body 6910*a* include one or more struts forming cells 6940*a*, 6940*b* as shown in two separate rows. The one or more struts can be monolithically or unitarily formed to enhance the structural integrity of the frame body 6910*a*. The anchoring feature 6930 can be monolithically or unitarily formed with the frame body 6910*a*. The frame body 6910*a* can include one or more eyelets 6912. The eyelets 6912 can be utilized to attach components of the replacement valve, such as a valve skirt, to the frame body 6910*a*. In some embodiments, the eyelets 6912 can be used to attach the first anchoring feature 6920 to the frame body 6910*a*.

The supplemental frame 6910*b* can include one or more struts forming cells 6940*c* as shown in a single row. The struts forming the lower portion of the lower row of cells 6940*c* and the struts forming the upper portion of the cells 6940*b* can have the same general size and shape. Accordingly, when aligned together, these struts can form a "combined" strut with the combined wall thicknesses of the struts.

The first anchoring feature 6920 can include one or more struts 6942. The struts 6942 and the struts forming the upper portion of the cells 6940*a* can have the same general size and shape. Accordingly, when aligned together, these struts can form a "combined" strut with the combined wall thicknesses of the struts. The first anchoring feature 6920 can include locking tabs 6950. As shown in the illustrated embodiment, the first anchoring feature 6920 can include one or more eyelets 6944. The eyelets 6944 of the first anchoring feature 6920 can be aligned with the eyelets 6912 of the frame body 6910a to facilitate securement of the first anchoring feature 6920 to the frame body 6910a by allowing sutures to be passed therethrough. Use of two eyelets 6912, 6944 on each of the frame body 6910a and the first anchoring feature 6920 can enhance securement. For example, a cloth or another intermediate, buffer material can be positioned between the eyelets 6912, 6944. A suture can be passed through both sets of eyelets using a "FIG. 8" suture technique. In some embodiments, the eyelets 6912, 6944 and/or the space between the eyelets 6912, 6944 can be wrapped with a suture or a sleeve to further enhance securement.

While the cells 6940a, 6940b, 6940c are generally diamond-shaped, it is to be understood that some or all of the struts forming cells 6940a, 6940b, 6940c may not be entirely straight segments. The struts forming cells 6940a, 6940b, 6940c can include some curvature such that the upper and/or lower apices are curved. For example, one or more struts can incorporate curvature such that the apices are generally "onion" shaped.

As shown in the illustrated embodiment, each row of cells 6940a, 6940b, 6940c can include twelve cells. While each of the cells 6940a, 6940b, 6940c are shown as having the same shape as other cells 6940a, 6940b, 6940c of the same row, it is to be understood that the shapes of cells 6940a, 6940b, 6940c within a row can differ. Moreover, it is to be understood that any number of rows of cells can be used and any number of cells may be contained in the rows. For example, some rows of cells may have twelve cells whereas other rows of cells may have six cells.

Figure 128:
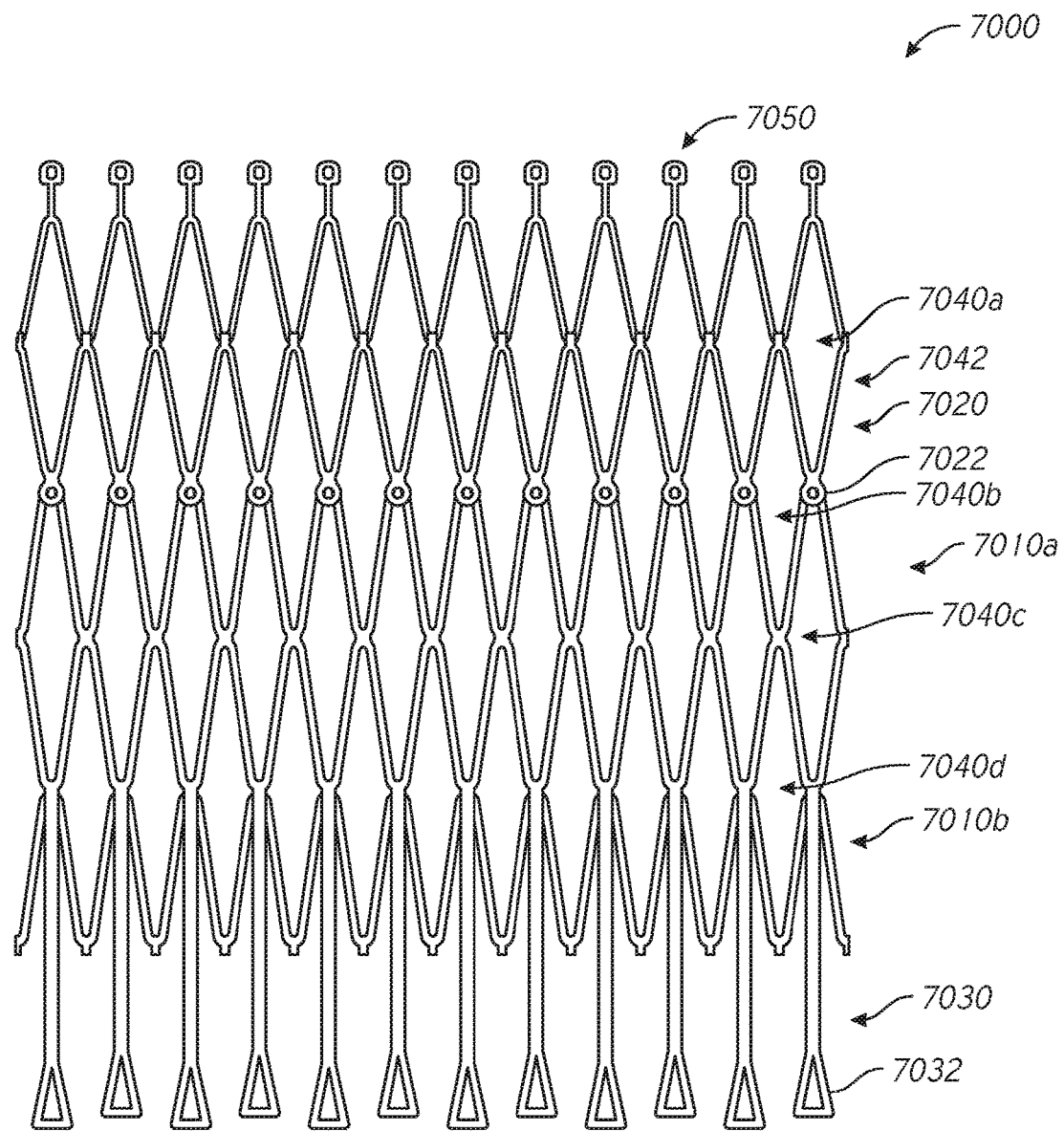
Figure 129:
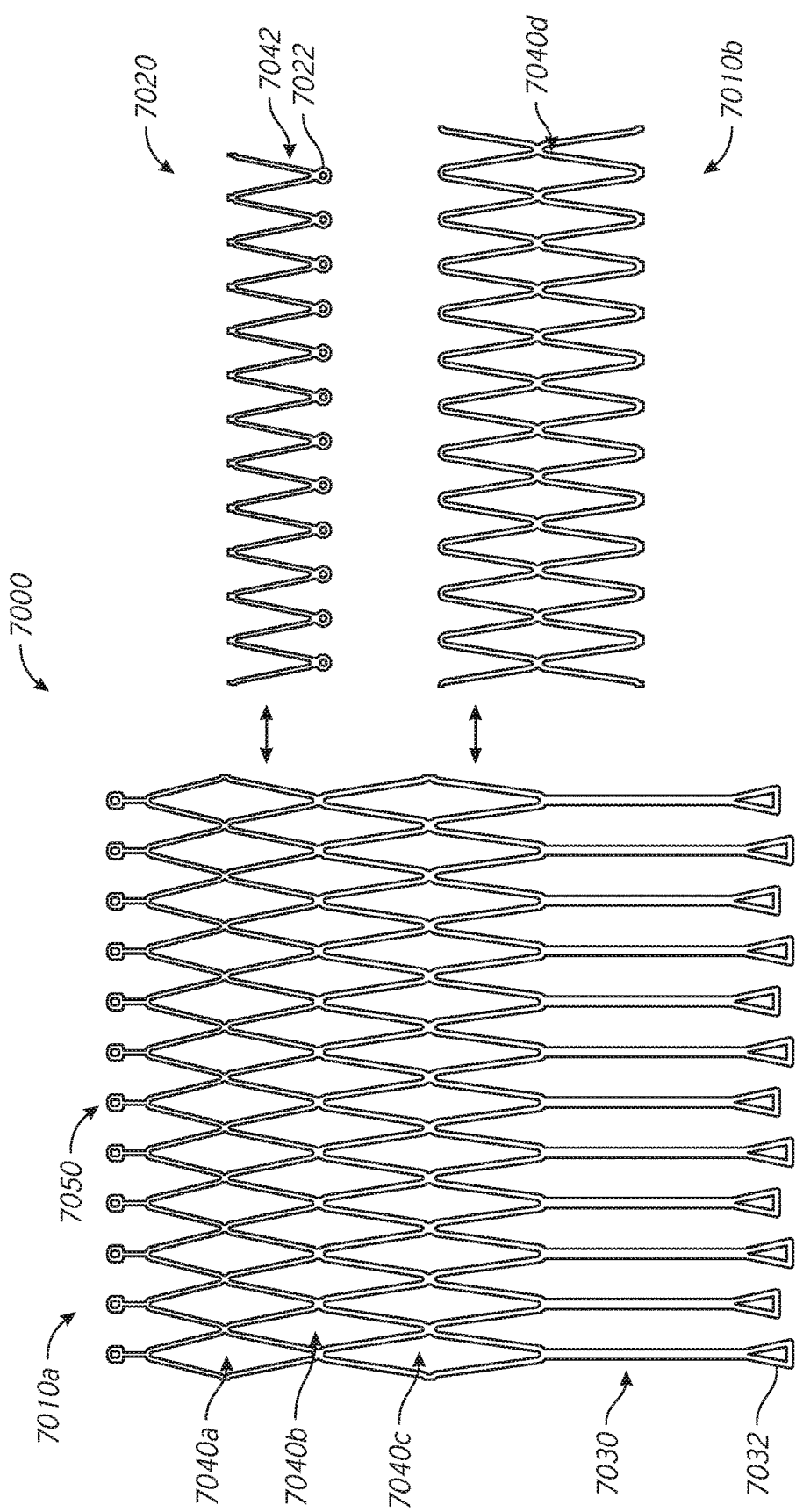
Figure 130:
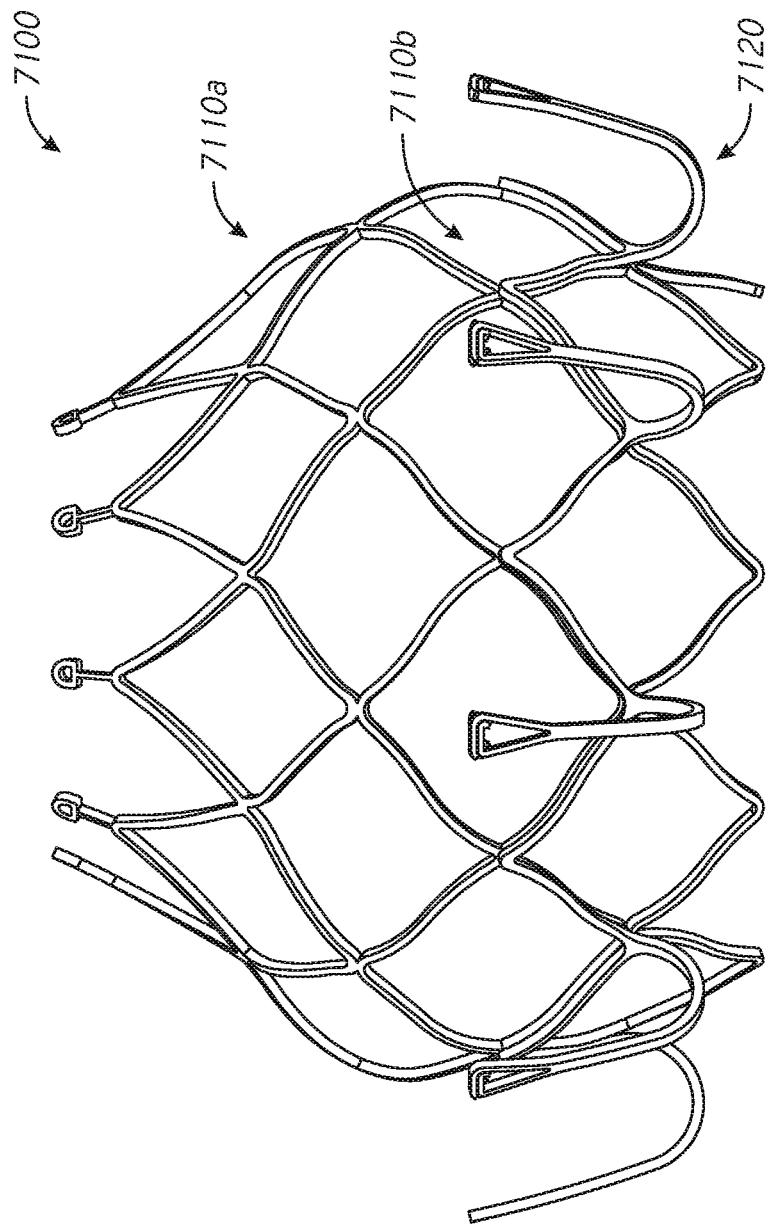

With reference next to the frame 7000 illustrated in FIGS. 128 and 129, the frame 7000 is shown as a flat pattern. The frame 7000 is shown in an assembled configuration in FIG. 128 and a disassembled configuration in FIG. 129. As shown in the illustrated embodiment, the frame 7000 can include a frame body 7010a, a supplemental frame 7010b, a first anchoring feature 7020, and/or a second anchoring feature 7030. In the assembled configuration, the frame 7000 can include a first row of cells 7040a, a second row of cells 7040b, a third row of cells 7040c, and/or a fourth row of cells 7040d. In some embodiments, in the assembled configuration, the frame 7000 can include a plurality of locking tabs 7050. The first anchoring feature 7020 can include anchors with tips 7022 having one or more eyelets. The second anchoring feature 7030 can include anchors with tips 7032.

As shown in the illustrated embodiment, the frame body 7010a, the supplemental frame 7010b, and/or the first anchoring feature 7020 can be formed separately from each other and subsequently attached. The first anchoring feature 7020 can be positioned in front of the frame body 7010a. The supplemental frame 7010b can be positioned behind the frame body 7010a. The frame body 7010a, the supplemental frame 7010b, and/or the first anchoring feature 7020 can be attached using any of the fasteners and techniques described herein, such as via sutures, welding, and/or adhesives.

With reference to FIG. 129, the frame body 7010a include one or more struts forming cells 7040a, 7040b, 7040c as shown in three separate rows. The one or more struts can be monolithically or unitarily formed to enhance the structural integrity of the frame body 7010a. The anchoring feature 7030 can be monolithically or unitarily formed with the frame body 7010a. The locking tabs 7050 can be monolithically or unitarily formed with the frame body 7010a.

The supplemental frame 7010b can include one or more struts forming cells 7040d as shown in a single row. The struts forming the lower portion of the lower row of cells 7040c and the struts forming the upper portion of the cells 7040d can have the same general size and shape. Accordingly, when aligned together, these struts can form a "combined" strut with the combined wall thicknesses of the struts.

The first anchoring feature 7020 can include one or more struts 7042. The struts forming the lower portion of the upper row of cells 7040a and the struts 7042 can have the same general size and shape. The struts 7042 can be attached to the frame body 7010a along the upper portion, such as the upper apices, of the struts 7042.

While the cells 7040a, 7040b, 7040c, 7040d are generally diamond-shaped, it is to be understood that some or all of the struts forming cells 7040a, 7040b, 7040c, 7040d may not be entirely straight segments. The struts forming cells 7040a, 7040b, 7040c, 7040d can include some curvature such that the upper and/or lower apices are curved. For example, one or more struts can incorporate curvature such that the apices are generally "onion" shaped.

As shown in the illustrated embodiment, each row of cells 7040a, 7040b, 7040c, 7040d can include twelve cells. While each of the cells 7040a, 7040b, 7040c, 7040d are shown as having the same shape as other cells 7040a, 7040b, 7040c, 7040d of the same row, it is to be understood that the shapes of cells 7040a, 7040b, 7040c, 7040d within a row can differ. Moreover, it is to be understood that any number of rows of cells can be used and any number of cells may be contained in the rows. For example, some rows of cells may have twelve cells whereas other rows of cells may have six cells.

While the embodiments described above have an anchoring feature monolithically or unitarily formed with the frame body, it is to be understood that the frame body can be formed without anchoring features. For example, with reference next to the frame 7100 illustrated in FIGS. 130 and 131, the frame 7100 is shown in an assembled configuration in FIG. 130 and a disassembled configuration in FIG. 131. As shown in the illustrated embodiment, the frame 7100 can include a frame body 7110a, a supplemental frame 7110b, and/or an anchoring feature 7120. The anchoring feature 7120 can be monolithically or unitarily formed with the supplemental frame 7110b. The supplemental frame 7110b can be attached to struts which are positioned further proximal than the distalmost struts of the frame body 7110a. As shown, the supplemental frame 7110b is positioned in front of, or radially outward of, the frame body 7110a.

Embodiments of Floating Valves

With reference to FIGS. 14-32, embodiments of prostheses 800, 900, 1000, 1200, 1300, 1400, 1500, 1600, 1700, 1800, 1900, 2000, 2100, or components thereof such as frames 810, 910, 1010, 1210, 1310, 1410, 1510, 1610, 1710, 1810, 1910, 2010, 2110 and/or valve bodies 820, 920, 1020, 1100, 1220, 1320, 1420, 1520, 1620, 1720, 1820, 1920, 2020, 2120, are illustrated. With reference first to the prosthesis 800 illustrated in FIGS. 14 and 15, the prosthesis 800 can include a frame 810 and a valve body 820. The valve body 820 can be positioned within the frame 810 and can be a replacement heart valve which includes a plurality of valve leaflets 830.

The valve leaflets 830 can include a first edge 832, second edge 834, and one or more tabs 836 for attaching the valve leaflets 830 to struts of the frame 810. The tabs 836 can form part of the valve leaflet 830 at the commissures of the valve body 820. The second edge 834 can be a freely moving edge which can allow the valve body 820 to open and close. The plurality of valve leaflets 830 can function in a manner similar to the native mitral valve, or to any other valves in the vascular system as desired. The plurality of valve leaflets 830 can open in a first position and then engage one another to close the valve in a second position. The plurality of valve leaflets 830 can be made to function as a one way valve such that flow in one direction opens the valve and flow in a second direction opposite the first direction closes the valve. For example, as shown in the illustrated embodiment, the valve body 820 can open allow blood to flow through the valve body 820 in a direction from the upper end of the frame 810 to the lower end of the frame 810. The valve body 820 can close to inhibit blood flow through the valve body 820 in a direction from the lower end of the frame 810 to the upper end of the frame 810. The valve body 820 can be constructed so as to open naturally with the beating of the heart. For example, the plurality of valve leaflets 830 can open during diastole and close during systole. The valve body 820 can replace a damaged or diseased native heart valve such as a diseased native mitral valve.

As shown in the illustrated embodiment, the valve body 820 can include one or more intermediate components 840. The one or more intermediate components 840 can be used to attach one or more of the valve leaflets 830, or a portion thereof, to the frame 810 such that the valve leaflet 830 is indirectly coupled to the frame 810 or "floats" within the frame 810. For example, as shown in FIG. 15, a first end of a first intermediate component 842 can be attached to the tabs 836 of the valve leaflet 830 and a second end of the first intermediate component 842 can be attached to the frame 810. In this manner, the tabs 836 of the valve leaflet 830 are not directly attached to the frame 810. As shown in the illustrated embodiment, the tabs 836 and/or the commissures of the valve body 820 can be spaced from an inner surface of the frame 810. In some embodiments, a first end of a second intermediate component 844 can be attached to other portions of the valve leaflet 830 such as a portion of, or the entirety of, the first edge 832 of the valve leaflet 830. A second end of the second intermediate component 844 can be attached to the frame 810. In this manner, at least a portion of, or the entirety of, the first edge 832 of the valve leaflet 830 is not directly attached to the frame 810. As shown in the illustrated embodiment, a portion of, or the entirety of, the first edge 832 of the valve leaflet 830 can be spaced from an inner surface of the frame 810. Although the two intermediate components 842, 844 were described herein for the tabs 836 and the first edge 832 respectively, it is to be understood that these two intermediate components 842, 844 can be formed as a single component or can be formed from more than two components.

The valve leaflet 830 can be attached to the intermediate component 840 using any mechanism or technique as desired such as, but not limited to, mechanical fasteners, such as sutures, staples, screws, rivets, and any other type of mechanical fastener as desired, chemical fasteners such as adhesives and any other type of chemical fastener as desired, fastening techniques such as welding, sintering, and any other type of fastening technique as desired, and/or a combination of such fasteners and techniques. In some embodiments, the valve leaflet 830 can be attached to the intermediate component 840 via an intermediate post or wireframe positioned between the leaflet 830 and the intermediate component 840. The intermediate post or wireframe can be formed from a generally rigid structure. This can beneficially enhance stability of valve leaflet 830 by serving as a generally rigid support structure for the valve leaflet 830. In some embodiments, the intermediate component 840 can be attached to the frame 810 using any mechanism or technique described above.

The intermediate component 840 can be formed from a material having a stiffness between that of the valve leaflets 830, which are relatively flexible, and the frame 810 which is generally rigid. The intermediate component 840 can serve as a dampener between the valve leaflet 830 and the frame 810 and transmit stresses from the leaflet 830 to the frame 810. For example, the intermediate component 840 can be formed from a flexible or semi-flexible material having a stiffness greater than the valve leaflet 830. In some embodiments, the intermediate component 840 can be formed from a biocompatible material such as, but not limited to, fabrics such as cloth, flexible or rigid polymers such as polyurethane and polyethylene terephthalate (PET), metals such as stainless steel, titanium, Nitinol, composites, and any other biocompatible material such as those which are wholly or substantially fluid impermeable, flexible, semi-flexible, stretchable, deformable, and/or resilient. When formed from a stiff material, such as metals or polymers, the intermediate component 840 can have a geometry which allows for less effective stiffness in certain direction than others. For example, the intermediate component 840 can be formed to have tapering cross-section and/or shapes to flex in certain directions and not in others. In some embodiments, the intermediate component 840 can be formed from a material that facilitates tissue ingrowth or formation. In this embodiment, the valve leaflets 830 can be formed from a tissue-based media such as bovine, equine and/or porcine pericardium. Vascular tissue, as well as other natural and manmade materials that are flexible and durable, may also be employed for the valve leaflets 830.

By isolating portions of the valve leaflets 830, such as the portions at the commissures or tabs 836 and/or the cusp or first edge 832, from the frame 810 with an intermediate component 840 of lesser stiffness than the frame, the stress concentrations on the valve leaflets 830 during operation of the valve body 820 can be reduced or eliminated. Such stresses can occur, for example, due to changes in blood flow during the cardiac cycle. For example, when the prosthesis 800 is positioned within a native mitral valve, such stresses can occur during systole when the valve leaflets 830 close to inhibit to restrict blood flow from the left ventricle to the left atrium. These stresses can be particularly elevated at portions of the leaflet connected to the frame 810 such as the portions at the commissures or tabs 836. This reduction of stress concentrations can beneficially increase the functional lifespan of the valve leaflet 830.

Moreover, the intermediate component 840 can beneficially allow the design of the valve leaflets 830 to be independent from the design of the frame 810 and allow for a single design of valve leaflets 830 to be applied to a wide variety of frames of different shapes and sizes. In this manner, the frame 810 can be designed in a manner that enhances anchoring or securement to a body cavity, such as a native valve annulus, and the valve leaflets 830 can be designed in a manner that enhances hemodynamic performance.

For example, valve leaflets 830 can be designed to have a small diameter to increase blood flow velocity through the valve leaflets 830. The increase in blood flow velocity, due to the reduction in diameter of the valve leaflets 830, can beneficially increase leaflet 830 activity and reduce the risk of thrombosis. The frame 810 can be designed with a large diameter to enhance anchoring or securement to a body cavity, such as a native valve annulus. The smaller diameter valve leaflets 830 can also be used to throttle flow through the prosthesis 800. Moreover, valve leaflets 830 having a smaller diameter relative beneficially allow for the frame 810 to be crimped to a smaller diameter with a reduced risk of damaging the valve leaflets 830.

With reference next to the prosthesis 900 illustrated in FIGS. 16 and 17, the prosthesis 900 can include a frame 910 and a valve body 920. As shown in the illustrated embodiment, the frame 910 can include a projection 912 which extends radially inwards. The valve body 920 can include a leaflet 930 and an intermediate component 940. The intermediate component 940 can be attached to at least a portion of leaflet 930 at a first end of the intermediate component 940. The intermediate component 940 can be attached to at least a portion of the frame 910, such as projection 912. The combination of the intermediate component 940 and the generally rigid projection 912 can be used to achieve a variable stiffness such as in the radial direction.

Figure 18:
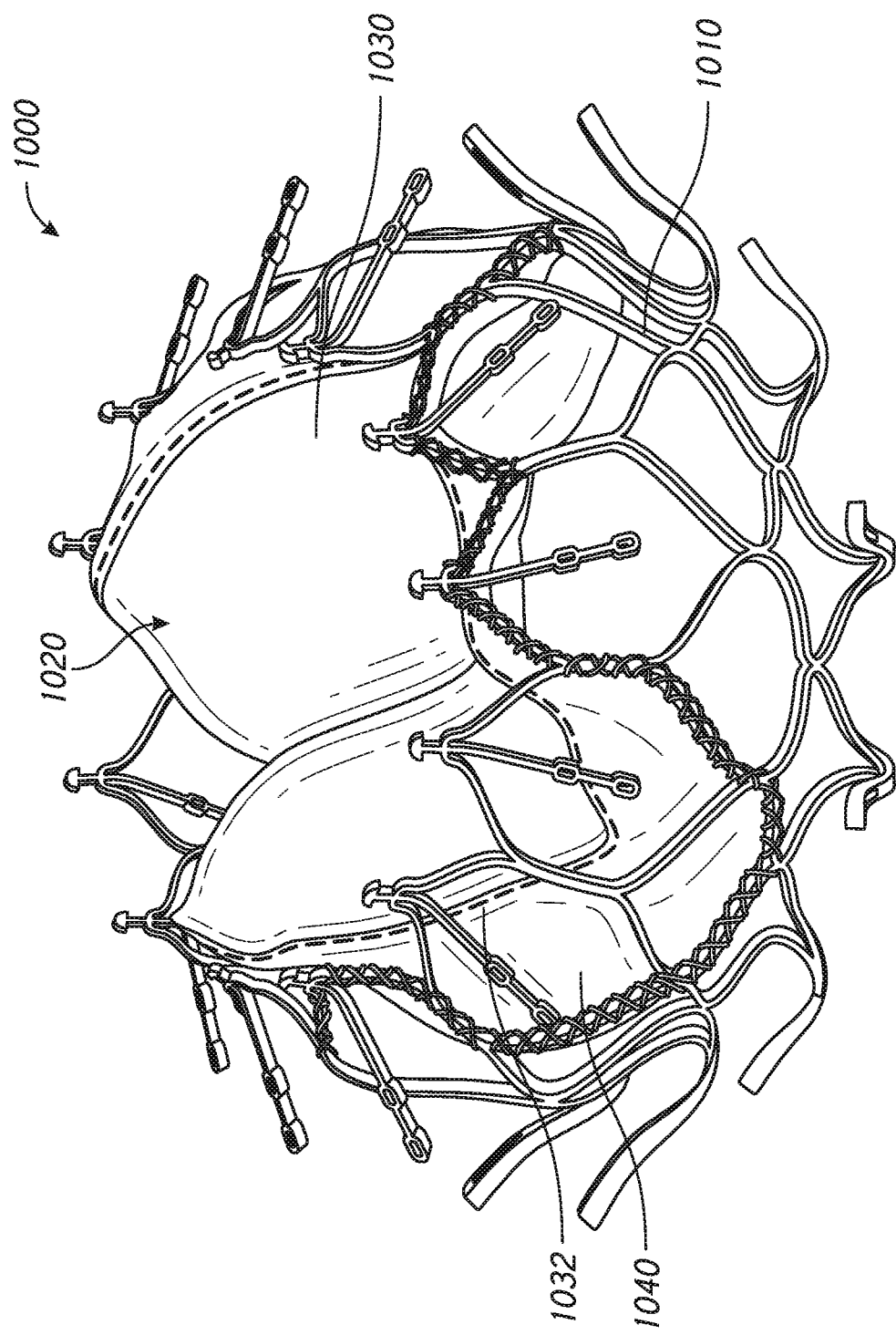
FIG. 18 is a top-oriented perspective view of an embodiment of a frame and floating valve.

With reference next to the prosthesis 1000 illustrated in FIG. 18, the prosthesis 1000 can include a frame 1010 and a valve body 1020. As shown in the illustrated embodiment, the valve body 1020 can include a plurality of leaflets 1030 and one or more intermediate components 1040. The one or more intermediate components 1040 extend across most of, if not the entirety of, the first edge 1032 of the leaflets 1030 and is attached to the first edge 1032 via sutures. The one or more intermediate components 1040 can also be attached to the frame 1010 via sutures along one or more struts of the frame 1010 via sutures. As shown in the illustrated embodiment, a portion of the first edge 1032 of the leaflet 1030 is positioned proximate a strut of the frame 1010. This can beneficially enhance stability of the leaflet 1030. In some embodiments, a portion of edge 1032 of the leaflet 1030, such as the positioned proximate a strut of the frame 1010, can be directly attached to the frame 1010.

Figure 19A:
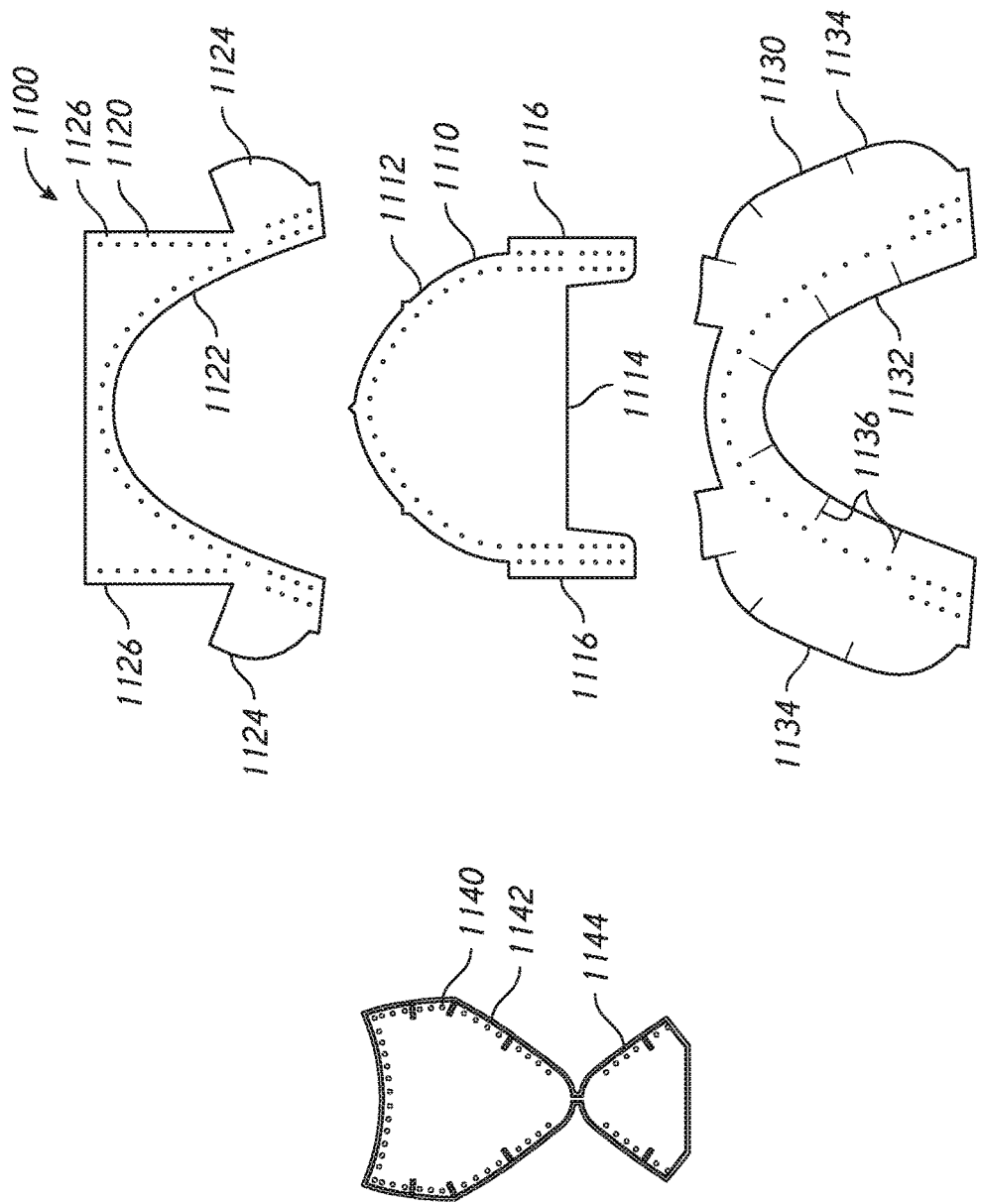
FIG. 19A is a flat, cutting pattern for various components of another embodiment of a floating valve.

With reference next to the portion of valve body 1100 illustrated in FIG. 19A, a flat pattern of various components are shown. The portion of valve body 1100 can include a valve leaflet 1110, a first intermediate component 1120, a second intermediate component 1130, and a third intermediate component 1140. The valve leaflet 1110 can include a first edge 1112, a second edge 1114, and one or more tabs 1116. The first edge 1112 can form a cusp of the leaflet 1110. The second edge 1114 can be a freely moving edge which can allow the valve body 1100 to open and close. The tabs 1116 can be used to attach valve leaflets 1110 together at commissures of the valve body 1100.

The first intermediate component 1120 can include an edge 1122. The edge 1122 can generally match the general curvature of the first edge 1112 of the valve leaflet 1110. In some embodiments, the first intermediate component 1120 can be attached to the valve leaflet 1110 at or proximate the edges 1112, 1122. As shown, the valve leaflet 1110 and the first intermediate component 1120 can include suturing holes to facilitate attachment of the valve leaflet 1110 and the second intermediate component 1130 via sutures. The first intermediate component 1120 can be attached along an inflow surface and/or outflow surface of the valve leaflet 1110. The first intermediate component 1120 can include one or more tabs 1124 on lateral sides of the first intermediate component 1120. The one or more tabs 1124 can generally correspond to the tabs 1116 of the valve leaflet 1110. The one or more tabs 1124 can be used at the commissures of the valve body 1100. In some embodiments, a plurality of first intermediate components 1120 can be attached along the edges 1126. This can form a generally cylindrical portion of a valve body 1100 along an inflow or upstream end of the valve body 1100. The first intermediate component 1120 can be similar to intermediate component 250a illustrated in FIG. 2.

The second intermediate component 1130 can include an inner edge 1132 and an outer edge 1134. The inner edge 1132 can generally match the general curvature of the first edge 1112 of the valve leaflet 1110. In some embodiments, the second intermediate component 1130 can be attached to the valve leaflet 1110 at or proximate the edges 1112, 1132. As shown, the valve leaflet 1110 and the second intermediate component 1130 can include suturing holes to facilitate attachment of the valve leaflet 1110 and the second intermediate component 1130 via sutures. The second intermediate component 1130 can be attached along an outflow surface and/or inflow surface of the valve leaflet 1110. The second intermediate component 1130 can be attached to struts of a frame along the inner edge 1132 and/or the outer edge 1134. To facilitate attachment of the second intermediate component 1130 to the frame, the second intermediate component 1130 can include a plurality of slits 1136. The second intermediate component 1130 can be similar to intermediate components 250b and 1040 illustrated in FIGS. 4 and 18 respectively.

The third intermediate component 1140 can include a first portion 1142 and a second portion 1144. The third intermediate component 1140 can be used to attach the valve leaflet 1110 to the frame at or proximate the portions of the valve leaflet 1110 at the commissures of the valve body 1100. The third intermediate component 1140 can be attached to a frame along a portion, or the entirety of, the edges defining the first portion 1142 and/or second portion 1144. In some embodiments, the third intermediate component 1140 can be positioned along portions of the frame near the valve body 1100 commissures. This can beneficially provide a seal between the first intermediate component 1120 and the second intermediate component 1130 as shown in FIG. 19C.

Figure 19B:
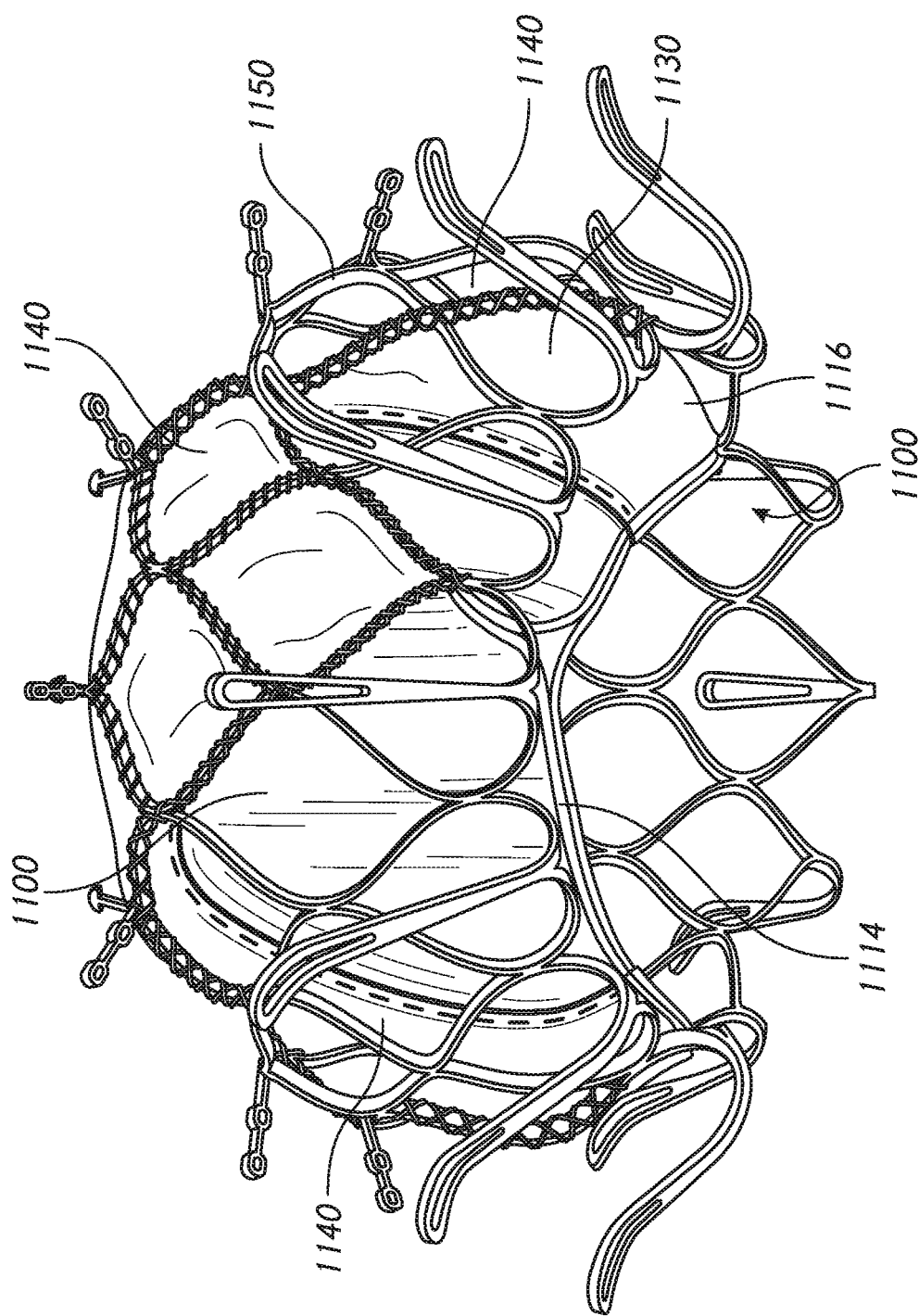
FIG. 19B is a bottom-oriented perspective view of an embodiment of a frame with the floating valve of FIG. 19A.
Figure 19C:
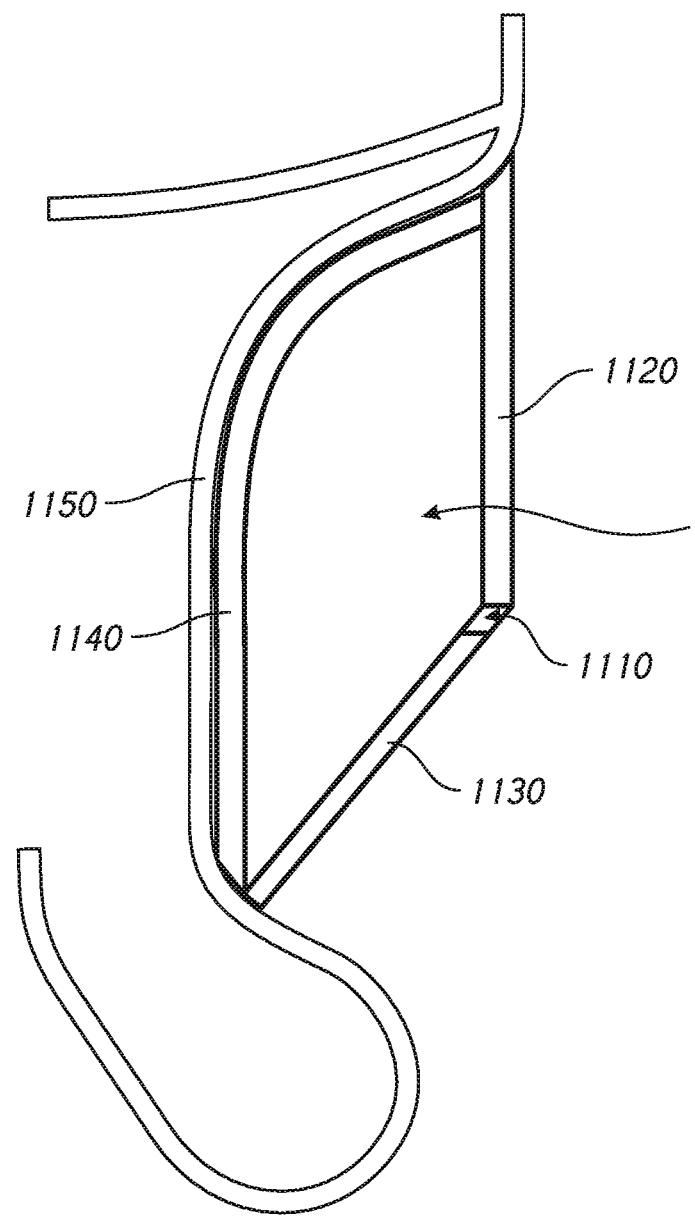
FIG. 19C is a cross-sectional schematic of the floating valve of FIG. 19A.

With reference next to the valve body 1100 and frame 1150 illustrated in FIG. 19B, the valve body 1100 is shown attached to the frame 1140. With reference next to the valve body 1100 and frame 1150 illustrated in FIG. 19C, a schematic cross-section of the valve body 1100 and frame 1150. As shown, the first intermediate component 1120 can form a generally vertically oriented structure around the frame 1150 and be attached to the frame 1150 at an upper end and to an inflow surface of a valve leaflet 1110 at a lower end. The second intermediate component 1120 can be attached to the valve leaflet 1110 at an upper end and to the frame 1150 at a lower end. The third intermediate component 1140 can be attached to the frame 1150 as well as the first and second intermediate components 1120, 1130. This can form an enclosed pocket 1146. In some embodiments, one or more of the intermediate components 1120, 1130, 1140 may be formed from a slightly porous material which allows fluid, such as blood, to enter into the pocket 1146. In some instances, the blood can form a clot within the pocket 1146.

Figure 20:
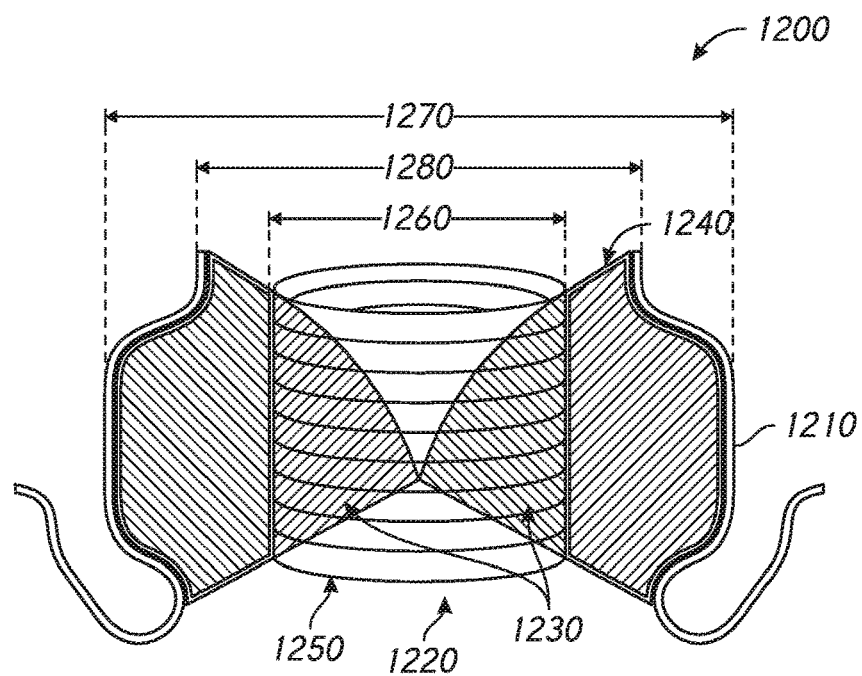
FIG. 20 is a side-oriented cross-sectional schematic view of another embodiment of a frame and floating valve.
Figure 21:
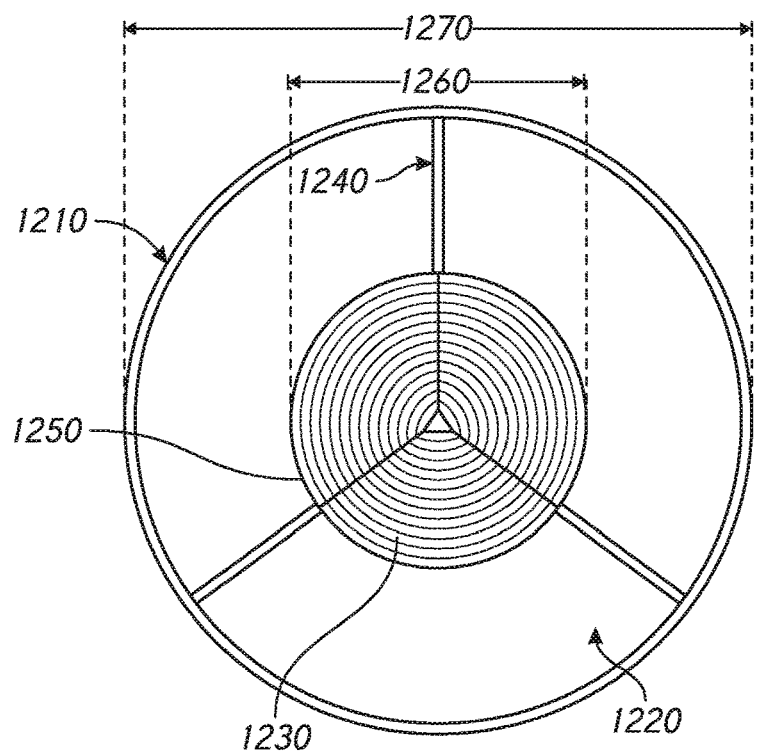
FIG. 21 is a top-oriented cross-sectional schematic view of the frame and floating valve of FIG. 20.

With reference next to the prosthesis 1200 illustrated in FIGS. 20 and 21, the prosthesis 1200 can include a frame 1210 and a valve body 1220. As shown in the illustrated embodiment, the valve body 1220 can include a plurality of valve leaflets 1230 and a plurality of intermediate components 1240. For example, the valve body 1220 can include three valve leaflets 1230 and three intermediate components 1240. The number of intermediate components 1240 can match the number of commissures for the valve body 1220 having three valve leaflets 1230. However, it is to be understood that any number of valve leaflets 1230 and/or intermediate components 1240 can be used. The intermediate components 1240 can be attached to at least the commissures of the valve leaflets 1230 at a first end of the intermediate components 1240. The intermediate components 1240 can be attached to the frame 1210 at a second end of the intermediate components 1240. As shown in the illustrated embodiment, an entirety of, or at least a portion of, the intermediate components 1240 can be generally flat. For example, at least a portion of the intermediate components 1240 proximate commissures of the valve body 1220 can be flat. The flat portion of the intermediate components 1240 can be generally aligned with a plane parallel to the longitudinal axis. In some embodiments, the flat portion of the intermediate components 1240 can be aligned with a plane which is parallel with, and extends through, the longitudinal axis. In some embodiments, the valve body 1220 can include an intermediate component 1250 in the form of a conduit which can extend circumferentially around the plurality of valve leaflets 1230. This can beneficially provide support for the valve leaflets 1230. As shown in the illustrated embodiment, the conduit 1250 can be generally cylindrical although other geometries can be used.

As noted above, the "floating" valve design can beneficially allow the design of the valve leaflets to be independent from the design of the frame. As shown in the illustrated embodiment, the diameter 1260 of the valve leaflets 1230 and/or conduit 1250 can be smaller than the widest diameter 1270 of the frame 1210. Moreover, the diameter 1260 of the valve leaflets 1230 and/or conduit 1250 can be smaller than the diameter 1280 of an upper or inflow end of the frame 1210. In some embodiments, the ratio of the diameter 1260 of the valve leaflets 1230 and/or conduit 1250 to the widest diameter 1270 of the frame 1210 can be about 1:3, about 2:5, about 1:2, about 3:5, about 4:5 or any other ratio as desired. In some embodiments, the diameter 1260 of the valve leaflets 1230 and/or conduit 1250 can be between about 20 mm to about 35 mm, any sub-range within these ranges, or any other diameter as desired.

Figure 22:
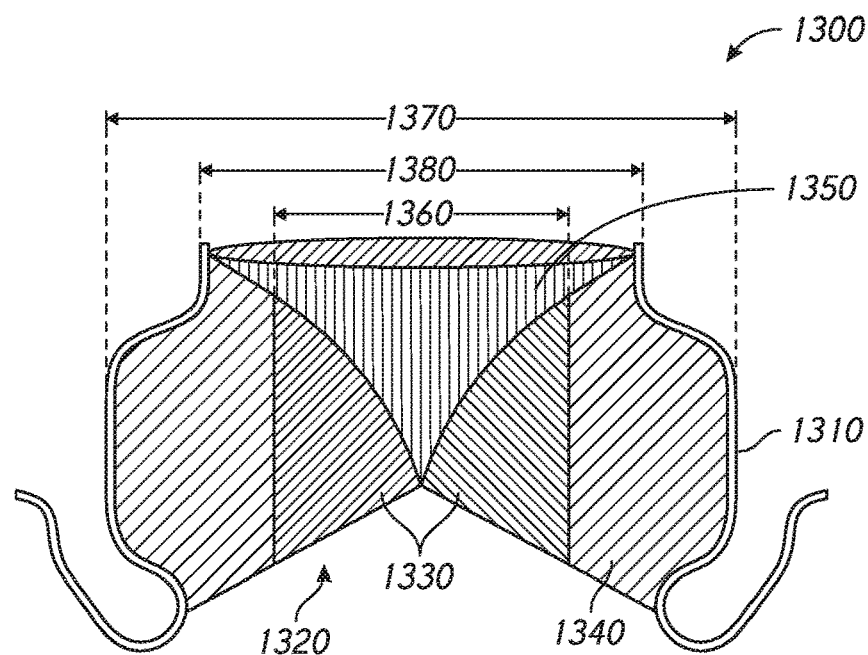
FIG. 22 is a side-oriented cross-sectional schematic view of another embodiment of a frame and floating valve.
Figure 23:
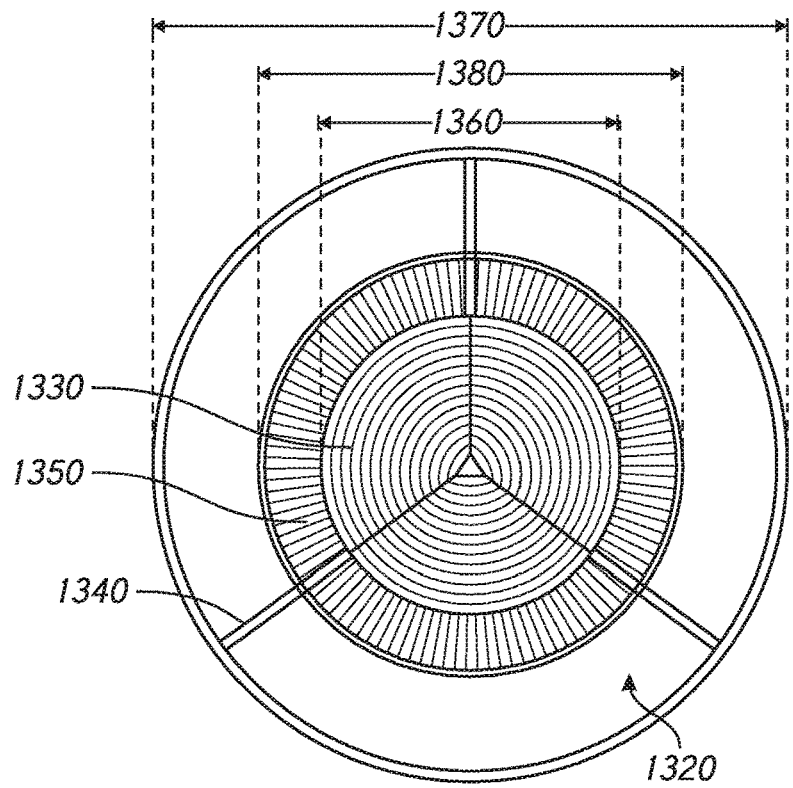
FIG. 23 is a top-oriented cross-sectional schematic view of the frame and floating valve of FIG. 22.

With reference next to the prosthesis 1300 illustrated in FIGS. 22 and 23, the prosthesis 1300 can include a frame 1310 and a valve body 1320. As shown in the illustrated embodiment, the valve body 1320 can include a plurality of valve leaflets 1330, a plurality of first or commissural intermediate components 1340, and one or more second intermediate components 1350. For example, the valve body 1320 can include three valve leaflets 1330 and three commissural intermediate components 1340. The number of commissural intermediate components 1340 can match the number of commissures for the valve body 1320 having three valve leaflets 1330. However, it is to be understood that any number of valve leaflets 1330 and/or intermediate components 1340 can be used. The commissural intermediate components 1340 can be attached to at least the portions of the valve leaflets 1330 at commissures of the valve body 1320 at a first end of the commissural intermediate components 1330. The commissural intermediate components 1340 can be attached to the frame 1310 at a second end of the commissural intermediate components 1340. As shown in the illustrated embodiment, an entirety of, or at least a portion of, the intermediate components 1340 can be generally flat. For example, at least a portion of the intermediate components 1340 proximate commissures of the valve body 1320 can be flat. The flat portion of the intermediate components 1340 can be generally aligned with a plane parallel to the longitudinal axis. In some embodiments, the flat portion of the intermediate components 1240 can be aligned with a plane which is parallel with, and extends through, the longitudinal axis.

The second intermediate component 1350 can extend at least around a portion of the cusps of the leaflets 1320. The second intermediate component 1350 can be attached to at least the cusps of the valve leaflets 1330 at a first end of the second intermediate component 1350. The second intermediate components 1350 can be attached to the frame 1310 at a second end of the second intermediate component 1350. In some embodiments, the first intermediate components 1340 and the second intermediate component 1350 can "tent" the valve leaflet 1330. That is, the first intermediate components 1340 can be tensioned in a first direction, such as a direction generally radially outward away from the longitudinal axis of the frame 1310. The second intermediate component 1350 can be tensioned in a second direction different from the first direction. For example, the second intermediate component 1350 can be tensioned in an axial direction generally aligned with a longitudinal axis of the frame 1310 and/or in a circumferential direction about the longitudinal axis of the frame 1310. The application of tension in different directions (i.e., "tenting") can beneficially provide enhanced structural support for the valve leaflets 1320 such that the valve leaflets 1320 retain their shape.

The second intermediate component 1350 can be used to assist with fluid flow through and/or around the prosthesis 1300. As shown, the second intermediate component 1350 can be positioned within the interior of the frame 1310 and can form a wall of the prosthesis 1300 along the inflow path from the upper end towards the lower end of the frame 1310. The second intermediate component 1350 can be positioned such that the second intermediate component 1350 is radially inward, relative to the longitudinal axis of the frame 1310, from struts of the frame 1310. In this manner, fluid can be directed towards the valve leaflets 1330 of the valve body 1310 along the inflow path.

As shown in the illustrated embodiment, the diameter 1360 of the valve leaflets 1330 and/or second intermediate component 1350 can be smaller than the widest diameter 1370 of the frame 1310. Moreover, the diameter 1360 of the valve leaflets 1330 can be smaller than the diameter 1380 of an upper or inflow end of the frame 1310. In some embodiments, the ratio of the diameter 1360 of the valve leaflets 1330 and/or conduit 1350 to the widest diameter 1370 of the frame 1310 can be about 1:3, about 2:5, about 1:2, about 3:5, about 4:5 or any other ratio as desired. In some embodiments, the diameter 1360 of the valve leaflets 1330 can be between about 20 mm to about 25 mm, any sub-range within these ranges, or any other diameter as desired. In some embodiments, the diameter 1380 of the second intermediate component 1350 can be the same, or about the same, as the diameter 1380 of the upper or inflow end of the frame 1310. In some embodiments, the diameter 1380 of the upper or inflow end of the frame 1310 can be between about 20 mm to about 40 mm, between about 25 mm to about 35 mm, between about 27 mm to about 33 mm, about 27 mm, any sub-range within these ranges, or any other diameter as desired.

Figure 24:
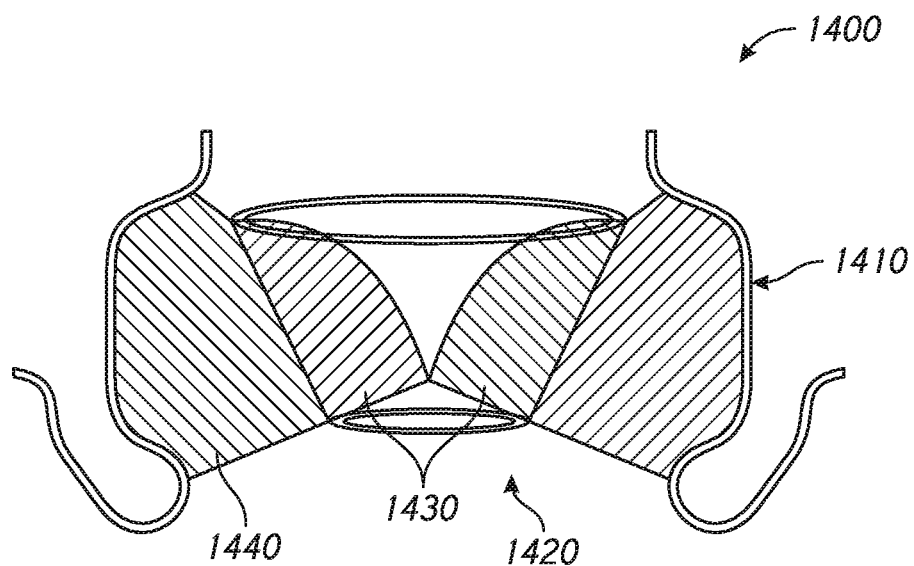
FIG. 24 is a side-oriented cross-sectional schematic view of another embodiment of a frame and floating valve.
Figure 25:
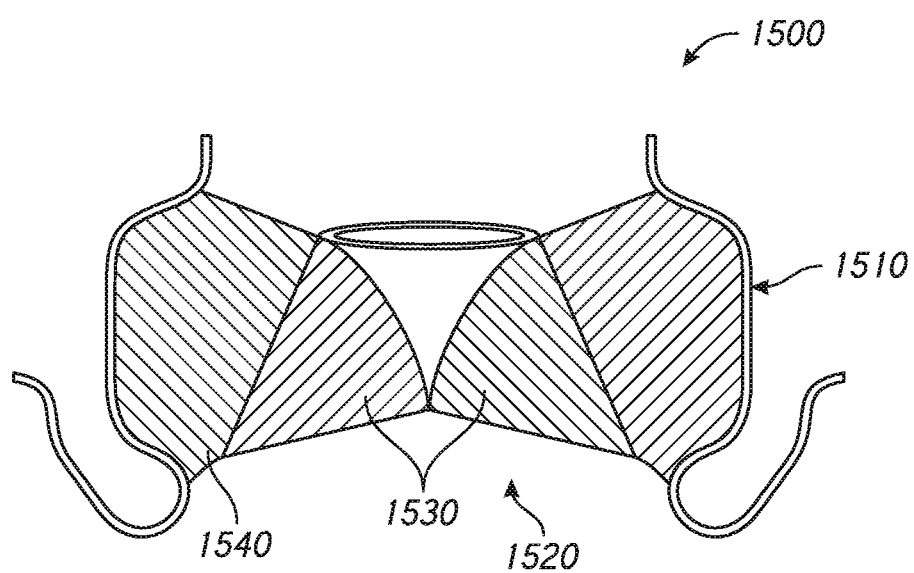
FIG. 25 is a side-oriented cross-sectional schematic view of another embodiment of a frame and floating valve.

With reference next to the prostheses 1400, 1500 illustrated in FIGS. 24 and 25, the prostheses 1400, 1500 can each include a frame 1410, 1510 and a valve body 1420, 1520. With reference to prosthesis 1400, the valve body 1420 can include a plurality of valve leaflets 1430 and a plurality of intermediate components 1440. As shown, the valve body 1420 can have a generally frustoconical shape with a diameter of the upper or inflow end of the valve body 1420 being larger than a diameter of the lower or outflow end of the valve body 1420. With reference to prosthesis 1500, the valve body 1520 can include a plurality of valve leaflets 1530 and a plurality of intermediate components 1540. As shown, the valve body 1520 can have a generally frustoconical shape with a diameter of the upper or inflow end of the valve body 1520 being smaller than a diameter of the lower or outflow end of the valve body 1520.

With reference next to the prostheses 1600, 1700, 1800, 1900 illustrated in FIGS. 26-29, the prostheses 1600, 1700, 1800, 1900 can each include a frame 1610, 1710, 1810, 1910 and a valve body 1620, 1720, 1820, 1920 which can each include valve leaflets schematically represented as structures 1630, 1730, 1830, 1930 and various configurations of intermediate components.

Figure 26:
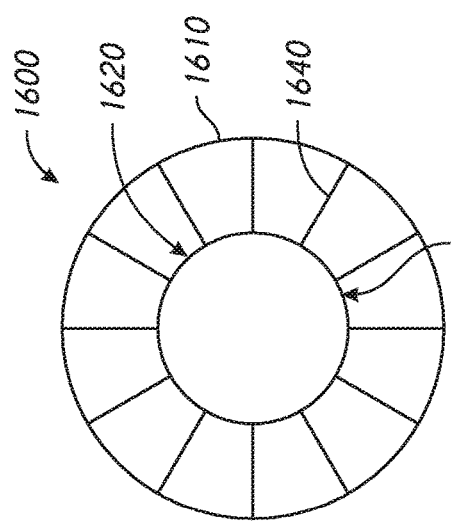
FIG. 26 is a top-oriented cross-sectional schematic view of another embodiment of a frame and floating valve.

With reference first to prosthesis 1600 illustrated in FIG. 26, the valve body 1620 can include a plurality of intermediate components 1640 extending radially between the frame 1620 and the valve leaflets 1630. As shown in the illustrated embodiment, the valve body 1620 can include twelve intermediate components 1640. It is to be understood that a greater number or a lesser number of intermediate components 1640 can be used.

Figure 27:
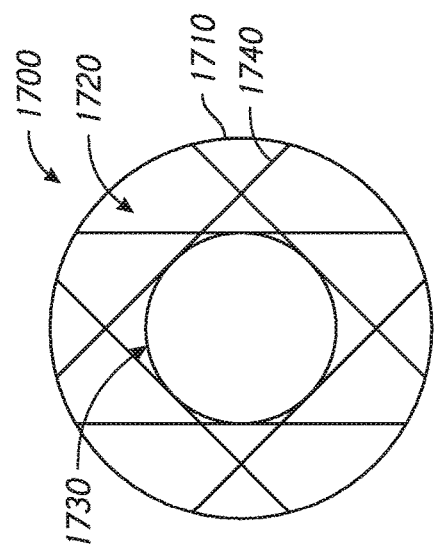
FIG. 27 is a top-oriented cross-sectional schematic view of another embodiment of a frame and floating valve.

With reference next to prosthesis 1700 illustrated in FIG. 27, the valve body 1720 can include a plurality of intermediate components 1740 oriented tangentially to the valve leaflets 1730. The intermediate components 1740 can be coupled at a first and second end to the frame 1710 and be coupled to the valve leaflets 1730 along a portion of the intermediate components 1740 between the first and second ends. As shown in the illustrated embodiment, the valve body 1720 can include six intermediate components 1740. It is to be understood that a greater number or a lesser number of intermediate components 1740 can be used.

Figure 28:
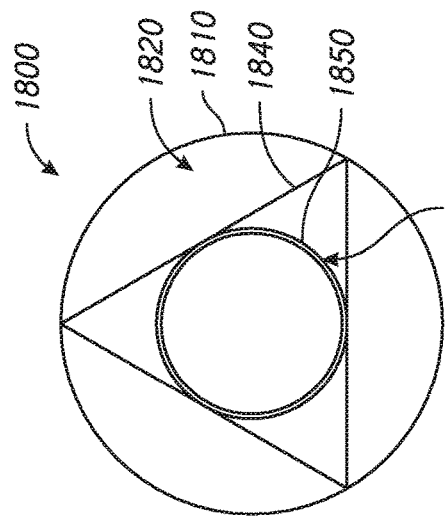
FIG. 28 is a top-oriented cross-sectional schematic view of another embodiment of a frame and floating valve.

With reference next to prosthesis 1800 illustrated in FIG. 28, the valve body 1820 can include a plurality of first intermediate components 1840 oriented tangentially to the valve leaflets 1830. The first intermediate components 1840 can be coupled at a first and second end to the frame 1810 and be coupled to the valve leaflets 1830 along a portion of the first intermediate components 1840 between the first and second ends. As shown in the illustrated embodiment, the ends of the first intermediate components 1840 can be attached to the frame 1810 at or proximate the same location. The valve body 1820 can include a second intermediate component 1850 extending or wrapping around at least a portion of the valve leaflets 1830. As shown in the illustrated embodiment, the valve body 1820 can include three first intermediate components 1840 and one second intermediate component 1850. It is to be understood that a greater number or a lesser number of intermediate components 1840, 1850 can be used.

Figure 29:
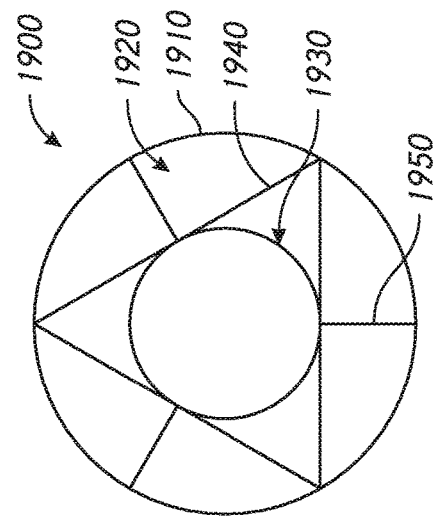
FIG. 29 is a top-oriented cross-sectional schematic view of another embodiment of a frame and floating valve.

With reference next to prosthesis 1900 illustrated in FIG. 29, the valve body 1920 can include a plurality of first intermediate components 1940, similar to intermediate components 1840, which are oriented tangentially to the valve leaflets 1930. The first intermediate components 1940 can be coupled at a first and second end to the frame 1910 and be coupled to the valve leaflets 1930 along a portion of the first intermediate components 1940 between the first and second ends. As shown in the illustrated embodiment, the ends of the first intermediate components 1940 can be attached to the frame 1910 at or proximate the same location. The valve body 1920 can include second intermediate components 1950, similar to intermediate components 1640, extending radially between the frame 1920 and the valve leaflets 1930. As shown in the illustrated embodiment, the valve body 1920 can include three first intermediate components 1940 and three second intermediate components 1950. It is to be understood that a greater number or a lesser number of intermediate components 1940, 1950 can be used.

Figure 30:
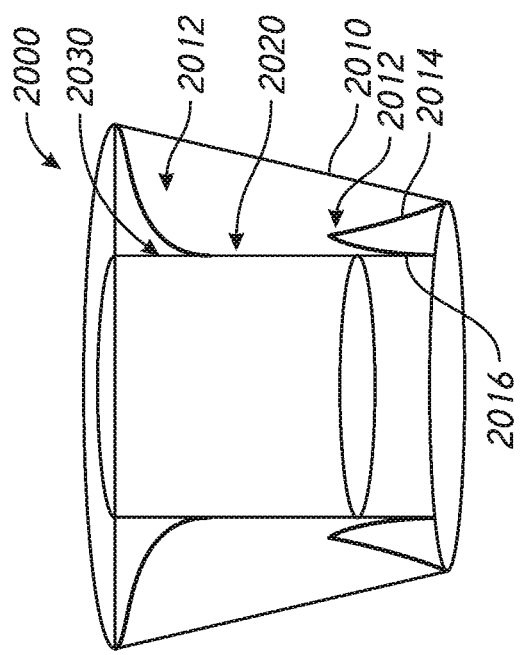
FIG. 30 is a side-oriented cross-sectional schematic view of another embodiment of a frame and floating valve.
Figure 31:
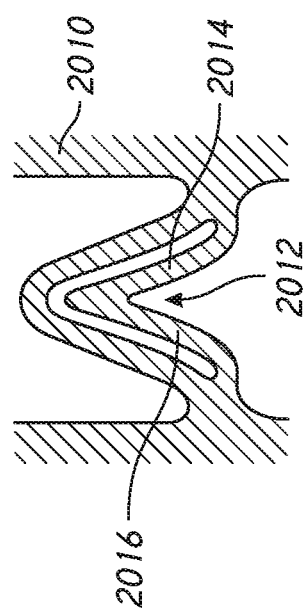
FIG. 31 is a schematic view of an embodiment of a portion of a frame.
Figure 33:
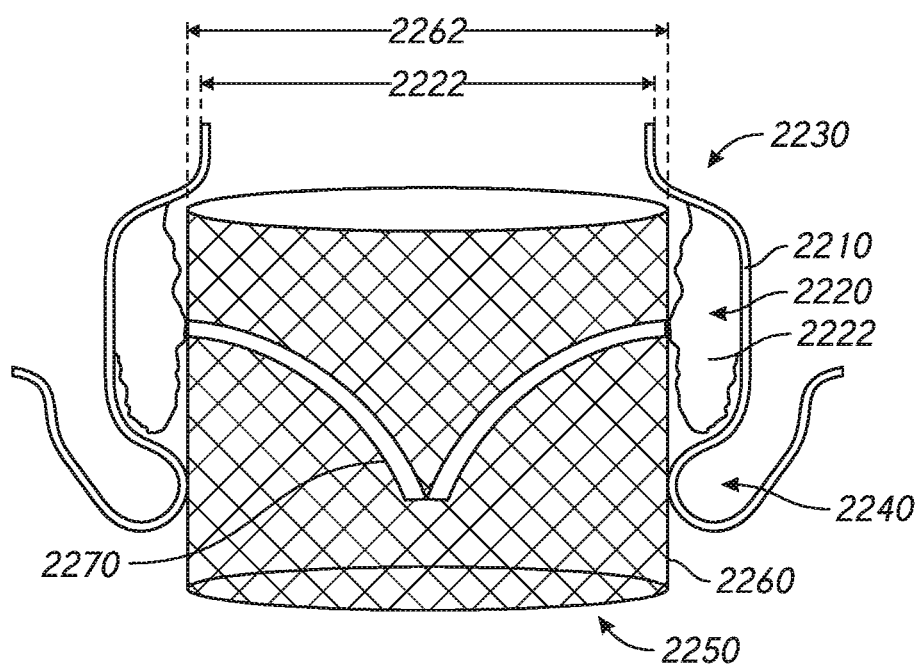
FIG. 33 is a side-oriented schematic view of an embodiment of a frame in which a supplemental prosthesis has been attached.

With reference next to the prostheses 2000 illustrated in FIGS. 30 and 31, the prostheses 2000 can include a frame 2010 and a valve body 2020 which can each include valve leaflets schematically represented as structures 2030. As shown in the illustrated embodiment, the frame 2010 can include projections 2012 extending inwardly towards an interior volume of the frame 2010. As shown in the illustrated embodiment, the projections 2012 can be formed from a first strut 2014 and a second strut 2016 to form a "V" shaped configuration. The projections 2012 can provide a mounting location for valve body 2020. For example, at least a portion of the valve body 2020 can be attached directly to the projections 2012 or can be attached via an intermediate component. This can beneficially allow a valve body 2020 having a different shape from frame 2010 to be attached to frame 2010.

Figure 32:
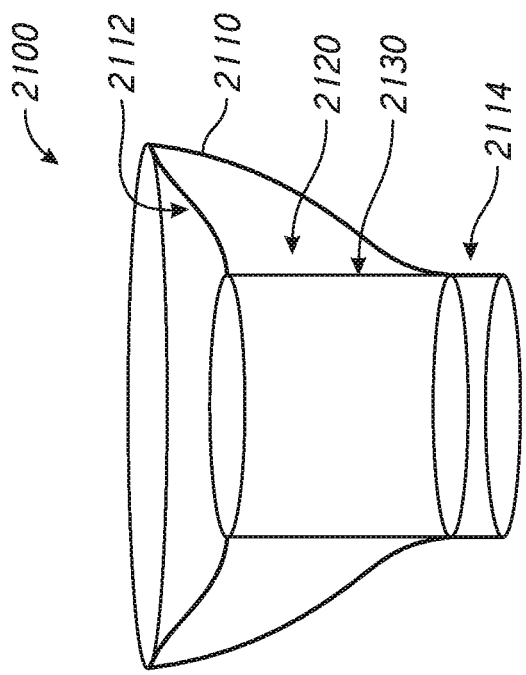
FIG. 32 is a side-oriented cross-sectional schematic view of another embodiment of a frame and floating valve.

With reference next to the prostheses 2100 illustrated in FIG. 32, the prostheses 2100 can include a frame 2110 and a valve body 2120 which can each include valve leaflets schematically represented as structures 2130. As shown in the illustrated embodiment, the frame 2110 can include projections 2112 extending inwardly towards an interior volume of the frame 2110. The projections 2112 can provide a mounting location for valve body 2120. For example, at least a portion of the valve body 2120 can be attached directly to the projections 2112 or can be attached via an intermediate component. This can beneficially allow a valve body 2020 having a different shape from frame 2010 to be attached to frame 2010. A lower region 2114 of frame 2110 can be sized and shaped to generally correspond to the shape of the valve body 2120 to facilitate mounting along the lower region 2114. This can beneficially enhance stability of the valve body 2120 when mounted to the frame 2110.

Embodiments of Valve-in-Valve Mechanisms

With reference to FIGS. 33-37, embodiments of prostheses 2200, or components thereof such as frames 2210, 2300, 2400, 2500, 2600 and/or valve bodies 2220, are illustrated. With reference first to the prosthesis 2200 illustrated in FIG. 33, the prosthesis 2200 include a frame 2210 and a valve body 2220. The valve body 2220 can include a plurality of leaflets 2222. The valve body 2220 can be designed to be used for an extended period of time. However, in some instances, it may be beneficial to utilize a supplemental prosthesis 2250 in order to prolong use of the prosthesis 2200. As shown in the illustrated embodiment, the prosthesis 2200 can be sized and shaped to receive a supplemental prosthesis 2250 such as, but not limited to, Edwards Lifesciences' Sapien 3 valve, replacement aortic valves, replacement mitral valves, and replacement valves described in U.S. Publication Nos. 2012/0123529, 2013/0030519, and 2013/0030520, the entireties of each of which are hereby incorporated by reference and made a part of this specification. The supplemental prosthesis 2250 can include a frame 2260 which can be self-expanding or balloon expandable. The supplemental prosthesis 2250 can also include a plurality of valve leaflets 2270. While the valve body 2220 has been described as being used for an extended period of time, it is to be understood that the valve body 2220 can be designed to be used temporarily. For example, the prosthesis 2200 and supplemental prosthesis 2250 can be delivered during the same surgical procedure. In such instances, the valve body 2220 can be used to ensure functioning of the heart when the prosthesis 2200 is implanted but before the supplemental prosthesis 2250 is mounted to the prosthesis 2200. Due to the lower expected period of use for valve body 2220, the valve body 2220 can be designed to utilize less materials which can allow the valve body 2220 to take on a more compact form factor.

As shown in the illustrated embodiment, the upper region 2230 of the frame 2210 can serve as a backstop for an upper end of the frame 2260 of the supplemental prosthesis 2250. For example, in the expanded configuration, the diameter 2222 of the upper or inflow end of the frame 2210 can be less than the diameter 2262 of the upper or inflow end of the frame 2260. This can beneficially inhibit the frame 2260 of supplemental prosthesis 2250 from moving axially upward past frame 2210 during the cardiac cycle. This can be particularly beneficial during periods of the cardiac cycle in which an upwardly directed force is applied to the prostheses 2200, 2250. For example, this upwardly directed force could be applied during systole in cases where the prostheses 2200, 2250 are positioned within a native mitral valve. In some embodiments, the diameter 2222 of the upper or inflow end of the frame 2210 can be between about 20 mm to about 40 mm, between about 25 mm to about 35 mm, between about 27 mm to about 33 mm, about 27 mm, any sub-range within these ranges, or any other diameter as desired. In some embodiments, the diameter 2222 of the upper or inflow end of the frame 2210 can be between about 20 mm to about 45 mm, between about 25 mm to about 40 mm, between about 28 mm to about 33 mm, about 29 mm, any sub-range within these ranges, or any other diameter as desired.

As shown in the illustrated embodiment, the lower region 2240 of the frame 2210 can have a diameter about the same, or less than, the diameter of the supplemental prosthesis 2250 such that the supplemental prosthesis 2250 is maintained within the lower region 2240 in a press fit, a friction fit, and/or an interference fit. As shown in the illustrated embodiment, the valve body 2220 of the prosthesis 2200, such as leaflets 2222, can beneficially enhance stability of the supplemental prosthesis 2250. For example, the valve body 2220 can beneficially reduce lateral movements of the supplemental prosthesis 2250. Moreover, in some embodiments, friction between the valve body 2220 and the supplemental prosthesis 2250 can beneficially reduce movement of the supplemental prosthesis 2250 in an axial direction.

With reference to FIGS. 33-37, embodiments of frames 2300, 2400, 2500, 2600 are illustrated. With reference first to frame 2300 illustrated in FIG. 34, the frame 2300 can have an upper region 2310 which serves as a backstop for a supplemental prosthesis and a lower region 2320 which interfaces with a portion of the supplemental prosthesis to retain the supplemental prosthesis within the frame 2300. As shown in the illustrated embodiment, the lower region 2320 includes an interface structure 2322 formed by one or more struts extending forming a "V" shaped configuration. This configuration is similar to that shown in FIG. 5A having struts 385. The interface structure 2322 can be inclined or curved towards a longitudinal axis of the frame 2300 such that a lower portion of the interface structure 2322 is positioned closer to the longitudinal axis of the frame 2300 than the lower portion of the interface structure 2322. The lower portion of the interface structure 2322, such as the lower apices formed by struts, can beneficially engage portions of the supplemental prosthesis. For example, in instances where the supplemental prosthesis includes a frame having a plurality of cells, the lower portion of the interface structure 2322 can extend within the cells to retain the supplemental prosthesis within the frame 2300. While the interface structure 2322 was described as having "V" shaped apices, it is to be understood that the interface structure 2322 can have other geometries and could, for example, be formed as fingers formed from separate struts.

With reference next to frame 2400 illustrated in FIG. 35, the frame 2400 can have an upper region 2410 which serves as a backstop for a supplemental prosthesis and an inner frame 2420 which interfaces with a portion of the supplemental prosthesis to retain the supplemental prosthesis within the frame 2400. As shown in the illustrated embodiment, the inner frame 2420 can include one or more arms coupling the inner frame 2420 to the frame 2400. The inner frame 2420 can be expandable. For example, the inner frame 2420 can be formed from one or more circumferentially-expansible struts 2424. In this manner, the inner frame 2420 can be expanded to accommodate a supplemental prosthesis. In some embodiments, the inner frame 2420 can be biased to a smaller diameter than the supplemental prosthesis. This biasing force can beneficially create a friction fit with a supplemental prosthesis. In some embodiments, the frame 2420 can be positioned below the frame 2420. For example, the frame 2420 can include one or more protrusions which extend from a lower end of the frame 2420. The protrusions can extend radially inwardly towards a longitudinal axis of the frame 2420 to form a diameter smaller than that of the lower end of the frame 2420.

With reference next to frame 2500 illustrated in FIG. 36, the frame 2500 can have an upper region 2510 which serves as a backstop for a supplemental prosthesis 2550 and a lower region 2520 which can serve as an opposing backstop for the supplemental prosthesis 2550. With reference next to frame 2600 illustrated in FIG. 37, the frame 2600 can have an upper region 2610 which serves as a backstop for a supplemental prosthesis. The frame 2600 can include an anchoring feature 2620 having an effective inner diameter less than, or the same as, that of the supplemental prosthesis. In some embodiments, the anchoring feature 2620 can retain the supplemental prosthesis in a manner similar to interface structure 2322 such that portions of the anchoring feature 2620 interface with portions of the supplemental prosthesis, such as cells forming the frame of the supplemental prosthesis. In some embodiments, the anchoring feature 2620 can retain the supplemental prosthesis in a manner similar to lower region 2520 such that portions of the anchoring feature 2620 serves as an opposing backstop for the supplemental prosthesis.

Embodiments of Annular Skirts

With reference to FIGS. 38-40, embodiments of prostheses 2700, 2800, 2900, or components thereof such as frames 2710, 2810, 2910, valve bodies 2720, 2820, 2920, and skirts 2730, 2830, 2930, are illustrated. With reference first to the prosthesis 2700 illustrated in FIG. 38, the prosthesis 2700 can include a frame 2710, a valve body 2720, and a skirt 2730. The skirt 2730 can be positioned around and secured to an exterior of the frame 2710. The skirt 2730 can be annular and can extend entirely circumferentially around the frame 2710. The skirt 2730 can prevent or inhibit backflow of fluids around the prosthesis 2700. For example, with the skirt 2730 positioned annularly around an exterior of the frame 2710, the skirt 2730 can create an axial barrier to fluid flow exterior to the frame 2710 when deployed within a body cavity. The skirt 2730 can form a flange when the skirt 2730 is positioned within a body cavity, such as a native valve, with the flange sealing against at least a portion of tissue surrounding the body cavity. In addition, the skirt 2730 can encourage tissue in-growth between the skirt 2730 and the natural tissue. This may further help to prevent leakage of blood flow around the prosthesis 2700.

The skirt 2730 can have a first end 2732 positioned at or proximate an upper or inflow end of the frame 2710 and extend to a second end 2734 positioned at or proximate a lower or outflow end of the frame 2710. In some embodiments, the second end 2734 can follow the shape of the struts along the lower or outflow end of the frame 2710 as shown, for example, in FIGS. 3 and 4. It is to be understood that other configurations, such as a curved edge or straight edge, can also be used as desired. The skirt 2730 can be attached to the frame 2710 and/or the valve body 2720 using any mechanism or technique as described above, such as sutures and/or adhesives.

In some embodiments, the skirt 2730 can be formed from a material such as such as knit polyester (e.g., polyethylene terephthalate (PET)) or any other biocompatible material such as those which are wholly or substantially fluid impermeable, flexible, stretchable, deformable, and/or resilient. In some embodiments, the skirt 2730 can be formed from separate components and can be attached together using any mechanism or technique as described above, such as via sutures and/or adhesives. In other embodiments, the skirt 2730 can be a single component. The skirt 2730 can also include other structures, such as wires formed from resilient materials such as nitinol, to allow at least portions of the skirt 2730 to retain a particular shape. These structures may be positioned on an inner surface of the skirt 2730.

As shown, the shape of the frame 2710, in conjunction with the skirt 2730, can beneficially enhance hemodynamic performance. For example, the shape of the frame 2710 with a larger, generally cylindrical intermediate region 2712 can allow for significant washout on an underside of the valve 2720. That is, the shape of the frame 2710 can enhance the exchange of blood from a prior cardiac cycle—which may have stagnated and accumulated in crevices, pockets, and/or surfaces of the frame 2710, valve 2720, and/or skirt 2730— with fresh blood from a current cardiac cycle. This washout can beneficially reduce the risk of thrombosis or clot formation under the valve 2720.

With reference next to the prosthesis 2800 illustrated in FIG. 39, the prosthesis 2800 can include a frame 2810, a valve body 2820, and a skirt 2830. The skirt 2830 can be positioned around and secured to an exterior of the frame 2810. The skirt 2830 can be annular and can extend entirely circumferentially around the frame 2810. The skirt 2830 can prevent or inhibit backflow of fluids around the prosthesis 2800. For example, with the skirt 2830 positioned annularly around an exterior of the frame 2810, the skirt 2830 can create an axial barrier to fluid flow exterior to the frame 2810 when deployed within a body cavity. In addition, the skirt 2830 can encourage tissue in-growth between the skirt 2830 and the natural tissue. This may further help to prevent leakage of blood flow around the prosthesis 2800. Unlike the skirt 2730, the skirt 2830 can be formed such that it remains generally taut against the frame 2810.

The skirt 2830 can have a first end 2832 positioned at or proximate an upper or inflow end of the frame 2810 and extend to a second end 2834 positioned at or proximate a lower or outflow end of the frame 2810. In some embodiments, the second end 2834 can follow the shape of the struts along the intermediate region 2812 of the frame 2812. The skirt 2830 can be attached to the frame 2810 and/or the valve body 2820 using any mechanism or technique as described above, such as sutures and/or adhesives.

The skirt 2830 is preferably formed from a material, such as such as knit polyester (e.g., polyethylene terephthalate (PET)), or any other biocompatible material such as those which are wholly or substantially fluid impermeable, flexible, stretchable, deformable, and/or resilient. In some embodiments, the skirt 2830 can be formed from separate components and can be attached together using any mechanism or technique as described above, such as via sutures and/or adhesives. In other embodiments, the skirt 2830 can be a single component. The skirt 2830 can also include other structures, such as wires formed from resilient materials such as nitinol, to allow at least portions of the skirt 2830 to retain a particular shape. These structures may be positioned on an inner surface of the skirt 2830.

As shown, the shape of the frame 2810 can beneficially enhance hemodynamic performance. For example, the shape of the frame 2810 with a larger, generally cylindrical intermediate region 2812 can allow for significant washout on an underside of the valve 2820. This washout can beneficially reduce the risk of thrombosis or clot formation under the valve 2820.

With reference next to the prosthesis 2900 illustrated in FIG. 40, the prosthesis 2900 can include a frame 2910, a valve body 2920, and a skirt 2930. The skirt 2830 can have a first end 2832 positioned at or proximate an upper or inflow end of the frame 2810 and extend to a second end 2834 positioned at or proximate a lower or outflow end of the frame 2810.

Although some embodiments of skirts described herein are formed from materials which can be substantially fluid impermeable, it is to be understood that the skirts can be entirely, or at least partially, formed from materials which are permeable and/or materials with holes formed therethrough. This can allow some blood to pass through and/or around the skirt. In embodiments where the skirt expands in size (e.g., due to systolic pressure), the amount of expansion can be reduced due to blood passing through the skirt. In some implementations, the skirt may not completely contact surrounding tissue and/or may apply a reduced amount of pressure against surrounding tissue. This can allow some blood to pass around the skirt.

In some embodiments, the entirety, or at least a portion, of the skirt can be formed from a partially porous cloth. The picks-per-inch (PPI) and/or the ends-per-inch (EPI) can be chosen to attain a desired porosity. In some embodiments, the cloth can have a PPI and/or EPI of between about 50 to about 500, a PPI and/or EPI of between about 100 to about 375, a PPI and/or EPI of between about 150 to about 250, any sub-range within these ranges, or any other PPI and/or EPI as desired. The cloth may be structured to incorporate pores via a specific weave pattern. In some embodiments, the skirt may be drilled to form one or more holes.

Use of an at least partially porous skirt and/or a skirt with holes can allow some degree of mitral regurgitation to persist, at least temporarily. This can be particularly beneficial in instances where a sudden correction in mitral regurgitation may be undesirable. For example, an immediate reduction in mitral regurgitation can place a significantly higher load on the left ventricle; however, patients who have functional mitral regurgitation may have a weak left ventricle. This immediate reduction in mitral regurgitation can result in a situation in which the patient's left ventricle is unable to expel all, or a majority, of blood through the aortic valve (e.g., volume overload). As such, it can be beneficial to allow some degree of mitral regurgitation to persist, at least temporarily, to allow the patient's heart to acclimate to an environment of reduced mitral regurgitation.

The amount of blood flow through and/or around the skirt can gradually reduce over time. For example, in some embodiments, the skirts can become effectively impermeable over time. In some embodiments, the skirt can incorporate a material such as, but not limited to hydrogel, which can seal or at least significantly reduce blood flow through pores and/or holes of the skirt. In some embodiments, the size of the pores and/or holes can be chosen such that a platelet response can reduce or eliminate flow through the pores and/or holes, and/or tissue healing (e.g., tissue ingrowth) can reduce or eliminate flow through the pores and/or holes.

The gradual reduction in size of the pores and/or holes can gradually reduce the amount of blood flow through the skirt. In embodiments where the skirt expands in size, the amount of expansion can gradually increase due to less blood passing through the skirt. In some implementations, the skirt may begin to completely contact surrounding tissue and/or may apply an increased amount of pressure against surrounding tissue. This can reduce, or wholly eliminate, blood flow around the skirt.

In some embodiments, this gradual reduction of blood flow through and/or around the skirt can occur over a period of between about 12 hours to about 72 hours. This can beneficially allow the patient's heart to gradually acclimate to reducing mitral regurgitation while allowing the physician to assess whether the patient's heart is properly acclimating to the reduction in mitral regurgitation. In some embodiments, this gradual reduction of blood flow through and/or around the skirt can occur over an extended period of time. For example, this gradual reduction in blood flow can occur over a period of between about one week to about one month. This can provide the patient's heart with additional time to acclimate to reducing mitral regurgitation. It is to be understood that in some embodiments, blood flow through and/or around the skirt can decrease at a greater rate over a shorter time period (e.g., about 12 hours to about 72 hours) and continue to decrease at a reduced rate over an extended period of time (e.g., up to one month).

With reference to FIGS. 48-57, embodiments of prostheses 3400, 3500, 3600, or components thereof such as frames 3420, 3520, 3620, valve bodies 3440, 3540, 3640, 3740 and skirts 3460, 3560, 3660, are illustrated. These embodiments can include features, such as openings and/or conduits, which can enhance hemodynamic performance of the prostheses 3400, 3500, 3600. With reference first to the prosthesis 3400 illustrated in FIGS. 48 and 49, the prosthesis 3400 can include a frame 3420, a valve body 3440, and a skirt 3460. As shown in the illustrated embodiment, the prosthesis 3400 can be positioned within a native mitral valve. The frame 3420 can be self-expanding or balloon expandable. The frame 3420 can include a frame body formed from a plurality of struts defining a plurality of cells. One or more of the cells can allow the frame 3420 to longitudinally foreshorten when the frame 3420 radially expands. Although not shown, the frame 3420 can include one or more anchoring features to secure the prosthesis to a native valve, such as a native mitral valve.

The valve body 3440 preferably includes a plurality of valve leaflets 3442 each having at least a first edge 3444 and a second edge 3446. The cusp or first edge 3444, which may be considered a proximal edge, may be arcuate in shape. The second edge 3446 can be a freely moving edge which can allow the valve body 3440 to open and close. The valve leaflet 3442 can be similar to leaflet 1110 illustrated in FIG. 19A which includes a first edge 1112, a second edge 1114, and tabs 1116. The plurality of valve leaflets 3442 can function in a manner similar to the native mitral valve, or to any other valves in the vascular system as desired.

The skirt 3460 can be attached to the frame 3420. The skirt 3460 can be positioned around and secured to an exterior of the frame 3420. The skirt 3460 can be annular and can extend entirely circumferentially around the frame 3420. The skirt 3460 can generally prevent or inhibit backflow of fluids, such as blood, around the prosthesis 3400. For example, with the skirt 3460 positioned annularly around an exterior of the frame 3420, the skirt 3460 can create an axial barrier to fluid flow exterior to the frame 3420 when deployed within a body cavity such as a native valve annulus. As shown in the illustrated embodiment, the skirt 3460 can be tautly secured around the frame 3420. However, it is to be understood that the skirt 3460 can be loosely attached to the exterior of the frame 3420. As shown in the illustrated embodiment, at least a portion of the first edge 3444 can be attached to the skirt 3460.

The skirt 3460 can include one or more openings 3462 in the material forming the skirt 3460. The openings 3462 can be positioned within an area of the skirt 3460 between the first edge 3444 of a valve leaflet 3442 (i.e., an area of the skirt positioned behind a valve leaflet 3442). In some embodiments, the skirt 3460 can include at least one opening 3462 for each valve leaflet 3442. The one or more openings 3462 can beneficially enhance hemodynamic performance of the prosthesis 3400. For example, the one or more openings 3462 can allow for significant washout on an underside of the valve 3420. That is, the one or more openings 3462 can enhance the exchange of blood from a prior cardiac cycle—which may have stagnated and accumulated in crevices, pockets, and/or surfaces of the frame 3420, valve body 3440, and/or skirt 3460—with fresh blood from a current cardiac cycle. This washout can beneficially reduce the risk of thrombosis or clot formation under the valve body 3440. In some instances, since the space between the valve leaflet 3442 and the skirt 3460 is generally shielded from the primary flow field of the prosthesis 3400, blood within this space can begin to stagnate thereby increasing the risk of thrombosis. The one or more openings 3462 can reduce, or eliminate, the amount of stagnant blood within this space. Blood flow through the one or more openings 3462 can occur due to a pressure differential across the prosthesis 3400 (e.g., pressure differential between the left atrium and left ventricle during diastole and systole) and/or momentum (e.g., momentum of blood flow during systole). The one or more openings 3462 can take on shapes such as those illustrated in FIGS. 50-52 (e.g., circular, diamond-shaped, triangular, etc.). In some embodiments, the one or more openings 3462 can have different shapes.

As shown in the illustrated embodiment, the one or more openings 3462 can be positioned along the skirt 3460 at or proximate a proximal region of the space between the valve leaflet 3442 and the skirt 3460. For example, the one or more openings 3462 can be positioned at or proximate the attachment between the cusp or first edge 3444 and the skirt 3460 near a proximal area of this attachment (as shown in FIG. 50). By positioning the one or more openings 3462 at or proximate a proximal region of the space between the valve leaflet 3442 and the skirt 3460, a greater degree of washout of the space between the valve leaflet 3442 and the skirt 3460 can be achieved. This can beneficially ensure that a majority, if not the entirety, of the valve leaflet 3442 is washed or flushed and reduce the likelihood of build-up of stagnant blood.

In some embodiments, the one or more openings 3462 can be positioned at least above the distalmost part of the valve leaflet 3442 (e.g., the second edges 3446) when coapted during the systolic phase. In some embodiments, the one or more openings 3462 can be positioned at or proximate a proximalmost region of the space between the valve leaflet 3442 and the skirt 3460. It is to be understood that the positioning, number, and size of the openings 3462 can be chosen based on numerous factors including, but not limited to, the geometry of the prosthesis 3400 (i.e., frame 3420, valve body 3440, and/or skirt 3460) and the desired amount of washout.

Figure 49:
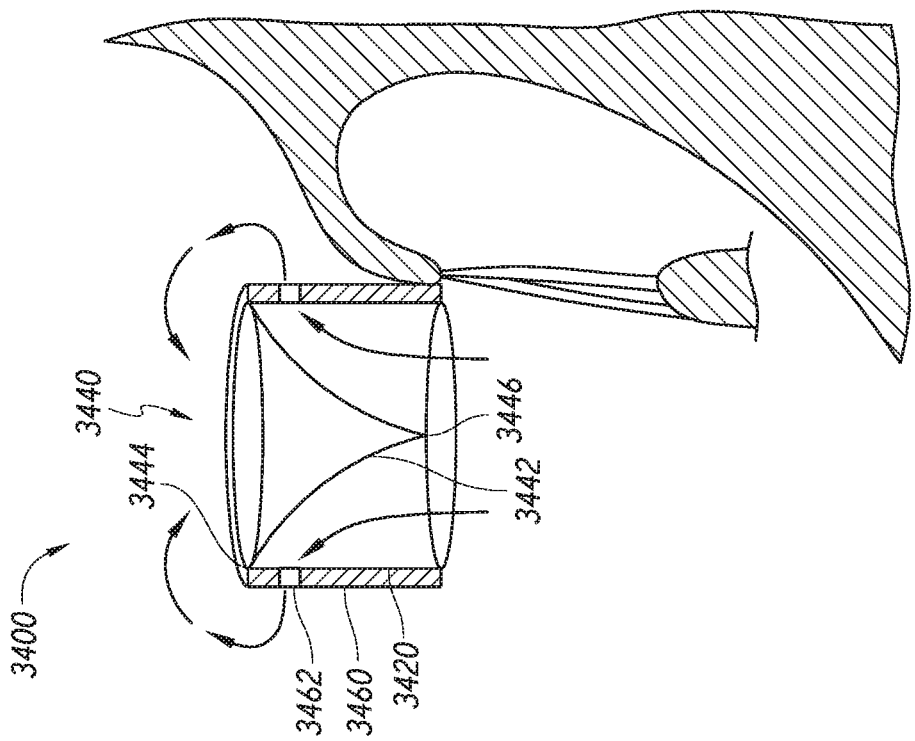
FIGS. 48 and 49 illustrate schematic representations of an embodiment of a prosthesis positioned within a heart.
Figure 48:
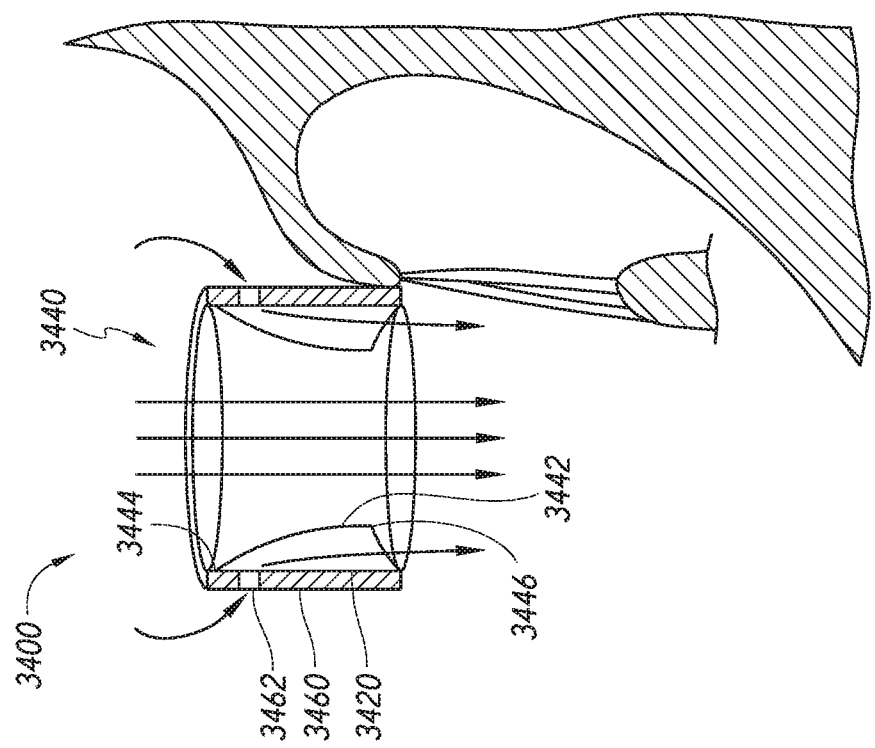

As shown in FIG. 48, in some embodiments the one or more openings 3462 can allow antegrade blood flow through the space between the valve leaflet 3442 and the skirt 3460 and into the ventricle during diastole. This can allow stagnant or trapped blood on the underside of the valve leaflet 3442 and the skirt 3460, from a prior systolic phase, to be flushed during the diastolic phase. As shown in FIG. 49, in some embodiments the one or more openings 3462 can allow retrograde blood flow through the space between the valve leaflet 3442 and the skirt 3460 and into the atrium during systole. This can allow blood which was previously trapped on the underside of the valve leaflet 3442 and the skirt 3460, from a prior diastolic phase, to be flushed during the systolic phase.

In some embodiments (not shown), the one or more openings 3462 can include one-way valves which allow blood to flow through the one or more openings 3462 during systole or diastole while preventing or inhibiting blood to flow through the one or more openings 3462 during the opposite phase. This can beneficially decrease undesirable retrograde flow during systole or antegrade flow during diastole through the one or more openings 3462. In some embodiments, some of the one or more openings 3462 can include one-way valves whereas other of the one or more openings 3462 can permit flow in both directions. In this manner, the effective area of the one or more openings 3462 can differ depending on the directionality of blood flow. For example, in embodiments where the one-way valves permit antegrade flow, the effective area of the one or more openings 3462 during diastole is greater than the effective area during systole. This can be beneficial due to the difference in pressure differential between the left atrium and left ventricle during diastole as compared to the pressure differential between the left atrium and left ventricle during systole. Since this pressure differential is generally greater during systole, a greater amount of blood would flow through the one or more openings 3462 as compared to the amount of blood flow during diastole. It is to be understood that in some embodiments, at least one of the one-way valves can allow retrograde flow and at least one of the one-way valves may allow antegrade flow.

Figure 55:
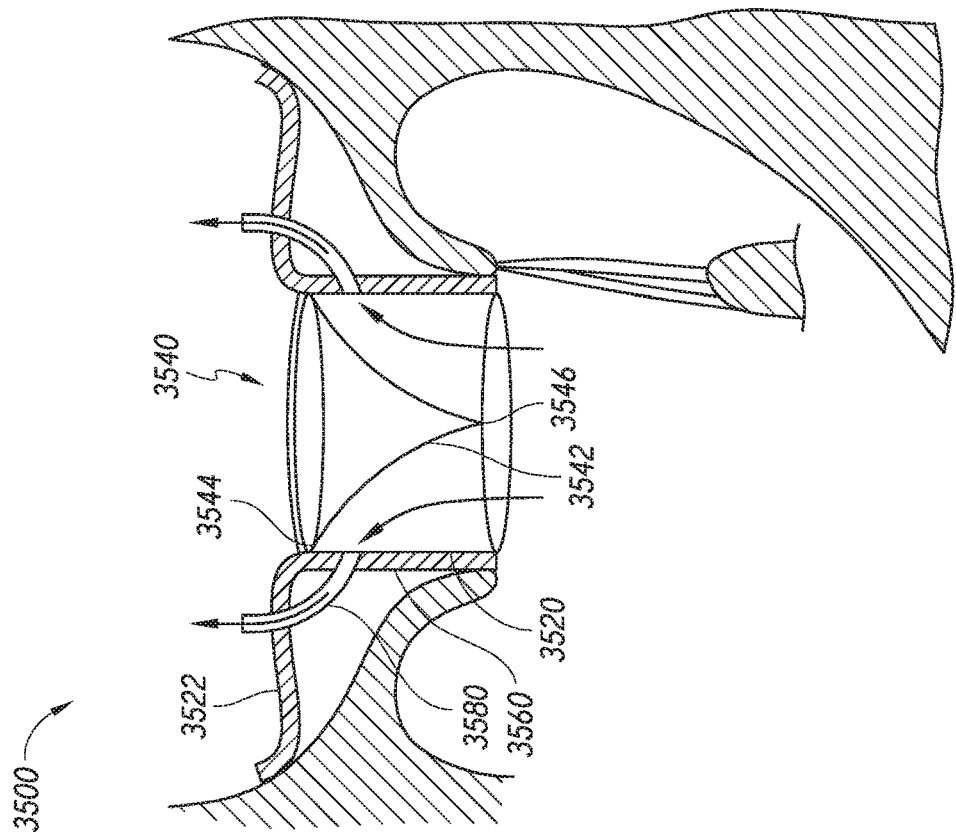
FIGS. 54 and 55 illustrate schematic representations of another embodiment of a prosthesis positioned within a heart.
Figure 54:
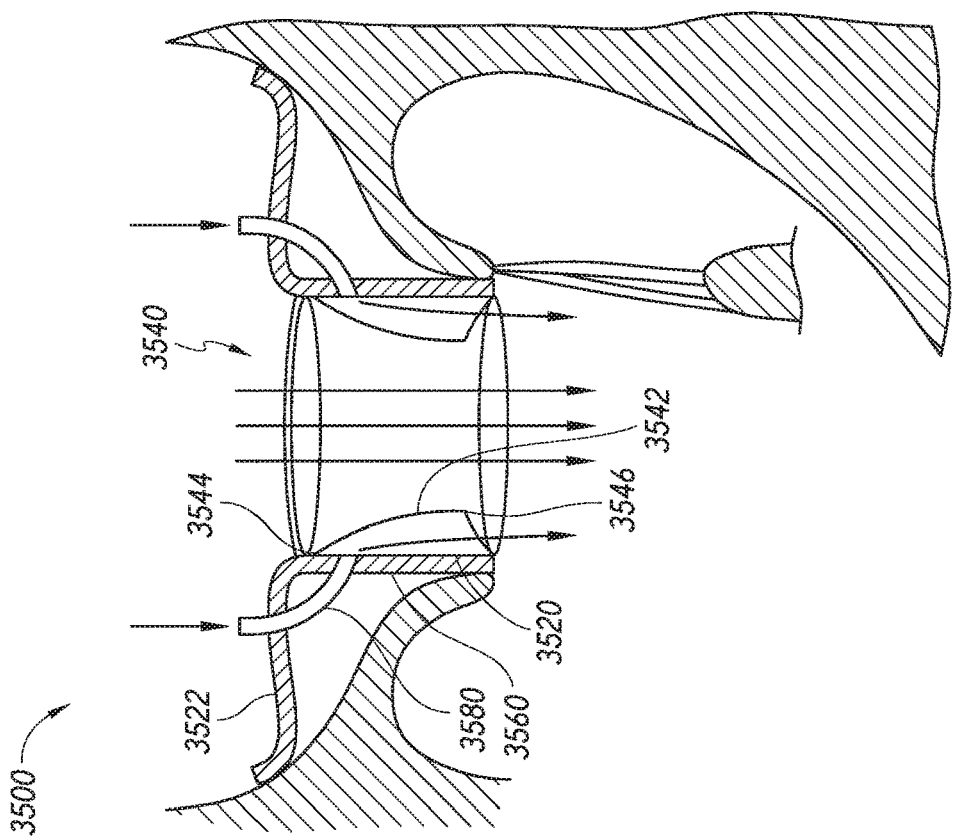

With reference next to the prosthesis 3500 illustrated in FIGS. 54 and 55, the prosthesis 3500 can include a frame 3520, a valve body 3540, and a skirt 3560. As shown in the illustrated embodiment, the prosthesis 3500 can be positioned within a native mitral valve. The frame 3520 can be self-expanding or balloon expandable. The frame 3520 can include a frame body formed from a plurality of struts defining a plurality of cells. One or more of the cells can allow the frame 3520 to longitudinally foreshorten when the frame 3520 radially expands. The frame 3520 can include one or more anchoring features 3522, such as an annular flange, to secure the prosthesis to a native valve, such as a native mitral valve.

The valve body 3540 preferably includes a plurality of valve leaflets 3542 each having at least a first edge 3544 and a second edge 3546. The cusp or first edge 3544, which may be considered a proximal edge, may be arcuate in shape. The second edge 3546 can be a freely moving edge which can allow the valve body 3540 to open and close. The valve leaflet 3542 can be similar to leaflet 1110 illustrated in FIG. 19A which includes a first edge 1112, a second edge 1114, and tabs 1116. The plurality of valve leaflets 3542 can function in a manner similar to the native mitral valve, or to any other valves in the vascular system as desired.

The skirt 3560 can be attached to the frame 3520. The skirt 3560 can be positioned around and secured to an exterior of the frame 3520. The skirt 3560 can be annular and can extend entirely circumferentially around the frame 3520. The skirt 3560 can generally prevent or inhibit backflow of fluids, such as blood, around the prosthesis 3500. For example, with the skirt 3560 positioned annularly around an exterior of the frame 3520, the skirt 3560 can create an axial barrier to fluid flow exterior to the frame 3520 when deployed within a body cavity such as a native valve annulus. As shown in the illustrated embodiment, the skirt 3560 can be tautly secured around the frame 3520 including the anchoring feature 3522. However, it is to be understood that the skirt 3560 can be loosely attached to the exterior of the frame 3520. As shown in the illustrated embodiment, at least a portion of the first edge 3544 of the valve leaflet 3542 can be attached to the skirt 3560.

The prosthesis 3500 can include one or more channels or conduits 3580 which can allow fluid ingress into and egress out of the space between the valve leaflet 3442 and the skirt 3460. For example, the prosthesis 3500 can include at least one conduit 3580 for each valve leaflet 3542. These conduits 3580 can extend between openings in the material forming the skirt 3560. As shown, the skirt 3560 can include an opening along a portion of the skirt 3560 proximate the valve leaflet 3542 (similar to that described above in connection with FIGS. 48 and 49) and an opening along a portion of the skirt 3560 extending along the anchoring feature 3522. The conduit 3580 can form a fluid pathway between these openings. In some embodiments, such as that shown, the conduits 3580 can extend past these openings. For example, the conduits 3580 can extend distally past the anchoring feature 3522 and extend into the atrium and/or the conduits 3580 can extend into a space between the skirt 3560 and the valve leaflet 3442. Blood flow through the one or more conduits 3580 can occur due to a pressure differential across the prosthesis 3500 (e.g., pressure differential between the left atrium and left ventricle during diastole and systole) and/or momentum (e.g., momentum of blood flow during systole).

The one or more conduits 3580 can be formed as structures separate from other components of the prosthesis 3500 such as the frame 3520, valve body 3540, and/or the skirt 3560. For example, the conduit 3580 can be a tube which is attached to one or more other components of the prosthesis 3500. However, it is to be understood that the one or more conduits 3580 can form part of one of the other components of the prosthesis 3500. For example, the one or more conduits 3580 can form part of the frame 3520. As another example, the one or more conduits 3580 can form part of the skirt 3560. In some embodiments, the one or more conduits 3580 can be a crease, such as a v-shaped crease, of the skirt 3560 which extends between the anchoring feature 3522 and the space between the skirt 3560 and the leaflets 3542.

By utilizing conduits 3580, the pathway for blood flow can be controlled. This can be beneficial in instances where the prosthesis 3500 includes structures positioned between the skirt 3560 and the left atrium such as anchoring feature 3522. Other examples include another skirt positioned exteriorly of the skirt 3560 such that the skirt 3560 is an inner skirt. The one or more channels or conduits 3580 can beneficially enhance hemodynamic performance of the prosthesis 3500. For example, the one or more conduits 3580 can allow for significant washout on an underside of the valve body 3540. That is, the one or more conduits 3580 can enhance the exchange of blood from a prior cardiac cycle, which may have stagnated and accumulated in crevices, pockets, and/or surfaces of the frame 3520, valve body 3540, and/or skirt 3560, with fresh blood from a current cardiac cycle. This washout can beneficially reduce the risk of thrombosis or clot formation under the valve body 3540.

As shown in the illustrated embodiment, the one or more conduits 3580 can be positioned such that blood flows at or proximate a proximal region of the space between the valve leaflet 3542 and the skirt 3560. For example, the one or more conduits 3580 can be positioned such that blood flows at or proximate the attachment between the first edge 3544 and the skirt 3560 near a proximal area of this attachment. By positioning the one or more conduits 3580 such that blood flows at or proximate a proximal region of the space between the valve leaflet 3542 and the skirt 3560, a greater degree of washout of the space between the valve leaflet 3542 and the skirt 3560 can be achieved. This can beneficially ensure that a majority, if not the entirety, of the valve leaflet 3442 is washed or flushed and reduce the likelihood of build-up of stagnant blood.

In some embodiments, the one or more conduits 3580 can be positioned such that blood flows at least above the distalmost part of the valve leaflet 3542 (e.g., the second edges 3546) when coapted during the systolic phase. In some embodiments, the one or more conduits 3580 can be positioned at or proximate a proximalmost region of the space between the valve leaflet 3442 and the skirt 3460. It is to be understood that the positioning, number, and size of the conduits 3580 can be chosen based on numerous factors including, but not limited to, the geometry of the prosthesis 3500 (i.e., frame 3520, valve body 3540, and/or skirt 3560) and the desired amount of washout.

As shown in FIG. 54, in some embodiments the one or more conduits 3580 can allow antegrade blood flow through the space between the valve leaflet 3542 and the skirt 3560 and into the ventricle during diastole. This can allow stagnant or trapped blood on the underside of the valve leaflet 3542 and the skirt 3560, from a prior systolic phase, to be flushed during the diastolic phase. As shown in FIG. 55, in some embodiments the one or more conduits 3580 can allow retrograde blood flow through the space between the valve leaflet 3542 and the skirt 3560 and into the atrium during systole. This can allow blood which was previously trapped on the underside of the valve leaflet 3542 and the skirt 3560, from a prior diastolic phase, to be flushed during the systolic phase.

In some embodiments, the one or more conduits 3580 can include one-way valves which allow blood to flow through the one or more conduits 3580 during systole or diastole while preventing or inhibiting blood to flow through the one or more conduits 3580 during the opposite phase. This can beneficially decrease undesirable retrograde flow during systole or antegrade flow during diastole through the one or more conduits 3580. In some embodiments, some of the one or more conduits 3580 can include one-way valves whereas other of the one or more conduits 3580 can permit flow in both directions. In this manner, the effective area of the one or more conduits 3580 can differ depending on the directionality of blood flow. It is to be understood that in some embodiments, at least one of the one-way valves can allow retrograde flow and at least one of the one-way valves may allow antegrade flow.

Although prosthesis 3500 incorporates one or more conduits 3580 extending between openings formed in the material of the skirt 3560, it is to be understood that the valve body 3540 and/or skirt 3560 can include openings which are not connected with conduits 3580. For example, the one or more openings can be formed along parts of the valve body, such as valve leaflets and/or intermediate components (not shown) as described above. Moreover, it is to be understood that in some embodiments, the conduits can be omitted and the skirt 3560 can simply include openings along a portion of the skirt 3560 extending along the frame. These openings can be positioned within an area of the skirt 3560 between the first edge 3544 of a valve leaflet 3542 (i.e., an area of the skirt positioned behind a valve leaflet 3442). These openings can be positioned within a portion of the skirt 3560 extending along the frame at the anchoring feature 3522. This can beneficially allow washout in a space between the skirt 3560 and the valve leaflet 3542 as well as in a space between the skirt 3560 and the native mitral valve leaflet (e.g., above the native mitral valve leaflet).

Figure 56:
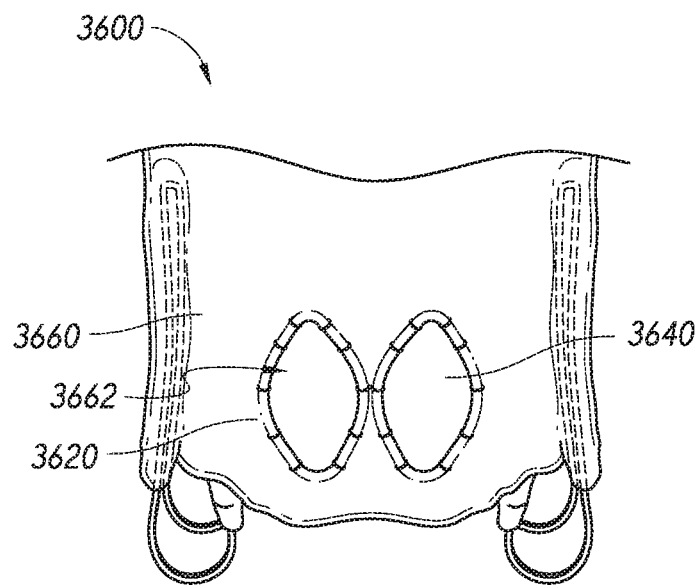
FIG. 56 illustrates a front view of an embodiment of a prosthesis, the prosthesis having a skirt with an opening.
Figure 57:
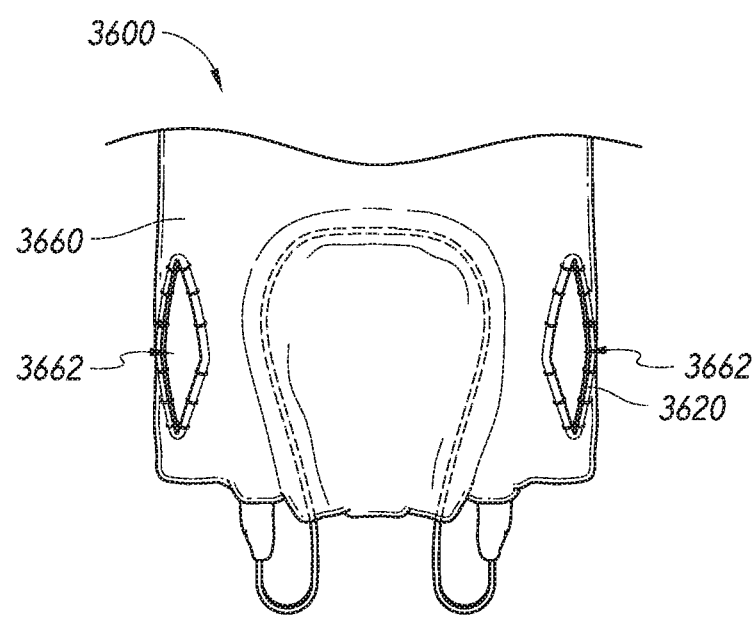
FIG. 57 illustrates a side view of the prosthesis of FIG. 56.

With reference next to the prosthesis 3600 illustrated in FIGS. 56 and 57, the prosthesis 3600 can include a frame 3620, a valve body 3640, and a skirt 3660. While the embodiments of prostheses 3400, 3500, and 3600 have included openings within skirts, it is to be understood that other components of the prosthesis can include one or more openings. For example, components of the valve body, such as the intermediate components and/or the valve leaflets can include one or more openings.

With reference to FIGS. 58-73, embodiments of prostheses 3800, 3900, 4000, 4100, 4200, 4300, 4400, 4500, 4600, 4700 or components thereof such as frames 3820, 3920, 4020, 4120, 4220, 4320, 4420, 4520, 4620, 4720 and skirts 3860, 3960, 4060, 4160, 4260, 4360, 4460, 4560, 4660, 4760 are illustrated. These embodiments illustrate components and geometries of skirts which can beneficially reduce paravalvular leakage around the prostheses when implanted within a native valve.

With reference first to the prosthesis 3800 illustrated in FIGS. 58-61, the prosthesis 3800 can include a frame 3820, a valve body (not shown), and a skirt 3860 which can be attached to the frame 3820. FIG. 58 illustrates the frame 3820 with the proximal end of the skirt 3860 detached from the frame 3820. FIG. 59 is a perspective-oriented, exploded schematic view of the skirt 3860 to illustrate the various parts forming the skirt 3860. FIGS. 60 and 61 illustrate the skirt 3860 in a first configuration and a second configuration. The frame 3820 can be self-expanding or balloon expandable. As shown in the illustrated embodiment, the frame 3820 can include a frame body formed from a plurality of struts defining a plurality of cells. One or more of the cells can allow the frame 3820 to longitudinally foreshorten when the frame 3820 radially expands.

The skirt 3860 can be positioned around and secured to an exterior of the frame 3820. As shown in the illustrated embodiment, the skirt 3860 can be loosely attached to the exterior of the frame 3820. The skirt 3860 can generally prevent or inhibit backflow of fluids, such as blood, around the prosthesis 3800. For example, with the skirt 3860 positioned annularly around an exterior of the frame 3820, the skirt 3860 can create an axial barrier to fluid flow exterior to the frame 3820 when deployed within a body cavity such as a native valve annulus. As such, the skirt 3860 can have a geometry which forms an advantageous seal over the native valve annulus, such as that of the native mitral valve annulus.

The skirt 3860 can be formed from multiple components such as an upper component 3862 and a lower component 3864. As shown in FIGS. 60 and 61, the upper component 3862 can be attached to an upper portion of the frame 3820, such as an upper edge or inflow end of the frame 3820. The upper component 3862 can extend downwardly and be attached to the lower component 3864. The lower component 3864 can be attached to the upper component 3862. As shown in the illustrated embodiment, the lower component 3864 can extend downwardly. As shown, the lower edge of the lower component 3864 can be attached along a lower portion of the frame 3820, such as a lower edge or outflow end of the frame 3820. It is contemplated that the lower component 3864 can have a lower edge with a shape that matches the lower edge of the frame 3820. While the skirt 3860 is formed from two components—an upper component 3862 and a lower component 3864—it is to be understood that the skirt 3860 can be formed from a fewer number of components or a greater number of components. For example, the skirt 3860 can be formed as a monolithic unit.

In embodiments where the prosthesis 3800 is designed for use in the native mitral valve, the prosthesis 3800 can include a valve body which inhibits or prevents blood flow in a retrograde direction (i.e., in a direction from the lower edge to the upper edge). As shown in FIG. 61, blood flow can be directed from within the frame 3820 and outwardly towards the skirt 3860 to expand the skirt 3860. In so doing, the skirt 3860 can impart a force on the native mitral valve annulus to enhance sealing and beneficially reduce paravalvular leakage. As shown, when in a radially expanded configuration, the skirt 3860 can have a shape which bulges radially outwardly closer to the upper end of the frame 3820 than the lower end of the frame 3820 due to the size of the components 3862, 3864 and the location of the seam lines. This can be beneficial in instances where the skirt 3860 is intended to be seated generally supra-annularly. However, it is to be understood that the skirt 3860 can have a shape which bulges radially outwardly closer to the lower end of the frame 3820 than the upper end of the frame 3820 when the skirt 3860 in a radially expanded configuration. This can be achieved by modifying the position of the attachment points of the skirt 3860. For example, the attachment point between the components 3862, 3864 can be shifted upwards.

Figure 62:
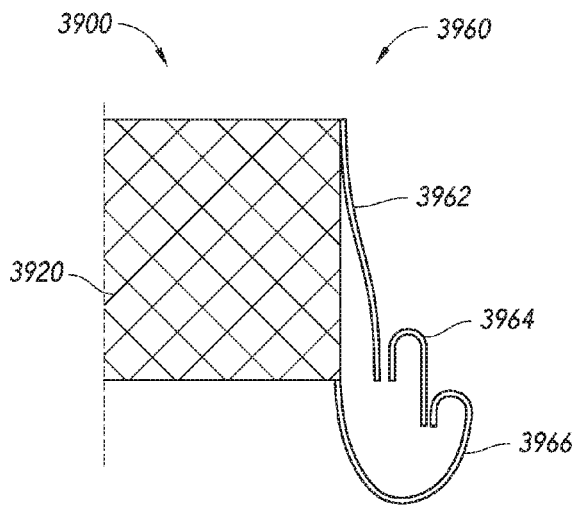
FIG. 62 illustrates a side-oriented cross-sectional schematic view of another embodiment of a frame and skirt.
Figure 63:
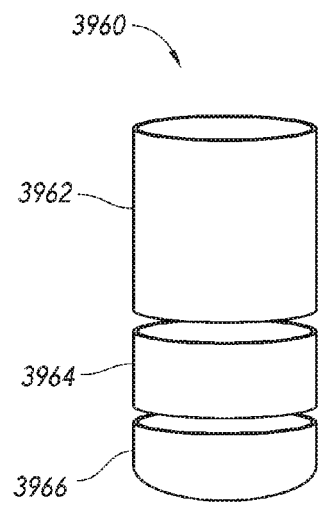
FIG. 63 illustrates a perspective-oriented, exploded schematic of the annular skirt of FIG. 62.
Figure 64:
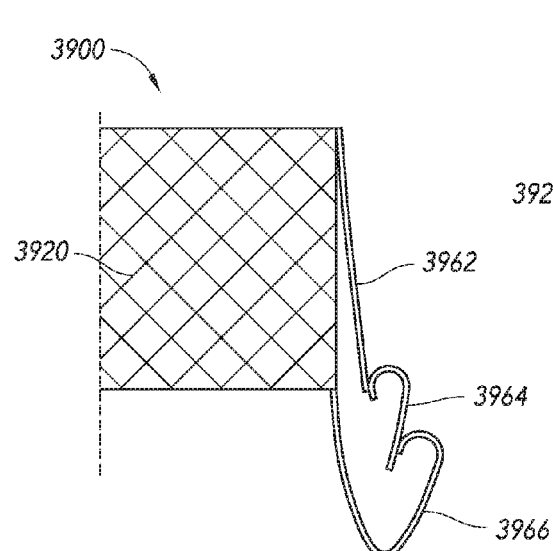
FIG. 64 illustrates a side-oriented cross-sectional schematic view of the frame and skirt of FIG. 62 in a first configuration.
Figure 65:
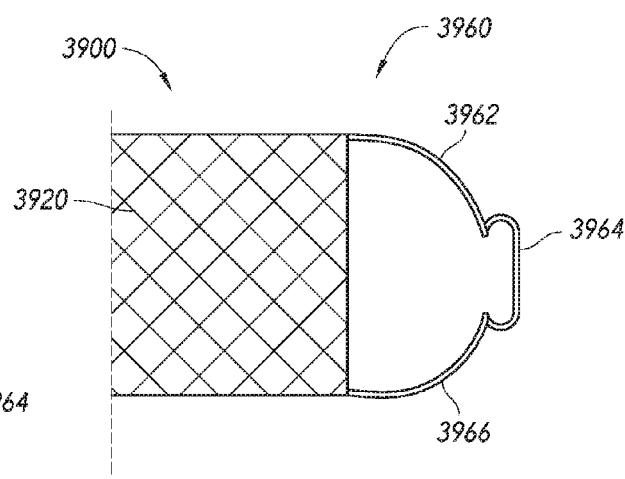
FIG. 65 illustrates a side-oriented cross-sectional schematic view of the frame and skirt of FIG. 62 in a second configuration.

With reference next to the prosthesis 3900 illustrated in FIGS. 62-65, the prosthesis 3900 can include a frame 3920, a valve body (not shown), and a skirt 3960 which can be attached to the frame 3920. FIG. 62 illustrates the frame 3920 with components of the skirt 3960 detached from each other. FIG. 63 is a perspective-oriented, exploded schematic view of the skirt 3960 to illustrate the various parts forming the skirt 3960. FIGS. 64 and 65 illustrate the skirt 3960 in a first configuration and a second configuration. The skirt 3960 can be formed from multiple components such as an upper component 3962, a middle component 3964, and a lower component 3966. The upper component 3962 can be attached to an upper portion of the frame 3920, such as an upper edge or inflow end of the frame 3920. The upper component 3962 can extend downwardly and be attached to the middle component 3964. The lower component 3966 can be attached to the middle component 3964 and can extend downwardly. As shown, the lower edge of the lower component 3966 can be attached along a lower portion of the frame 3920, such as a lower edge or outflow end of the frame 3920. It is contemplated that the lower component 3964 can have a lower edge with a shape that matches the lower edge of the frame 3920. While the skirt 3960 is formed from three components, it is to be understood that the skirt 3960 can be formed from a fewer number of components or a greater number of components. For example, the skirt 3960 can be formed as a monolithic unit.

In embodiments where the prosthesis 3900 is designed for use in the native mitral valve, the prosthesis 3900 can include a valve body which inhibits or prevents blood flow in a retrograde direction (i.e., in a direction from the lower edge to the upper edge). As shown in FIG. 65, blood flow can be directed from within the frame 3920 and outwardly towards the skirt 3960 to expand the skirt 3960. As shown, when in a radially expanded configuration, the skirt 3960 can have a supplemental rib or extension formed by the middle component 3964. The supplemental rib can have a partially toroidal shape, formed by the middle component 3964, which extends further radially outward from the middle portion of the skirt 3960 which itself forms an annular ring. This shape can be achieved via sizing of the components 3962, 3964, 3966 and the location of the seam lines. For example, portions of the components 3962, 3964, 3966 can overlap prior to being sutured or attached. This partially toroidal extension can beneficially increase the volume of the skirt in a region between an upper side and a lower side of the native valve annulus (e.g., an atrial side and a ventricular side of the native mitral valve annulus). This can beneficially ensure that the skirt 3960 forms a seal within the native valve annulus without significantly increasing the amount of material for the skirt 3960. This can beneficially allow the prosthesis 3900 to maintain a smaller form factor when in a collapsed configuration for delivery. While the partially toroidal extension is shown generally along a middle portion of the skirt 3960 when the skirt 3960 is in an expanded configuration, it is to be understood that the partially toroidal extension can be positioned higher or lower along the skirt 3960 when the skirt 3960 is in an expanded configuration. Moreover, while the partially toroidal extension has been described as having a greater volume within the native valve annulus to form a seal within the native valve annulus, it is to be understood that the partially toroidal extension can be positioned above or below the native valve annulus to seal above or below the native valve annulus.

Figures 66, 67:
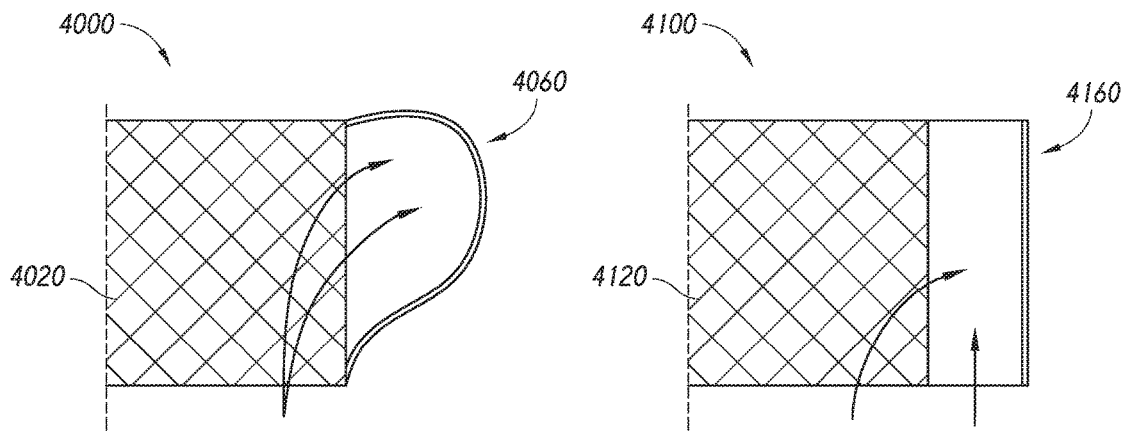
FIG. 66 illustrates a side-oriented cross-sectional schematic view of another embodiment of a frame and skirt.
FIG. 67 illustrates a side-oriented cross-sectional schematic view of another embodiment of a frame and skirt.

With reference next to the prosthesis 4000 illustrated in FIG. 66, the prosthesis 4000 can include a frame 4020, a valve body (not shown), and a skirt 4060 which can be attached to the frame 4020. In embodiments where the prosthesis 4000 is designed for use in the native mitral valve, the prosthesis 4000 can include a valve body which inhibits or prevents blood flow in a retrograde direction (i.e., in a direction from the lower edge to the upper edge). As shown, since the lower edge of the skirt 4060 is attached to the lower edge of the frame 4020, blood flow can be directed from within the frame 4020 and outwardly towards the skirt 4060 to expand the skirt 4060. As shown, when in an expanded configuration, the skirt 4060 can have a shape which bulges radially outwardly closer to the upper end of the frame 4020 than the lower end of the frame 4020. The skirt 4060 can also have a generally concave shape near a lower end of the skirt 4060. This can be beneficial in instances where the skirt 4060 is intended to be seated generally supra-annularly. However, it is to be understood that the dimensions of the skirt 4060 can be reversed.

With reference next to the prosthesis 4100 illustrated in FIG. 67, the prosthesis 4100 can include a frame 4120, a valve body (not shown), and a skirt 4160 which can be attached to the frame 4120. In embodiments where the prosthesis 4100 is designed for use in the native mitral valve, the prosthesis 4100 can include a valve body which inhibits or prevents blood flow in a retrograde direction (i.e., in a direction from the lower edge to the upper edge). As shown, since the lower edge of the skirt 4160 is not attached to the lower edge of the frame 4120, blood flow can be directed from outside the frame 4120 and into the skirt 4160.

Figures 68, 69:
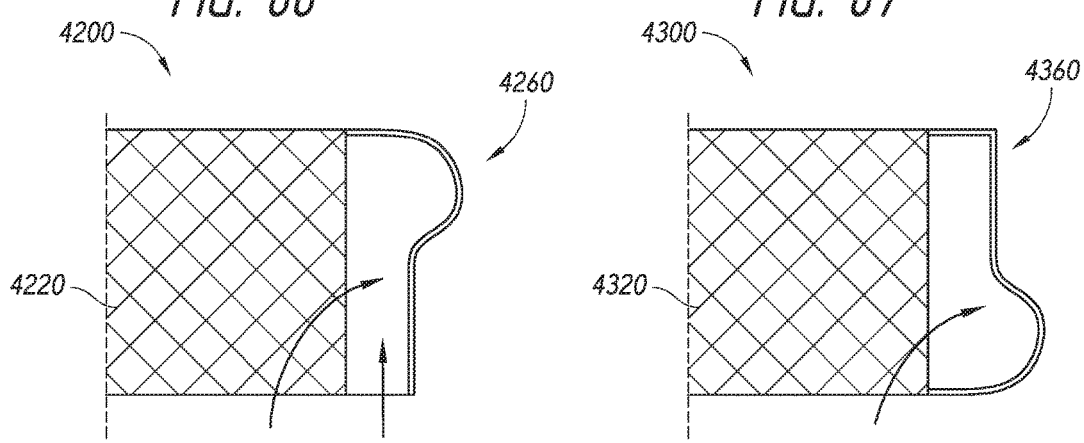
FIG. 68 illustrates a side-oriented cross-sectional schematic view of another embodiment of a frame and skirt.
FIG. 69 illustrates a side-oriented cross-sectional schematic view of another embodiment of a frame and skirt.
Figure 70:
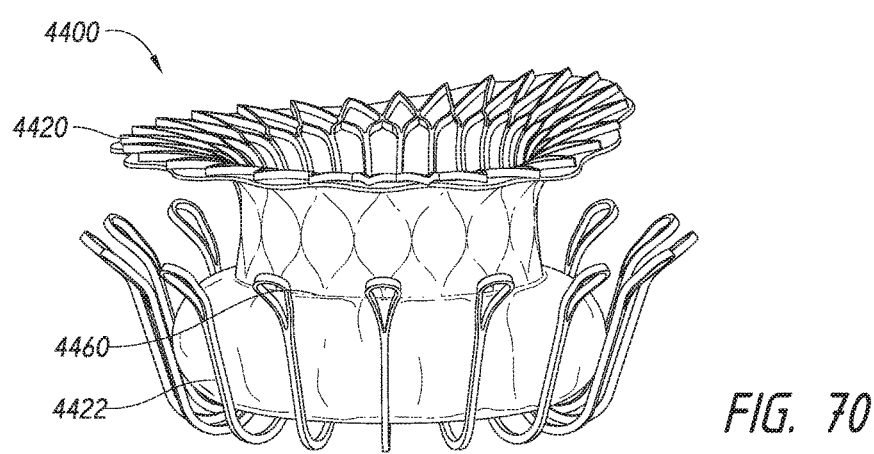
FIG. 70 illustrates a perspective view of an embodiment of a frame, a plurality of anchors, and a skirt.
Figure 74:
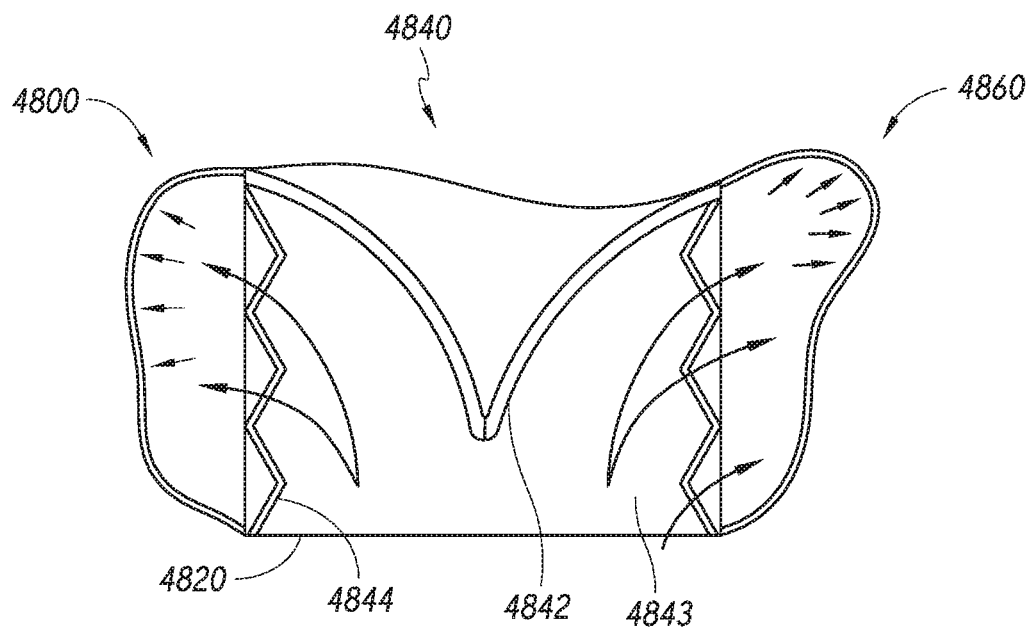
FIG. 74 illustrates a side-oriented cross-sectional schematic view of another embodiment of a frame, skirt, and a valve body.

Moreover, blood flow can be directed from within the frame 4120 and outwardly towards the skirt 4160 to expand the skirt 4160. As shown, when in an expanded configuration, the skirt 4160 can have a shape which is generally cylindrical. However, it is to be understood that the skirt 4160 can have a non-cylindrical shape. For example, as shown in FIG. 68, the skirt 4260 can have a shape which bulges radially outwardly closer to the upper end of the frame 4220 than the lower end of the frame 4220. However, it is to be understood that the dimensions of the skirt 4260 can be reversed.

With reference next to the prosthesis 4300 illustrated in FIG. 69, the prosthesis 4300 can include a frame 4320, a valve body (not shown), and a skirt 4360 which can be attached to the frame 4320. In embodiments where the prosthesis 4300 is designed for use in the native mitral valve, the prosthesis 4300 can include a valve body which inhibits or prevents blood flow in a retrograde direction (i.e., in a direction from the lower edge to the upper edge). As shown, since the lower edge of the skirt 4360 is attached to the lower edge of the frame 4320, blood flow can be directed from within the frame 4320 and outwardly towards the skirt 4360 to expand the skirt 4360. As shown, when in an expanded configuration, the skirt 4360 can have a shape which bulges radially outwardly closer to the lower end of the frame 4320 than the upper end of the frame 4320. In some embodiments, such as that of prosthesis 4400 of FIG. 70, the skirt 4460 can include a bulge which can beneficially be positioned proximate a lower anchoring feature 4422 of the frame 4420. This can enhance sealing sub-annularly by imparting a force upon the native leaflets towards a sub-annular surface of the native annulus. However, it is to be understood that the dimensions can be reversed.

FIGS. 71-73 illustrate top-oriented cross-sectional schematic views of prostheses 4500, 4600, 4700. The skirts 4560, 4660, 4700 can correspond to the skirts described above in connection with FIGS. 66-69 or any other skirt as described herein. With reference first to the prosthesis 4500 illustrated in FIG. 71, the prosthesis 4500 can include a frame 4520, a valve body (not shown), and a skirt 4560 which can be attached to the frame 4520. The skirt 4560 can extend around the entire periphery of the frame 4520 to a generally equivalent radial dimension when in an expanded configuration.

With reference next to the prosthesis 4600 illustrated in FIG. 72, the prosthesis 4600 can include a frame 4620, a valve body (not shown), and a skirt 4660 which can be attached to the frame 4620. As shown, when in an expanded configuration, the skirt 4660 can extend partially around the entire periphery of the frame 4620. This can be beneficial in instances where the prosthesis 4600 is positioned within native anatomy which is non-circular in shape and/or in instances where targeted contact locations can be advantageous. Moreover, this configuration can reduce the total material usage for skirt 4660 which can advantageously reduce the overall form factor when in a compact configuration for delivery.

With reference next to the prosthesis 4700 illustrated in FIG. 73, the prosthesis 4700 can include a frame 4720, a valve body (not shown), and a skirt 4760 which can be attached to the frame 4720. As shown, the skirt 4760 can extend around the entire periphery of the frame 4720. When in an expanded configuration, the skirt 4760 can extend to different radial dimensions with a first peripheral region 4762 extending to a first radial dimension and a second peripheral region 4764 extending to a second radial dimension greater than the first radial dimension. The second region 4764 can form one or more bulges which extends further radially outward than the other portions of the skirt 4760. This can be beneficial in instances where the prosthesis 4700 is positioned within native anatomy which is non-circular in shape and/or in instances where targeted contact locations can be advantageous. Moreover, this configuration can reduce the total material usage for skirt 4760 which can advantageously reduce the overall form factor when in a compact configuration for delivery.

Although the skirts 3860, 3960, 4060, 4160, 4260, 4360, 4460 described above are illustrated as extending the entire height of the frames 3820, 3920, 4020, 4120, 4220, 4320, 4420, it is to be understood that the skirts can extend only a part of the height of the frames.

With reference to FIGS. 74-79, embodiments of prostheses 4800, 4900, 5000, 5100, or components thereof such as frames 4820, 4920, 5020, 5120, valve bodies 4840, and skirts 4860, 4960, 5060, 5160, are illustrated. These embodiments illustrate methods by which skirts can extend radially outwardly and impart a force upon native tissue, such as tissue of a native valve annulus. With reference first to the prosthesis 4800 illustrated in FIG. 74, the prosthesis 4800 can include a frame 4820, a valve body 4840, and a skirt 4860 which can be attached to the frame 4820. The frame 4820 can be self-expanding or balloon expandable. As shown in the illustrated embodiment, the frame 4820 can include a frame body formed from a plurality of struts defining a plurality of cells. One or more of the cells can allow the frame 4820 to longitudinally foreshorten when the frame 4820 radially expands.

The valve body 4840 preferably includes a plurality of valve leaflets 4842 and a valve skirt 4843. The valve skirt 4843 can include one or more openings or windows 4844 which can allow fluid communication between an interior of the valve body 4840 and an interior of the skirt 4860. These openings or windows 4844 can be similar to those described above in connection with FIGS. 48-56. The plurality of valve leaflets 4842 can function in a manner similar to the native mitral valve, or to any other valves in the vascular system as desired. The skirt 4860 can be positioned around and secured to an exterior of the frame 4820. As shown in the illustrated embodiment, the skirt 4860 can be loosely attached to the exterior of the frame 4820. The skirt 4860 can generally prevent or inhibit backflow of fluids, such as blood, around the prosthesis 4800. For example, with the skirt 4860 positioned annularly around an exterior of the frame 4820, the skirt 4860 can create an axial barrier to fluid flow exterior to the frame 4820 when deployed within a body cavity such as a native valve annulus. As such, the skirt 4860 can have a geometry which forms an advantageous seal over the native valve annulus, such as that of the native mitral valve annulus.

In embodiments where the prosthesis 4800 is designed for use in the native mitral valve, the prosthesis 4800 can include a valve body 4840 which inhibits or prevents blood flow in a retrograde direction (i.e., in a direction from the lower edge to the upper edge). As shown, blood flow can be directed from within the frame 4820 and outwardly towards the skirt 4860 to expand the skirt 4860. The openings or windows 4844 of the valve skirt 4843 can beneficially direct blood flow towards particular areas of the skirt 4860. In so doing, the skirt 4860 can impart a force on the native mitral valve annulus to enhance sealing and beneficially reduce paravalvular leakage. As shown, multiple openings or windows 4844 can be positioned along the valve skirt 4843 at various axial positions. In some embodiments, multiple openings or windows can form a row which extends a substantial portion of the height of the frame 4820. In some embodiments, a single opening can extend a substantial portion of the height of the frame 4820. However, it is to be understood that the openings or windows 4844 can instead be positioned a part of the height of the frame 4820.

Figure 75:
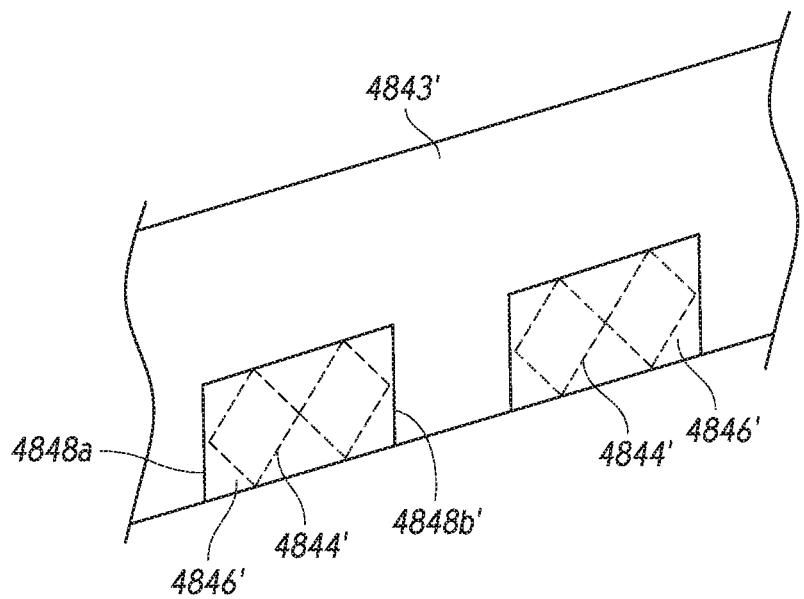
FIG. 75 illustrates a perspective-oriented schematic view of another embodiment of a skirt having one-way valves.

In some embodiments, components of the prosthesis 4800, such as the valve body 4840 and/or skirt 4860, can include one or more one-way valves which inhibit or prevent blood from flowing out of the skirt 4860. For example, as shown in the embodiment of valve skirt 4843' illustrated in FIGS. 75-77, the valve skirt 4843' can include one-way valves 4846' in the form of flaps which cover the openings 4844' in the valve skirt 4843'. As shown in FIG. 75, the one-way valves 4846' can be positioned along an exterior of the valve skirt 4843'. The one-way valves 4846' can be attached to the valve skirt 4843' via sutures along at least a portion of the periphery of the one-way valves 4846'. For example, as shown in the illustrated embodiment, the one-way valves 4846' can be attached to the valve skirt 4843' along side edges 4848a', 4848b' of the one-way valves 4846'. However, it is to be understood that the one-way valves 4846' can be attached to the valve skirt 4843' along other portions of the periphery such as the top and/or bottom edges of the one-way valves 4846'.

Figure 76:
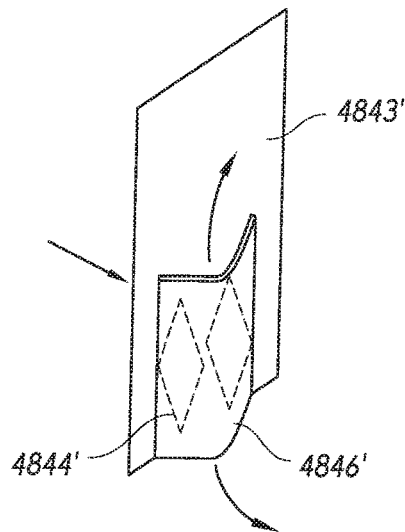
FIG. 76 illustrates a perspective-oriented schematic view of the skirt of FIG. 75 with a one-way valve in an open configuration.
Figure 77:
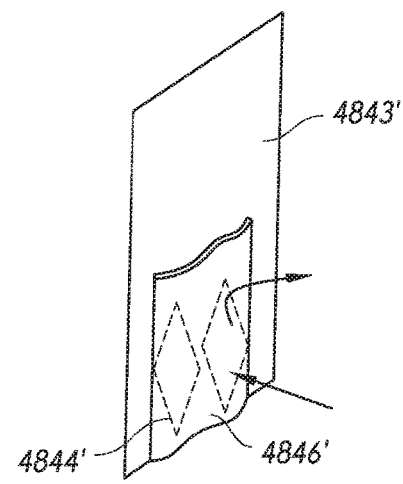
FIG. 77 illustrates a perspective-oriented schematic view of the skirt of FIG. 75 with a one-way valve in a closed configuration.

The one-way valves 4846' can allow flow in a first direction and reduce or inhibit flow in a second direction opposite the first direction. For example, as shown in FIG. 76, the one-way valves 4846' can transition to an open configuration when subject to fluid flow in a direction from a first side of the valve skirt 4843' to a second side of the valve skirt 4843'. As shown in FIG. 77, the one-way valves 4846' can transition to a closed configuration when subject to fluid flow in a direction from a second side of the valve skirt 4843' to a first side of the valve skirt 4843'. In some instances, this transitioning between open and closed configurations may be caused by a pressure differential between the two sides of the valve skirt 4843'. For example, the one-way valves 4846' can transition into the open configuration during systole and transition into the closed configuration during diastole. However, it is to be understood that the operation of the one-way valves 4846' may be reversed such that the one-way valves 4846' transition into the open configuration during diastole and transition into the closed configuration during systole.

In some embodiments, the one or more one-way valves 4846' can allow flow in a first direction from inside the valve body, such as valve body 4840, and into a skirt, such as skirt 4860, and reduce or inhibit flow in a second direction out of the skirt into the valve body. For example, the one or more one-way valves 4846' can allow flow into a skirt, such as skirt 4860, during systole and reduce or inhibit flow out of the skirt during diastole. This can beneficially ensure that the skirt 4860 remains in a generally enlarged configuration throughout the various phases of the cardiac cycle and thereby reduce material fatigue. Moreover, since the skirt 4860 is maintained in the second configuration with a fluid, the skirt 4860 can better conform to the native anatomy. This can beneficially enhance tissue ingrowth along the skirt 4860 due to constant contact with surrounding body tissue.

Additionally, by ensuring that the skirt 4860 remains in a generally enlarged configuration, the amount of blood traveling into skirt 4860 during systole can be reduced since the skirt 4860 is already filled with blood. This can advantageously increase efficiency of the left ventricle since little to no blood volume is pumped into the skirt 4860 once the skirt 4860 is filled. Moreover, by relying on blood flow into the skirt 4860, the prosthesis 4800 advantageously take on a relatively compact form factor when initially delivered to the native heart valve. In some instances, since the skirt 4860 is maintained in the second configuration with blood, the consistency of the skirt 4860 can more closely match that of native valve tissue and allow movement of the prosthesis 4800 to be dampened during the cardiac cycle.

It is to be understood that the one-way valves 4846' can take on other forms, such as duckbill valves and slit valves. In some embodiments, the one-way valves 4846' can incorporate features, such as nitinol struts, which bias the one-way valves 4846' into a closed configuration. As another example, the one-way valves 4846' can be shaped similarly to a windsock with a larger cross-sectional area at an inlet end and a smaller cross-sectional area at an outlet end. When subject to flow in a first direction from the inlet end to the outlet end, the one-way valve 4846' can transition to an expanded configuration in which the one-way valve 4846' allows blood to flow through the valve 4846'. When subject to flow in a second direction from the outlet end to the inlet end, the one-way valve 4846' can collapse upon itself such that blood is not allowed to flow through the valve 4846'.

Figure 78:
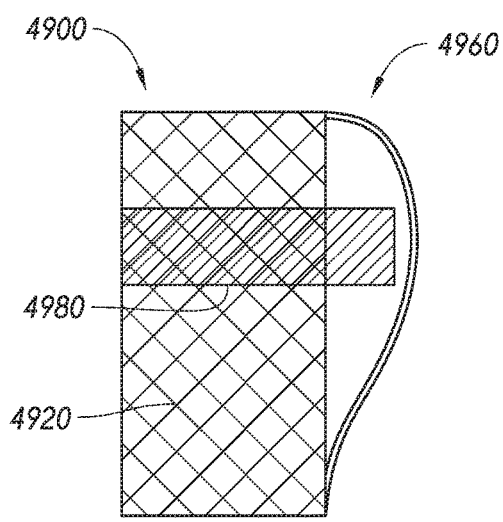
FIG. 78 illustrates a side-oriented cross-sectional schematic view of an embodiment of a frame, a skirt, and a biasing member.
Figure 79:
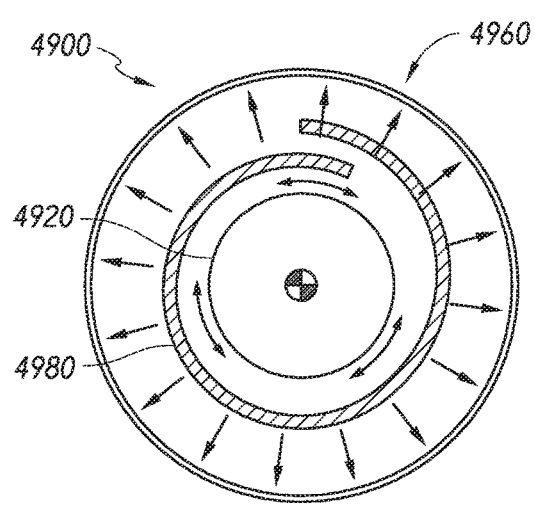
FIG. 79 illustrates a top-oriented cross-sectional schematic view of the frame, skirt, and biasing member of FIG. 78.

With reference first to the prosthesis 4900 illustrated in FIGS. 78 and 79, the prosthesis 4900 can include a frame 4920, a valve body (not shown), and a skirt 4960 which can be attached to the frame 4920. The frame 4920 can be self-expanding or balloon expandable. As shown in the illustrated embodiment, the frame 4920 can include a frame body formed from a plurality of struts defining a plurality of cells. One or more of the cells can allow the frame 4920 to longitudinally foreshorten when the frame 4920 radially expands.

The skirt 4960 can be positioned around and secured to an exterior of the frame 4920. As shown in the illustrated embodiment, the skirt 4960 can be loosely attached to the exterior of the frame 4920. The skirt 4960 can generally prevent or inhibit backflow of fluids, such as blood, around the prosthesis 4900. For example, with the skirt 4960 positioned annularly around an exterior of the frame 4920, the skirt 4960 can create an axial barrier to fluid flow exterior to the frame 4920 when deployed within a body cavity such as a native valve annulus. As such, the skirt 4960 can have a geometry which forms an advantageous seal over the native valve annulus, such as that of the native mitral valve annulus.

Figure 80:
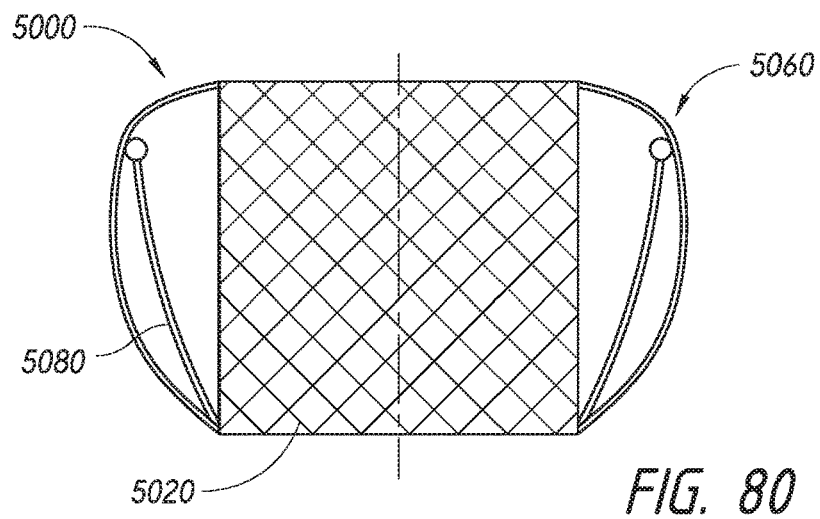
FIG. 80 illustrates a side-oriented cross-sectional schematic view of another embodiment of a frame, a skirt, and a biasing member.
Figure 81:
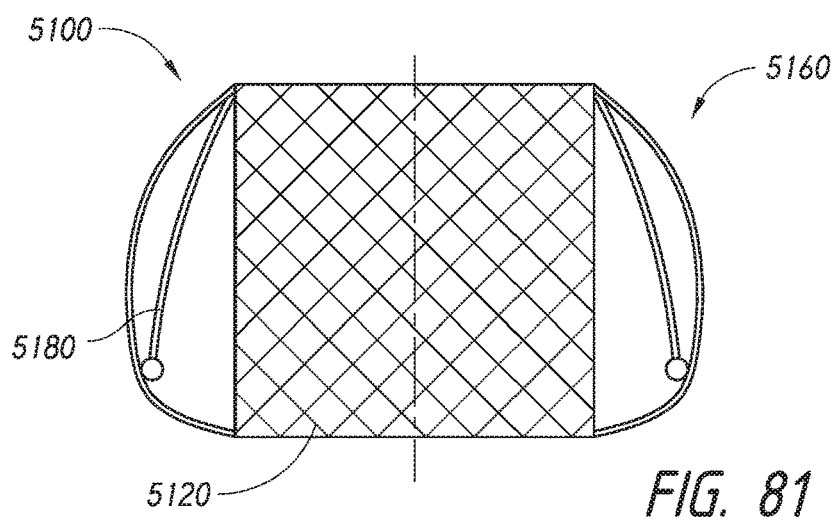
FIG. 81 illustrates a side-oriented cross-sectional schematic view of another embodiment of a frame, a skirt, and a biasing member.
Figure 82:
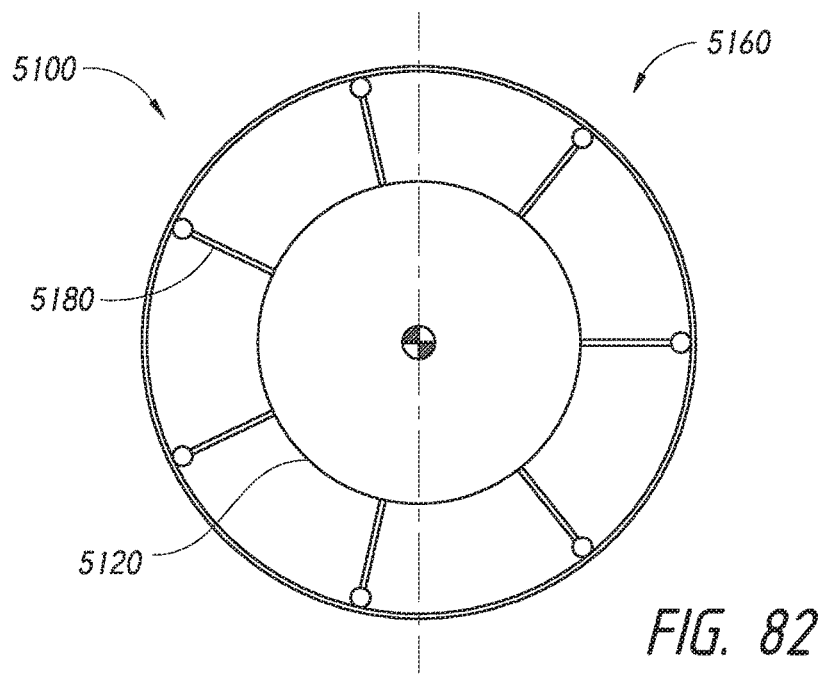
FIG. 82 illustrates a top-oriented cross-sectional schematic view of the frame, skirt, and biasing member of FIG. 80.

As shown, the prosthesis 4900 can include a biasing member 4980, such as a radial or torsion spring, which imparts a radially outward force upon the skirt 4960 to bias the skirt 4960 radially outwardly. In so doing, the skirt 4960 can impart a force on the native mitral valve annulus to enhance sealing and beneficially reduce paravalvular leakage. It is to be understood that other types of biasing members, such as coil springs, can be used. Moreover, as shown in the embodiments of prostheses 5000, 5100 illustrated in FIGS. 80-82, other types of biasing members 5080, 5180, such as cantilevers or arms, can be used to bias skirts 5060, 5160 radially outwardly of frames 5020, 5120. As shown in FIGS. 80-82, the biasing members 5080, 5180 can extend from various portions of the frame such as the upper edge and/or the lower edge. Other embodiments of biasing members are described in further detail in U.S. application Ser. No. 15/247,461, filed Aug. 25, 2016, which has been incorporated by reference herein in its entirety.

In some embodiments, the biasing members 4980, 5080, 5180 can be used in combination with blood flow into the skirts 4060, 5060, 5160, to impart a force on surrounding tissue. For example, the configuration of prostheses 4900, 5000, 5100 can be used in combination with the configuration of prosthesis 4800. This can beneficially increase the amount of force imparted on surrounding tissue. However, it is to be understood that the biasing members 4980, 5080, 5180 can be utilized without blood flow into the skirts to impart such forces on surrounding tissue.

Exemplary Placement of Replacement Valves

Reference is now made to FIGS. 41A-43 which illustrate schematic representations of an embodiment of a prosthesis 3000 positioned within a native mitral valve of a heart 10. As noted above, in some embodiments the prostheses described herein can be positioned within a native mitral valve. A portion of the native mitral valve is shown schematically and represents typical anatomy, including a left atrium 20 positioned above an annulus 40 and a left ventricle 30 positioned below the annulus 40. The left atrium 20 and left ventricle 30 communicate with one another through a mitral annulus 40. Also shown schematically in FIGS. 41A-43 is a native mitral leaflet 50 having chordae tendineae 60 that connect a downstream end of the mitral leaflet 50 to the papillary muscle of the left ventricle 30. The portion of the prosthesis 3000 disposed upstream of the annulus 40 (toward the left atrium) can be referred to as being positioned supra-annularly. The portion generally within the annulus 40 can be referred to as positioned intra-annularly. The portion downstream of the annulus 40 can be referred to as being positioned sub-annularly (toward the left ventricle). In the illustrated embodiment, only a part of the foreshortening portion is positioned intra-annularly or sub-annularly, and the rest of the prosthesis 3000 is supra-annular.

As shown in the situations illustrated in FIGS. 22A-23B, the prosthesis 3000 can be disposed so that the mitral annulus 40 is between the upper or atrial anchoring feature 3010 and the lower or ventricular anchoring feature 3020. In some situations, the prosthesis 3000 can be positioned such that ends or tips 3022 of the lower anchoring feature 3020 can contact the ventricular side of the annulus 40 as shown, for example, in FIGS. 41A-C. In some situations, the prosthesis 3000 can be positioned such that ends or tips 3022 of the lower anchoring feature 3020 do not contact the annulus 40 as shown, for example, in FIGS. 42A-B, and may just contact a downstream side of the leaflet 50. In some situations, the prosthesis 3000 can be positioned such that the lower anchoring feature 3020 do not extend around the leaflet 50 as illustrated, but rather are positioned radially inward of the leaflet 50 as shown, for example, in FIG. 43. While FIGS. 41A-43 are described separately below, it should be understood that one or more of the situations illustrated in FIGS. 41A-43 may be present when the prosthesis 3000 is positioned at the implantation location, such as a native mitral valve. For example, in some situations the prosthesis 3000 may be positioned such that some portion of the anchoring feature 3020 may contact the annulus 40 while another portion of the lower anchoring feature 3020 may not. Moreover, it may be contemplated some in some situations, some portion of the anchoring feature 3020 may be positioned With reference first to the situations illustrated in FIGS. 41A-42B, the prosthesis 3000 can be positioned so that the ends or tips 3022 of the lower anchoring feature 3020 are on a ventricular side of the mitral annulus 40 and the ends or tips 3012 of the upper anchoring feature 3010 are on an atrial side of the mitral annulus 40. The lower anchoring feature 3020 can be positioned such that the ends or tips 3022 of the lower anchoring feature 3020 are on a ventricular side of the native leaflets radially outwardly beyond a location where chordae tendineae 60 connect to free ends of the native leaflets 50. The lower anchoring feature 3020 may extend between at least some of the chordae tendineae 60 and, in some situations such as those shown in FIGS. 41A-C, can contact or engage a ventricular side of the annulus 40. It is also contemplated that in some situations, such as those shown in FIGS. 42A-B, the lower anchoring feature 3020 may not contact the annulus 40, though the lower anchoring feature 3020 may still contact the native leaflet 50. In some situations, the lower anchoring feature 3020 can contact tissue of the left ventricle 30 beyond the annulus 40 and/or a ventricular side of the leaflets 50.

Figure 41A:
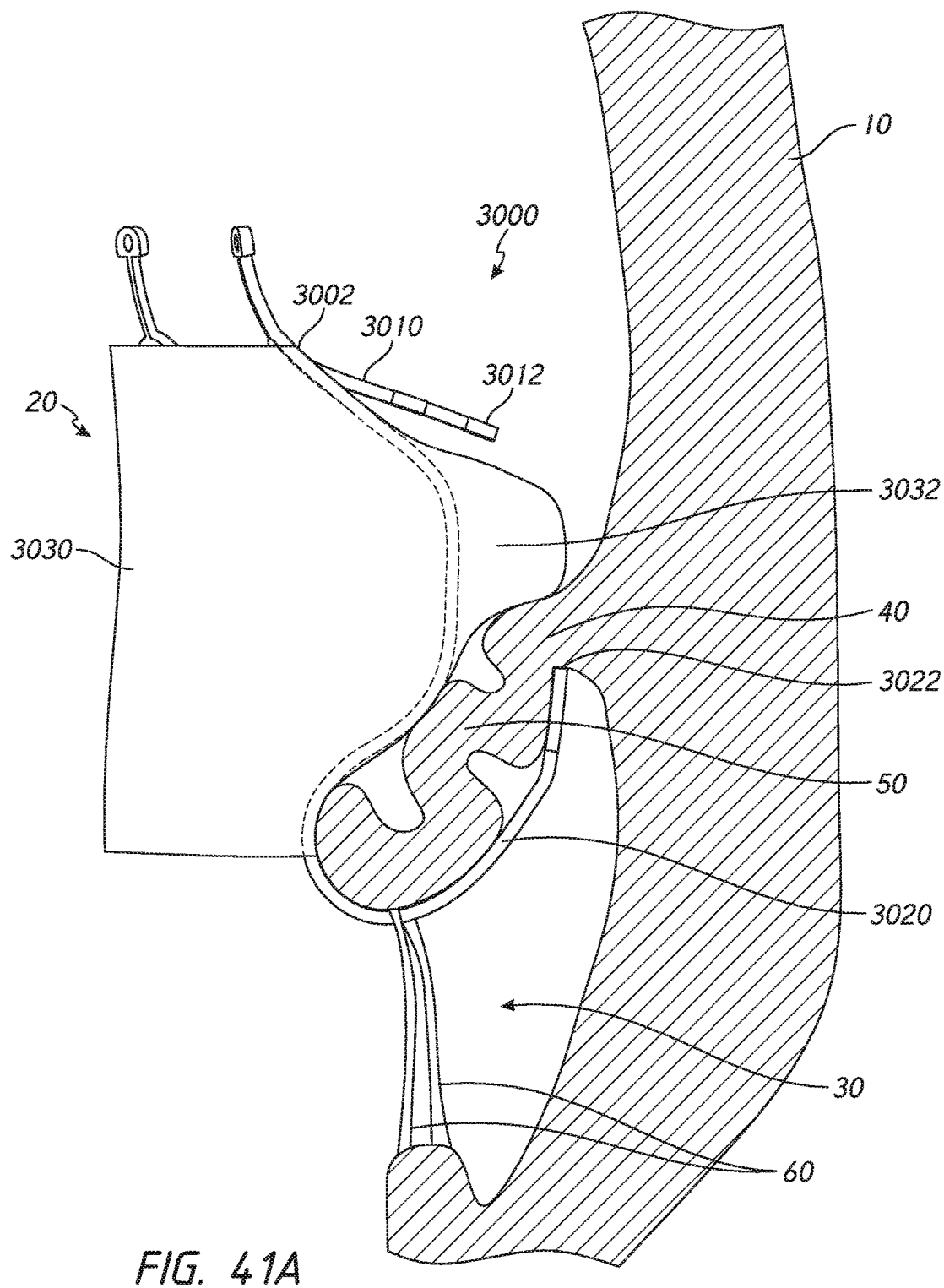
FIG. 41A-43 illustrate schematic representations of the prosthesis of FIG. 3 positioned within a heart, with FIGS. 41A-41C illustrating the prosthesis in situ with distal anchors contacting the ventricular side of a mitral valve annulus, FIGS. 42A-42B illustrating the prosthesis in situ with distal anchors not contacting the ventricular side of the mitral valve annulus, and FIG. 43 illustrating the prosthesis in situ with distal anchors not extending between the chordae tendineae.
Figure 41B:
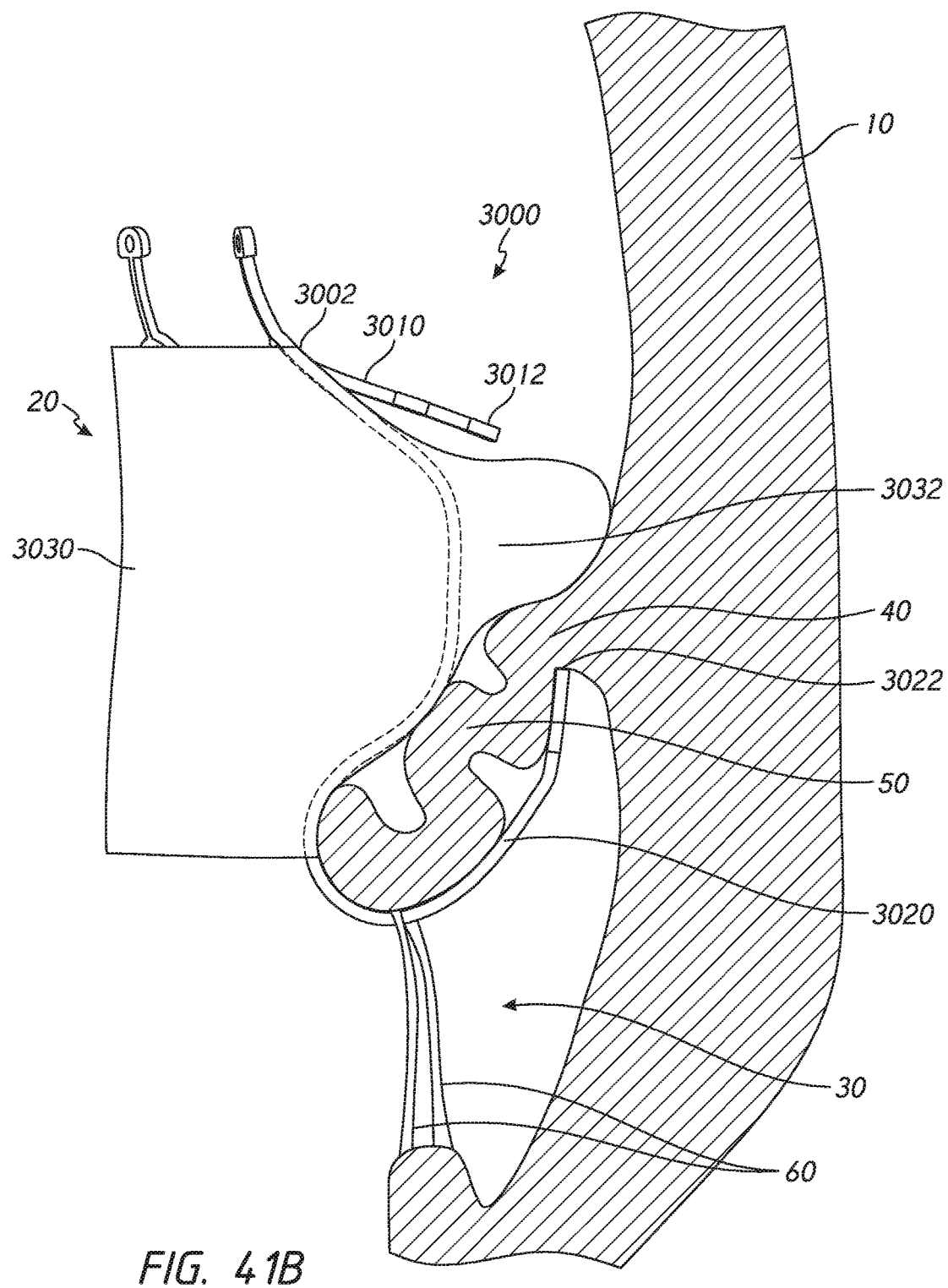
Figure 41C:
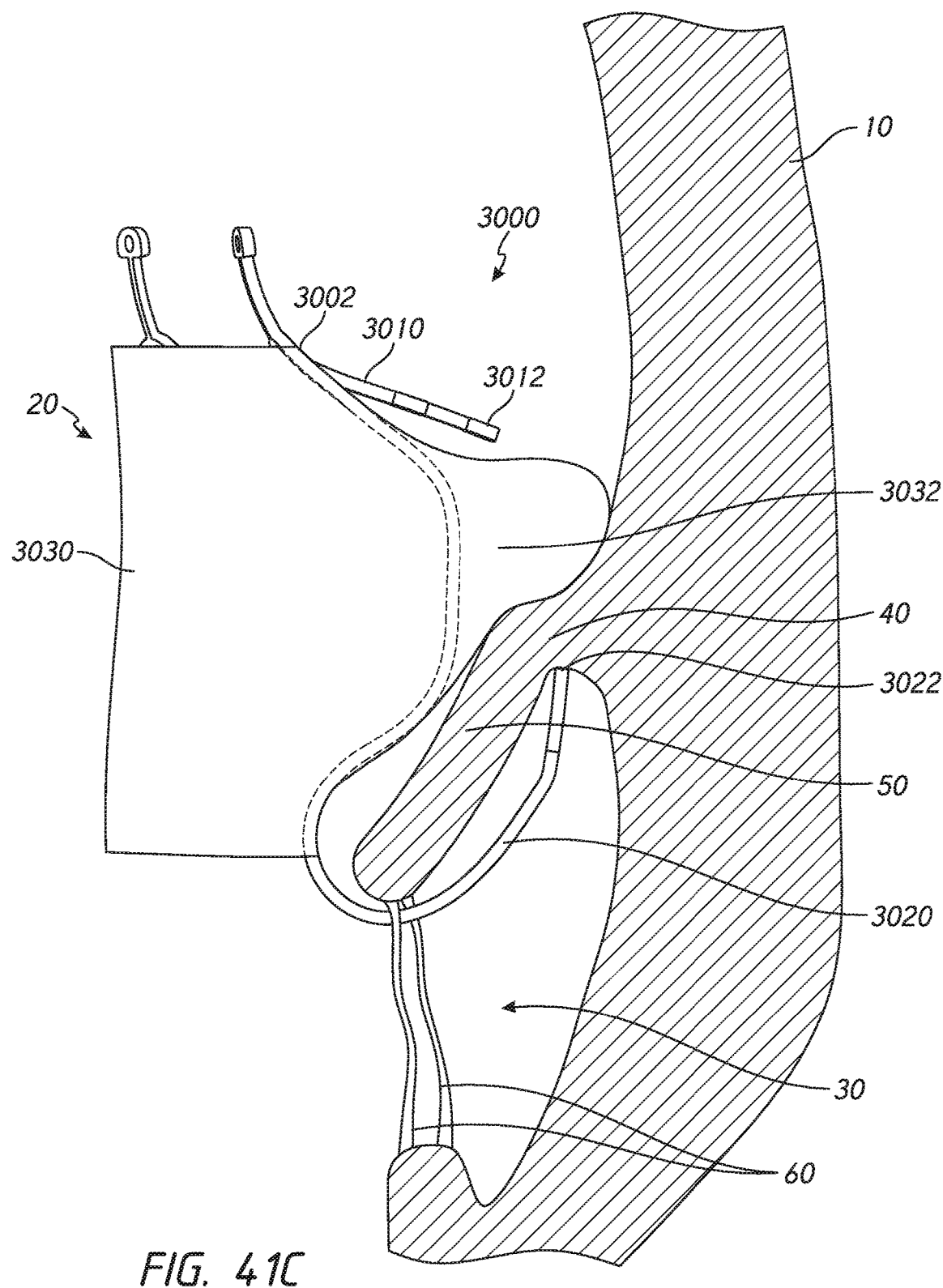
Figure 42A:
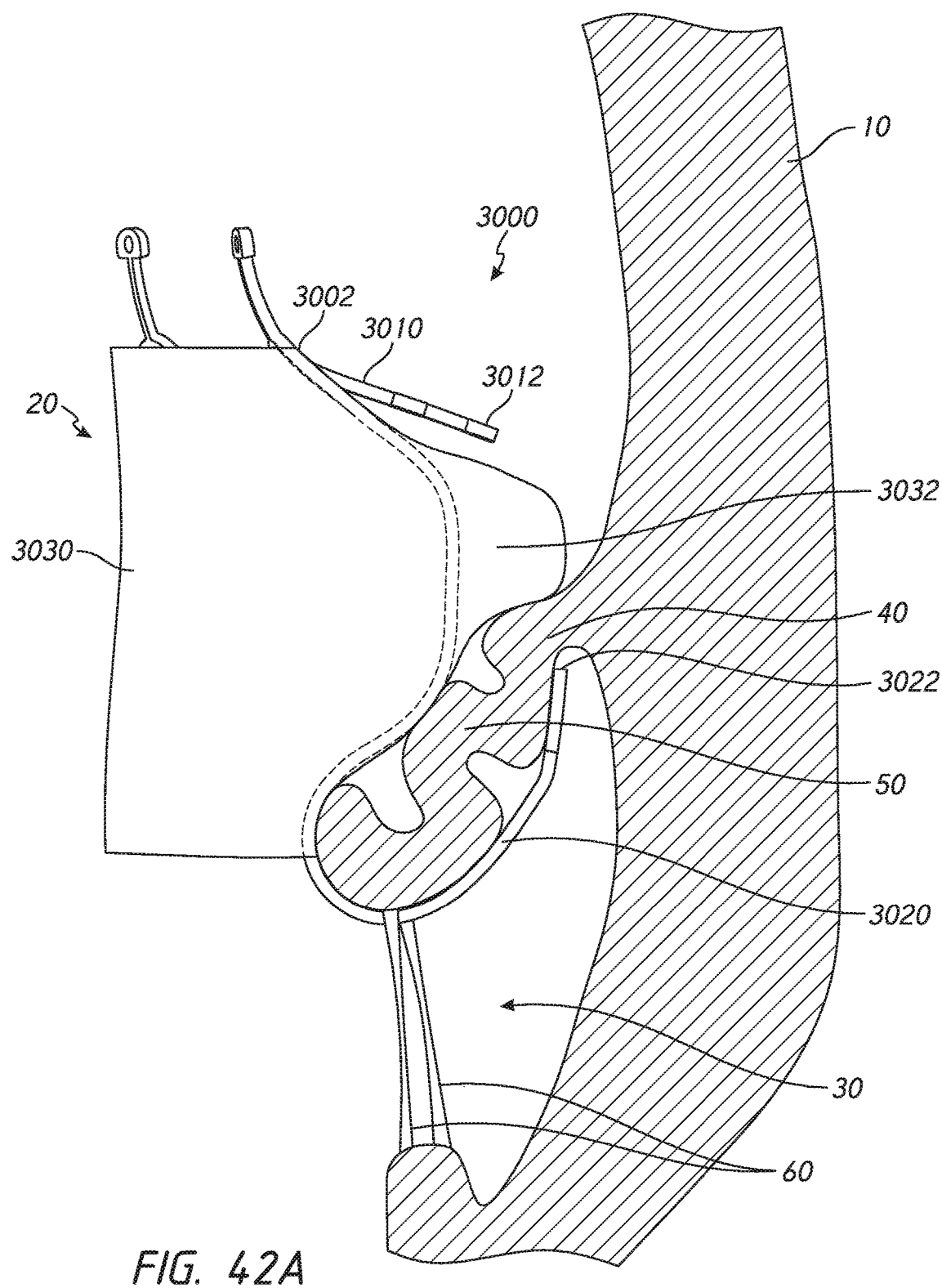
Figure 42B:
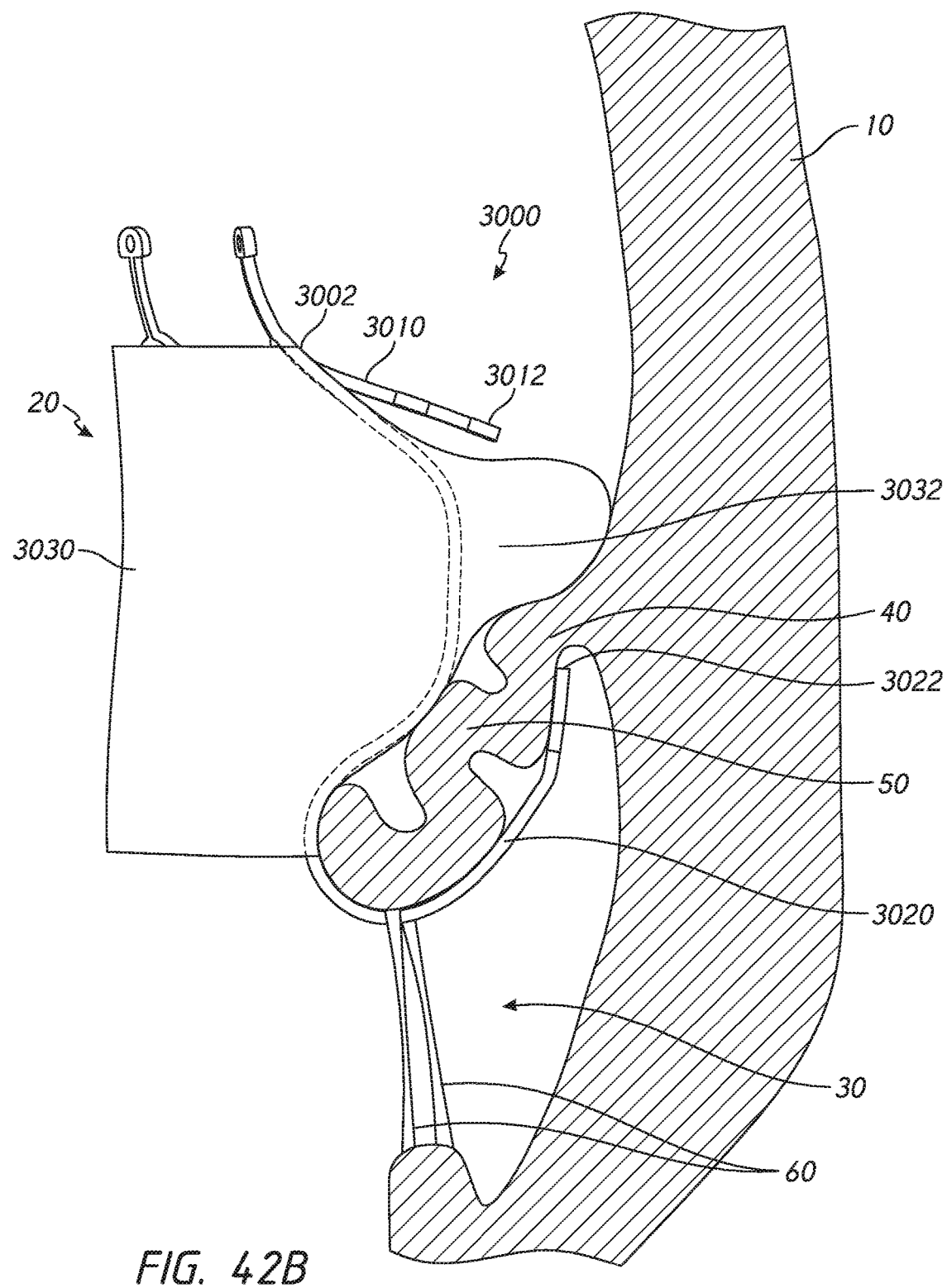

During delivery, the lower anchoring feature 3020 (along with the frame 3002) can be moved toward the ventricular side of the annulus 40 with the lower anchoring feature 3020 extending between at least some of the chordae tendineae 60 to provide tension on the chordae tendineae 60 after the prosthesis 3000 is finally delivered. The degree of tension provided on the chordae tendineae 60 can differ. For example, little to no tension may be present in the chordae tendineae 60 as shown in FIG. 41C where the leaflet 50 is shorter than or similar in size to the lower anchoring feature 3020. A greater degree of tension may be present in the chordae tendineae 60 as shown in FIGS. 41A and 42B where the leaflet 50 is longer than the lower anchoring feature 3020 and, as such, takes on a compacted form and is pulled proximally. An even greater degree of tension may be present in the chordae tendineae 60 as shown in FIGS. 42A-B where the leaflets 50 are even longer relative to the lower anchoring feature 3020. As shown in FIGS. 42A-B, the leaflet 50 is sufficiently long such that the lower anchoring feature 3020 do not contact the annulus 40.

The upper anchoring feature 3010 can be positioned such that the ends or tips 3012 of the upper anchoring feature 3010 are on or adjacent the atrial side of the annulus 40 and/or tissue of the left atrium 20 beyond the annulus 40. In some situations, some portion or all of the upper anchoring feature 3010 may only occasionally contact or engage atrial side of the annulus 40 and/or tissue of the left atrium 20 beyond the annulus 40. For example, as shown in FIGS. 41A-B, the upper anchoring feature 3010 may be spaced from the atrial side of the annulus 40 and/or tissue of the left atrium 20 beyond the annulus 40. The upper anchoring feature 3010 may be utilized to provide axial stability for the prosthesis 3000 and prevent off-axis orientation. Further, the upper anchoring feature 3010 can act as a safety feature without utilizing them for axial stability and off-axis orientation. For example, if the prosthesis 3000 is improperly deployed so that the prosthesis 3000 is deployed too low toward the left ventricle 30, the upper anchoring feature 3010 can prevent the prosthesis 3000 from falling into the left ventricle 30. In some situations such as those shown in FIGS. 41A and 42A, some or all of the upper anchoring feature 3010 may not contact the annular skirt 3030. This may occur when the skirt 3030 is in a collapsed configuration although it may also occur when the skirt 3030 is in an expanded configuration. It is also contemplated that some or all of the upper anchoring feature 3010 may contact the atrial side of the annulus 40 and/or tissue of the left atrium 20 beyond the annulus 40. The particular curve of the upper anchoring feature 3010 discussed above can prevent trauma to tissue of the heart 10, and can also help with stabilization of the prosthesis 3000 in the heart 10.

With continued reference to the situations illustrated in FIGS. 41A-43, the skirt 3030 can be positioned such that a proximal portion 3032 of the annular skirt 3030 is positioned along or adjacent an atrial side of the annulus 40. The proximal portion 3032 can be positioned between the atrial side of the annulus 40 and the upper anchoring feature 3010. The proximal portion 3032 can extend radially outward such that the skirt 3030 is positioned along or adjacent tissue of the left atrium 20 beyond the annulus 40.

In some situations such as those shown in FIGS. 41A and 41A, the skirt 3030 may not contact the wall of the heart 10. In some situations such as those shown in FIGS. 41B, 41C, 42B, 43, the skirt 3030 may contact the wall of the heart 10. As shown in FIG. 22A-23B, the annular skirt 3030 can also assist in filling gaps which exist between the leaflet 50 and the frame 3002 (portions of which are illustrated in dashed lines).

Figure 43:
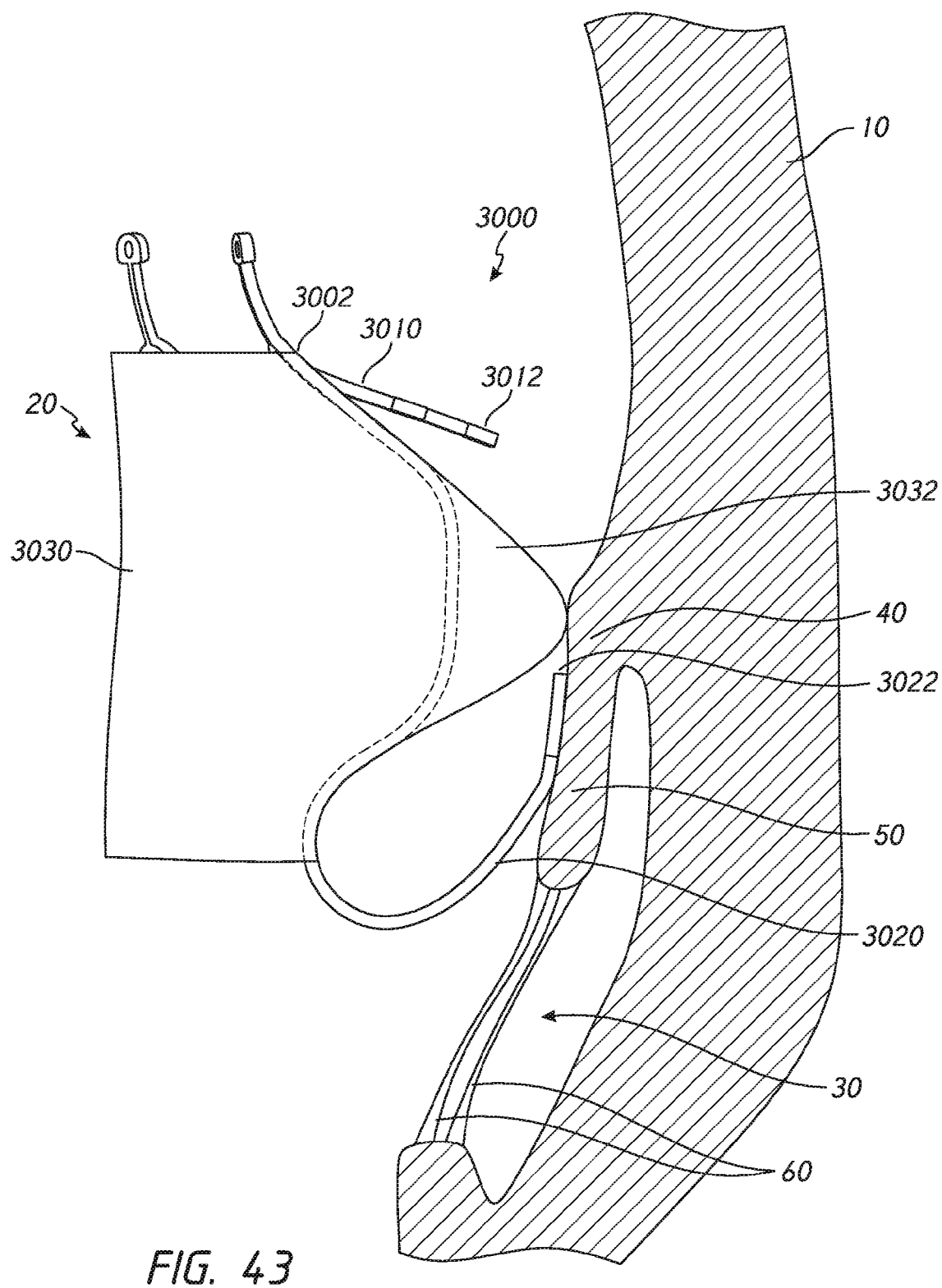

In some situations such as that shown in FIG. 43, the leaflet 50 may not be captured between the frame 3002 and a portion of the lower anchoring feature 3020. As shown, the portion of the lower anchoring feature 3020 may be positioned along an atrial surface of the leaflet 50. The portion of the lower anchoring feature 3020 may also be positioned along an inner surface of the annulus 40. It is also contemplated that the portion of the lower anchoring feature 3020 may exert a force against the leaflet 50 such that the leaflet 50 is pushed radially outward, relative to the longitudinal axis of the frame 3002, towards a wall of the heart 10. In such situations, the skirt 3030 can create a seal intra-annularly and/or along an atrial side of the leaflet 50. In alternative situations (not shown), the skirt 3030 can create a seal along a ventricular side of the annulus 40. For example, the prosthesis 3000 may be disposed in the annulus 40 such that a portion of the skirt 3030 is positioned on the ventricular side of the annulus 40.

As noted above, although the in vivo situations of FIG. 41A-43 have been described separately, it should be understood that one or more of these situations may be present when a prosthesis is positioned at the implantation location, such as a native mitral valve. For example, a portion of the lower anchoring feature 3020 may not capture the leaflet 50 whereas the remaining portion may capture the leaflet 50. As another example, when the prosthesis 3000 is positioned within the native mitral valve, the skirt 3030 can contact the wall of the heart 10 along one or more portions of an outermost circumference of the proximal portion 3032 and may not contact the wall of the heart 10 along other portions of the outermost circumference of the proximal portion 3032. For example, the skirt 3030 may contact the wall of the heart 10 along an approximately 180 degree portion of the outermost circumference of the proximal portion 3032 and may not contact the wall of the heart 10 along the remaining, approximately 180 degree portion of the outermost circumference of the proximal portion 3032.

Figure 44:
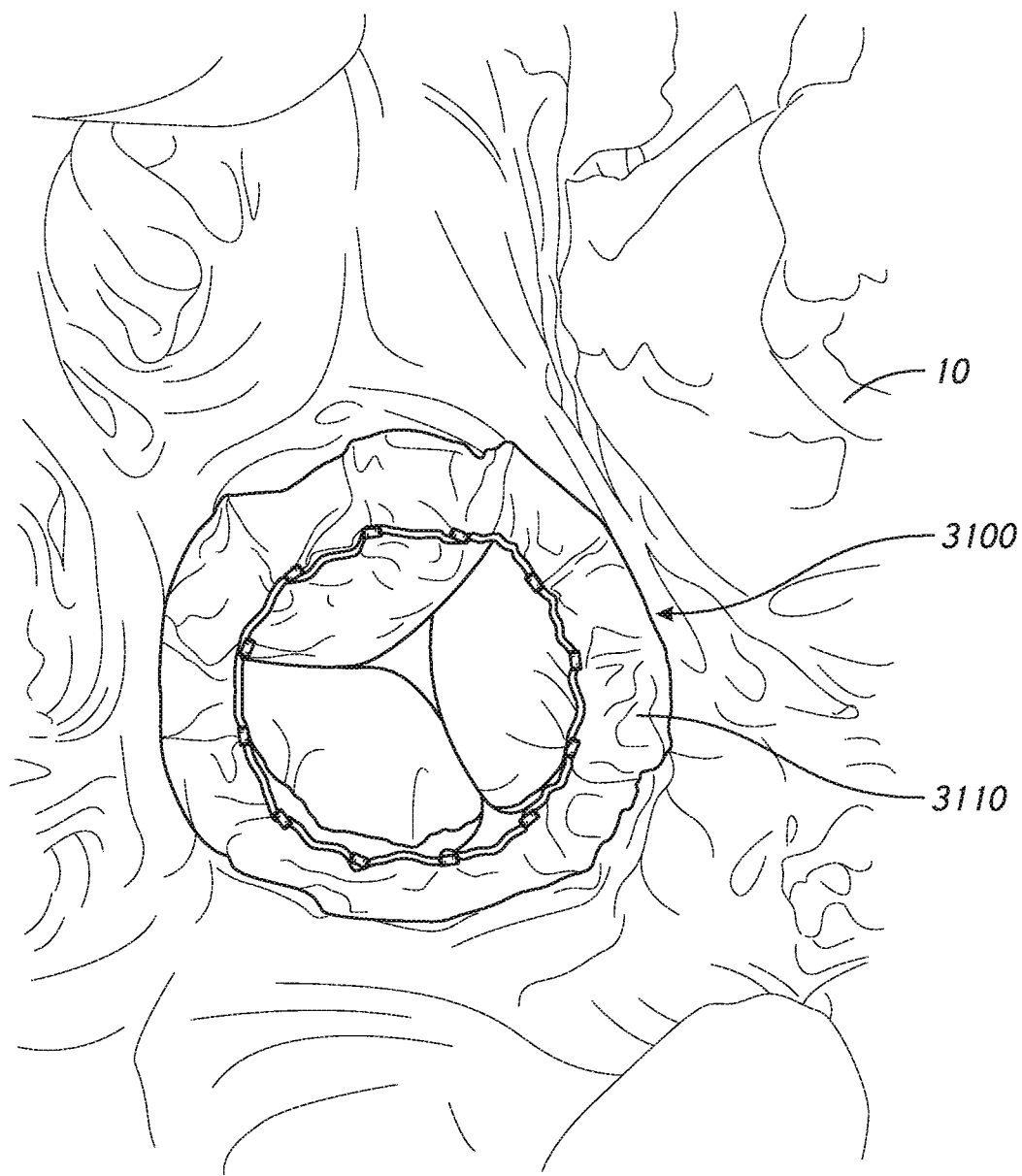
FIG. 44 is an atrial-oriented, view of an embodiment of a frame, a plurality of anchors, an annular skirt, and a floating valve implanted within a native mitral valve.
Figure 45:
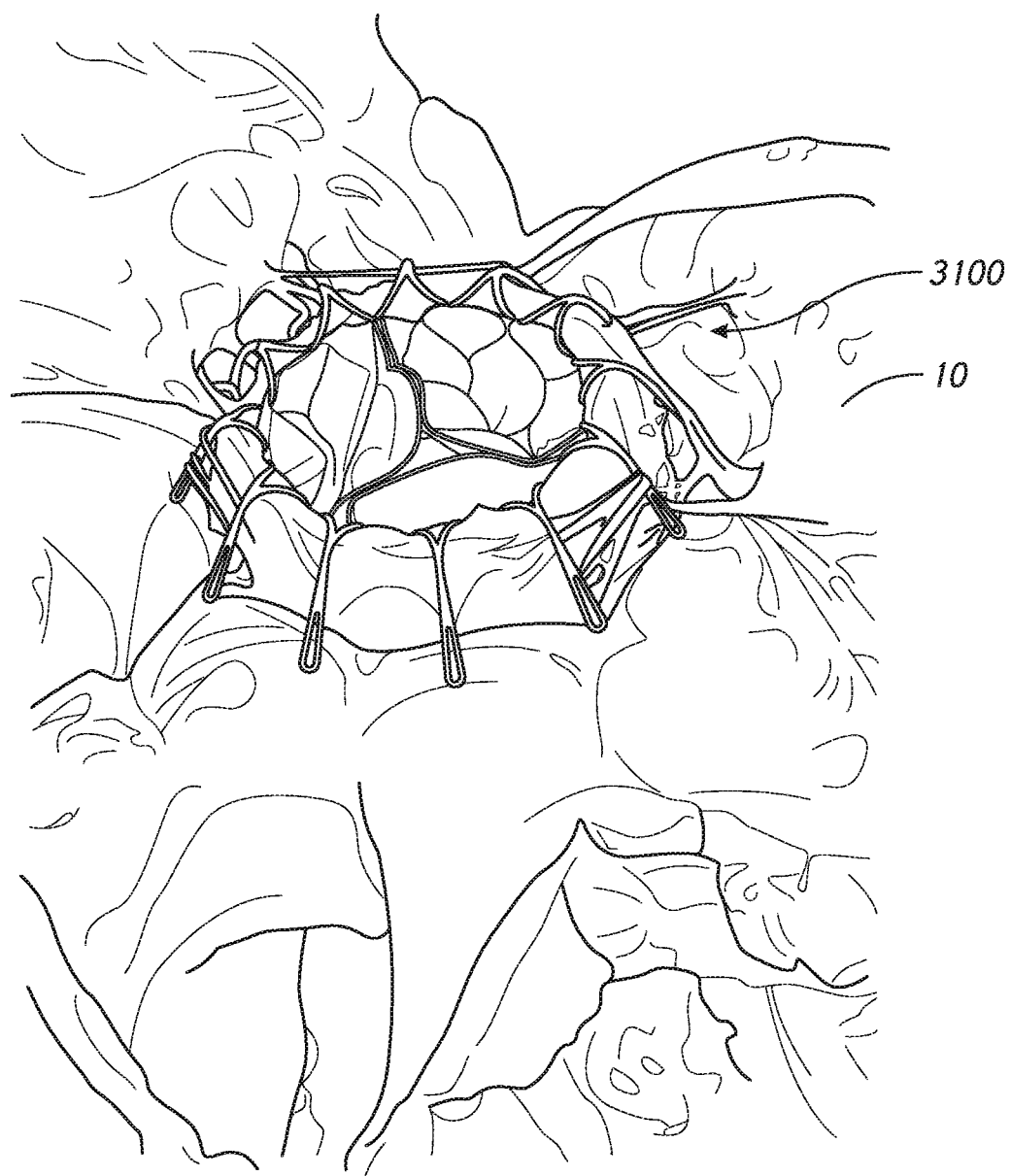
FIG. 45 is a ventricular-oriented, view of the frame, a plurality of anchors, an annular skirt, and a floating valve of FIG. 44 implanted within a native mitral valve.

With reference next to the prosthesis 3100 illustrated in FIGS. 44 and 45, the prosthesis 3100 is illustrated positioned within a heart 10 which has been splayed to more clearly show positioning of the prosthesis 3100 within the heart 10. FIG. 44 illustrates the prosthesis 3100 as viewed from an atrial side of the native mitral valve annulus. As shown in the illustrated embodiment, the prosthesis 3100 includes a skirt 3110 extending over an anchoring feature positioned over an atrial side of a native mitral valve annulus. FIG. 45 illustrates the prosthesis 3100 as viewed from a ventricular side of the native mitral valve annulus.

Delivery of Prosthesis

The prostheses described herein can be delivered to a patient's native heart valve in various ways, such as by open surgery, minimally-invasive surgery, and percutaneous or transcatheter delivery through the patient's vasculature. In some embodiments, the prosthesis can be delivered to a patient's native mitral valve through procedure such as, but not limited to, a transapical procedure and a transseptal procedure.

Figure 46:
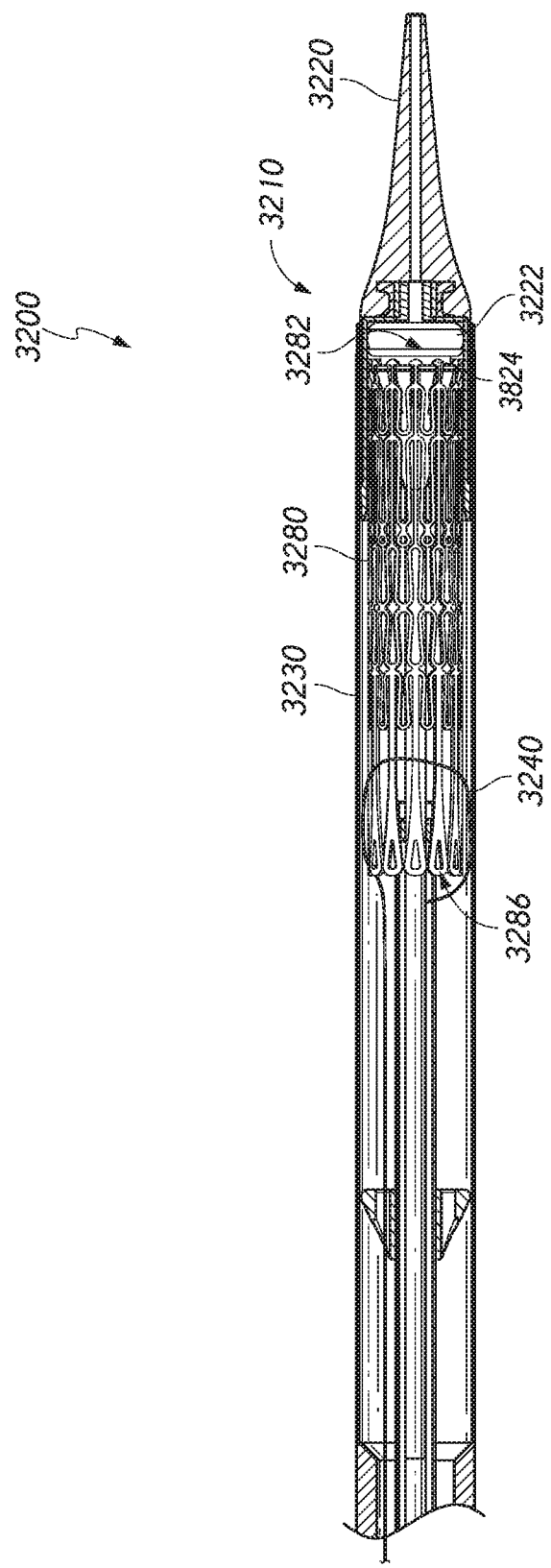
FIG. 46 is a cross-sectional view of a distal end of an embodiment of a delivery system loaded with an embodiment of a prosthesis.

As noted above, the prostheses can be used with a variety of delivery systems such as "slot"-based and/or "tether"-based systems. For purposes of the following figures, it is to be understood that the distal direction is towards the right of the drawing. With reference first to the system 3200 of FIG. 46, the system 3200 can include a delivery device 3210 with a prosthesis 3280 contained within the delivery device 3210. A first end 3282 of the prosthesis 3280 can be placed in a compressed state such that the first end 3282 of the prosthesis 3280 is retained between a nose cone 3220 and an inner retention member 3222 when the inner retention member 3222 is received within and covered by the nose cone 3220. The inner retention member 3222 can include one or more slots which interface with locking tabs 3284. The interface between the locking tabs 3284 and slots of the inner retention member 3222 can inhibit axial movement of the prosthesis 3280 relative to the inner retention member 3222. When the first end 3282 of the prosthesis 3280 is uncovered, such as by moving the nose cone 3220 distally relative to the inner retention member 3222 or by moving the inner retention member 3222 proximally relative to the nose cone 3220, the first end 3282 of the prosthesis 3280 can be released. This release can be caused by the prosthesis 3280 transitioning from a collapsed configuration to an expanded configuration when the prosthesis 3280 is formed from a self-expanding material.

At least a second end 3286 of the prosthesis 3280 can be placed in a compressed state such that the second end 3286 of the prosthesis 3280 is retained within a hollow shaft member 3230. When the second end 3286 is uncovered, such as by moving the hollow shaft member 3230 proximally relative to the prosthesis 3280 or by moving the prosthesis 3280 distally relative to the hollow shaft member 3230, the second end 3286 of the prosthesis 3280 can be released. This release can be caused by the prosthesis 3280 transitioning from a collapsed configuration to an expanded configuration when the prosthesis 3280 is formed from a self-expanding material. In some embodiments, the delivery system 3210 can include a tether 3240 which can wrap around a portion of the prosthesis 3280, such as an anchoring feature on the second end 3286. The tether 3240 can be used to control expansion of a portion of the prosthesis 3280, such as the second end 3286, when the portion of the prosthesis 3280 is uncovered.

In some embodiments, the system 3200 can be used in connection with a transapical procedure to access a native mitral valve. During such a procedure, the system 3200 can access a mitral valve through the apex of the heart. The anchoring feature on a ventricular side of the prosthesis 3280, such as the second end 3286, can be released on a ventricular side of the native mitral valve annulus. During delivery, the anchoring feature on a ventricular side of the annulus (along with the prosthesis 3280) can be moved toward the ventricular side of the annulus with the ventricular anchors extending between at least some of the chordae tendineae to provide tension on the chordae tendineae. The degree of tension provided on the chordae tendineae can differ. For example, little to no tension may be present in the chordae tendineae if the leaflet is shorter than or similar in size to the ventricular anchors. A greater degree of tension may be present in the chordae tendineae where the leaflet is longer than the ventricular anchors and, as such, takes on a compacted form and is pulled toward the native valve annulus. An even greater degree of tension may be present in the chordae tendineae where the leaflets are even longer relative to the ventricular anchors. The leaflet can be sufficiently long such that the ventricular anchors do not contact the annulus. After the anchoring feature on a ventricular side of the annulus is positioned, the remainder of the prosthesis can be deployed from the delivery system 3210.

Figure 47:
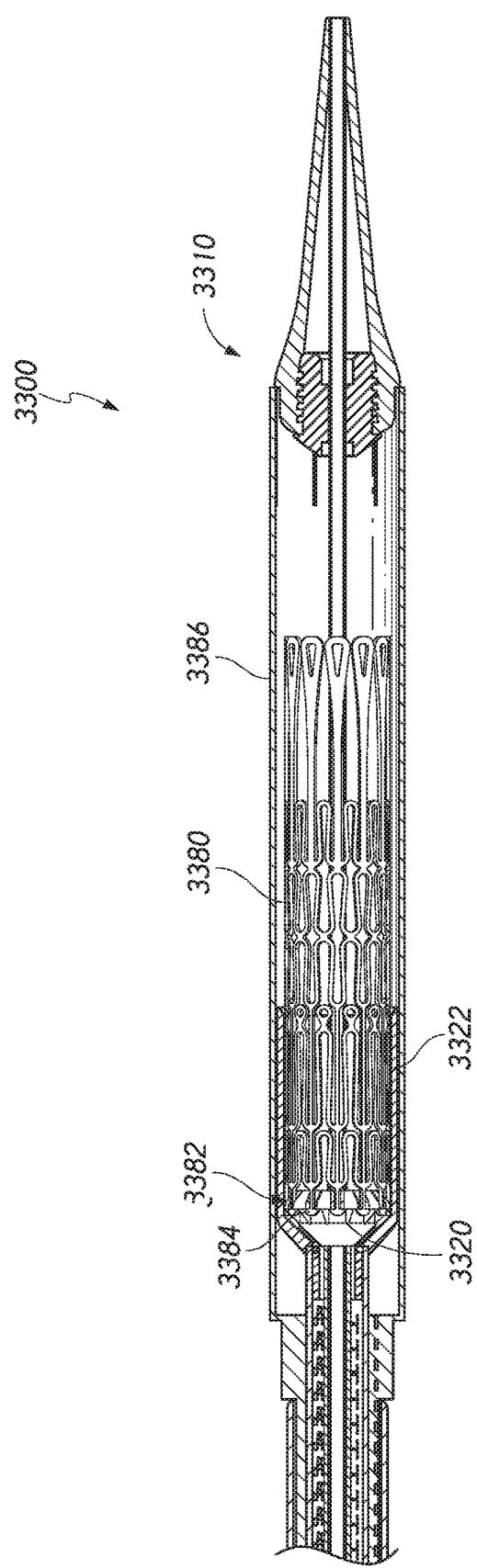
FIG. 47 is a cross-sectional view of a distal end of another embodiment of a delivery system loaded with another embodiment of a prosthesis.

With reference next to the system 3300 of FIG. 47, the system 3300 can include a delivery device 3310 with a prosthesis 3380 contained within the delivery device 3310. A first end 3382 of the prosthesis 3380 can be placed in a compressed state such that the first end 3382 of the prosthesis 3380 is retained between an inner retention member 3320 and another portion of the delivery device, such as an outer retention member 3322, when the inner retention member 3320 is received within and covered by the outer retention member 3322. The interface between the locking tabs 3384 and slots of the inner retention member 3320 can inhibit axial movement of the prosthesis 3380 relative to the inner retention member 3320. When the first end 3282 of the prosthesis 3380 is uncovered, such as by moving the outer retention member 3322 proximally relative to the inner retention member 3320 or by moving the inner retention member 3320 distally relative to the outer retention member 3322, the first end 3382 of the prosthesis 3380 can be released from the inner retention member 3322. If the inner retention member 3320 is fully uncovered, the first end 3382 of the prosthesis 3380 can be released from the delivery device 3310. This release can be caused by the prosthesis 3380 transitioning from a collapsed configuration to an expanded configuration when the prosthesis 3380 is formed from a self-expanding material.

At least a second end 3386 of the prosthesis 3380 can be placed in a compressed state such that the second end 3386 of the prosthesis 3380 is retained within an outer sheath assembly 3330. When the second end 3386 is uncovered, such as by moving the outer sheath assembly 3330 proximally relative to the prosthesis 3380 or by moving the prosthesis 3380 distally relative to the outer shaft assembly 3330, the second end 3386 of the prosthesis 3380 can be released. This release can be caused by the prosthesis 3380 transitioning from a collapsed configuration to an expanded configuration when the prosthesis 3380 is formed from a self-expanding material.

In some embodiments, the system 3300 can be used in connection with a transseptal procedure to access a native mitral valve. During such a procedure, the system 3300 can access a mitral valve through a septal puncture. The anchoring feature on a ventricular side of the prosthesis 3380, such as the second end 3386, can be released on a ventricular side of the native mitral valve annulus. During delivery, the anchoring feature on a ventricular side of the annulus (along with the prosthesis 3380) can be moved toward the ventricular side of the annulus with the ventricular anchors extending between at least some of the chordae tendineae to provide tension on the chordae tendineae. The degree of tension provided on the chordae tendineae can differ. For example, little to no tension may be present in the chordae tendineae if the leaflet is shorter than or similar in size to the ventricular anchors. A greater degree of tension may be present in the chordae tendineae where the leaflet is longer than the ventricular anchors and, as such, takes on a compacted form and is pulled toward the native valve annulus. An even greater degree of tension may be present in the chordae tendineae where the leaflets are even longer relative to the ventricular anchors. The leaflet can be sufficiently long such that the ventricular anchors do not contact the annulus. After the anchoring feature on a ventricular side of the annulus is positioned, the remainder of the prosthesis can be deployed from the delivery device 3310.

Other Embodiments

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A replacement heart valve prosthesis for deployment at a native heart valve, the prosthesis comprising:
    an expandable frame configured to radially expand and contract for deployment within a native heart valve, the expandable frame comprising:
        a frame body comprising a proximal region, a distal region, and an intermediate region extending between the proximal and distal regions, the frame body comprising a first row of struts and a second row of struts;
        a supplemental frame comprising a first row of struts configured to be generally aligned along the first row of struts of the frame body, the first row of struts of the supplemental frame having a shape which generally matches the shape of the first row of struts of the frame body;
        a proximal anchoring feature, the proximal anchoring feature sized to be positioned on a first side of an annulus of the native heart valve; and
        a distal anchoring feature, the distal anchoring feature sized to be positioned on a second side of an annulus of the native heart valve; and
    a valve body positioned within an interior of the expandable frame, the valve body comprising a plurality of leaflets configured to allow flow in a first direction and prevent flow in a second opposite direction;
    wherein the plurality of leaflets each have an arcuate proximal edge and a free distal edge, the plurality of leaflets being joined at commissures, the plurality of leaflets configured to allow flow in a proximal-to-distal direction and prevent flow in a distal-to-proximal direction; and
    wherein the valve body comprises one or more intermediate components connecting the leaflets to the expandable frame, wherein at least a portion of the arcuate proximal edge of each leaflet and/or the commissures are indirectly coupled to the expandable frame via the one or more intermediate components such that when the frame is in an expanded configuration, the one or more intermediate components position at least a portion of the arcuate proximal edge of each leaflet and/or the commissures radially inward from an inner surface of the expandable frame.

2. The prosthesis of claim 1, wherein the supplemental frame is formed separately from the frame body and the first row of struts of the supplemental frame is configured to be attached to at least a portion of the first row of struts of the frame body.

3. The prosthesis of claim 2, wherein the first row of struts of the supplemental frame is attached to the first row of struts of the frame body via sutures.

4. The prosthesis of claim 1, wherein the first row of struts of the supplemental frame is configured to be positioned radially inwardly of the first row of struts of the frame body.

5. The prosthesis of claim 1, wherein the first row of struts of the supplemental frame is configured to be positioned radially outwardly of the first row of struts of the frame body.

6. The prosthesis of claim 1, wherein the distal anchoring feature extends distally from the frame body and the supplemental frame comprises a second row of struts extending distally of the frame body, the first and second rows of struts of the supplemental frame forming cells.

7. The prosthesis of claim 1, wherein the proximal anchoring feature comprises a first row of struts configured to be generally aligned along the second row of struts of the frame body, the first row of struts of the proximal anchoring feature having a shape which generally matches the shape of the second row of struts of the frame body.

8. The prosthesis of claim 7, wherein the proximal anchoring feature is formed separately from the frame body and the first row of struts of the proximal anchoring feature is configured to be attached to at least a portion of the second row of struts of the frame body.

9. The prosthesis of claim 8, wherein the first row of struts of the proximal anchoring feature is attached to the second row of struts of the frame body via sutures.

10. The prosthesis of claim 7, wherein the first row of struts of the proximal anchoring feature is configured to be positioned radially outwardly of the second row of struts of the frame body.

11. The prosthesis of claim 7, wherein the proximal anchoring feature comprises a second row of struts configured to be generally aligned along a third row of struts of the frame body, the second row of struts of the proximal anchoring feature having a shape which generally matches the shape of the third row of struts of the frame body, the first and second rows of struts of the proximal anchoring feature forming cells.

12. The prosthesis of claim 1, further comprising a plurality of locking tabs extending from at least one of the frame body and the proximal anchoring feature.

13. The prosthesis of claim 12, wherein at least some of the locking tabs extend from the frame body and at least some of the locking tabs extend from the proximal anchoring feature, wherein the locking tabs of the proximal anchoring feature are configured to be generally aligned along the locking tabs of the frame body, the locking tabs of the proximal anchoring feature having a shape which generally matches the shape of the locking tabs of the frame body.

14. The prosthesis of claim 1, wherein the distal anchoring feature comprises a plurality of distal anchors, at least one of the distal anchors comprising two or more prongs.

15. The prosthesis of claim 14, wherein the two or more prongs are movable in at least one of a lateral direction and a radial direction relative to each other.

16. The prosthesis of claim 1, wherein the distal anchoring feature comprises one or more anchors configured to be movable in an axial direction relative to the frame body.

17. The prosthesis of claim 1, wherein the distal anchoring feature comprises one or more anchors having an insert comprising a platform, the platform configured to extend radially and laterally outwardly relative to the distal anchor when the expandable frame is in an expanded configuration.

18. The prosthesis of claim 1, wherein the one or more intermediate components form a generally tangent surface with the expandable frame when the valve body is closed to prevent flow in the second direction.

19. The prosthesis of claim 1, wherein the one or more intermediate components form an angle between about 120° to about 195° with the expandable frame when the valve body is closed to prevent flow in the second direction.

20. The prosthesis of claim 1, wherein the one or more intermediate components is formed from a material having a stiffness greater than that of the plurality of leaflets and less than that of the expandable frame.

21. The prosthesis of claim 1, wherein:
the prosthesis comprises an annular skirt extending around the exterior of the expandable frame; and
at least one of the valve body and the annular skirt comprises one or more openings configured to allow at least one of:
fluid ingress into a space between the valve leaflets and the annular skirt; and
fluid egress out of the space between the valve leaflets and the annular skirt.

22. The prosthesis of claim 21, wherein:
the annular skirt comprises a supplemental rib extending from a portion of the annular skirt; and
the annular skirt extends to different radial dimensions with a first peripheral region extending to a first radial dimension and a second peripheral region extending to a second radial dimension greater than the first radial dimension.

23. A replacement heart valve prosthesis for deployment at a native heart valve, the prosthesis comprising:
an expandable frame configured to radially expand and contract for deployment within a native heart valve, the expandable frame comprising:
a frame body comprising a proximal region, a distal region, and an intermediate region extending between the proximal and distal regions, the frame body comprising a first row of struts and a second row of struts;
a supplemental frame comprising a first row of struts configured to be generally aligned along the first row of struts of the frame body, the first row of struts of the supplemental frame having a shape which generally matches the shape of the first row of struts of the frame body;
a proximal anchoring feature, the proximal anchoring feature sized to be positioned on a first side of an annulus of the native heart valve; and
a distal anchoring feature, the distal anchoring feature sized to be positioned on a second side of an annulus of the native heart valve; and
a valve body positioned within an interior of the expandable frame, the valve body comprising a plurality of leaflets configured to allow flow in a first direction and prevent flow in a second opposite direction;
wherein the prosthesis comprises an annular skirt extending around the exterior of the expandable frame; and
at least one of the valve body and the annular skirt comprises one or more openings configured to allow at least one of:
fluid ingress into a space between the valve leaflets and the annular skirt; and
fluid egress out of the space between the valve leaflets and the annular skirt.

24. The prosthesis of claim 23, wherein:
the annular skirt comprises a supplemental rib extending from a portion of the annular skirt; and
the annular skirt extends to different radial dimensions with a first peripheral region extending to a first radial dimension and a second peripheral region extending to a second radial dimension greater than the first radial dimension.

25. A replacement heart valve prosthesis for deployment at a native heart valve, the prosthesis comprising:
an expandable frame configured to radially expand and contract for deployment within a native heart valve, the expandable frame comprising:
a frame body comprising a proximal region, a distal region, and an intermediate region extending between the proximal and distal regions, the frame body comprising a first row of struts and a second row of struts;
a supplemental frame comprising a first row of struts configured to be generally aligned along the first row of struts of the frame body, the first row of struts of the supplemental frame having a shape which generally matches the shape of the first row of struts of the frame body;
a proximal anchoring feature, the proximal anchoring feature sized to be positioned on a first side of an annulus of the native heart valve; and
a distal anchoring feature, the distal anchoring feature sized to be positioned on a second side of an annulus of the native heart valve; and
a valve body positioned within an interior of the expandable frame, the valve body comprising a plurality of leaflets configured to allow flow in a first direction and prevent flow in a second opposite direction;
wherein the supplemental frame is formed separately from the frame body and the first row of struts of the supplemental frame is configured to be attached to at least a portion of the first row of struts of the frame body; and
wherein the first row of struts of the supplemental frame is attached to the first row of struts of the frame body via sutures.

* * * * *